(12) United States Patent
Rau et al.

(10) Patent No.: US 11,116,849 B2
(45) Date of Patent: Sep. 14, 2021

(54) HYDROGEL-LINKED PRODRUGS RELEASING TAGGED DRUGS

(71) Applicant: Ascendis Pharma A/S, Hellerup (DK)

(72) Inventors: Harald Rau, Dossenheim (DE); Nora Kaluza, Heidelberg (DE); Ulrich Hersel, Heidelberg (DE); Thomas Knappe, Heidelberg (DE); Burkhardt Laufer, Dossenheim (DE)

(73) Assignee: Ascendis Pharma A/S, Hellerup (DK)

( * ) Notice: Subject to any disclaimer, the term of this patent is extended or adjusted under 35 U.S.C. 154(b) by 327 days.

(21) Appl. No.: 14/786,481

(22) PCT Filed: Apr. 16, 2014

(86) PCT No.: PCT/EP2014/057753
§ 371 (c)(1),
(2) Date: Oct. 22, 2015

(87) PCT Pub. No.: WO2014/173759
PCT Pub. Date: Oct. 30, 2014

(65) Prior Publication Data
US 2016/0082123 A1    Mar. 24, 2016

(30) Foreign Application Priority Data

Apr. 22, 2013 (EP) ..................... 13164669
Oct. 8, 2013 (EP) ..................... 13187784

(51) Int. Cl.
*A61K 47/60* (2017.01)
*A61K 47/69* (2017.01)

(52) U.S. Cl.
CPC .......... *A61K 47/6903* (2017.08); *A61K 47/60* (2017.08)

(58) Field of Classification Search
CPC ........................... A61K 47/60; A61K 47/6903
See application file for complete search history.

(56) References Cited

FOREIGN PATENT DOCUMENTS

| EP | 1 625 856 A1 | 2/2006 |
|---|---|---|
| WO | WO 99/22770 | 5/1998 |
| WO | WO 2005/099768 A2 | 10/2005 |
| WO | WO 2006/003014 A2 | 1/2006 |
| WO | WO 2006/136586 A2 | 12/2006 |
| WO | WO 2009/095479 A2 | 8/2009 |
| WO | WO 2011/012715 A1 | 2/2011 |
| WO | WO 2011/012721 A1 | 2/2011 |
| WO | WO 2011/012722 A1 | 2/2011 |
| WO | WO 2011/089214 A1 | 7/2011 |
| WO | WO 2011/089215 A1 | 7/2011 |
| WO | WO 2011/089216 A1 | 7/2011 |
| WO | WO 2013/160340 A1 | 10/2013 |

OTHER PUBLICATIONS

Harris et al., "Effect of PEGylation on Pharmaceuticals". Nature Reviews Drug Discovery, Mar. 2003, pp. 214-221, vol. 2.
Veronese et al., "PEGylation, Successful Approach to drug delivery", Drug Discovery Today, Nov. 2005, 1451-1458, vol. 10(21).
Jain et al., "PEGylation: An Approach for Drug Delivery. A Review", Critical Reviews in Therapeutic Drug Carrier Systems (2008), 403-447, vol. 25(5).
Hamidi et al., "Pharmacokinetic Consequences of PEGylation", Drug Delivery, (2006), 399-409 vol. 13.
Li et al., "Current Drug Research on PEGylation with Small Molecular Agents", Polymer Science, (2013), 421-444, vol. 38.

*Primary Examiner* — Alicia L Otton
(74) *Attorney, Agent, or Firm* — Haug Partners LLP

(57) ABSTRACT

The present invention relates to a process for the preparation of a hydrogel-linked prodrug releasing a tag moiety-biologically active moiety conjugate, to a hydrogel-linked prodrug releasing a tag moiety-bio logically active moiety conjugate obtainable by such process, to pharmaceutical compositions comprising said prodrug and their use as a medicament.

27 Claims, No Drawings

HYDROGEL-LINKED PRODRUGS RELEASING TAGGED DRUGS

The present application claims priority from PCT Patent Application No. PCT/EP2014/057753 filed on Apr. 16, 2014, which claims priority from European Patent Application No. EP 13187784.7 filed on Oct. 8, 2013, and European Patent Application No. EP 13164669.7 filed on Apr. 22, 2013, the disclosures of which are incorporated herein by reference in their entirety.

FIELD OF THE INVENTION

The present invention relates to a process for the preparation of a hydrogel-linked prodrug releasing a tag moiety-biologically active moiety conjugate, to a hydrogel-linked prodrug releasing a tag moiety-biologically active moiety conjugate obtainable by such process, to pharmaceutical compositions comprising said prodrug and their use as a medicament.

BACKGROUND OF THE INVENTION

Hydrogels are versatile carriers for carrier-linked prodrugs, see for example WO2006003014A2 and WO2011012715A1. As at least most of the drugs are connected to the inside of the hydrogel, they are protected from modifying and/or degrading enzymes present in a patient's body which extends the time period over which active drugs are released from such prodrugs.

However, once the drug is released from the hydrogel carrier, it is subject to renal clearance and exposed to modifying and/or degrading enzymes that reduce the half-life of the released drug.

To avoid this Harris (WO199922770) has devised hydrogel prodrugs which release biologically active moiety-poly(ethylene glycol) (PEG) conjugates. These prodrugs have two major disadvantages. On the one hand polymerization of the Harris' hydrogel occurs in the presence of drug molecules which get coupled to the forming hydrogel during polymerization. This may cause drug molecules to be entrapped in the hydrogel which may lead to a burst-type release of drug during hydrogel degradation.

On the other hand drug molecules are released upon degradation of labile bonds present in the hydrogel matrix. As the degradation process leads to fragments of various sizes, the exact nature of the PEG tag attached to the released biologically active moiety varies between different degradation products. The variable size of the PEG tags leads to different residual activities of the conjugates which are undesired from a pharmacological view point.

DETAILED DESCRIPTION OF THE INVENTION

Accordingly, there is a need for hydrogel-linked prodrugs, which at least partially overcome the shortcomings described before.

It is therefore an object of the present invention to overcome at least some of the above-mentioned shortcomings and to provide a hydrogel, which releases drugs with improved pharmacologic properties, like for example extended half-lives. This is achieved by releasing drugs with a tag, i.e. tag moiety-biologically active moiety conjugates, from the hydrogel-linked prodrugs of the present invention.

In one aspect, the present invention relates to a process for the preparation of a hydrogel-linked prodrug releasing a tag moiety-biologically active moiety conjugate comprising the steps of:
(a) providing a mixture comprising
  (a-i) at least one backbone reagent, wherein the at least one backbone reagent has a molecular weight ranging from 1 to 100 kDa, and comprises at least three functional groups $A^{x0}$, wherein each $A^{x0}$ is an amine (—NH$_2$ or —NH—), hydroxyl (—OH), carboxyl (—COOH) or activated carboxyl (—COY$^1$, wherein Y$^1$ is selected from formulas (f-i) to (f-vi):

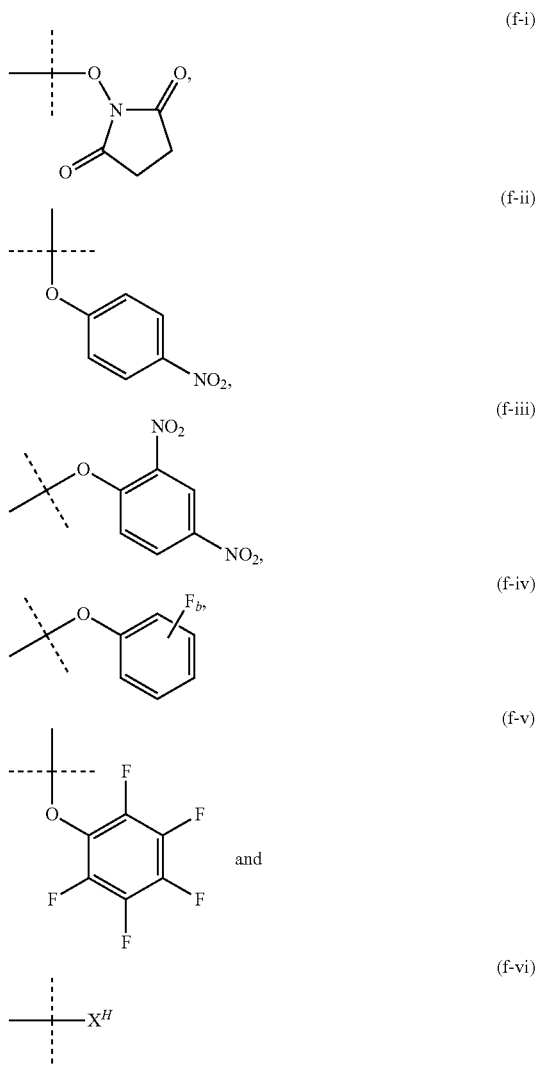

wherein
  the dashed lines indicate attachment to the rest of the molecule,
  b is 1, 2, 3 or 4
  X$^H$ is Cl, Br, I, or F);
(a-ii) at least one crosslinker reagent, wherein the at least one crosslinker reagent has a molecular weight ranging from 0.2 to 40 kDa and comprises at least two functional end groups selected from the group consisting of activated ester groups, activated carbamate groups, activated carbonate groups, activated thiocarbonate groups and amine groups;

in a weight ratio of the at least one backbone reagent to the at least one crosslinker reagent ranging from 1:99 to 99:1 and wherein the molar ratio of $A^{x0}$ to functional end groups is >1;
(b) polymerizing the mixture of step (a) to a hydrogel;
(c) optionally covalently conjugating a spacer reagent of formula (VI)

$A^{x1}\text{-}SP^2\text{-}A^{x2}$ (VI), wherein
SP$^2$ is $C_{1\text{-}50}$ alkyl, $C_{2\text{-}50}$ alkenyl or $C_{2\text{-}50}$ alkynyl, which $C_{1\text{-}50}$ alkyl, $C_{2\text{-}50}$ alkenyl and $C_{2\text{-}50}$ alkynyl is optionally interrupted by one or more group(s) selected from the group consisting of —NH—, —N($C_{1\text{-}4}$ alkyl)-, —O—, —S, —C(O)—, —C(O)NH, —C(O)N($C_{1\text{-}4}$ alkyl)-, —O—C(O)—, —S(O)—, —S(O)$_2$—, 4- to 7-membered heterocyclyl, phenyl and naphthyl;
$A^{x1}$ is a functional group for reaction with $A^{x0}$ of the hydrogel; and
$A^{x2}$ is a functional group;
to $A^{x0}$ of the hydrogel from step (b); and
(d) covalently conjugating;
(d-i) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalent conjugation of a drug to said reversible prodrug linker moiety resulting in a reversible prodrug linker moiety-biologically active moiety conjugate conjugated to the hydrogel of step (b) or (c), followed by covalent conjugation of a tag reagent to the biologically active moiety resulting in a reversible prodrug linker moiety-biologically active moiety-tag moiety conjugate conjugated to the hydrogel of step (b) or (c); or
(d-ii) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalent conjugation of a biologically active moiety-tag moiety conjugate reagent to said reversible prodrug linker moiety through a functional group of the biologically active moiety resulting in a reversible prodrug linker moiety-biologically active moiety-tag moiety conjugate conjugated to the hydrogel of step (b) or (c); or
(d-iii) a reversible prodrug linker moiety-biologically active moiety conjugate reagent to $A^{x0}$ or $A^{x2}$ of the hydrogel of step (b) or (c), respectively, through a functional group of the reversible prodrug linker moiety, followed by covalent conjugation of a tag reagent to said biologically active moiety; or
(d-iv) a reversible prodrug linker moiety-biologically active moiety-tag moiety conjugate reagent to $A^{x0}$ or $A^{x2}$ of the hydrogel of step (b) or (c), respectively, through a functional group of the reversible prodrug linker moiety; or
(d-v) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalent conjugation of a tag reagent to said reversible prodrug linker moiety resulting in a reversible prodrug linker moiety-tag moiety conjugate conjugated to the hydrogel of step (b) or (c), followed by covalent conjugation of a drug to said tag moiety resulting in a reversible prodrug linker moiety-tag moiety-biologically active moiety conjugate conjugated to the hydrogel of step (b) or (c); or
(d-vi) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalent conjugation of a tag moiety-biologically active moiety conjugate reagent to said reversible prodrug linker moiety through a functional group of the tag moiety;
(d-vii) a reversible prodrug linker moiety-tag moiety conjugate reagent to $A^{x0}$ or $A^{x2}$ of the hydrogel of step (b) or (c), respectively, through a functional group of the reversible prodrug linker moiety, followed by covalent conjugation of a drug to said tag moiety; or
(d-viii) a reversible prodrug linker moiety-tag moiety-biologically active moiety conjugate reagent to $A^{x0}$ or $A^{x2}$ of the hydrogel of step (b) or (c), respectively, through a functional group of the reversible prodrug linker moiety;
wherein the linkage between the reversible prodrug linker moiety and the biologically active moiety in the prodrug according to (d-i), (d-ii), (d-iii) and (d-iv) and the linkage between the reversible prodrug linker moiety and the tag moiety in the prodrug according to (d-v), (d-vi), (d-vii) and (d-viii) is reversible.

It was now surprisingly found that such hydrogel-linked prodrugs have a release kinetic that is only governed by the release kinetic of the reversible prodrug linker and the released tag moiety-biologically active moiety conjugate has improved pharmacologic properties, like for example an extended half-life, compared to the corresponding drug without the tag moiety. In contrast to the various conjugates of Harris (WO199922770) the released tag moiety-biologically active moiety conjugates have a well-defined structure.

Within the present invention the terms are used with the meaning as follows.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises at least one functional group for reaction with the functional group of another reagent or moiety.

As used herein, the term "backbone reagent" means a reagent, which is suitable as a starting material for forming hydrogels. As used herein, a backbone reagent preferably does not comprise biodegradable linkages. A backbone reagent may comprise a "branching core" which refers to an atom or moiety to which more than one other moiety is attached.

As used herein, the term "crosslinker reagent" means a linear or branched reagent, which is suitable as a starting material for crosslinking backbone reagents. Preferably, the crosslinker reagent is a linear chemical compound. A crosslinker reagent comprises at least one biodegradable linkage.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "-" indicates attachment to another moiety.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

The term "drug" means any substance which can affect one or more physical or biochemical properties of a biological organism, including but not limited to viruses, bacteria, fungi, plants, animals, and humans. In particular, as used herein, the term includes any substance intended for diagnosis, cure, mitigation, treatment, or prevention of disease in organisms, in particular humans or animals, or to otherwise enhance physical or mental well-being of organisms, in particular humans or animals. Instead of the term "drug" also the notation "$(A^{x5})_{a1}$-D-$(A^{x6})_{a2}$" is used, wherein D is biologically active moiety, $A^{x5}$ and $A^{x6}$ are independently of each other a functional group and a1 and a2 are both 1 in steps (d-i), (d-ii), (d-iii) and (d-iv) and a1 is 1 and a2 is 0 or 1 in steps (d-v), (d-vi), (d-vii) and (d-viii). It is understood that a drug may also have more than two functional groups which for simplification are not explicitly mentioned as they are not involved in the process of the present invention.

The term "biologically active moiety" refers to the moiety which results after covalently conjugating a drug to one or more other moieties wherein one or more functional groups of the drug were conjugated to functional groups of said one or more other moieties which subsequently form linkages. The term "biologically active moiety" is also referred to as "D". Accordingly, the corresponding reagent is referred to as "drug".

The term "spacer moiety" as used herein refers to any moiety suitable for connecting two moieties and is known to the person skilled in the art.

The term "tag moiety" as used herein refers to a moiety covalently conjugated to the biologically active moiety and preferably has a molecular weight ranging from 15 Da to 80 kDa.

As used herein, the term "functional group" means a group of atoms which can react with other functional groups. Functional groups include but are not limited to the following groups: carboxylic acid (—(C═O)OH), primary or secondary amine (—NH$_2$, —NH—), maleimide, thiol (—SH), sulfonic acid (—(O═S═O)OH), carbonate, carbamate (—O(C═O)N<), hydroxy (—OH), aldehyde (—(C═O)H), ketone (—(C═O)—), hydrazine (>N—N<), isocyanate, isothiocyanate, phosphoric acid (—O(P═O)OHOH), phosphonic acid (—O(P═O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "activated functional group" means a functional group, which is connected to an activating group, i.e. a functional group was reacted with an activating reagent. Preferred activated functional groups include but are not limited to activated ester groups, activated carbamate groups, activated carbonate groups and activated thiocarbonate groups. Preferred activating groups are selected from the group consisting of formulas ((f-i) to (f-vi):

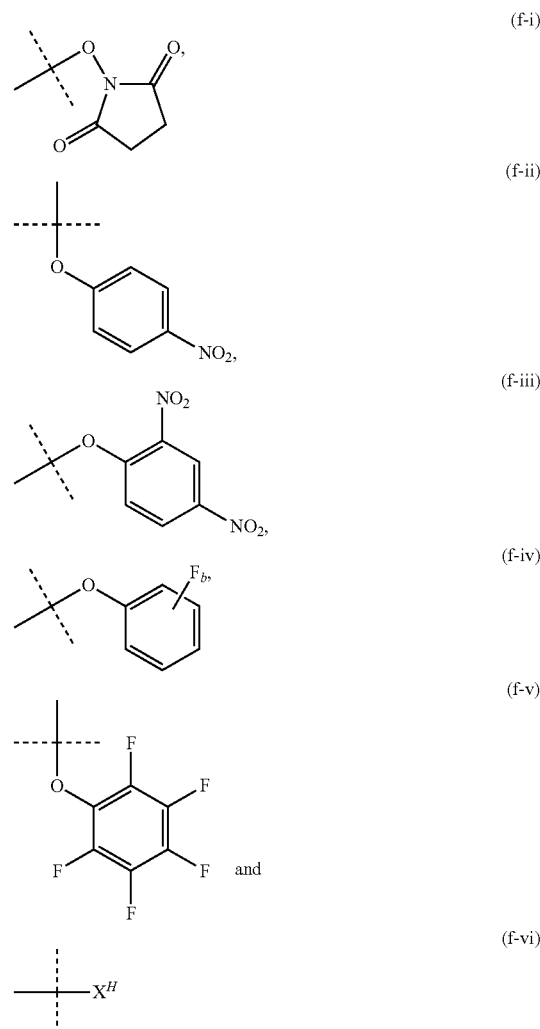

wherein
the dashed lines indicate attachment to the rest of the molecule;
b is 1, 2, 3 or 4; and
$X^H$ is Cl, Br, I, or F.

Accordingly, a preferred activated ester has the formula

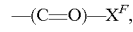

wherein
$X^F$ is selected from the group consisting of formulas (f-i), (f-ii), (f-iii), (f-iv), (f-v) and (f-vi).

Accordingly, a preferred activated carbamate has the formula

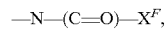

wherein
$X^F$ is selected from the group consisting of formulas (f-i), (f-ii), (f-iii), (f-iv), (f-v) and (f-vi).

Accordingly, a preferred activated carbonate has the formula

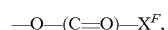

wherein
$X^F$ is selected from the group consisting of formulas (f-i), (f-ii), (f-iii), (f-iv), (f-v) and (f-vi).

Accordingly, a preferred activated thiocarbamate has the formula

—S—(C=O)—X$^F$, wherein

X$^F$ is selected from the group consisting of formulas (f-i), (f-ii), (f-iii), (f-iv), (f-v) and (f-vi).

Accordingly, a "functional end group" is a functional group which is localized at the end of a moiety or molecule, i.e. is a terminal functional group.

As used herein, the term "capping group" means a moiety which is irreversibly, i.e. permanently, connected to a functional group to render it incapable of reacting with functional groups of other reagents or moieties.

As used herein, the term "protecting group" means a moiety which is reversibly connected to a functional group to render it incapable of reacting with, for example, another functional group. Suitable alcohol (—OH) protecting groups are, for example, acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, trimethylsilyl, tert-butyldimethylsilyl, tri-iso-propylsilyloxymethyl, triisopropylsilyl ether, methyl ether, and ethoxyethyl ether. Suitable amine protecting groups are, for example, carbobenzyloxy, p-methoxybenzyl carbonyl, tert-butyloxycarbonyl, 9-fluorenylmethyloxyarbonyl, acetyl, benzoyl, benzyl, carbamate, p-methoxybenzyl, 3,4-dimethoxybenzyl, p-methoxyphenyl, and tosyl. Suitable carbonyl protecting groups are, for example, acetals and ketals, acylals and dithianes. Suitable carboxylic acid protecting groups are, for example, methyl esters, benzyl esters, tert-butyl esters, 2,6-dimethylphenol, 2,6-diisopropylphenol, 2,6.-di-tert-butylphenol, silyl esters, orthoesters, and oxazoline. Suitable phosphate protecting groups are, for example, 2-cyanoethyl and methyl.

As used herein, the terms "work-up" and "working-up" refer to the series of manipulations required to isolate and purify the product(s) of a chemical reaction, in particular of a polymerization.

As used herein, the term "polymer" means a molecule comprising repeating structural units, i.e. monomers, connected by chemical bonds in a linear, circular, branched, crosslinked or dendrimeric way or a combination thereof, which may be of synthetic or biological origin or a combination of both. It is understood that a polymer may for example also comprise functional groups or capping moieties. Preferably, a polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. At most, a polymer preferably has a molecular weight of 1 million Da.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "polymerization" or "polymerizing" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, i.e. the reaction product, and a low molecular weight molecule, for example water, is released.

As used herein, the term "suspension polymerization" means a heterogeneous and/or biphasic polymerization reaction, wherein the monomer reagents are dissolved in a first solvent, forming the disperse phase which is emulsified in a second solvent, forming the continuous phase. In the present invention, the monomer reagents are the at least one backbone reagent and the at least one crosslinker reagent. Both the first solvent and the monomer reagents are not soluble in the second solvent. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of a base as initiator which is soluble in the first solvent. A suitable commonly known base suitable as initiator may be a tertiary base, such as tetramethylethylenediamine (TMEDA).

As used herein, the term "immiscible" means the property where two substances are not capable of combining to form a homogeneous mixture at ambient temperature and pressure, i.e. at temperature and pressure conditions typically present in a typical laboratory environment.

As used herein, the term "polyamine" means a reagent or moiety comprising more than one amine (—NH— and/or —NH$_2$), e.g. from 2 to 64 amines, from 4 to 48 amines, from 6 to 32 amines, from 8 to 24 amines, or from 10 to 16 amines. Particularly preferred polyamines comprise from 2 to 32 amines.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties especially selected from the group consisting of:

C$_{1-50}$ alkyl, C$_{2-50}$ alkenyl, C$_{2-50}$ alkynyl, C$_{3-10}$ cycloalkyl, 4- to 7-membered heterocyclyl, 8- to 11-membered heterobicyclyl, phenyl; naphthyl; indenyl; indanyl; and tetralinyl; and linkages selected from the group of linkages consisting of

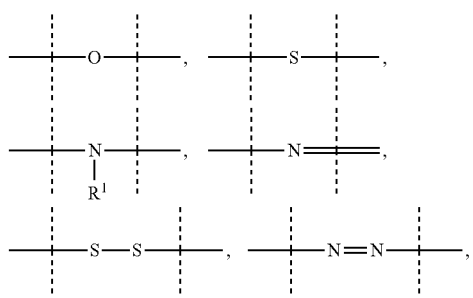

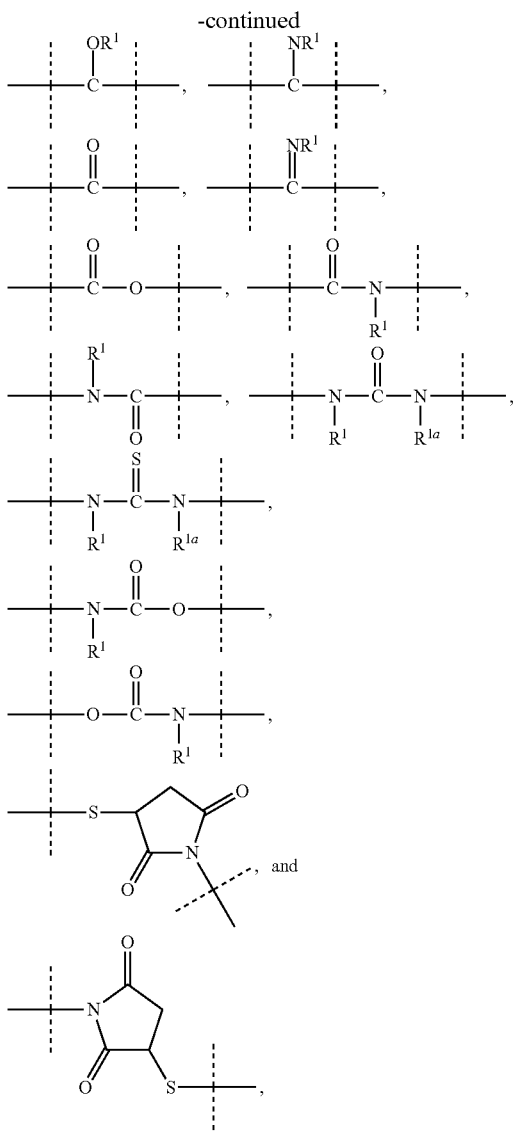

wherein
dashed lines indicate attachment to the remainder of the moiety or reagent, and $R^1$ and $R^{1a}$ are independently of each other H or $C_{1-6}$ alkyl.

The term "hyaluronic acid-based comprising at least X % hyaluronic acid" is used accordingly.

As used herein, the term "$C_{1-4}$ alkyl" alone or in combination means a straight-chain or branched alkyl group having 1 to 4 carbon atoms. If present at the end of a molecule, examples of straight-chain and branched $C_{1-4}$ alkyl groups are methyl, ethyl, n-propyl, isopropyl, n-butyl, isobutyl, sec-butyl and tert-butyl. When two moieties of a molecule are linked by the $C_{1-4}$ alkyl group, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —$CH_2$—$CH_2$—$CH_2$—$CH_2$—, and —$CH_2$—$CH_2$—$CH_2(CH_3)$—. Each hydrogen atom of a $C_{1-4}$ alkyl group may be replaced by a substituent as defined below.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ alkyl group may be replaced by a substituent as defined below.

Accordingly, as used herein, the term "$C_{1-20}$ alkyl" alone or in combination means a straight-chain or branched alkyl group having 1 to 20 carbon atoms. The term "$C_{8-18}$ alkyl" alone or in combination means a straight-chain or branched alkyl group having 8 to 18 carbon atoms. Accordingly, as used herein, the term "$C_{1-50}$ alkyl" alone or in combination means a straight-chain or branched alkyl group having 1 to 50 carbon atoms. Each hydrogen atom of a $C_{1-20}$ alkyl group, a $C_{8-18}$ alkyl group and $C_{1-50}$ alkyl group may be replaced by a substituent. In each case the alkyl group may be present at the end of a molecule or two moieties of a molecule may be linked by the alkyl group.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH=CH_2$, —$CH=CH—CH_3$, —$CH_2$—$CH=CH_2$, —$CH=CHCH_2$—$CH_3$ and —$CH=CH$—$CH=CH_2$. When two moieties of a molecule are linked by the $C_{2-6}$ alkenyl group, then an example for such $C_{2-6}$ alkenyl is —$CH=CH$—. Each hydrogen atom of a $C_{2-6}$ alkenyl group may be replaced by a substituent as defined below. Optionally, one or more triple bond(s) may occur.

Accordingly, as used herein, the term "$C_{2-20}$ alkenyl" alone or in combination means a straight-chain or branched hydrocarbon residue comprising at least one carbon-carbon double bond having 2 to 20 carbon atoms. The term "$C_{2-50}$ alkenyl" alone or in combination means a straight-chain or branched hydrocarbon residue comprising at least one carbon-carbon double bond having 2 to 50 carbon atoms. If present at the end of a molecule, examples are —$CH=CH_2$, —$CH=CH—CH_3$, —$CH_2$—$CH=CH_2$, —$CH=CHCH_2$—$CH_3$ and —$CH=CH$—$CH=CH_2$. When two moieties of a molecule are linked by the alkenyl group, then an example is e.g. —$CH=CH$—. Each hydrogen atom of a $C_{2-20}$ alkenyl or $C_{2-50}$ alkenyl group may be replaced by a substituent as defined below. Optionally, one or more triple bond(s) may occur.

As used herein, the term "$C_{2-6}$ alkynyl" alone or in combination means straight-chain or branched hydrocarbon residue comprising at least one carbon-carbon triple bond having 2 to 6 carbon atoms. If present at the end of a molecule, examples are —$C≡CH$, —$CH_2$—$C≡CH$, $CH_2$—$CH_2$—$C≡CH$ and $CH_2$—$C≡C$—$CH_3$. When two moieties of a molecule are linked by the alkynyl group, then an example is: —$C≡C$—. Each hydrogen atom of a $C_{2-6}$ alkynyl group may be replaced by a substituent as defined below. Optionally, one or more double bond(s) may occur.

Accordingly, as used herein, the term "$C_{2-20}$ alkynyl" alone or in combination means a straight-chain or branched hydrocarbon residue comprising at least one carbon-carbon triple bond having 2 to 20 carbon atoms and "$C_{2-50}$ alkynyl" alone or in combination means a straight-chain or branched hydrocarbon residue comprising at least one carbon-carbon triple bond having 2 to 50 carbon atoms. If present at the end of a molecule, examples are —$C≡CH$, —$CH_2$—$C≡CH$, CH$_2$—CH$_2$—C≡CH and CH$_2$—C≡C—CH$_3$. When two moieties of a molecule are linked by the alkynyl group, then an example is —C≡C—. Each hydrogen atom of a C$_{2-20}$ alkynyl or C$_{2-50}$ alkynyl group may be replaced by a substituent as defined below. Optionally, one or more double bond(s) may occur.

As used herein, the terms "C$_{3-8}$ cycloalkyl" or "C$_{3-8}$ cycloalkyl ring" means a cyclic alkyl chain having 3 to 8 carbon atoms, which may be saturated or unsaturated, e.g. cyclopropyl, cyclobutyl, cyclopentyl, cyclohexyl, cyclohexenyl, cycloheptyl, cyclooctyl. Each hydrogen atom of a cycloalkyl carbon may be replaced by a substituent as defined below. The term "C$_{3-8}$ cycloalkyl" or "C$_{3-8}$ cycloalkyl ring" also includes bridged bicycles like norbonane or norbonene. Accordingly, "C$_{3-5}$ cycloalkyl" means a cycloalkyl having 3 to 5 carbon atoms and C$_{3-10}$ cycloalkyl having 3 to 10 carbon atoms.

Accordingly, as used herein, the term "C$_{3-10}$ cycloalkyl" means a carbocyclic ring system having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl, cyclodecyl. The term "C$_{3-10}$ cycloalkyl" also includes at least partially saturated carbomono- and -bicycles.

As used herein, the term "halogen" means fluoro, chloro, bromo or iodo. Particularly preferred is fluoro or chloro.

As used herein, the term "4- to 7-membered heterocyclyl" or "4- to 7-membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 4- to 7-membered heterocycles include but are not limited to azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 4- to 7-membered heterocyclyl or 4- to 7-membered heterocyclic group may be replaced by a substituent as defined below.

As used herein, the term "8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

The term "substituted" means that one or more —H atom(s) of a molecule or moiety are replaced by a different atom or a group of atoms, which are referred to as "substituent". Suitable substituents are halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; C$_{1-50}$ alkyl; C$_{2-50}$ alkenyl; or C$_{2-50}$ alkynyl, which T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{o2-5}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein

R$^9$, R$^{9a}$, R$^{9b}$ are independently selected from the group consisting of H; T; C$_{1-50}$ alkyl; C$_{2-50}$ alkenyl; and C$_{2-50}$ alkynyl, which T; C$_{1-50}$ alkyl; C$_{2-50}$ alkenyl; and C$_{2-50}$ alkynyl are optionally substituted with one or more R$^{10}$, which are the same or different and which C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; C$_{3-10}$ cycloalkyl; 4- to 7-membered heterocyclyl; and 8- to 11-membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$); or C$_{1-6}$ alkyl, which C$_{1-6}$ alkyl is optionally substituted with one or more halogen, which are the same or different;

R$^{11}$, R$^{11a}$, R$^{12}$, R$^{12a}$, R$^{12b}$ are independently of each other selected from the group consisting of H; and C$_{1-6}$ alkyl, which C$_{1-6}$ alkyl is optionally substituted with one or more halogen, which are the same or different.

In one embodiment R$^9$, R$^{9a}$, R$^{9b}$ are independently of each other H.

In one embodiment R$^{10}$ is C$_{1-6}$ alkyl.

In one embodiment T is phenyl.

Preferably, a maximum of 6 —H atoms of a moiety or molecule are independently replaced by a substituent, e.g. 5

—H atoms are independently replaced by a substituent, 4
—H atoms are independently replaced by a substituent, 3
—H atoms are independently replaced by a substituent, 2
—H atoms are independently replaced by a substituent, or 1
—H atom is replaced by a substituent.

As used herein, the term "interrupted" means that between two carbon atoms or at the end of a carbon chain between the respective carbon atom and the hydrogen atom one or more atom(s) are inserted.

As used herein, the term "prodrug" means a compound that undergoes biotransformation before exhibiting its pharmacological effects. Prodrugs can thus be viewed as biologically active moieties connected to specialized non-toxic protective groups used in a transient manner to alter or to eliminate undesirable properties in the parent molecule. This also includes the enhancement of desirable properties in the drug and the suppression of undesirable properties.

As used herein, the term "carrier-linked prodrug" means a prodrug that contains a reversible linkage of a biologically active moiety with a carrier group and which carrier improves the physicochemical or pharmacokinetic properties of the biologically active moiety and which carrier is removed in vivo, usually by a hydrolytic cleavage. Preferably, the carrier is a polymer.

Accordingly, the term "hydrogel-linked prodrug" refers to a carrier-linked prodrug in which the carrier is a hydrogel.

As used herein, the term "reversible prodrug linker moiety" means a moiety which on its one end is attached to a backbone moiety of the hydrogel either directly or through a spacer moiety and on another end is attached to a tag moiety-biologically active moiety conjugate through a reversible linkage.

A "biodegradable linkage" or "reversible linkage" is a linkage that is enzymatically and/or non-enzymatically hydrolytically degradable, i.e. cleavable, under physiological conditions (aqueous buffer at pH 7.4, 37° C.) with a half-life ranging from one hour to twelve months. Preferably, a biodegradable linkage is non-enzymatically hydrolytically degradable, i.e. degradable independent of enzymatic activity, under physiological conditions with a half-life ranging from one hour to twelve months.

In contrast, a "permanent linkage" is non-enzymatically hydrolytically degradable under physiological conditions (aqueous buffer at pH 7.4, 37° C.) with a half-life of more than twelve months.

As used herein, the term "traceless prodrug linker" means a reversible prodrug linker which upon cleavage leaves no moiety originally part of the reversible prodrug linker moiety on the released tag moiety-biologically active moiety conjugate.

As used herein, the term "peptide" means a short polymer of amino acid monomers linked by peptide bonds. The term "polypeptide" means a peptide comprising up to and including 50 amino acid monomers. The term "protein" means a peptide of more than 50 amino acid monomers.

As used herein, the term "oligonucleotide" means a short nucleic acid polymer of up to 200 bases.

As used herein, the term "pharmaceutical composition" means one or more active ingredients, i.e. drugs or prodrugs, and one or more inert ingredients, the so-called excipients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the hydrogel-linked prodrug releasing tag moiety-biologically active moiety conjugates of the present invention and one or more pharmaceutically acceptable excipient(s).

As used herein, the term "excipient" refers to a diluent, adjuvant, or vehicle with which the active ingredient is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. An oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the drug or prodrug, together with a suitable amount of excipient, so as to provide the form for proper administration to the patient. The formulation should suit the mode of administration.

In general the term "comprise" or "comprising" also encompasses "consist of" or "consisting of".

Some of the backbone and crosslinker reagents, which can be used as starting material in process step (a) are commercially available. Further, the backbone and crosslinker reagents can be prepared according to a method described in the Examples section. A method for the synthesis of a suitable backbone reagent is described in example 1 of WO2011/012715A1, which is incorporated by reference herein. Example 2 of WO2011/012715A1 further provides methods for the synthesis of crosslinker reagents. Based on these methods the person skilled in the art is able to apply standard chemical knowledge to obtain the backbone and crosslinker reagents described in the present invention.

The Backbone Reagent

In one embodiment the backbone reagent is present in the form of its acidic salt, preferably in the form of an acid addition salt, if $A^{x0}$ is amine. Suitable acid addition salts are formed from acids which form non-toxic salts. Examples include but are not limited to acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

The at least one backbone reagent of step (a) comprises one or more polymer(s) selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), siliconeses, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, the at least one backbone reagent of step (a) is PEG-based comprising at least 10% PEG or is hyaluronic acid-based comprising at least 20% hyaluronic acid.

In one preferred embodiment, the at least one backbone reagent of step (a) is hyaluronic acid-based comprising at least 20% hyaluronic acid, more preferably, comprising at least 40% hyaluronic acid, even more preferably, at least 60% hyaluronic acid, even more preferred at least 80% hyaluronic acid.

Preferably, in such hyaluronic acid-comprising backbone reagent of step (a) each $A^{x0}$ is an amine.

In another preferred embodiment, the at least one backbone reagent of step (a) is PEG-based comprising at least 10% PEG, preferably at least 20% PEG, even more preferably at least 30%, even more preferably at least 40% PEG, even more preferably at least 50% PEG, even more preferably at least 60%, even more preferably at least 70% PEG, even more preferably at least 80% PEG and most preferably at least 90% PEG.

Preferably, in such PEG-based backbone reagent of step (a) each $A^{x0}$ is an amine.

Some of the functional groups $A^{x0}$ react with the functional end groups of the crosslinker reagents during polymerization in step (b) and the remaining activated functional end groups are used for optionally coupling spacer moieties in step (c) and/or for covalently conjugating the reagents of steps (d-i), (d-ii), (d-iii), (d-iv), (d-v) (d-vi), (d-vii) or (d-viii), i.e the molar ratio of $A^{x0}$ to functional end groups is >1.

In one embodiment, the at least one backbone reagent is selected from the group consisting of (i) a compound of formula (I)

$$B(-(A^0)_{x1}-(SP^1)_{x2}-A^1-P-A^2-Hyp^1)_x \qquad (I),$$

wherein
B is a branching core,
$SP^1$ is a spacer moiety selected from the group consisting of $C_{1-6}$ alkyl, $C_{2-6}$ alkenyl and $C_{2-6}$ alkynyl,
P is a PEG-based polymeric chain comprising at least 80% PEG, preferably at least 85% PEG, more preferably at least 90% PEG and most preferably at least 95% PEG,
$Hyp^1$ is a moiety comprising an amine (—$NH_2$ and/or —NH—) or a polyamine comprising at least two amines (—$NH_2$ and/or —NH—),
x is an integer from 3 to 16,
x1, x2 are independently of each other 0 or 1, provided that x1 is 0, if x2 is 0, $A^0$, $A^1$, $A^2$ are independently of each other selected from the group consisting of

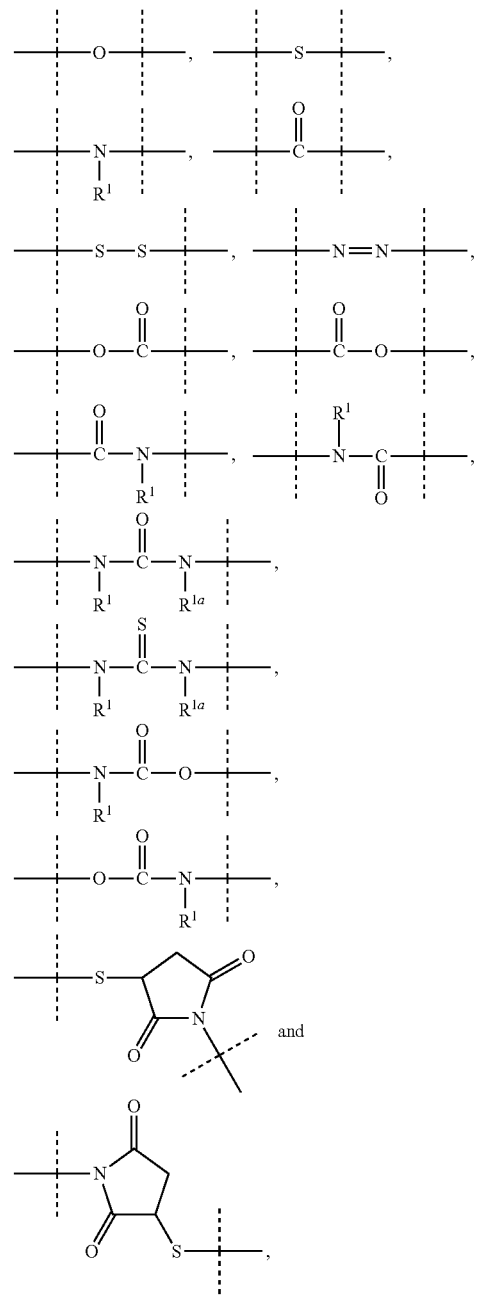

wherein $R^1$ and $R^{1a}$ are independently of each other H or $C_{1-6}$ alkyl;

(ii) a compound of formula (II)

$$\text{Hyp}^2\text{-}A^3\text{-}P\text{-}A^4\text{-}\text{Hyp}^3 \quad (II),$$

wherein

P is defined as above in the compound of formula (I),
$\text{Hyp}^2$, $\text{Hyp}^3$ are independently of each other a polyamine comprising at least two amines ($-NH_2$ and/or $-NH-$), and
$A^3$ and $A^4$ are independently selected from the group consisting of

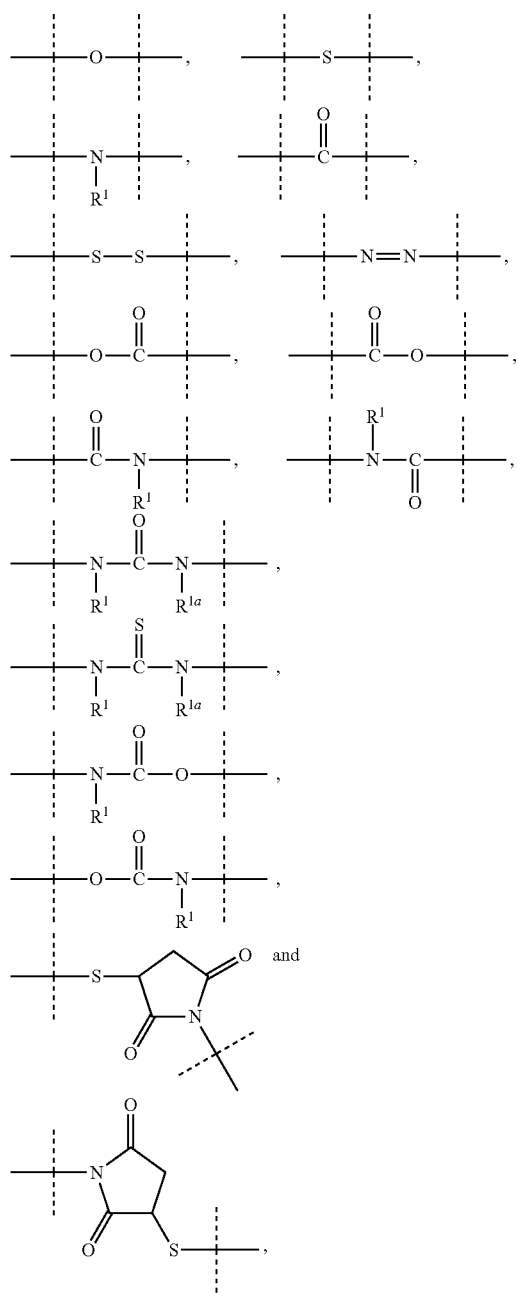

wherein $R^1$ and $R^{1a}$ are independently of each other H or $C_{1-6}$ alkyl;

(iii) a compound of formula (III)

$$P^1\text{-}A^5\text{-}\text{Hyp}^4 \quad (III),$$

wherein $P^1$ is a PEG-based polymeric chain comprising at least 80% PEG, preferably at least 85% PEG, more preferably at least 90% PEG and most preferably at least 95% PEG,
$\text{Hyp}^4$ is a polyamine comprising at least three amines ($-NH_2$ and/or $-NH$), and
$A^5$ is selected from the group consisting of

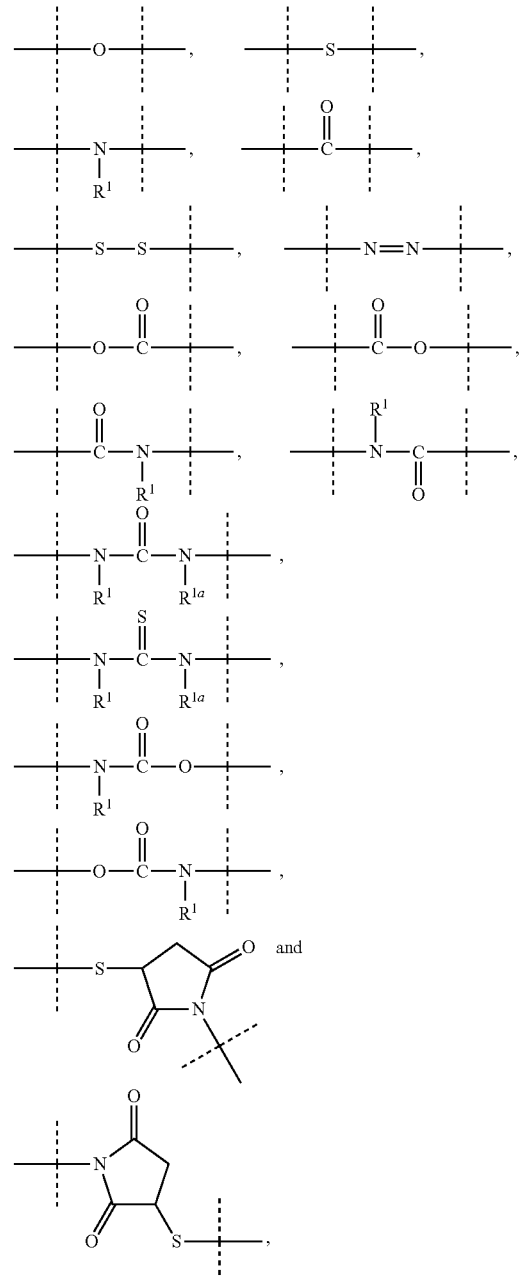

wherein $R^1$ and $R^{1a}$ are independently of each other H or $C_{1-6}$ alkyl;
and (iv) a compound of formula (IV)

$$T^1\text{-}A^6\text{-}\text{Hyp}^5 \quad (IV),$$

wherein

Hyp⁵ is a polyamine comprising at least three amines (—NH₂ and/or —NH), and

A⁶ is selected from the group consisting of

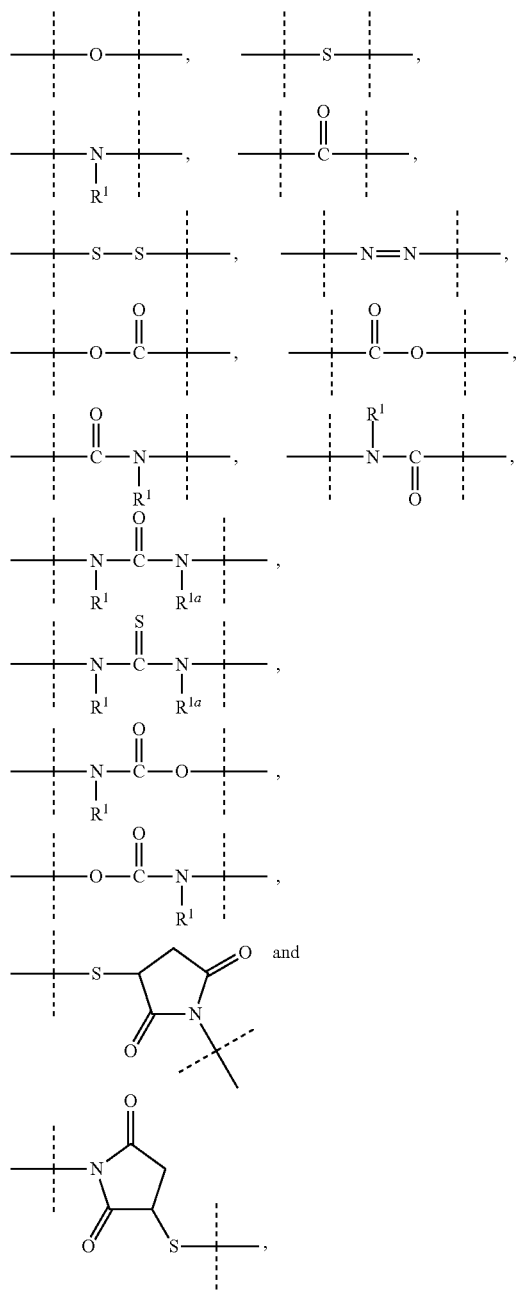

wherein $R^1$ and $R^{1a}$ are independently of each other H or $C_{1-6}$ alkyl; and $T^1$ is selected from the group consisting of $C_{1-50}$ alkyl, $C_{2-50}$ alkenyl and $C_{2-50}$ alkynyl, which $C_{1-50}$ alkyl, $C_{2-50}$ alkenyl or $C_{2-50}$ alkynyl are optionally interrupted by one or more group(s) selected from the group consisting of —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)₂—, 4- to 7-membered heterocyclyl, phenyl and naphthyl.

In the following sections the term "Hyp$^x$" refers to Hyp¹, Hyp², Hyp³, Hyp⁴ and Hyp⁵ collectively.

Preferably, the backbone reagent is a compound of formula (I), (II) or (III), more preferably the backbone reagent is a compound of formula (I) or (III), and most preferably the backbone reagent is a compound of formula (I).

In a preferred embodiment, the backbone reagent is of formula (I) and x is 4, 6 or 8, more preferably x is 4 or 8 and most preferably x is 4.

In a preferred embodiment $A^0$, $A^1$, $A^2$, $A^3$, $A^4$, $A^5$ and $A^6$ of formulas (I) to (IV) are selected from the group consisting of

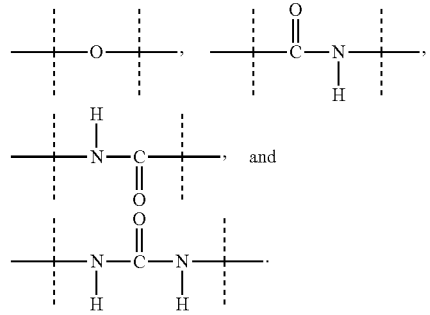

Preferably, $A^0$ of formula (I) is selected from the group consisting of

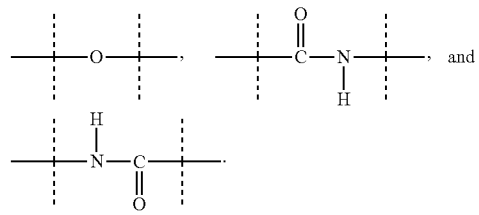

Preferably, $A^1$ of formula (I) is selected from the group consisting of

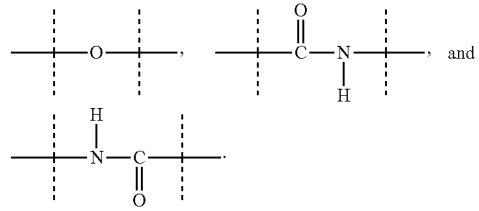

Preferably, $A^2$ of formula (I) is selected from the group consisting of

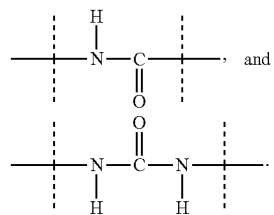

Preferably, $A^3$ of formula (II) is selected from the group consisting of

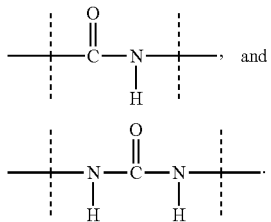, and

Preferably, $A^4$ of formula (II) is selected from the group consisting of

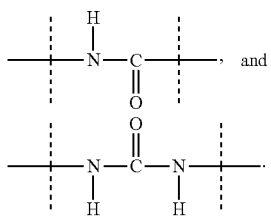, and

Preferably, $A^5$ of formula (III) is selected from the group consisting of

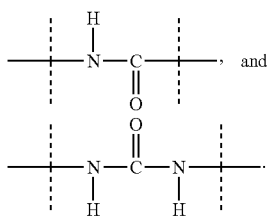, and

Preferably, $A^6$ of formula (IV) is selected from the group consisting of

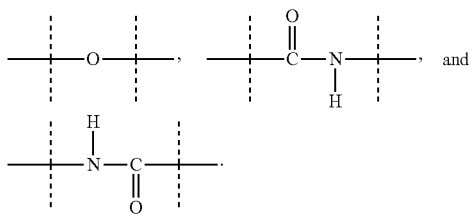

Preferably, in a compound of formula (IV), $T^1$ is H or $C_{1-6}$ alkyl.

$SP^1$ is a spacer moiety selected from the group consisting of $C_{1-6}$ alkyl, $C_{2-6}$ alkenyl and $C_{2-6}$ alkynyl. Preferably $SP^1$ is —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, —CH═CH— or —CH═CH—, and most preferably $SP^1$ is —CH$_2$—, —CH$_2$—CH$_2$— or —CH═CH—.

In one embodiment B of formula (I) is selected from the group consisting of:

(a-i) 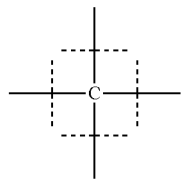

(a-ii) 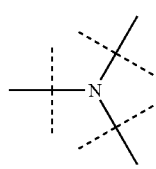

(a-iii) 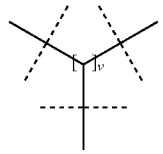

(a-iv) 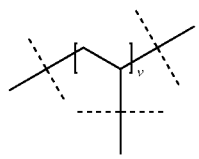

(a-v) 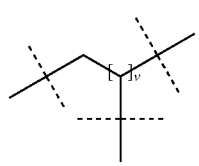

(a-vi) 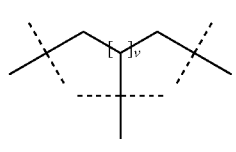

(a-vii) 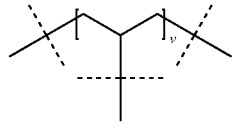

(a-viii) 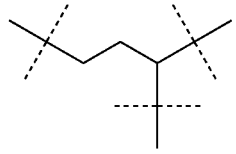

(a-ix) 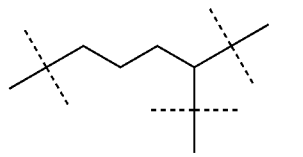

(a-x) 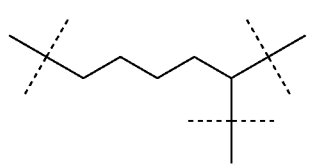

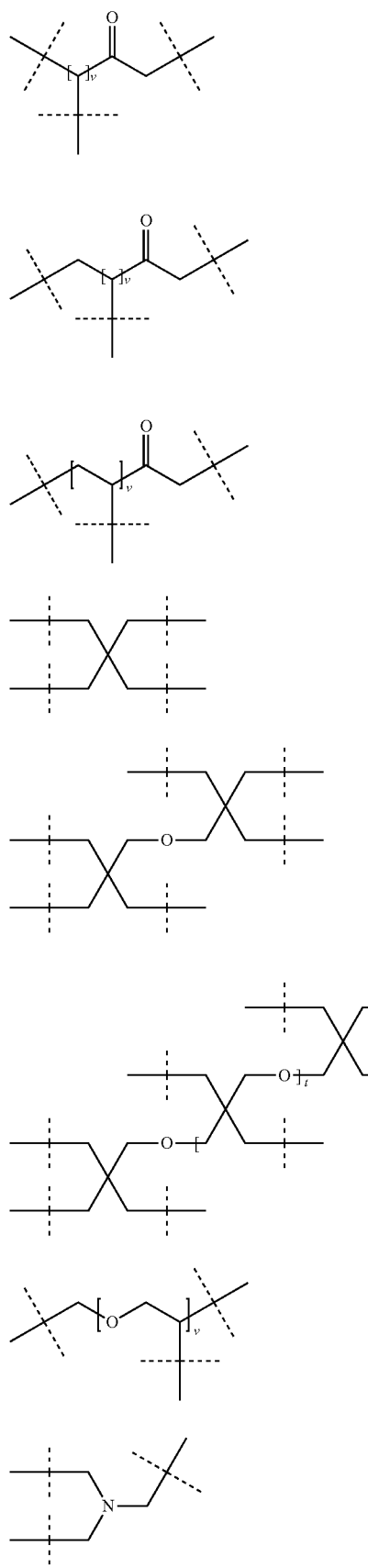
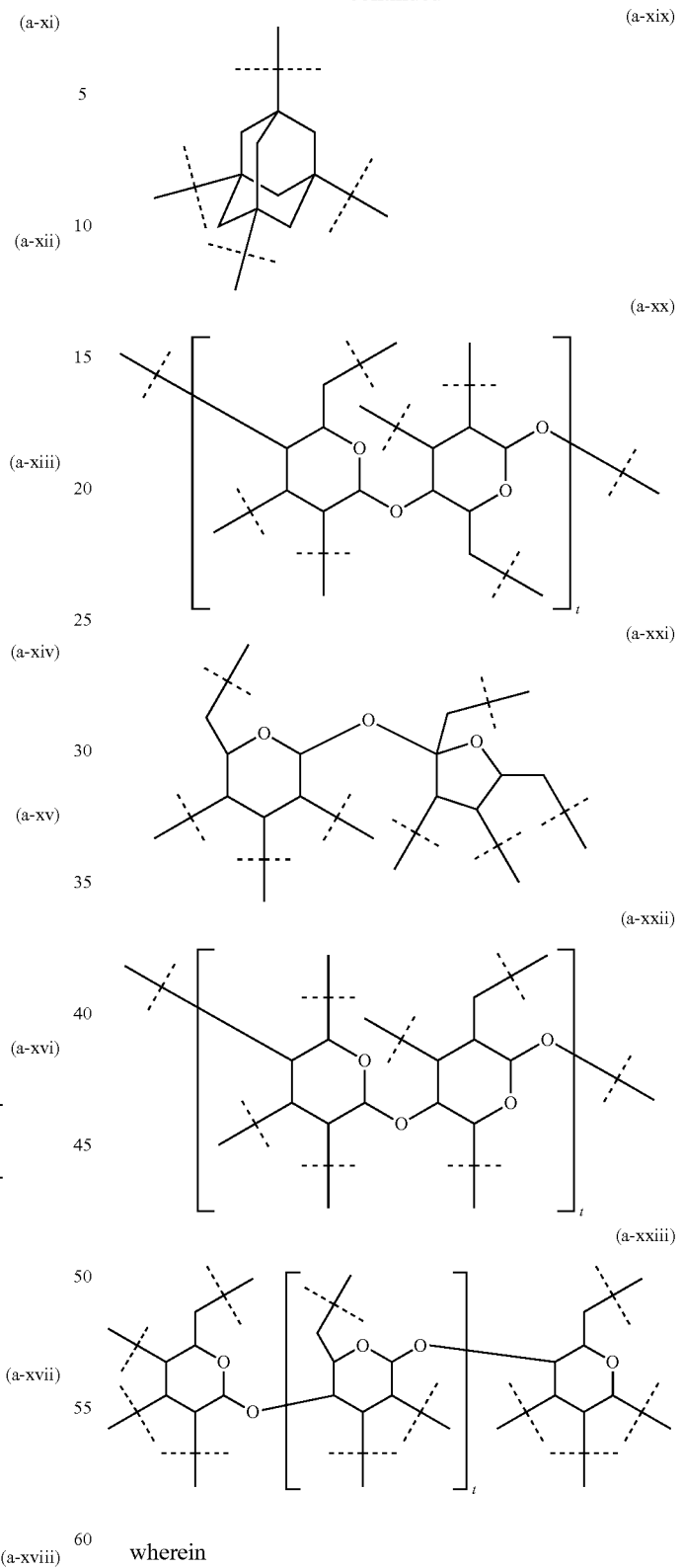
wherein
dashed lines indicate attachment to $A^0$ or, if x1 and x2 are both 0, to $A^1$,
t is 1 or 2; preferably t is 1,
v is 1, 2, 3, 4, 5, 6, 7, 8, 9, 10, 11, 12, 13 or 14; preferably, v is 2, 3, 4, 5, 6; more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv), (a-xv) or (a-xvi). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred combination of B and $A^0$, or, if x1 and x2 are both 0, of B and $A^1$, is selected from the group consisting of the following structures:

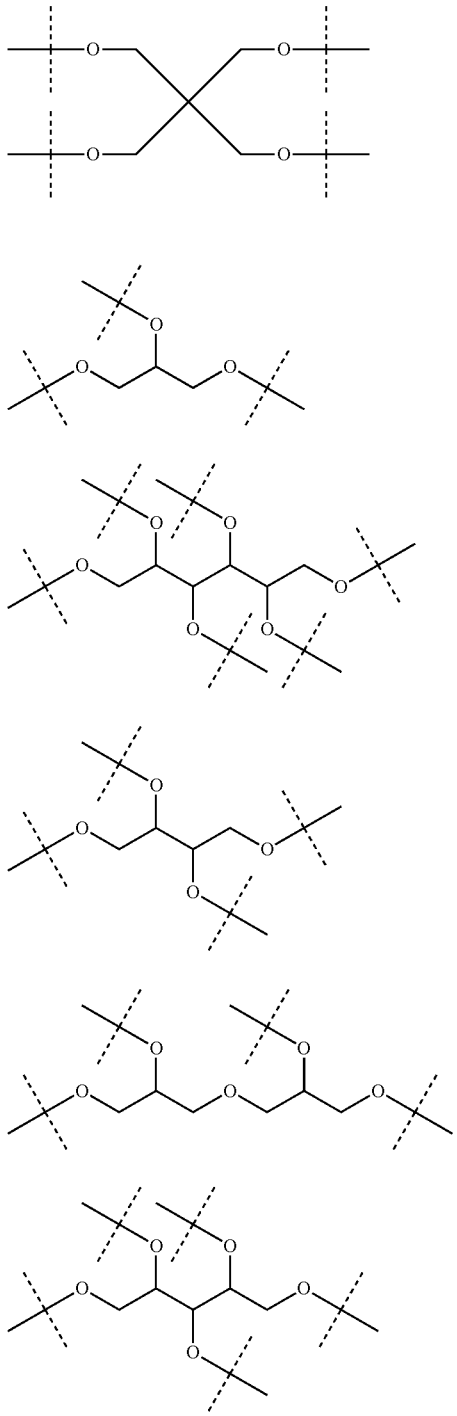

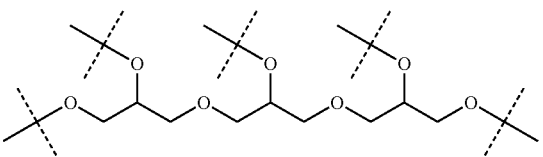

wherein
dashed lines indicate attachment to $SP^1$ or, if x1 and x2 are both 0, to P.

More preferably, the combination of B and $A^0$ or, if x1 and x2 are both 0, the combination of B and $A^1$, is of formula (b-i), (b-iv), (b-vi) or (b-viii) and most preferably is of formula (b-i).

In one embodiment, x1 and x2 of formula (I) are both 0.

In one embodiment, the PEG-based polymeric chain P has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, P of formula (I) or (II) is of formula (c-i):

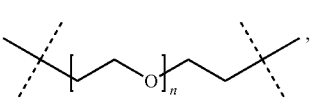

wherein n ranges from 6 to 900, more preferably n ranges from 20 to 700 and most preferably n ranges from 20 to 250.

In one embodiment, $P^1$ of formula (III) has the structure of formula (c-ii):

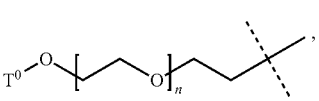

wherein
n ranges from 6 to 900, more preferably n ranges from 20 to 700 and most preferably n ranges from 20 to 250;

$T^0$ is selected from the group consisting of $C_{1-6}$ alkyl, $C_{2-6}$ alkenyl and $C_{2-6}$ alkynyl, which $C_{1-6}$ alkyl, $C_{2-6}$ alkenyl and $C_{2-6}$ alkynyl are optionally interrupted by one or more group(s) selected from the group consisting of —NH—, —N($C_{1-4}$ alkyl)-, —O—, —S—, —C(O)—, —C(O)NH—, —C(O)N($C_{1-4}$ alkyl)-, —O—C(O)—, —S(O)— and —S(O)$_2$—.

In one embodiment, the moiety $Hyp^x$ of formulas (I) to (IV) is a polyamine and preferably comprises in bound form and, where applicable, in R- and/or S-configuration, a moiety of formulas (d-i), (d-ii), (d-iii) and/or (d-iv):

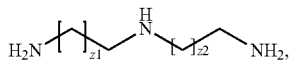 (d-i)

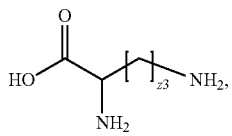 (d-ii)

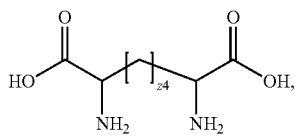 (d-iii)

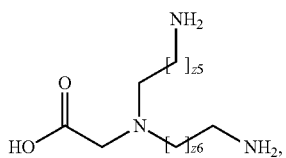 (d-iv)

wherein
z1, z2, z3, z4, z5, z6 are independently of each other 1, 2, 3, 4, 5, 6, 7 or 8.

More preferably, $Hyp^x$ comprises in bound form and in R- and/or S-configuration lysine, ornithine, diaminoproprionic acid and/or diaminobutyric acid. Most preferably, $Hyp^x$ comprises in bound form and in R- and/or S-configuration lysine.

Preferably, $Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of:
a moiety of formula (e-i)

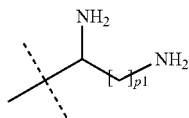 (e-i)

wherein
p1 is an integer from 1 to 5, preferably p1 is 4, and
the dashed line indicates attachment to $A^2$ if the backbone reagent is of formula (I) and to $A^3$ or $A^4$ if the backbone reagent is of formula (II);
a moiety of formula (e-ii)

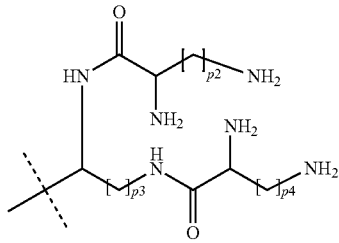 (e-ii)

wherein
p2, p3 and p4 are identical or different and each is independently of the others an integer from 1 to 5, preferably p2, p3 and p4 are 4, and the dashed line indicates attachment to $A^2$ if the backbone reagent is of formula (I), to $A^3$ or $A^4$ if the backbone reagent is of formula (II), to $A^5$ if the backbone is of formula (III) and to $A^6$ if the backbone reagent is of formula (IV);
a moiety of formula (e-iii)

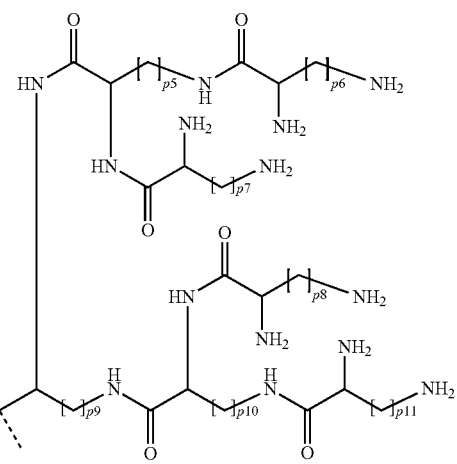 (e-iii)

wherein
p5 to p11 are identical or different and each is independently of the others an integer from 1 to 5, preferably p5 to p11 are 4, and
the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);
a moiety of formula (e-iv)

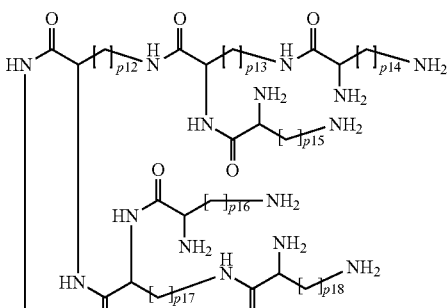 (e-iv)

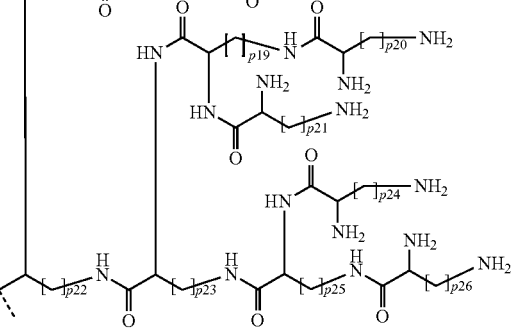

wherein p12 to p26 are identical or different and each is independently of the others an integer from 1 to 5, preferably p12 to p26 are 4, and the dashed line indicates attachment to $A^2$ if the backbone reagent is of formula (I), to $A^3$ or $A^4$ if the backbone reagent is of formula (II), to $A^5$ if the backbone is of formula (III) and to $A^6$ if the backbone reagent is of formula (IV);

a moiety of formula (e-v)

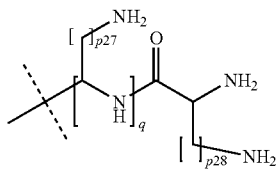

(e-v)

wherein p27 and p28 are identical or different and each is independently of the other an integer from 1 to 5, preferably p27 and p28 are 4, q is an integer from 1 to 8, preferably q is 2 or 6 and most preferably 1 is 6, and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-vi)

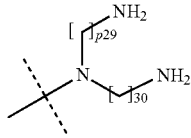

(e-vi)

wherein p29 and p30 are identical or different and each is independently of the other an integer from 2 to 5, preferably p29 and p30 are 3, and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-vii)

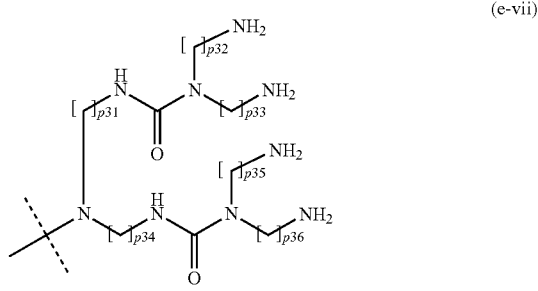

(e-vii)

wherein p31 to p36 are identical or different and each is independently of the others an integer from 2 to 5, preferably p31 to p36 are 3, and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-viii)

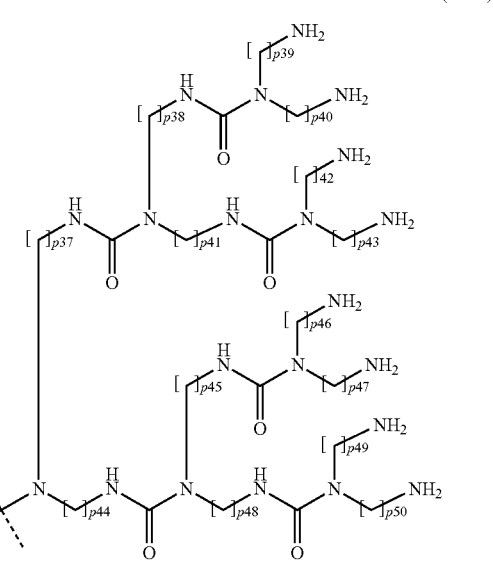

(e-viii)

wherein p37 to p50 are identical or different and each is independently of the others an integer from 2 to 5, preferably p37 to p50 are 3, and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV); and a moiety of formula (e-ix):

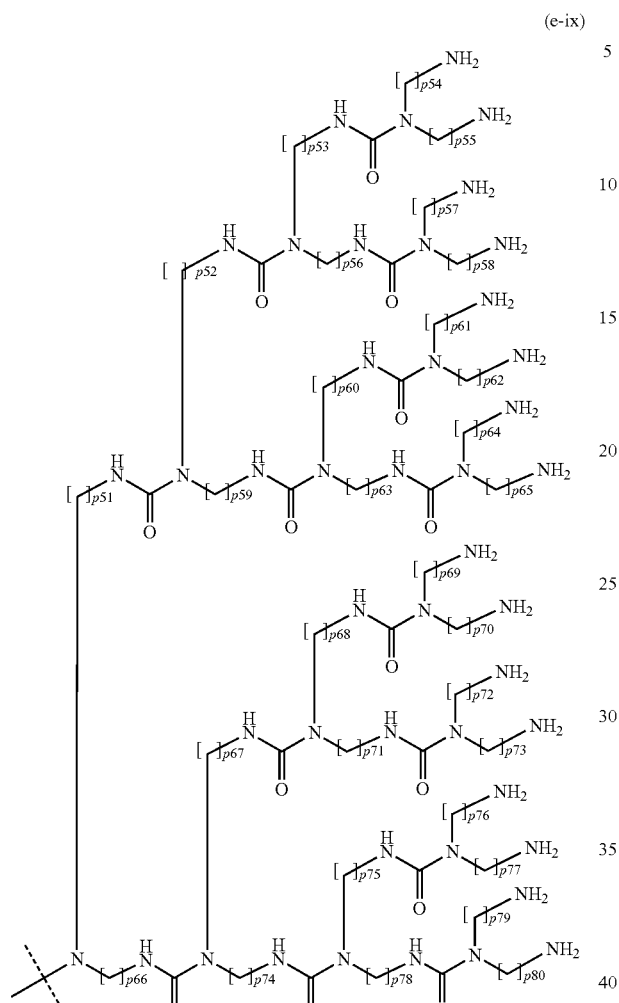

wherein
- p51 to p80 are identical or different and each is independently of the others an integer from 2 to 5, preferably p51 to p80 are 3, and
- the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV); and wherein the moieties (e-i) to (e-v) may at each chiral center be in either R- or S-configuration, preferably, all chiral centers of a moiety (e-i) to (e-v) are in the same configuration.

Preferably, $Hyp^x$ is of formula (e-i), (e-ii), (e-iii), (e-iv), (e-vi), (e-vii), (e-viii) or (e-ix). More preferably, $Hyp^x$ is of formula (e-ii), (e-iii), (e-iv), (e-vii), (e-viii) or (e-ix), even more preferably $Hyp^x$ is of formula (e-ii), (e-iii), (e-vii) or (e-viii) and most preferably $Hyp^x$ is of formula (e-iii).

Preferably, the moiety -$A^2$-$Hyp^1$ is

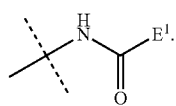

wherein
the dashed line indicates attachment to P; and
$E^1$ is selected from formulas (e-i) to (e-ix).
Preferrably, the moiety $Hyp^2$-$A^3$ is

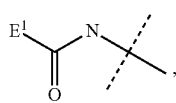

wherein
the dashed line indicates attachment to P; and
$E^1$ is selected from formulas (e-i) to (e-ix).
Preferably, the moiety -$A^4$-$Hyp^3$ is

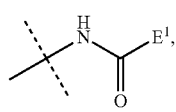

wherein
the dashed line indicates attachment to P; and
$E^1$ is selected from formulas (e-i) to (e-ix).
Preferably, the moiety -$A^5$-$Hyp^4$ is

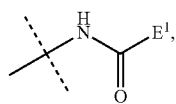

wherein
the dashed line indicates attachment to $P^1$; and
$E^1$ is selected from formulas (e-i) to (e-ix).
More preferably, the backbone reagent is of formula (I) and B is of formula (a-xiv).
Even more preferably, the backbone reagent is of formula (I), B is of formula (a-xiv), x1 and x2 are 0, and $A^1$ is —O—.
Even more preferably, the backbone reagent is of formula (I), B is of formula (a-xiv), $A^1$ is —O—, and P is of formula (c-i).
Even more preferably, the backbone reagent is of formula (I), B is of formula (a-xiv), x1 and x2 are 0, $A^1$ is —O— and P is of formula (c-i).
Even more preferably, the backbone reagent is formula (I), B is of formula (a-xiv), x1 and x2 are 0, $A^1$ is —O—, P is of formula (c-i), $A^2$ is —NH—(C=O)— and $Hyp^1$ is of formula (e-iii).
Most preferably, the backbone reagent has the following formula:

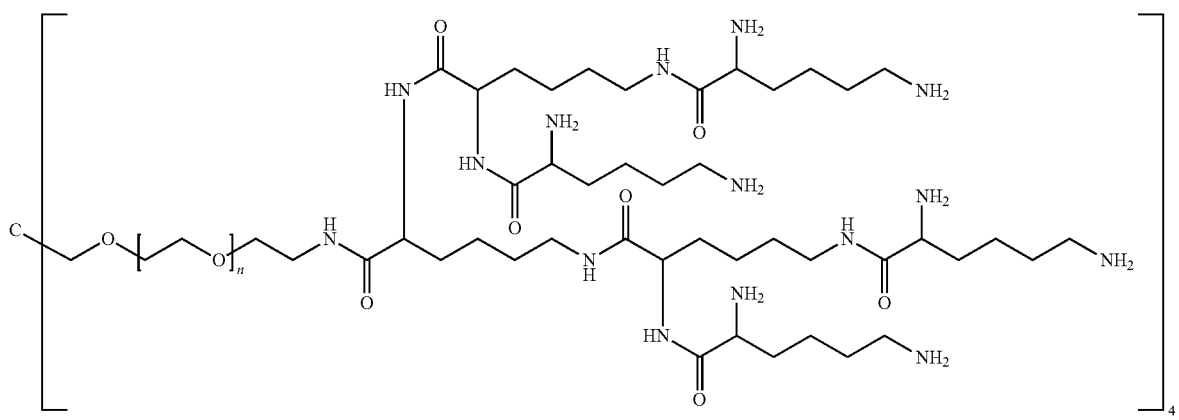

wherein n ranges from 10 to 40, preferably from 10 to 30, more preferably from 10 to 20.

Equally preferably, n ranges from 20 to 30 kDa and most preferably n is 28.

The Crosslinker Reagent

The at least one crosslinker reagent of step (a) comprises one or more polymer(s) selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), polypropylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylan, and copolymers thereof.

Preferably, the at least one crosslinker reagent of step (a) comprises hyaluronic acid or PEG.

In one preferred embodiment, the at least one crosslinker reagent of step (a) comprises hyaluronic acid. Preferably, such hyaluronic acid-comprising crosslinker reagent of step (a) comprises at least 70% hyaluronic acid, more preferably at least 80% hyaluronic acid and most preferably at least 90% hyaluronic acid and further comprises (i) at least two carbonyloxy groups (—(C=O)—O— or —O—(C=O)—), and additionally (ii) at least two functional end groups selected from the group consisting of activated ester groups, activated carbamate groups, activated carbonate groups, activated thiocarbonate groups and amine groups.

In another preferred embodiment, the at least one crosslinker reagent of step (a) comprises PEG. Preferably, such PEG-comprising crosslinker reagent of step (a) comprises at least 70% PEG, more preferably at least 80% PEG and most preferably at least 90% PEG and further comprises (i) at least two carbonyloxy groups (—(C=O)—O— or —O—(C=O)—), and additionally (ii) at least two functional end groups selected from the group consisting of activated ester groups, activated carbamate groups, activated carbonate groups, activated thiocarbonate groups and amine groups.

The at least one crosslinker reagent preferably comprises at least two carbonyloxy groups (—(C=O)—O— or —O—(C=O)—), which are biodegradable linkages. These biodegradable linkages render the hydrogel biodegradable which is advantageous. In addition, the at least one crosslinker reagent comprises at least two functional end groups which during the polymerization of step (b) react with the functional groups $A^{x0}$ of the at least one backbone reagent.

The crosslinker reagent has a molecular weight ranging from 0.2 to 40 kDa, more preferably ranging from 0.5 to 30 kDa, even more preferably ranging from 0.5 to 20 kDa, even more preferably ranging from 0.5 to 15 kDa and most preferably ranging from 1 to 10 kDa.

Preferably, the reaction of a functional end group of a crosslinker reagent with a functional group $A^{x0}$ of a backbone reagent leads to the formation of an amide linkage between a backbone moiety and a crosslinker moiety.

In one preferred embodiment, the crosslinker reagent is a compound of formula (V-I):

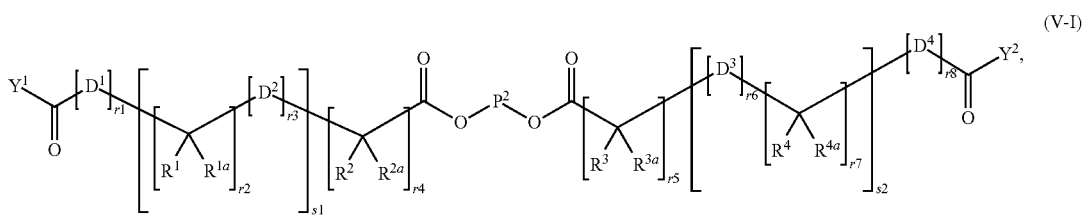

(V-I)

wherein
each $D^1$, $D^2$, $D^3$ and $D^4$ are identical or different and each is independently of the others selected from the group comprising —O—, —NR$^5$—, —S— and —CR$^6$R$^{6a}$—;

each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —OR$^7$, —NR$^7$R$^{7a}$, —SR$^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}$, $R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;

each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atom to which they are attached to form a 4- to 7-membered heterocyclyl or 8- to 11-membered heterobicyclyl;

each $R^7$, $R^{7a}$ is independently selected from H and $C_{1-6}$ alkyl;

A is selected from the group consisting of indenyl, indanyl and tetralinyl;

$P^2$ is

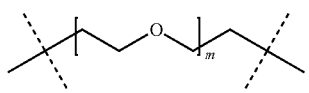

m ranges from 120 to 920, preferably from 120 to 460 and more preferably from 120 to 230;

r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;

$Y^1$, $Y^2$ are identical or different and each is independently of the other selected from formulas (f-i) to (f-vi):

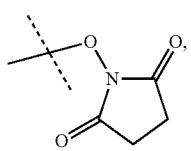
(f-i)

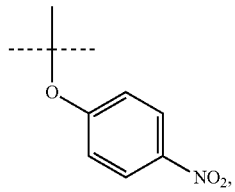
(f-ii)

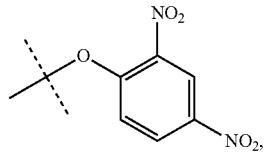
(f-iii)

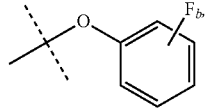
(f-iv)

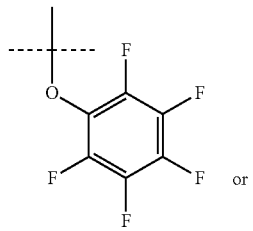
(f-v)

or

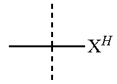
(f-vi)

wherein
the dashed lines indicate attachment to the rest of the molecule,
b is 1, 2, 3 or 4
$X^H$ is Cl, Br, I, or F.

Preferably, the crosslinker reagent is a compound of formula (V-II):

(V-II)

$$Y^1 \underset{O}{\overset{}{\parallel}} [D^1]_{r1} [\underset{R^1 \ R^{1a}}{C}]_{r2} [D^2]_{r3} [\underset{R^2 \ R^{2a}}{C}]_{r4}]_{s1} \underset{O}{\overset{O}{\parallel}} - O - \underset{}{P^2} - O - \underset{O}{\overset{O}{\parallel}} [[\underset{R^3 \ R^{3a}}{C}]_{r5} [D^3]_{r6} [\underset{R^4 \ R^{4a}}{C}]_{r7}]_{s2} [D^4]_{r8} \underset{O}{\overset{}{\parallel}} Y^2,$$

wherein
$D^1$, $D^2$, $D^3$ and $D^4$ are identical or different and each is independently of the others selected from the group comprising —O—, —NR$^5$—, —S— and —CR$^5$R$^{5a}$—;
$R^1$, $R^{1a}$, $R^2$, $R^{2a}$, $R^3$, $R^{3a}$, $R^4$, $R^{4a}$, $R^5$ and $R^{5a}$ are identical or different and each is independently of the others selected from the group comprising H and $C_{1-6}$ alkyl; optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
A is selected from the group consisting of phenyl, naphthyl, indenyl, indanyl and tetralinyl;
$P^2$ is

[structure showing $-\!\!\!\{\!CH_2CH_2-O\}_m\!\!\!-$ type linker]

m ranges from 120 to 920, preferably from 120 to 460 and more preferably from 120 to 230;
r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

(f-i) [N-hydroxysuccinimidyl ester structure]

(f-ii) [4-nitrophenoxy structure]

(f-iii) [2,4-dinitrophenoxy structure]

(f-iv) [fluorophenoxy structure with $F_b$]

(f-v) [pentafluorophenoxy structure]

(f-vi) $-X^H$ wherein
the dashed lines indicate attachment to the rest of the molecule,
b is 1, 2, 3 or 4
$X^H$ is Cl, Br, I, or F.

Preferably, $Y^1$ and $Y^2$ of formula (V-I) and (V-II) are of formula (f-i), (f-ii) or (f-v). More preferably, $Y^1$ and $Y^2$ are of formula (f-i) or (f-ii) and most preferably, $Y^1$ and $Y^2$ are of formula (f-i).

Preferably, both moieties $Y^1$ and $Y^2$ of formula (V-I) and (V-II) have the same structure. More preferably, both $Y^1$ and $Y^2$ are of formula (f-i).

It is understood that the moieties of formula (V-I) and (V-II)

[structures showing $Y^1-C(=O)-$ and $-C(=O)-Y^2$]

represent the at least two activated functional end groups.

Preferably, r1 and r8 of formula (V-I) and (V-II) are both 0.

Preferably, r1, r8, s1 and s2 of formula (V-I) and (V-II) are all 0.

Preferably, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ of formula (V-I) and (V-II) form a chemical bond or are joined together with the atom to which they are attached to form a $C_{3-8}$ cycloalkyl or a ring A.

Preferably, one or more of the pair(s) $R^1/R^2$, $R^{1a}/R^{2a}$, $R^3/R^4$, $R^{3a}/R^{4a}$ of formula (V-I) and (V-II) are joined together with the atom to which they are attached to form a 4- to 7-membered heterocyclyl or 8- to 11-membered heterobicyclyl.
Preferably, the crosslinker reagent of formula (V-I) and (V-II) is symmetric, i.e. the moiety
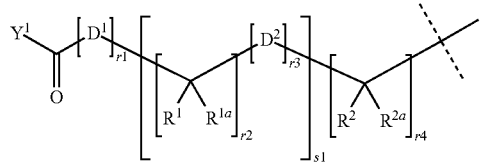
has the same structure as the moiety
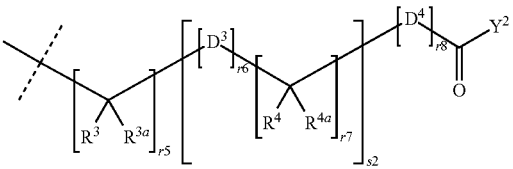
Preferred crosslinker reagents are of formula (V-1) to (V-54):
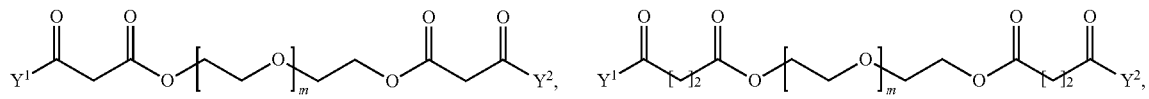
(V-1)                                                      (V-2)
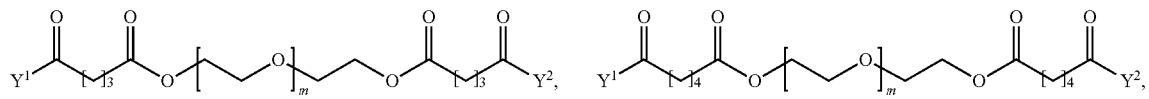
(V-3)                                                      (V-4)
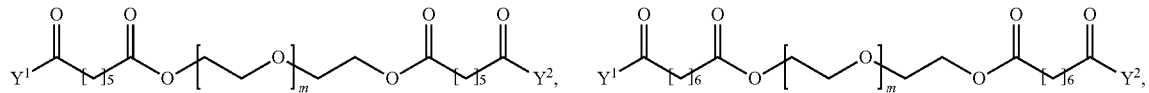
(V-5)                                                      (V-6)
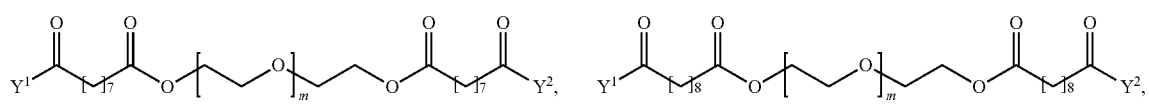
(V-7)                                                      (V-8)
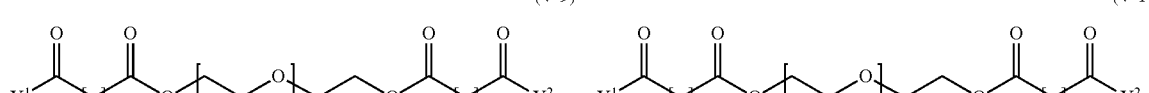
(V-9)                                                      (V-10)
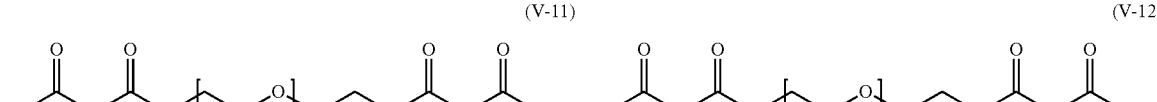
(V-11)                                                     (V-12)
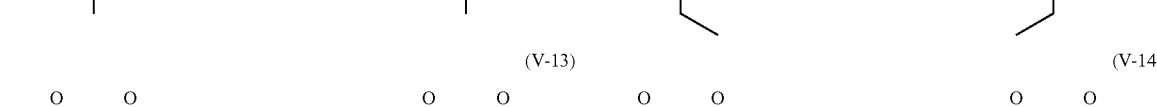
(V-13)                                                     (V-14)
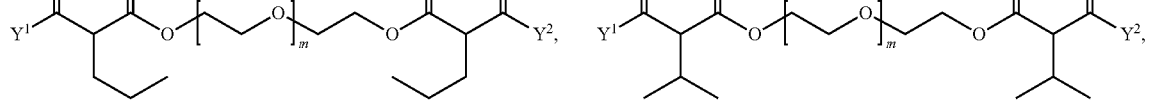
(V-15)                                                     (V-16)
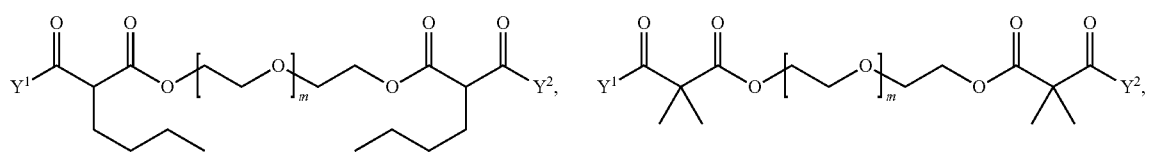

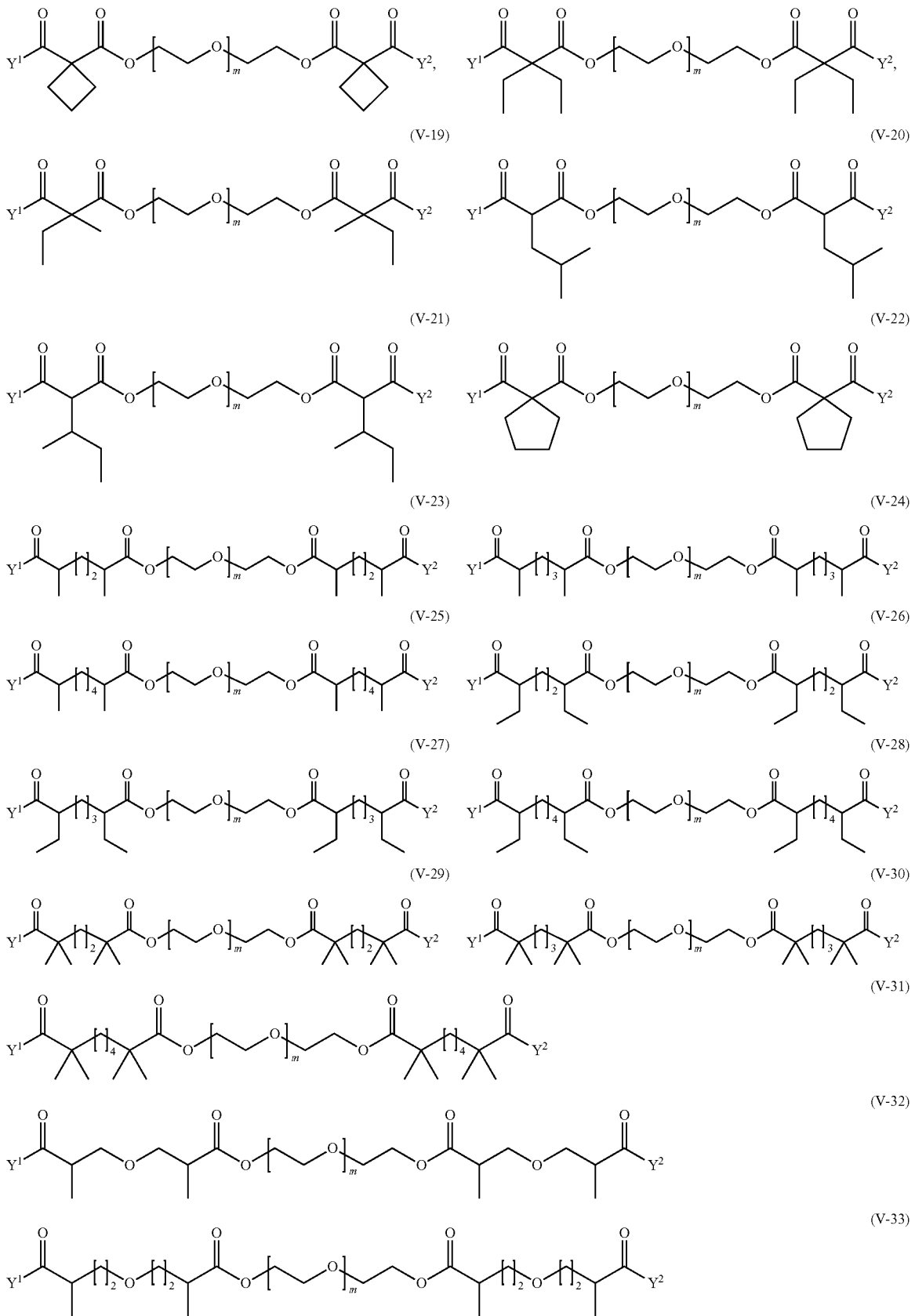

(V-34)
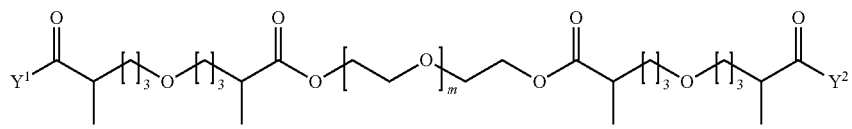
(V-35)
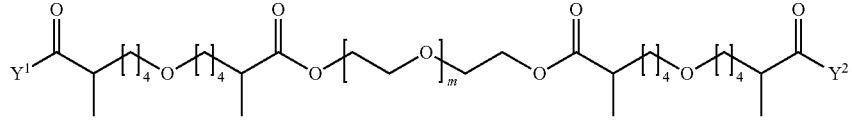
(V-36) (V-37)
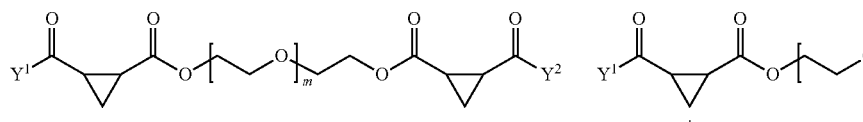
(V-38) (V-39)
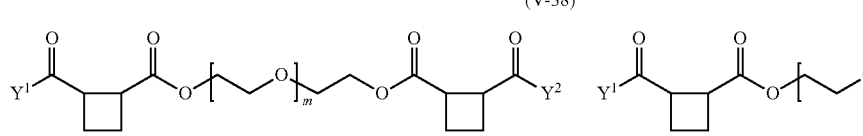
(V-40) (V-41)
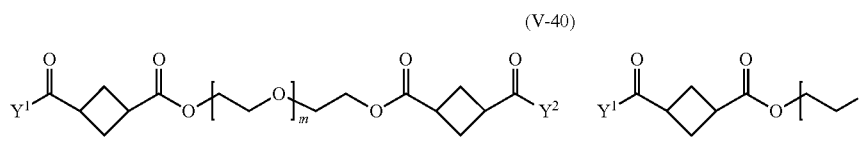
(V-42) (V-43)
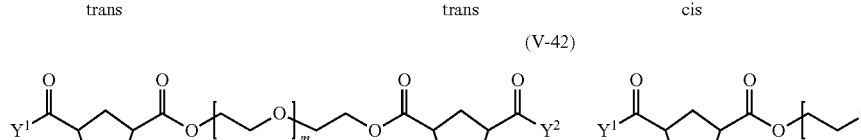
(V-44) (V-45)
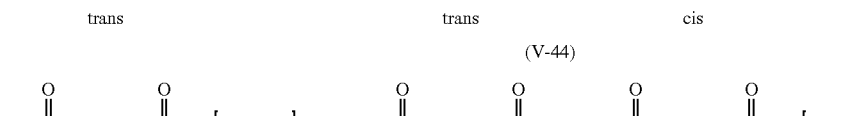
(V-46) (V-47)
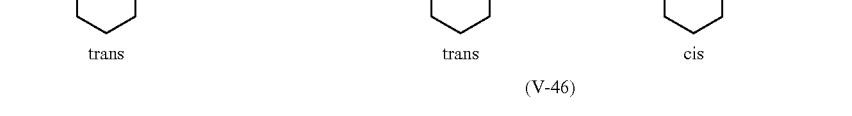
(V-48) (V-49)
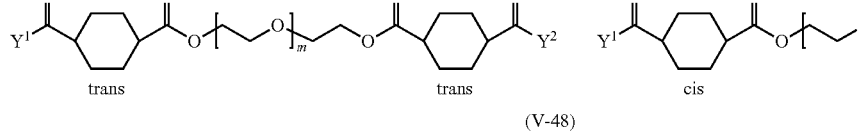
(V-50) (V-51)
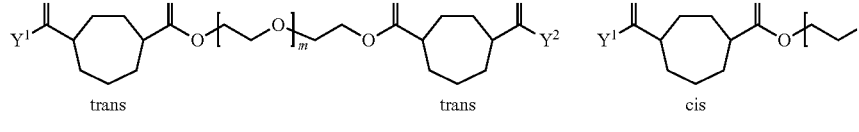

-continued
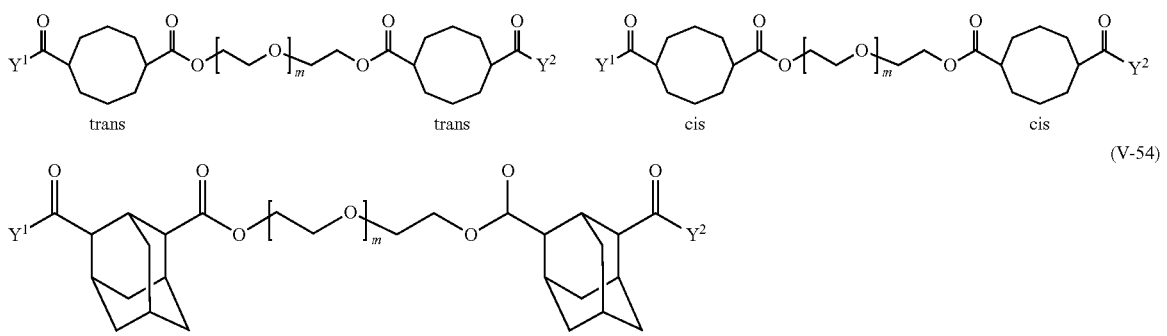
wherein
each crosslinker reagent may be in the form of its racemic mixture, where applicable; and
m, $Y^1$ and $Y^2$ are defined as above.
Even more preferred crosslinker reagents are of formula (Va-1) to (Va-54):
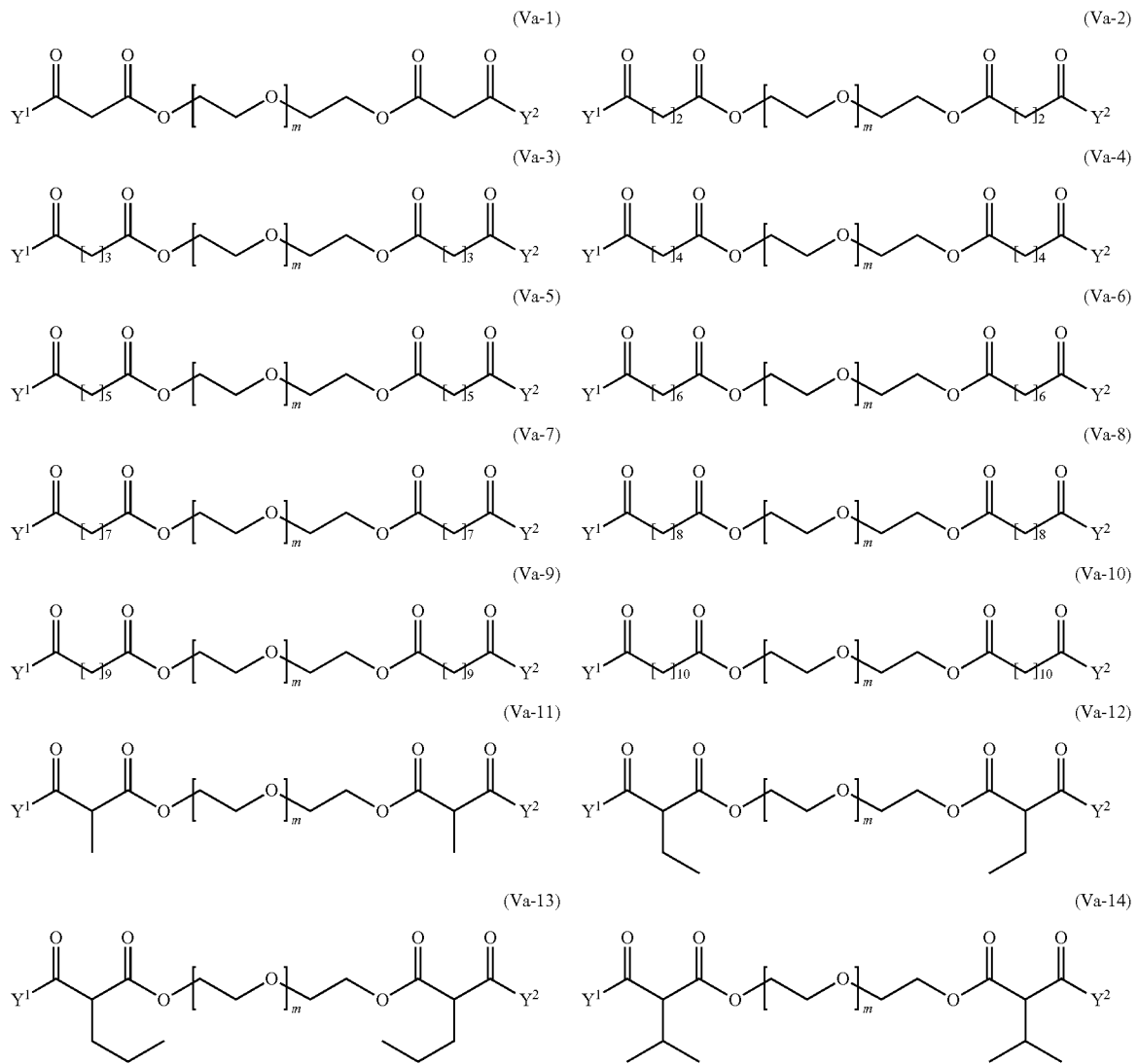

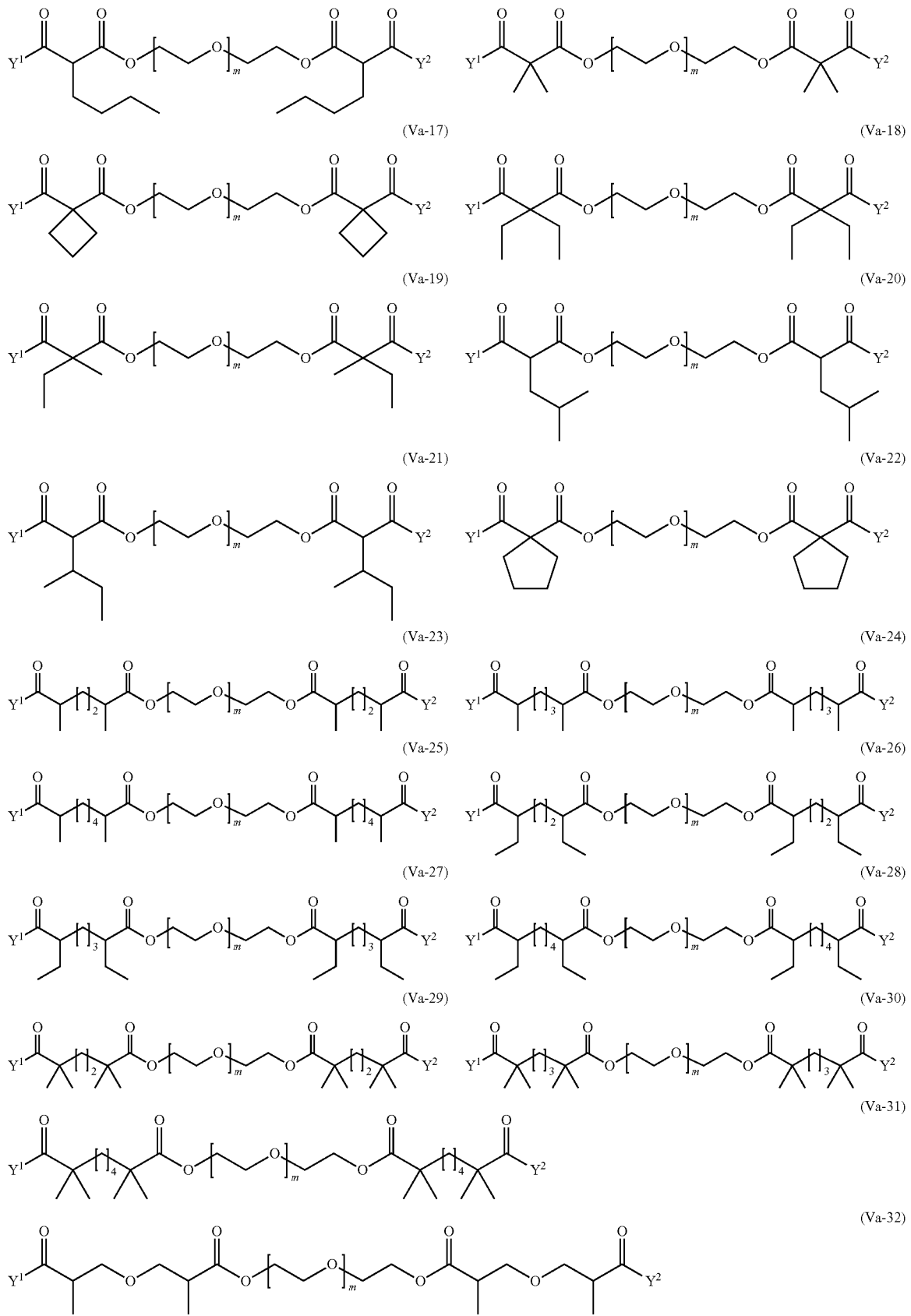

-continued
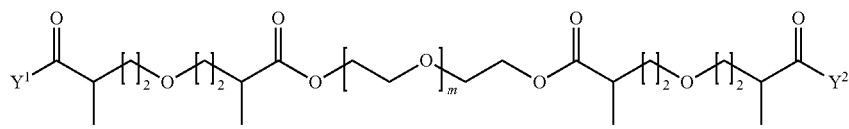
(Va-33)
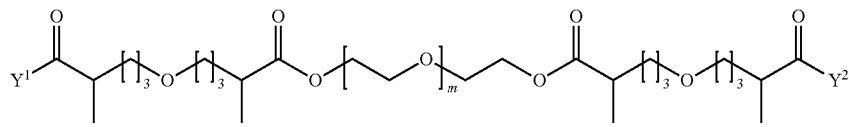
(Va-34)
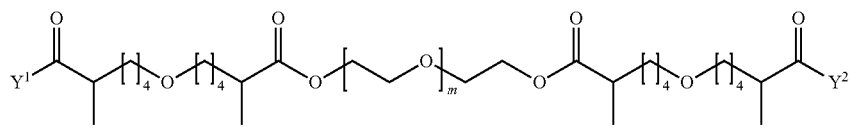
(Va-35)
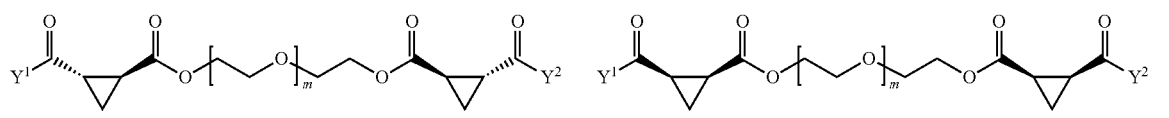
(Va-36) (Va-37)
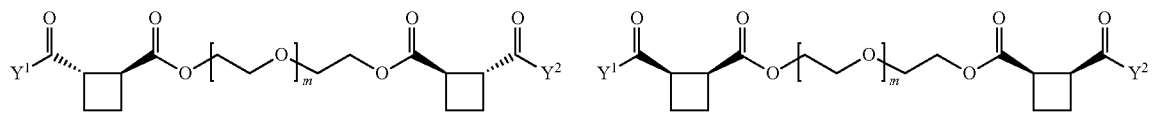
(Va-38) (Va-39)
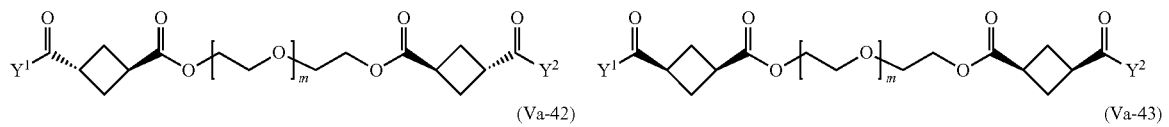
(Va-40) (Va-41)
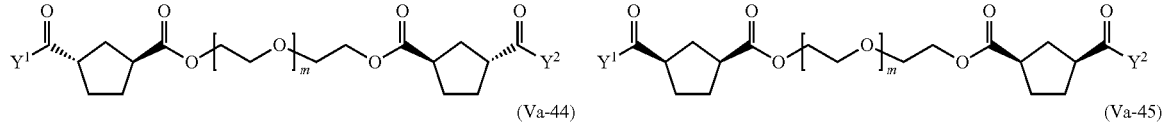
(Va-42) (Va-43)
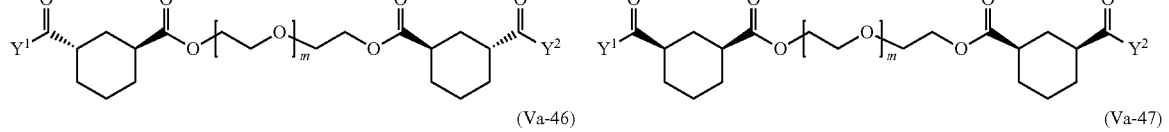
(Va-44) (Va-45)
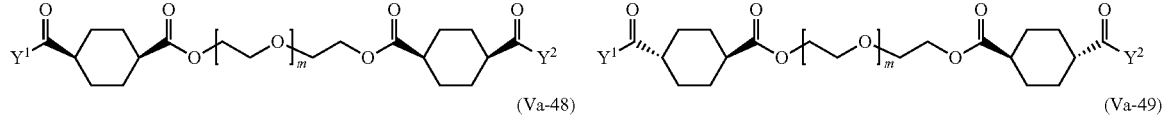
(Va-46) (Va-47)
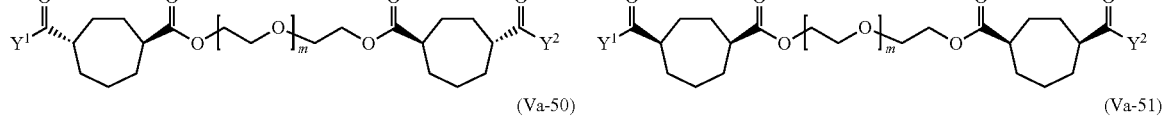
(Va-48) (Va-49)
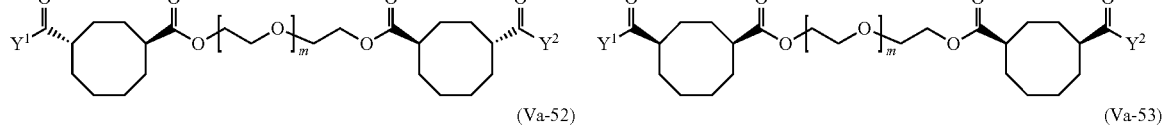
(Va-50) (Va-51)
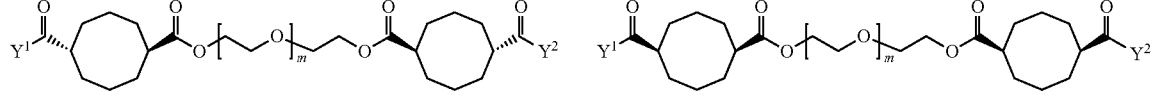
(Va-52) (Va-53)

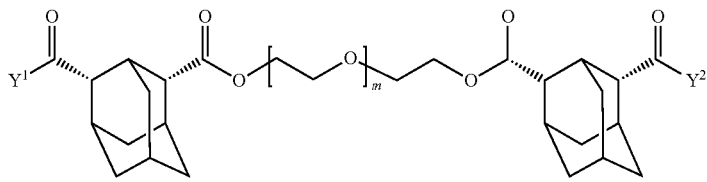

wherein
each crosslinker reagent may be in the form of its racemic mixture, where applicable; and
m, $Y^1$ and $Y^2$ are defined as above.

It was surprisingly found that the use of crosslinker reagents with branches, i.e. residues other than H, at the alpha carbon of the carbonyloxy group lead to the formation of hydrogels which are more resistant against enzymatic degradation, such as degradation through esterases.

Similarly, it was surprisingly found that the fewer atoms there are between the (C=O) of a carbonyloxy group and the (C=O) of the adjacent activated ester, activated carbamate, activated carbonate or activated thiocarbamate, the more resistant against degradation the resulting hydrogels are, such as more resistant against degradation through esterases.

Accordingly, crosslinker reagents V-11 to V-54, V-1, V-2, Va-11 to Va-54, Va-1 and Va-2 are preferred crosslinker reagents. Crosslinker reagents Va-11 to Va-54, Va-1 and Va-2 are most preferred crosslinker reagents. Most preferred is crosslinker reagent Va-14.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

In another embodiment, crosslinker reagents Va-1, Va-2, Va-5, Va-6, Va-7, Va-8, Va-9, Va-10, Va-11, Va-12, Va-13, Va-14, Va-15, Va-16, Va-17, Va-18, Va-19, Va-20, Va-21, Va-22, Va-23, Va-24, Va-25, Va-26, Va-27, Va-28, Va-29, Va-30, Va-31, Va-32, Va-33, Va-34, Va-35, Va-36, Va-37, Va-38, Va-39, Va-40, Va-41, Va-42, Va-43, Va-44, Va-45, Va-46, Va-47, Va-48, Va-49, Va-50, Va-51, Va-52, Va-53 an Va-54 are even more preferred crosslinker reagents. More preferably, the at least one crosslinker reagent is of formula Va-5, Va-6, Va-7, Va-8, Va-9, Va-10, Va-14, Va-22, Va-23, Va-43, Va-44, Va-45 or Va-46, and most preferably, the at least one crosslinker reagent is of formula Va-5, Va-6, Va-9 or Va-14.

The preferred embodiments of the compound of formula (V-I) and (V-II) as mentioned above apply accordingly to the preferred compounds of formulas (V-1) to (V-54) and to the more preferred compounds of formulas (Va-1) to (Va-54).

The hydrogel resulting from step (b) preferably contains from 0.01 to 1.2 mmol/g primary amine groups (—NH$_2$), more preferably from 0.02 to 1.0 mmol/g primary amine groups, even more preferably from 0.02 to 0.5 mmol/g primary amine groups and most preferably from 0.05 to 0.3 mmol/g primary amine groups.

The term "X mmol/g primary amine groups" means that 1 g of dry hydrogel comprises X mmol primary amine groups. Measurement of the amine content of the hydrogel is carried out according to Gude et al. (Letters in Peptide Science, 2002, 9(4): 203-206, which is incorporated by reference in its entirety) and is also described in detail in the Examples section.

Polymerization

The polymerization in step (b) is initiated by adding a base. Preferably, the base is a non-nucleophilic base soluble in alkanes, more preferably the base is selected from the group consisting of N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, DIPEA, trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, 1,8-diazabicyclo[5.4.0]undec-7-ene, 1,5-diazabicyclo[4.3.0]non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

Preferably, the polymerization of step (b) is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel preferably ranges from 4:1 to 1:2, more preferably the diameter to height ratio of the vessel ranges from 2:1 to 1:1.

Preferably, the reaction vessel is equipped with an axial flow stirrer selected from the group consisting of pitched blade stirrers, marine type propellers, and Lightnin A-310. More preferably, the stirrer is a pitched blade stirrer.

Step (b) can be performed in a broad temperature range, preferably at a temperature from −10° C. to 100 C.°, more preferably at a temperature of 0° C. to 80° C., even more preferably at a temperature of 10° C. to 50° C. and most preferably at ambient temperature.

"Ambient temperature" refers to the temperature present in a typical laboratory environment and preferably means a temperature ranging from 17 to 25° C.

Preferably, the hydrogel obtained from the polymerization of step (b) is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The aforementioned diameters are measured when the hydrogel microparticles are fully hydrated in water.

In one preferred embodiment the polymerization in step (b) occurs in a suspension polymerization, in which case the mixture of step (a) further comprises a first solvent and at least a second solvent, which second solvent is immiscible in the first solvent.

Said first solvent is preferably selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water and mixtures thereof.

The at least one backbone reagent and at least one crosslinker reagent are dissolved in the first solvent, i.e. the disperse phase of the suspension polymerization. In one embodiment the at least one backbone reagent and the at least one crosslinker reagent are dissolved separately, i.e. in different containers, using either the same or different solvent and preferably using the same solvent for both reagents. In another embodiment, the at least one backbone reagent and the at least one crosslinker reagent are dissolved together, i.e. in the same container and using the same solvent.

A suitable solvent for the at least one backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water and mixtures thereof. More preferably, the backbone reagent is dissolved in a solvent selected from acetonitrile, dimethyl sulfoxide, methanol and mixtures thereof. Most preferably, the backbone reagent is dissolved in dimethylsulfoxide.

In one embodiment the at least one backbone reagent is dissolved in the solvent in a concentration ranging from 1 to 300 mg/ml, more preferably from 5 to 60 mg/ml and most preferably from 10 to 40 mg/ml.

A suitable solvent for the at least one crosslinker reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water and mixtures thereof. More preferably, the crosslinker reagent is dissolved in a solvent selected from dimethylformamide, acetonitrile, dimethyl sulfoxide, methanol and mixtures thereof. Most preferably, the crosslinker reagent is dissolved in dimethylsulfoxide.

In one embodiment the at least one crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the at least one backbone reagent and the second number to the at least one crosslinker reagent.

Preferably, the ratios are selected such that the mixture of step (a) comprises a molar excess of functional groups $A^{x0}$ from the at least one backbone reagent compared to the functional end groups of the at least one crosslinker reagent. Consequently, the hydrogel resulting from the process of the present invention has free functional groups $A^{x0}$ groups which can be used to couple other moieties to the hydrogel, such as spacer moieties and/or reversible prodrug linker moieties.

The at least one second solvent, i.e. the continuous phase of the suspension polymerization, is preferably an organic solvent, more preferably an organic solvent selected from the group consisting of linear, branched or cyclic $C_{5-30}$ alkanes; linear, branched or cyclic $C_{5-30}$ alkenes; linear, branched or cyclic $C_{5-30}$ alkynes; linear or cyclic poly (dimethylsiloxanes); aromatic $C_{6-20}$ hydrocarbons; and mixtures thereof. Even more preferably, the at least second solvent is selected from the group consisting of linear, branched or cyclic $C_{5-16}$ alkanes; toluene; xylene; mesitylene; hexamethyldisiloxane; and mixtures thereof. Most preferably, the at least second solvent is a linear $C_{7-11}$ alkane, such as heptane, octane, nonane, decane or undecane.

Preferably, the mixture of step (a) further comprises a detergent. Preferred detergents are Cithrol DPHS, Hypermer 70A, Hypermer B246, Hypermer 1599A, Hypermer 2296, and Hypermer 1083.

Preferably, the detergent has a concentration of 0.1 g to 100 g per 1 L total mixture, i.e. disperse phase and continuous phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

In one embodiment, step (b) further comprises working-up the hydrogel after polymerization, wherein said working-up comprises one or more of the following steps:

(b-i) removing excess liquid from the polymerization reaction, (b-ii) washing the hydrogel to remove solvents used during polymerization, (b-iii) transferring the hydrogel into a buffer solution, (b-iv) size fractionating/sieving of the hydrogel, (b-v) transferring the hydrogel into a container, (b-vi) drying the hydrogel, (b-vii) transferring the hydrogel into a specific solvent suitable for sterilization, and/or (b-viii) sterilizing the hydrogel, preferably by gamma radiation.

Preferably, the working-up step comprises all of the following steps (b-i) removing excess liquid from the polymerization reaction, (b-ii) washing the hydrogel to remove solvents used during polymerization, (b-iii) transferring the hydrogel into a buffer solution, (b-iv) size fractionating/sieving of the hydrogel, (b-v) transferring the hydrogel into a container, (b-vii) transferring the hydrogel into a specific solvent suitable for sterilization, and (b-viii) sterilizing the hydrogel, preferably by gamma radiation.

Optional Reaction with a Spacer Reagent

In a preferred embodiment $A^{x0}$ is an amine and $A^{x1}$ is $ClSO_2-$, $R^1(C=O)-$, $I-$, $Br-$, $Cl-$, $SCN-$, $CN-$, $O=C=N-$, $Y^1-(C=O)-$, $Y^1-(C=O)-NH-$, or $Y^1-(C=O)-O-$, wherein $R^1$ is H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and $Y^1$ is selected from formulas (f-i) to (f-vi):

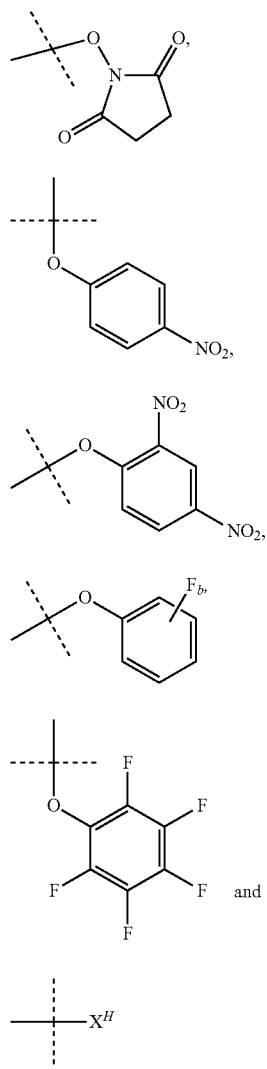

wherein
the dashed lines indicate attachment to the rest of the molecule,
b is 1, 2, 3 or 4,
$X^H$ is Cl, Br, I, or F.

In another preferred embodiment $A^{x0}$ is a hydroxyl group (—OH) and $A^{x1}$ is $O=C=N-$, $I-$, $Br-$, $SCN-$, or $Y^1-(C=O)-NH-$, wherein $Y^1$ is selected from formulas (f-i) to (f-vi):

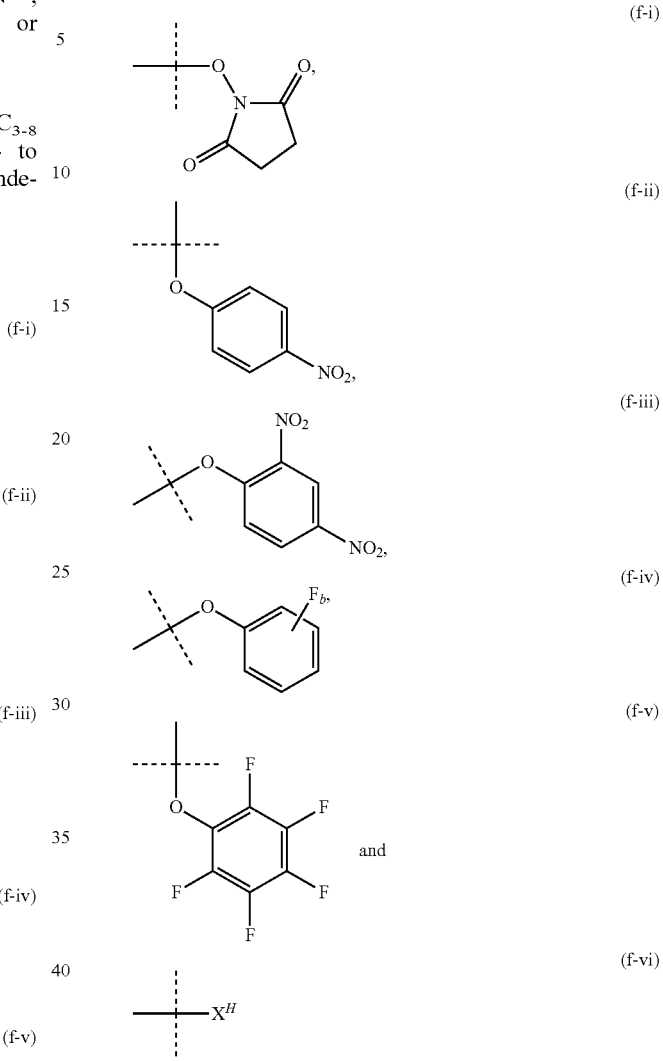

wherein
the dashed lines indicate attachment to the rest of the molecule,
b is 1, 2, 3 or 4,
$X^H$ is Cl, Br, I, or F.

In another preferred embodiment $A^{x0}$ is a carboxylic acid (—(C=O)OH) and $A^{x1}$ is a primary amine or secondary amine.

Most preferably, $A^{x0}$ is an amine and $A^{x1}$ is $Y^1-(C=O)-$.

Suitable activating reagents to obtain the activated carboxylic acid are for example N,N'-dicyclohexyl-carbodiimide (DCC), 1-ethyl-3-carbodiimide (EDC), benzotriazol-1-yl-oxytripyrrolidinophosphonium hexafluorophosphate (PyBOP), bromotripyrrolidinophosphonium hexafluorophosphate (PyBrOP), 1-cyano-2-ethoxy-2-oxoethylidenaminooxy)dimethylamino-morpholino-carbenium hexafluorophosphate (COMU), 1-hydroxybenzotriazole (HOBT), 1-hydroxy-7-azabenzotriazole (HOAT), O-(6-chlorobenzotriazol-1-yl)-N,N,N',N'-tetramethyluronium hexafluorophosphate (HCTU), 1-H-benzotriazolium (HBTU), (O-(7-azabenzotriazol-1-yl)-N,N,N',N'-tetramethyluronium hexafluorophosphate (HATU), and O-(benzotriazol-1-yl)-N,N,N',N'-tetramethyluronium tetrafluoroborate (TBTU). These reagents are commercially available and well-known to the skilled person.

Preferably, $A^{x2}$ is selected from the group consisting of -maleimide, —SH, —NH$_2$, —SeH, —N$_3$, —C≡CH, —CR$^1$=CR$^{1a}$R$^{1b}$, —OH, —(CH=X)—R$^1$, —(C=O)—S—R$^1$, —(C=O)—H, —NH—NH$_2$, —O—NH$_2$, —Ar—X$^0$, —Ar—Sn(R$^1$)(R$^{1a}$)(R$^{1b}$), —Ar—B(OH)(OH), Br, I,

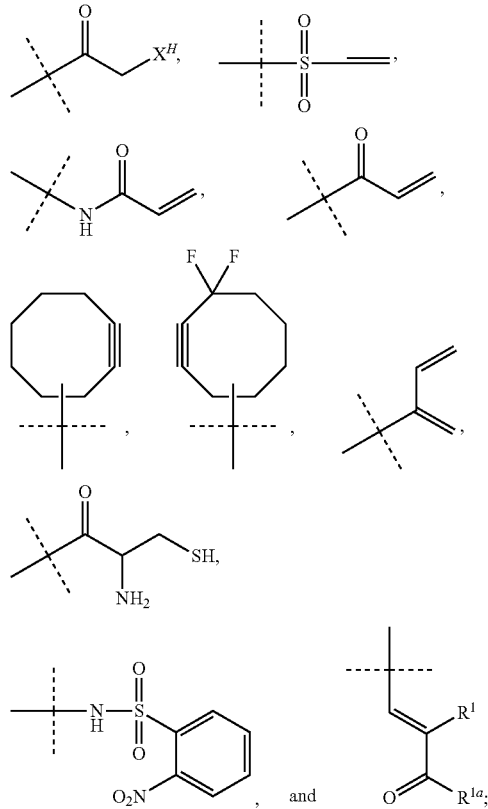

with optional protecting groups;
wherein
dashed lines indicate attachment to SP$^2$;
X is O, S, or NH,
X$^0$ is —OH, —NR$^1$R$^{1a}$, —SH, or —SeH,
X$^H$ is Cl, Br, I or F;
Ar is phenyl, naphthyl, indenyl, indanyl, or tetralinyl, and
R$^1$, R$^{1a}$, R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl.

More preferably, $A^{x2}$ is —NH$_2$, maleimide or thiol and most preferably $A^{x2}$ is maleimide.

If the hydrogel of step (b) is covalently conjugated to a spacer moiety, the resulting hydrogel-spacer moiety conjugate is of formula (VIa):

$$\text{\textemdash A}^{y1}\text{-SP}^2\text{-A}^{x2} \qquad \text{(VIa),}$$

wherein
the dashed line indicates attachment to the hydrogel of step (b);
$A^{y1}$ is the linkage formed between $A^{x0}$ and $A^{x1}$; and
SP$^2$ and $A^{x2}$ are used as in formula (VI).
Preferably, $A^{y1}$ is a stable linkage.
Preferably, $A^{y1}$ is selected from the group consisting of

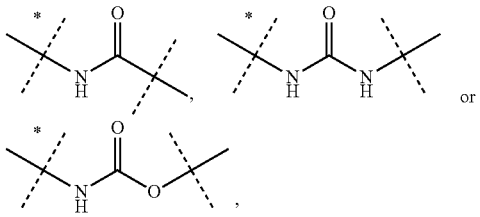

wherein
dashed lines marked with an asterisk indicate attachment to a backbone moiety; and unmarked dashed lines indicate attachment to SP$^2$.

Suitable reaction conditions are described in the Examples sections and are known to the person skilled in the art.

Process step (c) may be carried out in the presence of a base. Suitable bases include customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN), N,N-diisopropylethylamine (DIPEA), diazabicycloundecene (DBU) or collidine.

Process step (c) may be carried out in the presence of a solvent. Suitable solvents for carrying out the process step (d) of the invention include organic solvents. These preferably include water and aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, dimethylether, diethylene glycol; acetonitrile, N-methyl-2-pyrrolidone (NMP), dimethylformamide (DMF), dimethyl sulfoxide (DMSO), N,N-dimethylacetamide, nitromethane, nitrobenzene, hexamethylphosphoramide (HMPT), 1,3-dimethyl-2-imidazolidinone (DMI), 1,3-dimethyl-3,4,5,6-tetrahydro-2(1H)-pyrimidinone (DMPU), ethyl acetate, acetone, butanone; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; or mixtures thereof. Preferably, the solvent is selected from the group consisting of water, acetonitrile and N-methyl-2-pyrrolidone.

Step (d)

The hydrogel or hydrogel-spacer moiety conjugate of step (b) or (c) is subjected to one of steps (d-i), (d-ii), (d-iii), (d-iv), (d-v), (d-vi), (d-vii) or (d-viii). The result of each of these steps is a hydrogel-linked prodrug which releases a tag moiety-biologically active moiety conjugate.

Step (d-i)

Step (d-i) preferably comprises three sub-steps, namely (i) covalently conjugating a reversible prodrug linker reagent of formula (VII)

$$A^{x3}\text{-}L\text{-}A^{x4} \quad (VII),$$

wherein $A^{x3}$ and $A^{x4}$ are independently of each other a functional group; and L is a reversible prodrug linker moiety;

to $A^{x0}$ of the hydrogel of step (b) or to $A^{x2}$ of step (c) wherein $A^{x3}$ reacts with $A^{x0}$ or $A^{x2}$, respectively;

(ii) covalently conjugating a drug of formula (VIII)

$$A^{x5}\text{-}D\text{-}A^{x6} \quad (VIII),$$

wherein $A^{x5}$ and $A^{x6}$ are independently of each other a functional group; and D is a biologically active moiety;

to the conjugate of step (i), wherein $A^{x5}$ reacts with $A^{x4}$; and (iii) covalently conjugating a tag reagent of formula (IX)

$$A^{x7}\text{-}T \quad (IX),$$

wherein $A^{x7}$ is a functional group; and

T is a tag moiety;

to the conjugate of step (ii), wherein $A^{x7}$ reacts with $A^{x6}$.

The resulting conjugate of step (iii) has the structure of formula (Xa) or (Xb):

wherein the dashed line indicates attachment to a backbone moiety;

$A^{y0}$ is the linkage formed between $A^{x0}$ and $A^{x3}$;

$A^{y1}$ is used as in formula (VIa);

$A^{y2}$ is the linkage formed between $A^{x2}$ and $A^{x3}$;

$A^{y3}$ is the linkage formed between $A^{x4}$ and $A^{x5}$;

$A^{y4}$ is the linkage formed between $A^{x6}$ and $A^{x7}$;

$SP^2$ is used as in formula (VI);

L is used as in formula (VII);

D is used as in formula (VIII); and

T is used as in formula (IX).

Preferably, $A^{x3}$ is selected from the group consisting of —SH, —NH$_2$, —SeH, -maleimide, —C≡CH, —N$_3$, —CR$^1$=CR$^{1a}$R$^{1b}$, —(C=X)—R$^1$, —OH, —(C=O)—S—R$^1$, —NH—NH$_2$, —O—NH$_2$, —Ar—Sn(R$^1$)(R$^{1a}$)(R$^{1b}$), —Ar—B(OH)(OH), —Ar—X$^0$,

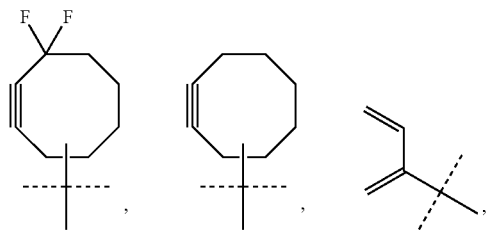

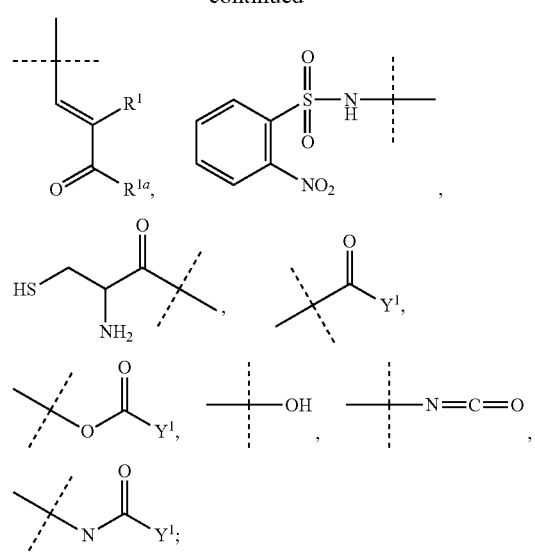

wherein dashed lines indicate attachment to L;

X is O, S, or NH,

X$^0$ is —OH, —NR$^1$R$^{1a}$, —SH, or —SeH;

R$^1$, R$^{1a}$, R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl; and Ar is phenyl, naphthyl, indenyl, indanyl, or tetralinyl.

$Y^1$ is selected from formulas (f-i) to (f-vi):

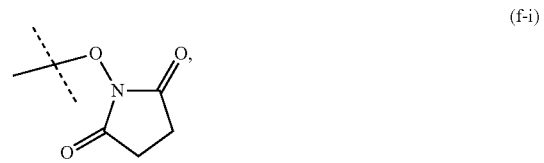

(f-i)

(f-ii)

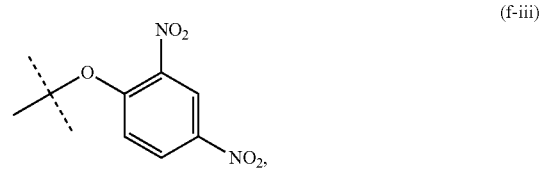

(f-iii)

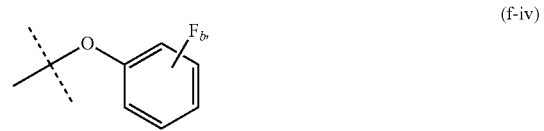

(f-iv)

(f-v)
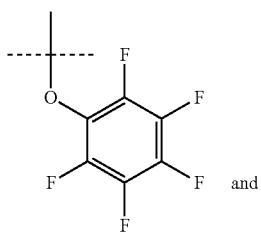 and
(f-vi)
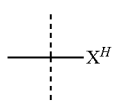—X$^H$
wherein
  the dashed lines indicate attachment to the rest of the molecule,
  b is 1, 2, 3 or 4,
  X$^H$ is Cl, Br, I, or F.
Preferred combinations of A$^{x2}$ and A$^{x3}$ are the following:
| A$^{x2}$ | A$^{x3}$ |
|---|---|
| -maleimide | HS—, H$_2$N—, or HSe— |
| —SH, —NH$_2$, or —SeH | maleimide- |
| —N$_3$ | HC≡C—, |
| | 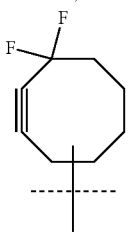, or |
| —C≡CH, | N$_3$— |
| 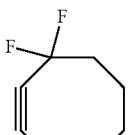 | |
| | , or |
| | 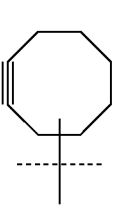 |
| —CR$^{1a}$=CR$^{1a}$R$^{1b}$ | R$^{1b}$R$^{1a}$C=CR$^1$— or 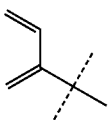 |
| 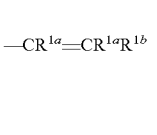 | R$^{1b}$R$^{1a}$C=CR$^1$— |
| —(C=X)—R$^1$ | 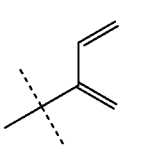 |
| | R$^1$—(C=X)— |
| 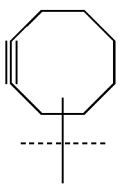 | |
| —OH | H$_2$N— or 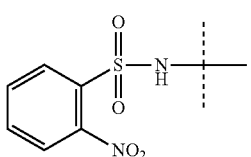 |

-continued

| $A^{x2}$ | $A^{x3}$ |
|---|---|
| —NH$_2$ or 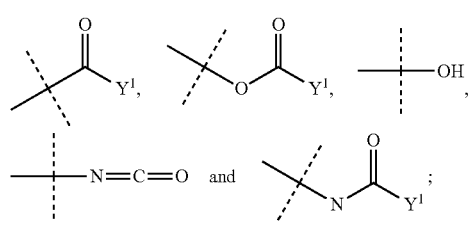 | HO— |
| —(C=O)—S—R$^1$ | 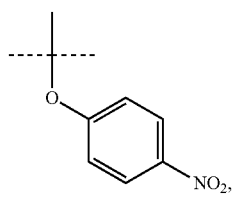 |
| 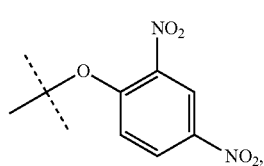 | R$^1$—S—(C=O)— |
| —(C=O)—H<br>—NH—NH$_2$ or —O—NH$_2$<br>—Ar—X$^0$<br>(R$^{1b}$)(R$^{1a}$)(R$^1$)Sn—Ar— or<br>—Ar—B(OH)(OH) | H$_2$N—NH— or H$_2$N—O—<br>H—(C=O)—<br>—Ar—Sn(R$^1$)(R$^{1a}$)(R$^{1b}$) or<br>—Ar—B(OH)(OH)<br>X$^0$—Ar— | wherein

X is O, S, or NH;

X$^0$ is —OH, —NR$^1$R$^{1a}$, —SH, or —SeH;

R$^1$, R$^{1a}$, R$^{1b}$ are independently of each other selected from the group consisting of H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, and tetralinyl; and Ar is phenyl, naphthyl, indenyl, indanyl, or tetralinyl.

More preferably, A$^{x3}$ is —SH or -maleimide and most preferably A$^{x3}$ is —SH.

Accordingly, a preferred combination of A$^{x2}$/A$^{x3}$ is -maleimide/—SH and —SH/-maleimide and most preferably, A$^{x2}$ is -maleimide and A$^{x3}$ is —SH.

Preferably, A$^{x4}$ is selected from the group consisting of

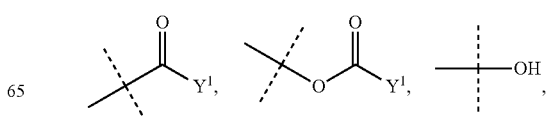

wherein dashed lines indicate attachment to L;

Y$^1$ is selected from formulas (f-i) to (f-vi):

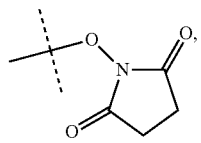
(f-i)

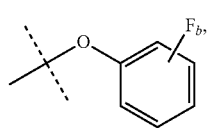
(f-ii)

(f-iii)

(f-iv)

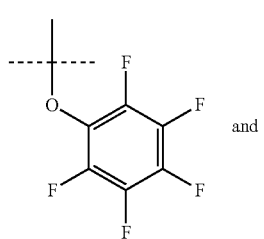
and

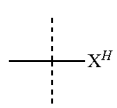
(f-vi)

wherein the dashed lines indicate attachment to the rest of the molecule, b is 1, 2, 3 or 4, X$^H$ is Cl, Br, I, or F.

It is understood that A$^{x5}$ and A$^{x6}$ are functional groups of the drug which are independ of each other selected from the group consisting of carboxylic acid, amine, thiol, sulfonic acid, carbonate, carbamate, hydroxyl, aldehyde, ketone, hydrazine, isocyanate, isothiocyanate, phosphoric acid, phosphonic acid, haloacetyl, alkyl halides, acryloyl, aryl fluorides, hydroxylamine, disulfides, vinyl sulfone, vinyl ketone, diazoalkanes, diazoacetyls, oxirane, and aziridine. Preferably, A$^{x5}$ and A$^{x6}$ are independently selected from carboxylic acid, amine, and hydroxyl.

Preferably, A$^{x7}$ is selected from the group consisting of

-continued

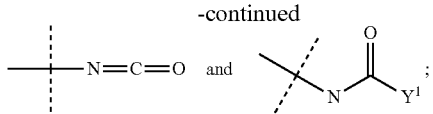

wherein
dashed lines indicate attachment to T; and
Y¹ is selected from formulas (f-i) to (f-vi):

(f-i)
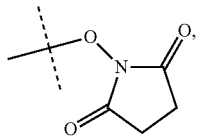

(f-ii)
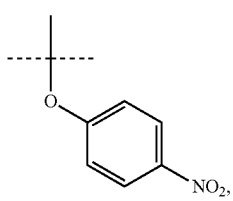

(f-iii)
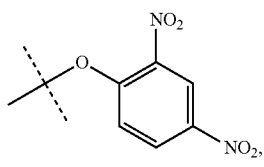

(f-iv)
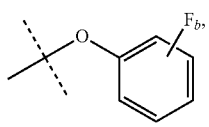

(f-v)
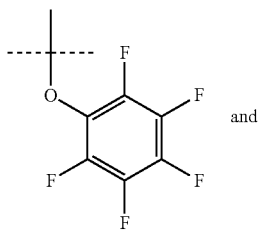

(f-vi)
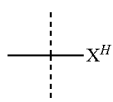

wherein
the dashed lines indicate attachment to the rest of the molecule,
b is 1, 2, 3 or 4
$X^H$ is Cl, Br, I, or F.

The person skilled in the art knows what type of linkage results from the reaction of any two of the above mentioned functional groups. Therefore only preferred linkages are listed below.

Preferably, $A^{y0}$ is a stable linkage.

Preferably, $A^{y0}$ is selected from the group consisting of thioether, ether, amine, amide, ester, oxime, hydrazone, carbamate, thiozolidine, carbon-carbon bond and triazole.

Preferably, $A^{y2}$ is a stable linkage.

Preferably, $A^{y2}$ is selected from the group consisting of

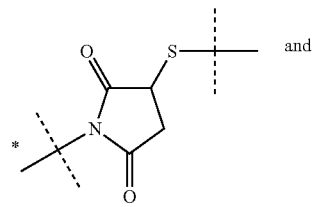

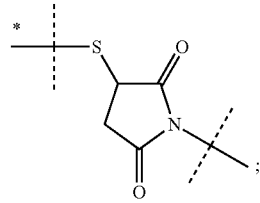

wherein
the dashed lines marked with an asterisk indicate attachment to $SP^2$; and
the unmarked dashed lines indicate attachment to L.

Preferably, the linkage $A^{y3}$ is selected from the group consisting of

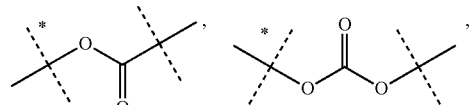

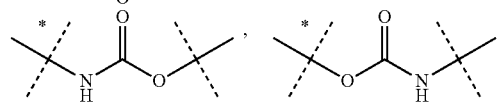

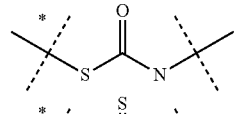

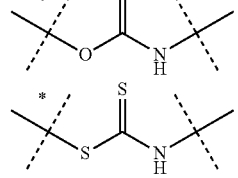

wherein
the dashed lines marked with an asterisk indicate attachment to L; and
the unmarked dashed lines indicate attachment to D.

More preferably, the linkage $A^{y3}$ is selected from the group consisting of

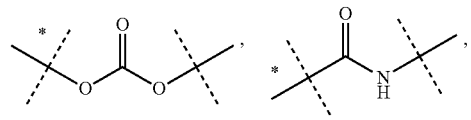

-continued

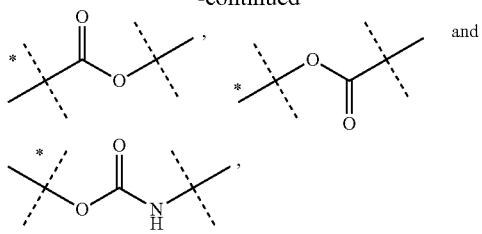

wherein
the dashed lines marked with an asterisk indicate attachment to L; and
the unmarked dashed lines indicate attachment to D.
Preferably, $A^{y4}$ is a stable linkage.
Preferably, $A^{y4}$ is selected from the group consisting of

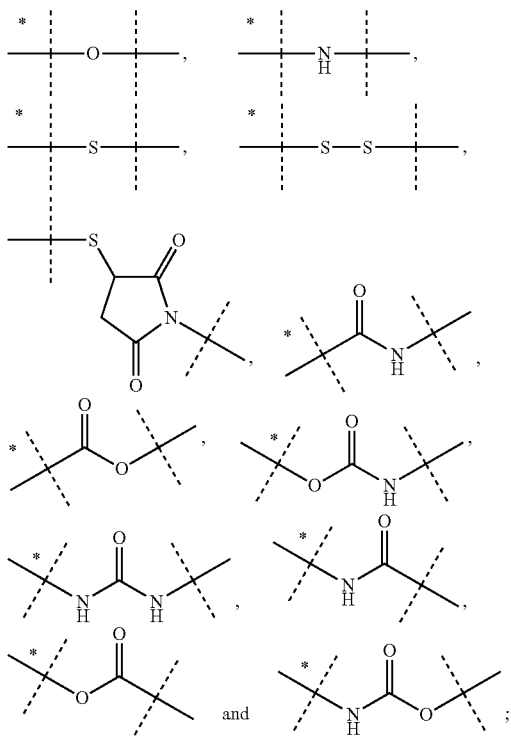

wherein
the dashed lines marked with an asterisk indicate attachment to D; and
the unmarked dashed lines indicate attachment to T.
Preferred embodiments of L, D and T are given below.

Step (d-ii)
Step (d-ii) preferably comprises two sub-steps, namely
(i) covalently conjugating a reversible prodrug linker reagent of formula (VII) to $A^{x0}$ of step (b) or to $A^{x2}$ of step (c), wherein $A^{x3}$ reacts with $A^{x0}$ or $A^{x2}$, respectively;
(ii) covalently conjugating a biologically active moiety-tag moiety conjugate reagent of formula (XI)

$A^{x5}$-D-$A^{y4}$-T  (XI), wherein
$A^{x5}$ and D are used as in formula (VIII);
$A^{y4}$ is used as in formula (Xa)/(Xb); and
T is used as in formula (IX);
to the conjugate of step (i), wherein $A^{x5}$ reacts with $A^{x4}$.

The resulting conjugate of step (ii) has the structure of formula (Xa) or (Xb).

Step (d-iii)
Step (d-iii) preferably comprises two sub-steps, namely
(i) covalently conjugating a reversible prodrug linker moiety-biologically active moiety conjugate reagent of formula (XII)

$A^{x3}$-L-$A^{y3}$-D-$A^{x6}$  (XII), wherein
$A^{x3}$ and L are used as in formula (VII),
$A^{y3}$ is used as in formula (Xa)/(Xb); and
D and $A^{x6}$ are used as in formula (VIII);
to $A^{x0}$ of step (b) or to $A^{x2}$ of step (c), wherein $A^{x3}$ reacts with $A^{x0}$ or $A^{x2}$, respectively; and
(ii) covalently conjugating a tag reagent of formula (IX) to the conjugate of step (ii), wherein $A^{x7}$ reacts with $A^{x6}$.

The resulting conjugate of step (ii) has the structure of formula (Xa) or (Xb).

Step (d-iv)
Step (d-iv) preferably comprises the step of covalently conjugating a reversible prodrug linker moiety-biologically active moiety-tag moiety conjugate reagent of formula (XIII)

$A^{x3}$-L-$A^{y3}$-D-$A^{y4}$-T  (XIII), wherein
$A^{x3}$ and L are used as in formula (VII);
$A^{y3}$ and $A^{y4}$ are used as in formula (Xa)/(Xb);
D is used as in formula (VIII); and
T is used as in formula (IX);
to $A^{x0}$ of step (b) or to $A^{x2}$ of step (c), wherein $A^{x3}$ reacts with $A^{x0}$ or $A^{x2}$, respectively.

The resulting conjugate is of formula (Xa) or (Xb).

Step (d-v)
Step (d-v) preferably comprises three sub-steps, namely
(i) covalently conjugating a reversible prodrug linker reagent of formula (VII) to $A^{x0}$ of step (b) or to $A^{x2}$ of step (c), wherein $A^{x3}$ reacts with $A^{x0}$ or $A^{x2}$, respectively;
(ii) covalently conjugating a tag reagent of formula (XIV)

$A^{x8}$-T-$A^{x9}$  (XIV), wherein
$A^{x8}$ and $A^{x9}$ are independently of each other a functional group; and
T is used as in formula (IX);
to the conjugate of step (i), wherein $A^{x8}$ reacts with $A^{x4}$; and
(iii) covalently conjugating a drug of formula (VIIIa)

$A^{x5}$-D  (VIIIa), wherein
$A^{x5}$ and D are used as in formula (VIII);
to the conjugate of step (ii), wherein $A^{x5}$ reacts with $A^{x9}$.

The resulting conjugate is of formula (XVa) or (XVb):

$\dashv A^{y0}$-L-$A^{y5}$-D-$A^{y6}$-T  (XVa), $\dashv A^{y1}$-SP$^2$-$A^{y2}$-L-$A^{y5}$-D-$A^{y6}$-T  (XVb), wherein
the dashed line indicates attachment to the hydrogel of step (b);
$A^{y0}$ and $A^2$ are used as in formula (Xa)/(Xb);
$A^{y1}$ is used as in formula (VIa);

$A^{y5}$ is the linkage formed between $A^{x4}$ and $A^{x8}$;
$A^{y6}$ is the linkage formed between $A^{x9}$ and $A^{x5}$;
SP is used as in formula (VI);
L is used as in formula (VII);
T is used as in formula (IX); and
D is used as in formula (VIII).

Preferably, $A^{x8}$ is selected from the group consisting of carboxylic acid, amine, thiol, sulfonic acid, carbonate, carbamate, hydroxyl, aldehyde, ketone, hydrazine, isocyanate, isothiocyanate, phosphoric acid, phosphonic acid, haloacetyl, alkyl halides, acryloyl, aryl fluorides, hydroxylamine, disulfides, vinyl sulfone, vinyl ketone, diazoalkanes, diazoacetyls, oxirane, and aziridine. Preferably, $A^{x8}$ is selected from the group consisting of carboxylic acid, amine, and hydroxyl.

Preferably, $A^{x9}$ is selected from the group consisting of -maleimide,

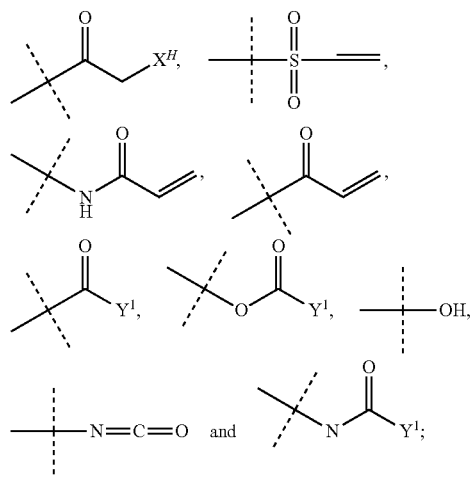

wherein
dashed lines indicate attachment to T; and
$Y^1$ is selected from formulas (f-i) to (f-vi):

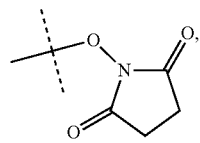

(f-i)

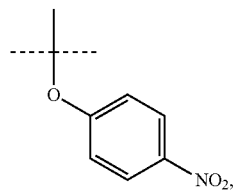

(f-ii)

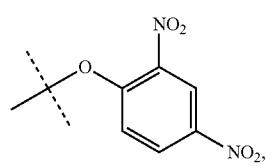

(f-iii)

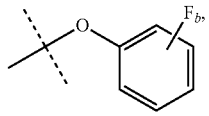

(f-iv)

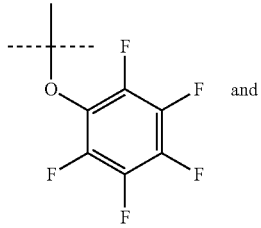

(f-v) and

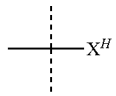

(f-vi)

wherein
the dashed lines indicate attachment to the rest of the molecule,
b is 1, 2, 3 or 4,
$X^H$ is Cl, Br, I, or F.

Preferably, $A^{y5}$ is selected from the group consisting of

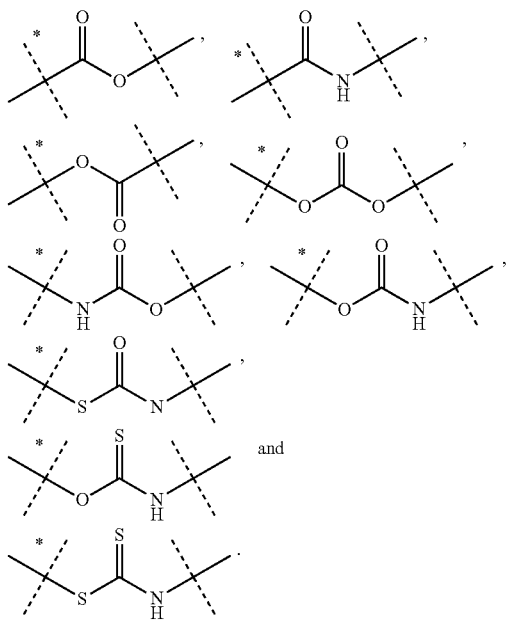

wherein
the dashed lines marked with an asterisk indicate attachment to L; and
the unmarked dashed lines indicate attachment to T.

More preferably, $A^{y5}$ is selected from the group consisting of

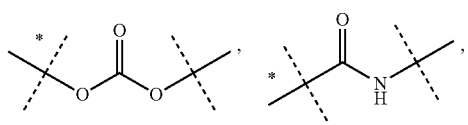

-continued

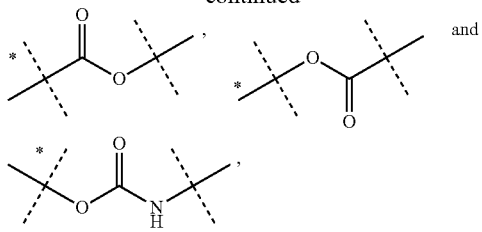

wherein
the dashed lines marked with an asterisk indicate attachment to L; and
the unmarked dashed lines indicate attachment to T.
Preferably, $A^{y6}$ is a stable linkage.
Preferably, the linkage $A^{y6}$ is selected from the group consisting of

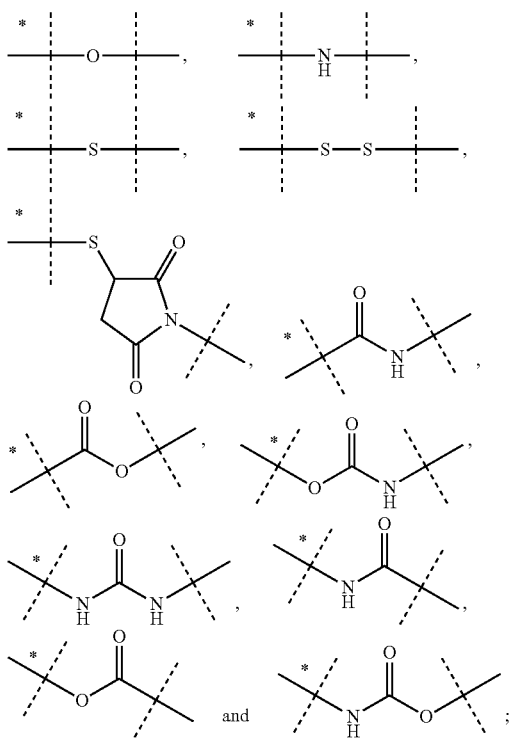

wherein
the dashed lines marked with an asterisk indicate attachment to D; and
the unmarked dashed lines indicate attachment to T.

Step (d-vi)
Step (d-vi) preferably comprises two sub-steps, namely
(i) covalently conjugating a reversible prodrug linker reagent of formula (VII) to $A^{x0}$ of step (b) or to $A^{x2}$ of step (c), wherein $A^{x3}$ reacts with $A^{x0}$ or $A^{x2}$, respectively; and
(ii) covalently conjugating a tag moiety-biologically active moiety conjugate reagent of formula (XVI)

$$A^{x8}\text{-}T\text{-}A^{y6}\text{-}D \quad (XVI),$$

wherein
$A^{x8}$ is used as in formula (XIV);
T is used as in formula (IX);
$A^{y6}$ is used as in formula (XVa)/(XVb); and
D is used as in formula (VIII);
to the conjugate of step (i) wherein $A^{x8}$ reacts with $A^{x4}$.

The resulting conjugate is of formula (XVa) or (XVb).
Step (d-vii)
Step (d-vii) preferably comprises two sub-steps, namely
(i) covalently conjugating a reversible prodrug linker moiety-tag moiety conjugate reagent of formula (XVII)

$$A^{x3}\text{-}L\text{-}A^{y5}\text{-}T\text{-}A^{x9} \quad (XVII);$$

wherein
$A^{x3}$ and L are used as in formula (VII);
$A^{y5}$ is used as in formula (XVa)(XVb);
T is used as in formula (IX); and
$A^{x9}$ is used as in formula (XIV);
to $A^{x0}$ of step (b) or to $A^{x2}$ of step (c), wherein $A^{x3}$ reacts with $A^{x0}$ or $A^{x2}$, respectively; and
(ii) covalently conjugating a drug of formula (VIIIa) to the conjugate of step (i) wherein $A^{x5}$ reacts with $A^{x9}$.

The resulting conjugate is of formula (XVa) or (XVb).
Step (d-viii)
Step (d-viii) preferably comprises the step of covalently conjugating a reversible prodrug linker moiety-tag moiety-biologically active moiety conjugate reagent of formula (XVIII)

$$A^{x3}\text{-}L\text{-}A^{y5}\text{-}T\text{-}A^{y6}\text{-}D \quad (XVIII),$$

wherein
$A^{x3}$ and L are used as in formula (VII);
$A^{y5}$ and $A^{y6}$ are used as in formula (XVa)/(XVb);
T is used as in formula (IX); and
D is used as in formula (VIII);
to $A^{x0}$ of step (b) or to $A^{x2}$ of step (c), wherein $A^{x3}$ reacts with $A^{x0}$ or $A^{x2}$, respectively.

The resulting conjugate is of formula (XVa) or (XVb).
Depending on the exact nature of the different steps and sub-steps the functional groups $A^{x0}$, $A^{x1}$, $A^{x2}$, $A^{x3}$, $A^{x4}$, $A^{x5}$, $A^{x6}$, $A^{x7}$, $A^{x8}$, and $A^{x9}$ may be present in their protected form, i.e. reversibly connected to a protection group which renders said functional group incapable of reacting with for example other chemical functional groups. Such protection groups are well known to the person skilled in the art.

In one preferred embodiment step (d) is (d-iv).
In another preferred embodiment step (d) is (d-vii).
In another preferred embodiment step (d) is (d-viii).
Reversible Prodrug Linker Moiety L
The reversible prodrug linker moiety L may have the structure of any prodrug linker moiety known in the art.
Preferably, L is a traceless prodrug linker moiety.
Due to the different embodiments of step (d), namely (d-i), (d-ii), (d-iii), (d-iv), (d-v), (d-vi), (d-vii) and (d-viii), the moiety L is present in different structural contexts. For simplification, the term "$A^{Z1}$-L-$A^{Z2}$" will be used, wherein $A^{Z1}$ is $A^{x3}$, $A^{y0}$ or $A^{y2}$ and wherein $A^{Z2}$ is $A^{x4}$, $A^{y3}$ or $A^{y5}$.

A preferred prodrug linker is disclosed and can be obtained as described in WO 2005/099768 A2. Accordingly, a preferred moiety/reagent $A^{Z1}$-L-$A^{Z2}$ has the structure of formula (L-i) or (L-ii):

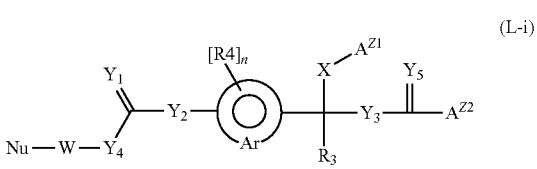

-continued (L-ii)

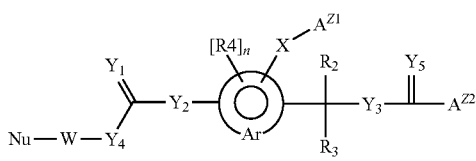

wherein $A^{Z1}$ is $A^{x3}$, $A^{y0}$ or $A^{y2}$;

$A^{Z2}$ is $A^{x4}$, $A^{y3}$ or $A^{y5}$; wherein $A^{Z2}$ is connected to T or D through an aromatic amine of the corresponding drug or tag reagent;

X is a spacer moiety such as $R_5$—$Y_6$, $Y_1$, $Y_2$ are independently O, S or $NR_6$, $Y_3$, $Y_5$ are independently O or S, $Y_4$ is O, $NR_6$ or $C(R_7)(R_8)$, $Y_6$ is O, S, $NR_6$, succinimide, maleimide, an unsaturated carbon-carbon bonds or any heteroatom containing a free electron pair or is absent, $R_2$, $R_3$ are independently of each other selected from the group consisting of substituted or non-substituted linear, branched or cyclical alkyl or heteroalkyl, aryls, substituted aryls, substituted or non-substituted heteroaryl, cyano, nitro, halogen, carboxy, carboxylalkyl, alkylcarbonyl and carboxamidoalkyl;

R4 is selected from the group consisting of hydrogen, substituted or non-substituted linear, branched or cyclical alkyl or heteroalkyl, aryl, substituted aryl, substituted or non-substituted heteroaryl, substituted or non-substituted linear, branched or cyclical alkoxy, substituted or non-substituted linear, branched or cyclical heteroalkyloxy, aryloxy or heteroaryloxy, cyano, and halogen, $R_5$ is selected from the group consisting of substituted or non-substituted linear, branched or cyclical alkyl or heteroalkyl, aryls, substituted aryls, substituted and non-substituted heteroaryls, $R_6$ is selected from the group consisting of substituted or non-substituted linear, branched or cyclical alkyl or heteroalkyl, aryls, and substituted or non-substituted heteroaryls, $R_7$, $R_8$ are independently selected from the group consisting of hydrogen, substituted or non-substituted linear, branched or cyclical alkyl or heteroalkyl, aryls, substituted aryls, substituted or non-substituted heteroaryls, carboxyalkyl, alkylcarbonyl, carboxamidoalkyl, cyano and halogen, W is selected from the group consisting of substituted or non-substituted linear, branched or cyclical alkyl, aryls, substituted aryls, substituted or non-substituted linear, branched or cyclical heteroalkyl, and substituted or non-substituted heteroaryls, Nu is a nucleophile, n is zero or a positive integer, and Ar is a multi-substituted aromatic hydrocarbon or a multi-substituted aromatic heterocycle.

Preferably, $R_2$, $R_3$, R4, $R_5$, $R_6$, $R_7$ and $R_8$ of formula (L-i) and (L-ii) are independently selected from the group consisting of H, $C_{1-6}$ alkyl, $C_{2-6}$ alkenyl and $C_{2-6}$ alkynyl.

Preferably, $Y_6$ of formula (L-i) and (L-ii) is $C_{1-20}$ alkyl, $C_{2-20}$ alkenyl or $C_{2-20}$ alkynyl.

Preferably, Nu of formula (L-i) and (L-ii) is selected from the group of nucleophiles consisting of primary, secondary and tertiary amino groups, thiol, carboxylic acid, hydroxylamine, hydrazine and nitrogen containing heteroaryl.

Preferably, W of formula (L-i) and (L-ii) is —($CR_9R_{10}$)$_b$—, wherein $R_9$ and $R_{10}$ are independently of each other selected from the group consisting of H, $C_{1-6}$ alkyl, $C_{2-6}$ alkenyl and $C_{2-6}$ alkynyl and wherein b is 1, 2, 3, 4 or 5.

Preferably, n of formula (L-i) and (L-ii) is 0, 1 or 2, more preferably, n is 0 or 1 and most preferably n is 0.

Preferably, Ar of formula (L-i) and (L-ii) is selected from the group consisting of

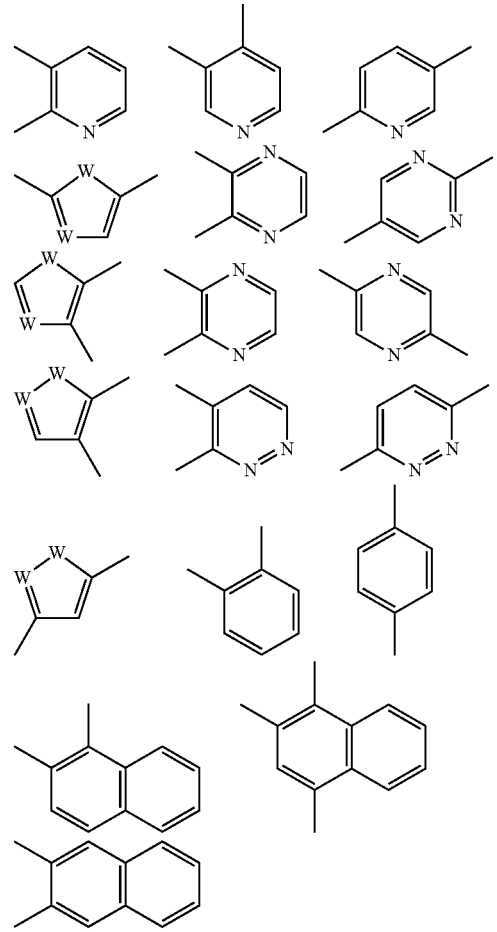

It is understood that in formula (L-i) and (L-ii) L corresponds to the moiety linking $A^{Z1}$ and $A^{Z2}$.

Other preferred reversible prodrug linkers are disclosed and can be obtained as described in WO 2006/136586 A2. Accordingly, a preferred moiety/reagent $A^{Z1}$-L-$A^{Z2}$ has the structure of formula (L-iii), (L-iv) or (L-v):

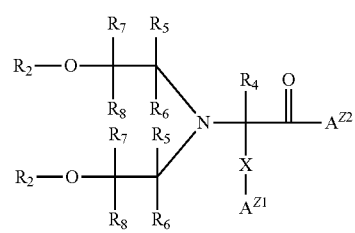

(L-iii)

-continued

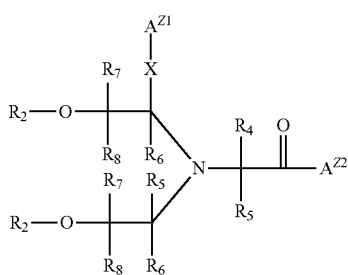

(L-iv)

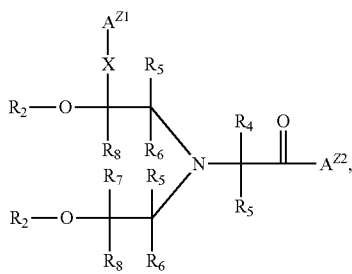

(L-v)

wherein
A$^{Z1}$ is A$^{x3}$, A$^{y0}$ or A$^{y2}$;
A$^{Z2}$ is A$^{x4}$, A$^{y3}$ or A$^{y5}$; wherein A$^{Z2}$ is connected to T or D through an amine of the corresponding drug or tag reagent by forming an amide linkage;
X is a spacer moiety such as R13-Y1;
Y1 is O, S, NR6, succinimide, maleimide, unsaturated carbon-carbon bonds or any heteroatom-containing a free electron pair or is absent;
R$_{13}$ is selected from the group consisting of substituted or non-substituted linear, branched or cyclical alkyl or heteroalkyl, aryls, substituted aryls, and substituted or non-substituted heteroaryls;
R$_2$ and R$_3$ are independently of each other selected from the group consisting of hydrogen, acyl groups, and protecting groups for hydroxyl groups;
R$_4$ to R$_{12}$ are independently of each other selected from the group consisting of hydrogen, substituted or non-substituted linear, branched or cyclical alkyl or heteroalkyl, aryls, substituted aryls, substituted or non-substituted heteroaryls, cyano, nitro, halogen, carboxy and carboxamide.
Preferably, R$_2$, R$_3$, R$_4$, R$_5$, R$_6$, R$_7$, R$_8$, R$_9$, R$_{10}$, R$_{11}$ and R$_{12}$ of formula (L-iii), (L-iv) and (L-v) are independently of each other H, C$_{1-6}$ alkyl, C$_{2-6}$ alkenyl or C$_{2-6}$ alkynyl.
Preferably, Y1 of formula (L-iii), (L-iv) and (L-v) is C$_{1-20}$ alkyl, C$_{2-20}$ alkenyl or C$_{2-20}$ alkynyl.
It is understood that in formula (L-iii), (L-iv) and (L-v) L corresponds to the moiety linking A$^{Z1}$ and A$^{Z2}$.

Another preferred prodrug linker is disclosed and can be obtained as described in WO 2009/095479 A2. Accordingly, a preferred moiety/reagent A$^{Z1}$-L-A$^{Z2}$ has the structure of formula (L-vi):

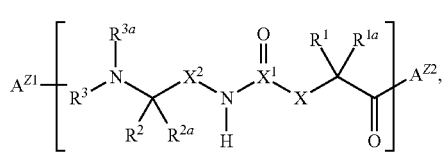

(L-vi)

wherein
A$^{Z1}$ is A$^{x3}$, A$^{y0}$ or A$^{2}$;
A$^{Z2}$ is A$^{x4}$, A$^{y3}$ or A$^{y5}$; wherein A$^{Z2}$ is connected to T or D through an amine of the corresponding drug or tag reagent by forming an amide linkage;
X$^1$ is C(R$^4$R$^{4a}$); N(R$^4$); O; C(R$^4$R$^{4a}$)—C(R$^5$R$^{5a}$); C(R$^5$R$^{5a}$)—C(R$^4$R$^{4a}$); C(R$^4$R$^{4a}$)—N(R$^6$); N(R$^6$)—C(R$^4$R$^{4a}$); C(R$^4$R$^{4a}$)—O; or O—C(R$^4$R$^{4a}$);
X$^1$ is C; or S(O);
X$^2$ is C(R$^7$, R$^{7a}$); or C(R$^7$, R$^{7a}$)—C(R$^8$, R$^{8a}$);
R$^1$, R$^{1a}$, R$^2$, R$^{2a}$, R$^3$, R$^{3a}$, R$^4$, R$^{4a}$, R$^5$, R$^{5a}$, R$^6$, R$^7$, R$^{7a}$, R$^8$, R$^{8a}$ are independently of each other selected H; or C$_{1-4}$ alkyl;
optionally, one or more of the pair(s) R$^{1a}$/R$^{4a}$, R$^{1a}$/R$^{5a}$, R$^{4a}$/R$^{5a}$, R$^{4a}$/R$^{5a}$, R$^{7a}$/R$^{8a}$ form a chemical bond;
optionally, one or more of the pair(s) R$^1$/R$^{1a}$, R$^2$/R$^{2a}$, R$^4$/R$^{4a}$, R$^5$/R$^{5a}$, R$^7$/R$^{7a}$, R$^8$/R$^{8a}$ are joined together with the atom to which they are attached to form a C$_{3-8}$ cycloalkyl; or 4- to 7-membered heterocyclyl;
optionally, one or more of the pair(s) R$^1$/R$^4$, R$^1$/R$^5$, R$^1$/R$^6$, R$^4$/R$^5$, R$^7$/R$^8$, R$^2$/R$^3$ are joined together with the atoms to which they are attached to form a ring A;
optionally, R$^3$/R$^{3a}$ are joined together with the nitrogen atom to which they are attached to form a 4- to 7-membered heterocycle;
A is phenyl; naphthyl; indenyl; indanyl; tetralinyl; C$_{3-10}$ cycloalkyl; 4- to 7-membered heterocyclyl; or 8- to 11-membered heterobicyclyl;
provided that one hydrogen of R$^1$, R$^{1a}$, R$^2$, R$^{2a}$, R$^3$, R$^{3a}$, R$^4$, R$^{4a}$, R$^5$, R$^{5a}$, R$^6$, R$^7$, R$^{7a}$, R$^8$ or R$^{8a}$ is replaced by A$^{Z1}$.

It is understood that in formula (L-vii) L corresponds to the moiety linking A$^{Z1}$ and A$^{Z2}$.

Another preferred prodrug linker is disclosed and can be obtained as described in WO 2011/012721 A1 and WO 2011/012722 A1. Accordingly, a preferred moiety/reagent A$^{Z1}$-L-A$^{Z2}$ has the structure of formula (L-vii):

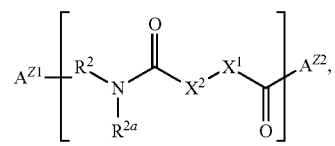

(L-vii)

wherein
A$^{Z1}$ is A$^{x3}$, A$^{y0}$ or A$^{y2}$;
A$^{Z2}$ is A$^{x4}$, A$^{y3}$ or A$^{y5}$; wherein A$^{Z2}$ is connected to T or D through an aromatic amine of the corresponding drug or tag reagent by forming an amide linkage;
X$^1$ is C(R$^1$R$^{1a}$) or a cyclic fragment selected from the group consisting of C$_{3-8}$ cycloalkyl, 4- to 7-membered heterocyclyl, phenyl, naphthyl, indenyl, indanyl, tetralinyl, and 8- to 11-membered heterobicyclyl, wherein
in case X$^1$ is a cyclic fragment, said cyclic fragment is incorporated into L$^1$ via two adjacent ring atoms and the ring atom of X$^1$, which is adjacent to the carbon atom of the amide bond, is also a carbon atom;
X$^2$ is a chemical bond or selected from the group consisting of C(R$^3$R$^{3a}$), N(R$^3$), O, C(R$^3$R$^{3a}$)—C(R$^4$R$^{4a}$), C(R$^3$R$^{3a}$)—N(R$^4$), N(R$^3$)—C(R$^4$R$^{4a}$), C(R$^3$R$^{3a}$)—O, and O—C(R$^3$R$^{3a}$), wherein
in case $X^1$ is a cyclic fragment, $X^2$ is a chemical bond, $C(R^3R^{3a})$, $N(R^3)$ or O;
optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;
$R^1$, $R^3$ and $R^4$ are independently of each other H, $C_{1-4}$ alkyl or $-N(R^5R^{5a})$;
$R^{1a}$, $R^2$, $R^{3a}$, $R^{4a}$ and $R^{5a}$ are independently of each other H, or $C_{1-4}$ alkyl;
$R^5$ is $C(O)R^6$;
$R^6$ is $C_{1-4}$ alkyl;
optionally, one of the pairs $R^{1a}/R^{4a}$, $R^{3a}/R^{4a}$ or $R^{1a}/R^{3a}$ form a chemical bond;
provided that one hydrogen of $R^1$, $R^{1a}$, $R^2$, $R^{2a}$, $R^3$, $R^{3a}$, $R^4$, $R^{4a}$, $R^5$, $R^{5a}$ or $R^6$ is replaced by $A^{Z1}$.

It is understood that in formula (L-vii) L corresponds to the moiety linking $A^{Z1}$ and $A^{Z2}$.

Another preferred prodrug linker is disclosed and can be obtained as described in WO 2011/089214 A1. Accordingly, a preferred moiety/reagent $A^{Z1}$-L-$A^{Z2}$ has the structure of formula (L-viii):

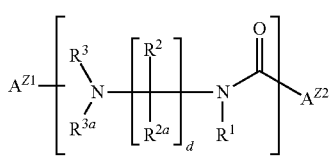
(L-viii)

wherein
$A^{Z1}$ is $A^{x3}$, $A^{y0}$ or $A^{y2}$;
$A^{Z2}$ is $A^{x4}$, $A^{y3}$ or $A^{y5}$; wherein $A^{Z2}$ is connected to T or D through an aromatic hydroxyl (—OH) of the corresponding drug or tag reagent by forming a carbamate linkage;
$R^1$ is selected from the group consisting of $C_{1-4}$ alkyl; heteroalkyl; $C_{3-8}$ cycloalkyl; and

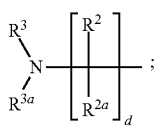

$R^2$, $R^{2a}$, $R^3$ and $R^{3a}$ are independently of each other selected from the group consisting of hydrogen, substituted or non-substituted linear, branched or cyclic $C_{1-4}$ alkyl and heteroalkyl;
each d is independently 2, 3 or 4;
provided that one hydrogen of $R^1$, $R^2$, $R^{2a}$, $R^3$, or $R^{3a}$ is replaced by $A^{Z1}$.

It is understood that in formula (L-viii) L corresponds to the moiety linking $A^{Z1}$ and $A^{Z2}$.

Another preferred prodrug linker is disclosed and can be obtained as described in WO 2011/089216 A1. Accordingly, a preferred moiety/reagent $A^{Z1}$-L-$A^{Z2}$ has the structure of formula (L-ix):

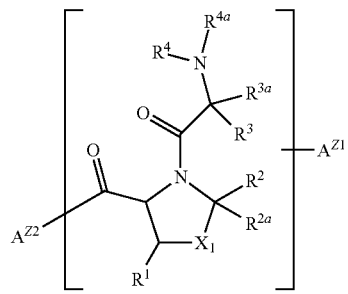
(L-ix)

wherein
$A^{Z1}$ is $A^{x3}$, $A^{y0}$ or $A^{y2}$;
$A^{Z2}$ is $A^{x4}$, $A^{y3}$ or $A^{y5}$; wherein $A^{Z2}$ is connected to T or D through an aliphatic amine of the corresponding drug or tag reagent by forming an amide linkage;
$X_1$ is O, S or CH—$R^{1a}$;
$R^1$ and $R^{1a}$ are independently of each other H, OH, or $CH_3$;
$R^2$, $R^{2a}$, $R^4$ and $R^{4a}$ are independently of each other H or $C_{1-4}$ alkyl,
$R^3$ and $R^{3a}$ are independently of each other H, $C_{1-4}$ alkyl, or $R^5$;
$R^5$ is selected from the group consisting of

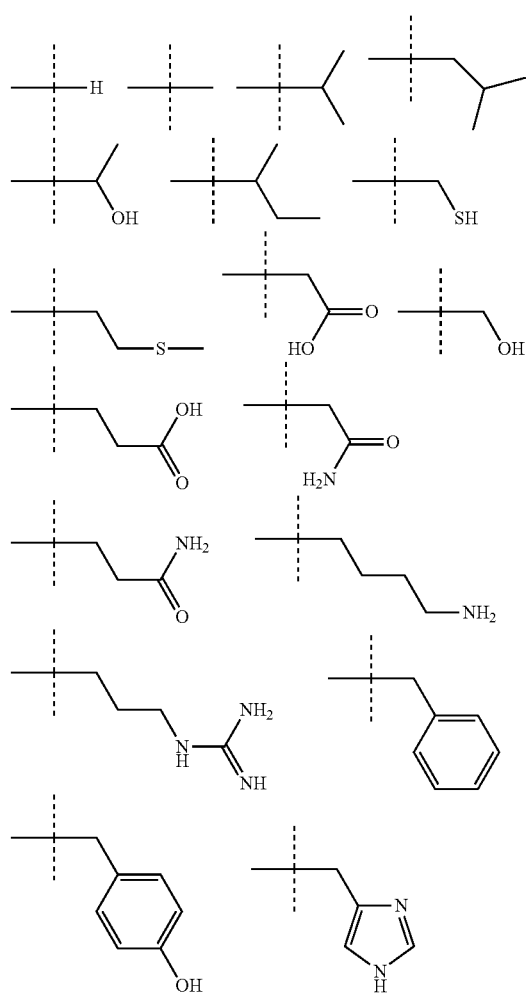

-continued

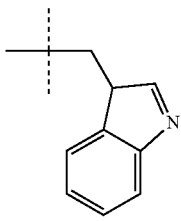

wherein
dashed lines indicate attachment to the rest of the moiety.
provided that one hydrogen of $R^1$, $R^{1a}$, $R^2$, $R^{2a}$, $R^3$, $R^{3a}$, $R^4$, $R^{4a}$ and $R^5$ is replaced by $A^{Z1}$.

It is understood that in formula (L-ix) L corresponds to the moiety linking $A^{Z1}$ and $A^{Z2}$.

Preferably, $R^3$ of formula (L-ix) is H and $R^{3a}$ of formula (L-ix) is $R^5$.

Preferably, one of $R^4/R^{4a}$ of formula (L-ix) is H.

Optionally, one or more of the pair(s) $R^3/R^{3a}$, $R^4/R^{4a}$, $R^3/R^4$ of formula (L-ix) may independently form one or more cyclic fragment(s) selected from the group consisting of $C_{3-8}$ cycloalkyl, 4- to 7-membered heterocyclyl, and 8- to 11-membered heterobicyclyl.

Optionally, $R^3$, $R^{3a}$, $R^4$ and $R^{4a}$ of formula (L-ix) are further substituted with $C_{1-6}$ alkyl, $C_{2-6}$ alkenyl, $C_{2-6}$ alkynyl, phenyl, 4- to 7-membered heterocycle or halogen.

Another preferred prodrug linker is disclosed and can be obtained as described in WO 2011/089215 A1. Accordingly, a preferred moiety/reagent $A^{Z1}$-L-$A^{Z2}$ has the structure of formula (L-x):

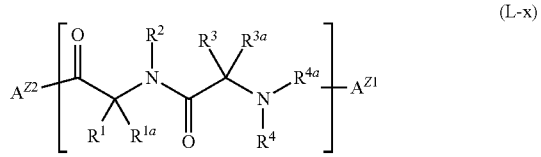

wherein
$A^{Z1}$ is $A^{x3}$, $A^{y0}$ or $A^{y2}$;
$A^{Z2}$ is $A^{x4}$, $A^{y3}$ or $A^{y5}$; wherein $A^{Z2}$ is connected to T or D through an aromatic amine of the corresponding drug or tag reagent by forming an amide linkage;
$R^1$, $R^{1a}$, $R^2$, $R^3$, $R^{3a}$, $R^4$ and $R^{4a}$ are independently of each other H or $C_{1-4}$ alkyl;
optionally, any two of $R^1$, $R^{1a}$, $R^2$, $R^3$, $R^{3a}$, $R^4$ and $R^{4a}$ may independently form one or more cyclic fragment(s) selected from the group consisting of $C_{3-8}$ cycloalkyl, 4- to 7-membered heterocyclyl, phenyl, naphthyl, indenyl, indanyl, tetralinyl, and 8- to 11-membered heterobicyclyl;
optionally, $R^1$, $R^{1a}$, $R^2$, $R^3$, $R^{3a}$, $R^4$ and $R^{4a}$ are further substituted with a substituent selected from the group consisting of $C_{1-6}$ alkyl, $C_{2-6}$ alkenyl, $C_{2-6}$ alkynyl, $C_{3-8}$ cycloalkyl, 4- to 7-membered heterocyclyl, phenyl, naphthyl, indenyl, indanyl, tetralinyl, and 8- to 11-membered heterobicyclyl;
provided that one hydrogen of $R^1$, $R^{1a}$, $R^2$, $R^3$, $R^{3a}$, $R^4$ and $R^{4a}$ is replaced by $A^{y1}$.

It is understood that in formula (L-x) L corresponds to the moiety linking $A^{Z1}$ and $A^{Z2}$.

Another preferred prodrug linker is disclosed and can be obtained as described in PCT/EP2012/065748. Accordingly, a preferred moiety/reagent $A^{Z1}$-L-$A^{Z2}$ has the structure of formula (L-xi):

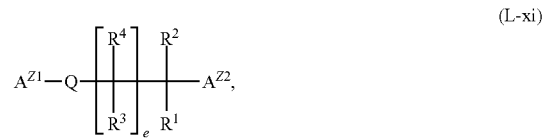

wherein
$A^{Z1}$ is $A^{x3}$, $A^{y0}$ or $A^{y2}$;
$A^{Z2}$ is $A^{x4}$, $A^{y3}$ or $A^{y5}$; wherein $A^{Z2}$ is connected to T or D through a carboxylic acid group (—(C=O)—OH) of the corresponding drug or tag reagent by forming an amide linkage;
$R^1$ is selected from the group consisting of unsubstituted alkyl; substituted alkyl; unsubstituted phenyl; substituted phenyl; unsubstituted naphthyl; substituted naphthyl; unsubstituted indenyl; substituted indenyl; unsubstituted indanyl; substituted indanyl; unsubstituted tetralinyl; substituted tetralinyl; unsubstituted $C_{3-10}$ cycloalkyl; substituted $C_{3-10}$ cycloalkyl; unsubstituted 4- to 7-membered heterocyclyl; substituted 4- to 7-membered heterocyclyl; unsubstituted 8- to 11-membered heterobicyclyl; and substituted 8- to 11-membered heterobicyclyl;
$R^2$ is H, unsubstituted alkyl, or substituted alkyl
$R^3$ and $R^4$ are independently selected from the group consisting of H, unsubstituted alkyl, and substituted alkyl;
e is 0 or 1;
optionally, $R^1$ and $R^3$ are joined together with the atoms to which they are attached to form a ring A;
A is selected from the group consisting of $C_{3-10}$ cycloalkyl; 4- to 7-membered aliphatic heterocyclyl; and 8- to 11-membered aliphatic heterobicyclyl, wherein A is unsubstituted or substituted;
Q is selected from the group consisting of $C_{1-50}$ alkyl, $C_{2-50}$ alkenyl and $C_{2-50}$ alkinyl, which fragment is optionally interrupted by one or more group(s) selected from the group consisting of —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl and naphthyl.

It is understood that in formula (L-xi) L corresponds to the moiety linking $A^{Z1}$ and $A^{Z2}$.

Another preferred prodrug linker is disclosed and can be obtained as described in EP12165516. Accordingly, a preferred moiety/reagent $A^{Z1}$-L-$A^{Z2}$ has the structure of formula (L-xii):

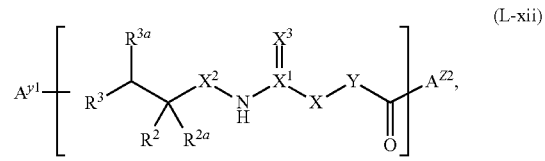

wherein

A$^{Z1}$ is A$^{x3}$, A$^{y0}$ or A$^2$;

A$^{Z2}$ is A$^{x4}$, A$^{y3}$ or A$^{y5}$; wherein A$^{Z2}$ is connected to T or D through a hydroxyl of the corresponding drug or tag reagent by forming an ester or carbamate linkage;

Y is —C(R$^1$)(R$^{1a}$)—; or —N(R$^1$)—;

X is —C(R$^4$)(R$^{4a}$)—; —N(R$^4$)—; —O—; —C(R$^4$)(R$^{4a}$)—C(R$^5$)(R$^{5a}$)—; —C(R$^4$)(R$^{4a}$)—N(R$^6$)—; —N(R$^6$)—C(R$^4$)(R$^{4a}$)—; —C(R$^4$)(R$^{4a}$)—O—; —O—C(R$^4$)(R$^{4a}$)—; —C(O)—N(R$^6$)—; or —N(R$^6$)—C(O)—;

X$^1$ is

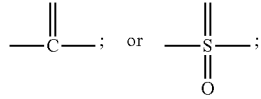

X$^2$ is —C(R$^7$)(R$^{7a}$)—; or —C(R$^7$)(R$^{7a}$)—C(R$^8$)(R$^{8a}$)—;

X$^3$ is =O; =S; or =N—CN;

R$^1$, R$^{1a}$, R$^2$, R$^{2a}$, R$^3$, R$^{3a}$, R$^4$, R$^{4a}$, R$^5$, R$^{5a}$, R$^6$, R$^7$, R$^{7a}$, R$^8$, R$^{8a}$ are independently of each other H; C$_{1-6}$ alkyl, C$_{2-6}$ alkenyl, C$_{2-6}$ alkynyl, C$_{1-20}$ heteroalkyl or Y$_1$-T; and independently none, one or more of the pair(s) R$^{1a}$/R$^{4a}$, R$^{1a}$/R$^{5a}$, R$^{4a}$/R$^{5a}$, R$^{7a}$/R$^{8a}$ are absent and the corresponding carbon atoms to which they are attached form a cis double bond;

Y$^1$ is a chemical bond or C$_{1-6}$ alkyl, C$_{2-6}$ alkenyl, C$_{2-6}$ alkynyl;

T is phenyl; naphthyl; indenyl; indanyl; tetralinyl; C$_{3-10}$ cycloalkyl; 4- to 7-membered heterocyclyl; or 8- to 11-membered heterobicyclyl, wherein T is optionally substituted with one or more R$^9$, which are the same or different;

R$^9$ is halogen; —CN; oxo (=O); —C(O)OH; —OH; —S(O)$_2$NH$_2$; —S(O)NH$_2$; —S(O)$_2$OH; —S(O)OH; —SH; —NH$_2$; —NO$_2$; C$_{1-6}$ alkyl, or C$_{1-10}$ heteroalkyl;

optionally, one or more of the pairs R$^1$/R$^{1a}$, R$^1$/R$^4$, R$^1$/R$^6$, R$^1$/R$^5$, R$^2$/R$^{2a}$, R$^2$/R$^3$, R$^4$/R$^{4a}$, R$^4$/R$^5$, R$^5$/R$^{5a}$, R$^7$/R$^{7a}$, R$^7$/R$^8$, R$^8$/R$^{8a}$ are joined together with the atom to which they are attached to form a ring T;

optionally, R$^3$/R$^{3a}$ are joined together with the nitrogen atom to which they are attached to form a 4- to 7-membered heterocycle;

provided that one hydrogen of R$^1$, R$^{1a}$, R$^2$, R$^{2a}$, R$^3$, R$^{3a}$, R$^4$, R$^{4a}$, R$^5$, R$^{5a}$, R$^6$, R$^7$, R$^{7a}$, R$^8$ or R$^{8a}$ is replaced by A$^{y1}$.

It is understood that in formula (L-xii) L corresponds to the moiety linking A$^{Z1}$ and A$^{Z2}$.

Biologically Active Moiety/Drug

In step (d) any drug (A$^{x5}$)$_{a1}$-D-(A$^{x6}$)$_{a2}$ can be used, provided that it comprises at least two functional groups for steps (d-i), (d-ii), (d-iii) and (d-iv) and at least one functional group for steps (d-v), (d-vi), (d-vii) and (d-viii).

Preferably, D is a small molecule biologically active moiety, a peptide biologically active moiety, a protein biologically active moiety or an oligonucleotide biologically active moiety.

Preferably, D has a molecular weight ranging between 0.05 and 500 kDa, more preferably between 0.2 and 250 kDa, more preferably between 0.5 and 100 kDa and most preferably between 1 and 60 kDa.

In one embodiment the drug is a small molecule drug. A small molecule drug preferably has a molecular weight of between 50 Da and 1 kDa, more preferably of between 50 Da and 800 Da and most preferably of between 50 Da and 500 Da.

Suitable small molecule drugs comprising an aromatic amine functional group are, for example, (−)-Carbovir, (±)-Hymenin, (±)-Norcisapride, (±)-Picumeterol, (R)-Aminoglutethimide, (R)-Clenbuterol, (S)-Aminoglutethimide, (S)-Clenbuterol, [6-p-aminophenylalanine]-angiotensin II, 10′-Demethoxystreptonigrin, 17-Aminogeldanamycin, 1-Aminoacridine, 1-Deazaadenine, 1-NA-PP 1, 1-NM-PP 1,2,7-Diaminoacridine, 2,7-Dimethylproflavine, 2-Amino-6 (5H)-phenanthridinone, 2-Aminoacridine, 2-amino-Carbanilide, 2-Amino histamine, 2-Aminoperimidine, 2′-AMP, 2-Chloroadenosine, 2′-Deoxyxylotubercidin, 2-Sulfanilamidoimidazole, 3,4-Diaminocoumarin, 3′-Amino-4′-methoxyflavone, 3-Aminoacridine, 3-Aminopicolinic acid, 3-Deazaguanine, 4′-Aminoflavone, 4-Aminopyridine, 5′-ADP, 5-Aminoacridine, 5-amino-DL-Tryptophan, 5-Aminonicotinamide, 5′-AMP, 5′-ATP, 5-Chlorodeoxycytidine, 5′-CMP, 5-Dimethylamiloride, 5′-GDP, 5′-GMP, 5′-GTP, 5-Iodotubercidin, 5-Methylcytosine, 6-Aminoflavone, 6-Aminophenanthridine, 6-Aminothymine, 6-Benzylthioguanine, 6-Chlorotacrine, 6-Iodoamiloride, 7,8-Dihydroneopterin, 7-Aminonimetazepam, 7-Methoxytacrine, 7-Methyltacrine, 9-Deazaguanine, 9-Phenethyladenine, Abacavir, Acadesine, Acediasulfone, Acefurtiamine, Acetyl coenzyme A, Aciclovir, Actimid, Actinomycin, Acyclovir, Adefovir, Adenallene, Adenine, Adenophostin A, Adenosine, Adenosine monophosphate, Adenosine triphosphate, Adenosylhomocysteine, Aditeren, Afloqualone, Alamifovir, Albofungin, Alfuzosin, Allithiamine, Alpiropride, Amanozine, Ambasilide, Ambucaine, Amdoxovir, Ameltolide, Amethopterin, Amfenac, Amflutizole, Amicycline, Amidapsone, Amifampridine, Amiloride, Aminacrine, Aminoacridine, Aminoantipyrine, Aminobenzoate, Aminogenistein, Aminoglutethimide, Amino hippurate, Aminoisatin, Aminometradine, Aminonimetazepam, Aminophenylalanine, Aminopotentidine, Aminopterin, Aminopurvalanol A, Aminoquinuride, Aminosalicylic Acid, Amiphenazole, Amiphenosine, Amisometradine, Amisulpride, Amiterol, Amlexanox, Ammelin, Amonafide, Amoxecaine, Amphenidone, Amphethinile, Amphotalide, Amprenavir, Ampurine, Amrinone, AMT, Amthamine, Amtizole, Angustmycin A, Anileridine, Apadenoson, Apraclonidine, Apricitabine, Arafluorocytosine, Aramine, Arazide, Aristeromycin, Arprinocid, Ascamycin, Ascensil, Aspiculamycin, Atolide, Azabon, Azacitidine, Azaline B, Azamulin, Azanidazole, Azepexole, Aztreonam, Baquiloprim, Basedol, Batanopride, b-D-Adenosine, Bemitradine, Benfotiamine, Bentiamine, Benzamil, Benzocaine, Betoxycaine, Binodenoson, Biopterin, Bisbentiamine, Blasticidin, Bleomycin, Bleomycin A1, Bleomycin A2, Bleomycin A5, Bleomycin A6, Bleomycin DMA2, Brodimoprim, Bromfenac, Bromobuterol, Bromopride, Bropirimine, Buciclovir, Bunazosin, Butyrylthiamine disulfide, Cadeguomycin, cAMP, Candicidin, Capadenoson, Carbanilide, Carbodine, Carbovir, Carbutamide, Carumonam, CDP-dipalmitin, Cefcapenepivoxil, Cefclidin, Cefdaloxime, Cefdinir, Cefditoren, Cefempidone, Cefepime, Cefetamet, Cefetecol, Cefixime, Cefluprenam, Cefmatilen, Cefmenoxime, Cefodizime, Cefoselis, Cefotaxime, Cefotiam, Cefozopran, Cefpodoxime, Cefquinome, Cefrom, Ceftazidime, Cefteram, Ceftibuten, Ceftiofur, Ceftiolene, Ceftioxide, Ceftizoxime, Ceftobiprole, Ceftriaxone, Cefuzonam, Centazolone, Cetotiamine, cGMP, Chloroprocaine, Cidofovir, Cifostodine, Cipamfylline, Cisapride, Cladribine, Clafanone, Claforan, Clebopride, Clenbuterol, Clenproperol, Clofarabine, Clorsulon, Coelenteramine, Coenzyme A, Colchicamid, Coumarin 10, Coviracil, Crotonoside, Cyclobut A, Cyclobut G, Cycloclenbuterol, Cycotiamine, Cytallene, Cytarabine, Cytarazid, Cytidine, Cytidine diphosphate, Cytidoline, CytosineD-(+)-Neopterin, Dactinomycin, D-Amethopterin, dAMP, Damvar, Daniquidone, Dapsone, Daptomycin, Daraprim, Darunavir, DATHF, Dazopride, dCMP, dCTP, Debromohymenialdisine, Decitabine, Declopramide, Deisopropylhydroxyatrazine, Delafloxacin, Delfantrine, Denavir, Deoxyadenosine, Deoxy-ATP, Deoxycytidine, Deoxyguanosine, Dephosphocoenzyme A, Dequalinium, Desbutylbumetanide, Desciclovir, Desoxyminoxidil, dGMP, dGTP, Diacethiamine, Diaminoacridine, Diaveridine, Dichlorobenzamil, Dichloromethotrexate, Dichlorophenarsine, Dideoxycytidine, Dihydrobiopterin, Dihydro folic acid, Dimethialium, Dimethocaine, Dimethyl methotrexate, Dinalin, DL-5,6,7,8-Tetrahydrofolic acid, DL-Methotrexate, Dobupride, Dovitinib, Doxazosin, Draflazine, Edatrexate, Elpetrigine, Elvucitabine, Emtricitabine, Entecavir, Enviradene, Epcitabine, Epiroprim, Eritadenine, Etanterol, Ethacridine, Ethaden, Ethylisopropylamiloride, Etoprine, Etoxazene, Etravirine, Etriciguat, FAD, Famciclovir, Fazarabine, Fenamol, Fepratset, Fiacitabine, Flucytosine, Fludara, Fludarabine, Fluocytosine, Folic acid, Formycin A, Fosamprenavir, Furalazine, Fursultiamine, Furyltriazine, Ganciclovir, Gancyclovir, Gastracid, Gemcitabine, Giracodazole, Gloximonam, Glybuthiazol, GSK 3B Inhibitor XII, GSK3BInhibitorXII, Guanine, Guanine arabinoside, Guanosine, Hexyl PABA, Hydroxymethylclenbuterol, Hydroxyprocaine, Hydroxytriamterene sulfate, Ibacitabine, Iclaprim, Imanixil, Imiquimod, Indanocine, Iobenzamic acid, Iocetamic acid, Iomeglamic acid, Iomeglamicacid, Ipidacrine, Iramine, Irsogladine, Isatoribine, Isobutamben, Isoritmon, Isosepiapterin, Ketoclenbuterol, Ketotrexate, Kopexil, Lamivudine, Lamotrigin, Lamotrigine, Lamtidine, Lappaconine, Lavendamycin, L-Cytidine, Lenalidomide, Leucinocaine, Leucovorin, L-g-Methylene-10-deazaaminopterin, Linifanib, Lintopride, Lisadimate, Lobucavir, Lodenosine, Lomeguatrib, Lometrexol, Loxoribine, L-S-Adenosylmethionine, Mabuterol, Medeyol, Melarsenoxyd, Melarsoprol B, Mesalazine, Metabutethamine, Metabutoxycaine, Metahexamide, Metazosin, Methioprim, Methotrexate, Methylanthranilate, Metioprim, Metoclopramide, Metoprine, Minoxidil, Mirabegron, Mitomycin, Mivobulin, Mocetinostat, Monocain, Mosapride, Mutamycin, N-(p-Aminophenethyl)spiroperidol, N6-[2-(4-aminophenyl)ethyl]adenosine Role, NAD+, NADH, NADH2, NADP+, NADPH2, Naepaine, Naminterol, Naretin, Nebidrazine, NECA, Nelarabine, Nelzarabine, Neolamin, Neotropine, Nepafenac, Nerisopam, Neurofort, Nifurprazine, Nimustine, Nitrine, N-Methyltetrahydrofolic acid, Nolatrexed, Nomifensine, Norcisapride, N-Propionylprocainamide, N-Sulfanilylnorfloxacin, o-Aminophenylalanine, Octotiamine, Olamufloxacin, Ormetoprim, Orthocaine, Oximonam, Oxybuprocaine, p-Aminoantipyrine, p-Aminobenzoate, p-Amino-D-phenylalanine, Pancopride, Parsalmide, Pasdrazide, Pathocidine, Pelitrexol, Pemetrexed, Penciclovir, Peplomycin, Peralopride, Phenamil, Phenazone, Phenazopyridine, Phenyl p-aminobenzoate, Phenyl-PAS-Tebamin, Phleomycin D1, Pibutidine, Picumeterol, Pirazmonam, Piridocaine, Piritrexim, Porfiromycin, Pralatrexate, Pramipexole, Prazobind, Prazosin, Preladenant, Procainamide, Procaine, Proflavine, Proparacaine, Propoxycaine, Prosultiamine, Prucalopride, Pseudoisocytidine, Psicofuranine, Pteridoxamine, Pteroyltriglutamic acid, Pyramine, Pyrimethamine, Questiomycin, Quinelorane, Racivir, Regadenoson, Renoquid, Renzapride, Resiquimod, Resorcein, Retigabine, Reverset, Riluzole, Rociclovir, Rufocromomycin, S-Adenosylmethionine, Sangivamycin, Sapropterin, S-Doxazosin, Sepiapterine, Silversulfadiazine, Sinefungin, Sipatrigine, Sparfloxacin, Sparsomycin, Stearyl-CoA, Stearylsulfamide, Streptonigrin, Succisulfone, Sufamonomethoxine, Sulamserod, Sulfabromomethazine, Sulfacetamide, Sulfachlorpyridazine, Sulfachrysoidine, Sulfaclomide, Sulfaclorazole, Sulfaclozine, Sulfacytine, Sulfadiasulfone, Sulfadiazine, Sulfadicramide, Sulfadimethoxine, Sulfadimidine, Sulfadoxine, Sulfaethoxypyridazine, Sulfaguanidine, Sulfaguanole, Sulfalene, Sulfamerazine, Sulfamethazine, Sulfamethizole, Sulfamethoxazole, Sulfamethoxydiazine, Sulfamethoxypyridazine, Sulfametomidine, Sulfametopyrazine, Sulfametrole, Sulfanilamide, Sulfanilamidoimidazole, Sulfanilylglycine, Sulfaperin, Sulfaphenazole, Sulfaproxyline, Sulfapyrazole, Sulfapyridine, Sulfasomizole, Sulfasymazine, Sulfathiadiazole, Sulfatroxazole, Sulfatrozole, Sulfisomidine, Sulfisoxazole, Tacedinaline, Tacrine, Talampanel, Talipexole, Talisomycin A, Tenofovir, Tenofovir disoproxil, Terazosin, Tetrahydrobiopterinm, Tetrahydrofolic acid, Tetroxoprim, Tezacitabine, Thiamine, Thiazosulfone, Thioguanine, Tiamiprine, Tigemonam, Timirdine, Tinoridine, Tiodazosin, Tirapazamine, Tiviciclovir, Tocladesine, Trancopal, Triacanthine, Triamterene, Triapine, Triciribine, Trimazosin, Trimethoprim, Trimetrexate, Tritoqualine, Troxacitabine, Tubercidin 5'-diphosphate, Tuvatidine, Tyrphostin AG 1112, Valacyclovir, Valganciclovir, Valopicitabine, Valtorcitabine, Velnacrine, Vengicide, Veradoline, Vidarabine, Viroxime, Vitaberin, Zalcitabine, Zhengguangmycin B2, Zinviroxime, Zorbamycin, Zoxazolamine, (±)-Saxitoxin, 2-Aminoperimidine, 6-Formylpterin, 8-13-Neurotensin, 8-Thioguanosine, 9-Deazaguanosine, 9-Desarginine-bradykinin, a4-10-Corticotropin, Afamelanotide, Agmatine, Alarelin, Ambazone, Amiloride, Aminopterine, Ampyrimine, Angiotensin, Angiotensin I, Angiotensin II, Antibiotic O-129, Antipain, Arginine, Argiprestocin, Astressin, Atriopeptin III, Aviptadil, Benzylisothiourea, Betacyamine, Bisindolylmaleimide IX, Bivalirudin, Blasticidin S, Bleomycin B2, Bombesin 14, Buformin, Camostat, Cariporide, Carperitide, Cecropin P 1, Cetrorelix, Cilengitide, Creapure, Cyanoginosin LR, Cyanoviridin RR, Dalargine, Damvar, Deazaaminopterin, Defensin HNP 1, Deslorelin, Desmopressin, Dezaguanine, Dichloromethotrexate, Dihydrostreptomycin, Dimaprit, Dimethylamiloride, Diminazene, DL-Methotrexate, D-Methotrexate, Ebrotidine, Edatrexate, Eel Thyrocalcitonin, Elastatinal, Elcatonin, Enterostatin, Enviomycin, Eptifibatide, Ethylisopropylamiloride, Etilamide, Etoprine, Famotidine, Flupirtine, Furterene, Galanin, Galegin, Ghrelin, Glucagon, Gonadoliberin A, Guanethidine, Guanfacine, Guanoxan, Guanylthiourea, Gusperimus, Hexamidine, Histatin 5, Histrelin, Homoarginine, Icatibant, Imetit, Insulinotropin, Isocaramidine, Kallidin 10, Kemptide, Ketotrexate, Kiotorphin, Lactoferricin, Lamifiban, L-Bradykinin, Leucoverin, Leucovorin A, Leupeptin, Leuprolide, Lometrexol, Lutrelin, m-Chlorophenylbiguanide, Melagatran, Melanotan II, Melanotropin, Melittin, Metformin, Methotrexate dimethyl ester, Methotrexate monohydrate, Methoxtrexate, Methylisothiourea, Metoprine, Miacalcin, MIBG, Minoxidil, Mitoguazone, Mivobulin, Mivobulin isethionate, Moroxydine, Nafarelin, Neotine, Nesiritide, Netropsin, Neurotensin, N-Methyltetrahydrofo late, Nociceptin, Nolatrexed, Novastan, Panamidin, Pathocidine, Pebac, Peldesine, Pelitrexol, Pemetrexed, Pentamidine, Peramivir, Phenformine, Phenylbiguanide, Pig galanin, Pimagedine, Piritrexim, Pitressin, Porcine angiotensinogen, Porcine gastrin-releasing hormone, Porcine neuropeptide Y, Porcine PHI, Pralatrexate, Protein Humanin, Proteinase inhibitor E 64, Pyrimethamin, Quinespar, Rat atriopeptin, Rat atriopeptin, Resiquimod, Ribamidine, Rimorphin, Saralasin, Saxitoxin, Sermorelin, S-Ethylisothiourea, Spantide, Stallimycin, Stilbamidine, Streptomycin A, Substance P free acid, Sulfaguanidine, Synthetic LH-releasing hormone, Tallimustine, Teprotide, Tetracosactide, Tetrahydrobiopterin, Tetrahydrofolic acid, Thrombin receptor-activating peptide-14, Thymopentin, Tioguanin, Tiotidine, Tirapazamine, Triamteren, Trimetrexate, Tryptorelin, Tuberactinomycin B, Tuftsin, Urepearl, Viomycidin, Viprovex, Vitamin M, Xenopsin, Zanamivir, Zeocin, Ziconotide, Zoladex.

Preferably, suitable small molecule drugs comprising an aromatic amine functional group are selected from the group consisting of (−)-Draflazine, (−)-Indocarbazostatin B, (+)-(R)-Pramipexole, (R)-(+)-Terazosin, (R)-Ganciclovir Cyclic Phosphonate, (R)-Sufinosine, (R)-Zacopride, (S)-Sufinosine, (S)-Zacopride Hydrochloride, 17-Aminogeldanamycin, 2-Aminoaristeromycin, 2-Aminoneplanocin A, 3-Chloroprocainamide, 3-Deazaadenosine, 4-Aminosalicylic Acid, 4-Chlorophenylthio-DADME-Immucillin-A, 5"-Homoneplanocin A, 5-Aminosalicylic Acid, 9-Aminocamptothecin, Abacavir Succinate, Abacavir Sulfate, Abanoquil Mesilate, Acadesine, Acriflavine, Acyclovir, Acyclovir Elaidate, Acyclovir Oleate, Adefovir, Adefovir Dipivoxil, Ademetionine Tosylate Sulfate, Adenallene, Adenophostin A, Adenophostin B, Adenosine, Afloqualone, Ageliferin Diacetate, Ageliferin Dihydrochloride, Alamifovir, Alfuzosin Hydrochloride, Ambasilide, Ambroxol Nitrate, Amdoxovir, Ameltolide, Amezinium Methylsulfate, Amfenac Sodium, Amiloride Hydrochloride, Aminoglutethimide, Amisulpride, Amoxanox, Amprenavir, Ampydin, Amrinone, Amselamine Hydrobromide, Amthamine, Anakinra, Apadenoson, Aplonidine Hydrochloride, Apricitabine, Azacytidine, Azalanstat, Aztreonam, Aztreonam L-Lysine, Balapiravir Hydrochloride, Batracylin, Belactin A, Benzocaine, Binodenoson, Bleomycin A2 Sulfate, Brodimoprim, Bromfenac Sodium, Bromhexine Hydrochloride, Bunazosin Hydrochloride, Capadenoson, Capeserod Hydrochloride, Carbovir, Carboxyamidotriazole, Carumonam Sodium, Cefcapene Pivoxil Hydrochloride, Cefdaloxime, Cefdaloxime Pentexil Tosilate, Cefdinir, Cefditoren Pivoxil, Cefepime, Cefetamet Pivoxil, Cefetecol, Cefixime, Cefluprenam, Cefmatilen Hydrochloride Hydrate, Cefmenoxime Hydrochloride, Cefodizime, Cefodizime Sodium, Cefoselis Sulfate, Cefotaxime Sodium, Cefotiam Hexetil, Cefotiam Hexetil Hydrochloride, Cefotiam Hydrochloride, Cefozopran, Cefozopran Hydrochloride, Cefpirome, Cefpodoxime Proxetil, Cefquinome, Ceftaroline, Ceftazidime, Cefteram Pivoxil, Ceftibuten, Ceftobiprole, Ceftobiprole Medorcaril, Ceftrazonal Bopentil, Ceftrazonal Sodium, Ceftriaxone Sodium, Centanamycin, Cibrostatin 1, Cidofovir, Cimaterol, Cinitapride Hydrogen Tartrate, Cipamfylline, Cisapride Hydrate, Citicoline, Cladribine, Clitocine, Clofarabine, Clopidogrel Sulfate, Cycallene, Cyclic-Cidofovir, Cygalovir, Cystazosin, Cytarabine, Cytarabine Ocfosfate, Cytaramycin, Cytochlor, Dactinomycin, DADME-Immucillin-G, Dapropterin Dihydrochloride, Dapsone, Darbufelone Mesilate, Darunavir, Delafloxacin, Denufosol Tetrasodium, Deoxyvariolin B, Desacetylvinblastinehydrazide/Folate Conjugate, Deticiclovir Diacetate, Dexelvucitabine, Dezocitidine, Diadenosine Tetraphosphate, Diaveridine, Dichlorobenzoprim, Dicloguamine Maleate, Dideoxycytidine, DI-VAL-L-DC, Docosyl Cidofovir, Dovitinib Lactate, Doxazosin Mesylate, Draflazine, DTPA-Adenosylcobalamin, Ecenofloxacin Hydrochloride, Eicosyl Cidofovir, Elacytarabine, Elpetrigine, Elvucitabine, Emtricitabine, Entecavir, Entinostat, Epinastine Hydrochloride, Epiroprim, Epofolate, Ethylthio-DADME-Immucillin-A, Ethynylcytidine, Etravirine, Etriciguat, Famciclovir, Filarizone, Flucytosine, Fludarabine Phosphate, Fluorobenzyltriamterene, Fluorominoxidil, Fluoroneplanocin A, Flupiritine Maleate, Folinic Acid, Fosamprenavir Calcium, Fosamprenavir Sodium, Freselestat, Ganciclovir, Ganciclovir Elaidic Acid, Ganciclovir Monophosphate, Ganciclovir Sodium, Gemcitabine, Gemcitabine Elaidate, Girodazole, Hepavir B, Heptaminol AMP Amidate, Hexadecyl Cidofovir, Hexadecyloxypropyl-Cidofovir, Hydroxyakalone, Iclaprim, Imiquimod, Immunosine, Indanocine, Isobatzelline A, Isobatzelline B, Isobatzelline C, Isobatzelline D, Lamivudine, Lamotrigine, Lenalidomide, Leucettamine A, Leucovorin Calcium, Levo leucovorin Calcium, Liblomycin, Linifanib, Lintopride, Lirexapride, Lobucavir, Lodenosine, Lomeguatrib, Lometrexol, Loxoribine, L-Simexonyl Homocysteine, Lymphostin, Mabuterol Hydrochloride, Makaluvamine A, Makaluvamine A, Makaluvamine B, Makaluvamine C, Managlinat Dialanetil, Meriolin-3, Metazosin, Methotrexate, Methylthio-DADME-Immucillin-A, Metoclopramide Hydrochloride, Midoriamin, Minoxidil, Mirabegron, Mitomycin, Mivobulin Isethionate, Mocetinostat Dihydrobromide, Mosapride Citrate, Mozenavir Mesilate, Neldazosin, Nelzarabine, Nepafenac, Nolatrexed Hydrochloride, NO-Mesalamine, Noraristeromycin, O6-Benzylguanine, Olamufloxacin, Olamufloxacin Mesilate, Omaciclovir, Oxyphenarsine, PalauÀmine, Pancopride, Peldesine, Pelitrexol, Pemetrexed Disodium, Penciclovir, Penicillin G Procaine, Peplomycin, Picumeterol Fumarate, Pimeloylanilide O-Amino anilide, PMEO-5-ME-DAPY, Pralatrexate, Pramipexole Hydrochloride, Prazosin Hydrochloride, Prefolic A, Preladenant, Procainamide Hydrochloride, Procaine Hydrochloride, Prucalopride, Prucalopride Hydrochloride, Prucalopride Succinate, Pyriferone, Pyrimethamine, Quinelorane Hydrochloride, Razaxaban Hydrochloride, Regadenoson, Resiquimod, Retigabine Hydrochloride, Riluzole, Riociguat, Rociclovir, Rumycin 1, Rumycin 2, Sampirtine, Secobatzelline A, Secobatzelline B, Silver Sulfadiazine, Sipatrigine, Sonedenoson, Sotirimod, Sparfloxacin, Styloguanidine, Sufinosine, Surfen, Synadenol, Synguanol, Tacedinaline, Tacrine Hydrochloride, Talampanel, Talipexole Dihydrochloride, Talopterin, Tenofovir, Tenofovir DF, Terazosin Hydrochloride, Tetracosyl Cidofovir, Tezacitabine, TGP, Timirdine Diethanesulfonate, Torcitabine, Trantinterol Hydrochloride, Trichomycin A, Trimazosin Hydrochloride, Trimetrexate Glucuronate, Troxacitabine, Trybizine Hydrochloride, Valacyclovir, Valganciclovir Hydrochloride, Valomaciclovir Stearate, Valopicitabine, Velnacrine Maleate, and Xylocydine.

Suitable small molecule drugs comprising an amine functional group are, for example, Aphidicolin Glycinate, Cetrorelix Acetate, Picumeterol Fumarate, (−)-Draflazine, (−)-Indocarbazostatin B, (+)-(23,24)-Dihydrodiscodermolide, (+)-(R)-Pramipexole, (R)-(+)-Amlodipine, (R)-(+)-Terazosin, (R)-Ganciclovir Cyclic Phosphonate, (R)-Sufinosine, (R)-Zacopride, (S)-(−)-Norketamine, (S)-Oxiracetam, (S)-Sufinosine, (S)-Zacopride Hydrochloride, [90Y]-DOTAGA-Substance P, [ARG(Me)9] MS-10, [D-TYR1,ARG(Me)9] MS-10, [D-TYR1,AzaGLY7,ARG(Me)9] MS-10, [D-TYR1] MS-10, [Psi(CH2NH)TPG4] Vancomycin Aglycon, [TRP19] MS-10, 111IN-Pentetreotide, 13-Deoxyadriamycin Hydrochloride, 17-Aminogeldanamycin, 19-O-Methylgeldanamycin, 1-Methyl-D-Tryptophan, 21-Aminoepothilone B, 2-Aminoaristeromycin, 2-Aminoneplanocin A, 3-Chloroprocainamide, 3-Deazaadenosine, 3-Matida, 4-Amino salicylic Acid, 4-Chlorophenylthio-DADME-Immucillin-A, 5,4'-Diepiarbekacin, 5'-Homoneplanocin A, 5-Aminosalicylic Acid, 8(R)-Fluoroidarubicin Hydrochloride, 99MTC-C (RGDFK*)2Hynic, 9-Aminocamptothecin, A-42867 Pseudoaglycone, Abacavir Succinate, Abacavir Sulfate, Abanoquil Mesilate, Abarelix, Acadesine, Acriflavine, Acyclovir, Acyclovir Elaidate, Acyclovir Oleate, Acyline, Adefovir, Adefovir Dipivoxil, Ademetionine Tosylate Sulfate, Adenallene, Adenophostin A, Adenophostin B, Adenosine, Aerothricin 1, Aerothricin 16, Aerothricin 41, Aerothricin 45, Aerothricin 5, Aerothricin 50, Aerothricin 55, Afloqualone, Ageliferin Diacetate, Ageliferin Dihydrochloride, Aladapcin, Alamifovir, Alatrofloxacin Mesilate, Alendronic Acid Sodium Salt, Alestramustine, Alfuzosin Hydrochloride, Aliskiren Fumarate, Alogliptin Benzoate, Alpha-Methylnorepinephrine, Alpha-Methyltryptophan, Altemecidin, Alvespimycin Hydrochloride, Amantadine Hydrochloride, Ambasilide, Ambazone, Ambroxol Nitrate, Amdoxovir, Ameltolide, Amelubant, Amezinium Methylsulfate, Amfenac Sodium, Amidox, Amifostine Hydrate, Amikacin, Amiloride Hydrochloride, Amino candin, Aminoglutethimide, Aminoguanidine, Amino levulinic Acid Hexyl Ester, Aminolevulinic Acid Methyl Ester, Amisulpride, Amlodipine, Amlodipine Besylate, Amoxanox, Amoxicillin Pulsys, Amphotericin B, Ampicillin Sodium, Amprenavir, Ampydin, Amrinone, Amrubicin Hydrochloride, Amselamine Hydrobromide, Amthamine, Anakinra, Anamorelin Hydrochloride, Anatibant Mesilate, Angiopeptin Acetate, Anisperimus, Antagonist-G, Antide, Antide-1, Antide-2, Antide-3, Antileukinate, Apadenoson, Apixaban, Aplonidine Hydrochloride, Apoptozole 1, Apoptozole 2, Apoptozole 3, Apricitabine, Arbekacin, Arbekacin sulfate, Arborcandin A, Arborcandin B, Arborcandin C, Arborcandin D, Arborcandin E, Arborcandin F, Argatroban Monohydrate, Argimesna, Arginine Butyrate, Argiotoxin-636, Armodafinil, Arotinolol Hydrochloride, Arterolane Maleate, Aspoxicillin, Atenolol, Atosiban, Atreleuton, Avorelin, Azacytidine, Azalanstat, Azaromycin SC, Azelnidipine, Azetirelin, Azodicarbonamide, Azoxybacilin, Aztreonam, Aztreonam L-Lysine, Azumamide A, Baclo fen, Bactobolin, Balapiravir Hydrochloride, Balhimycin, Barusiban, Batracylin, Belactin A, Belactosin A, Belactosin C, Benanomicin B, Benexate Cyclodextrin, Benzocaine, Besifloxacin Hydrochloride, Beta-Amyloid (12-20), Binodenoson, Bleomycin A2 Sulfate, Boceprevir, Bogorol A, Boholmycin, Brasilicardin A, Bremelanotide, Brivanib Alaninate, Brivaracetam, Brodimoprim, Bromfenac Sodium, Bromhexine Hydrochloride, Brostallicin Hydrochloride, Bunazosin Hydrochloride, Buserelin Acetate, Butabindide, Butamidine, Buteranol, Cabin 1, Calcium-Like Peptide 1, Calcium-Like Peptide 2, Cambrescidin 800, Cambrescidin 816, Cambrescidin 830, Cambrescidin 844, Camostat, Canfosamide Hydrochloride, Capadenoson, Capeserod Hydrochloride, Capravirine, Caprazamycin A, Caprazamycin B, Caprazamycin C, Caprazamycin E, Caprazamycin F, Capromorelin, Carafiban Maleate, Carbachol, Carbamazepine, Carbetocin, Carbovir, Carboxyamidotriazole, Cariporide Hydrochloride, Carisbamate, Carpipramine, Carumonam Sodium, Caspofungin Acetate, Cefaclor, Cefcanel Daloxate Hydrochloride, Cefcapene Pivoxil Hydrochloride, Cefdaloxime, Cefdaloxime Pentexil Tosilate, Cefdinir, Cefditoren Pivoxil, Cefepime, Cefetamet Pivoxil, Cefetecol, Cefixime, Cefluprenam, Cefmatilen Hydrochloride Hydrate, Cefmenoxime Hydrochloride, Cefminox Sodium, Cefodizime, Cefodizime Sodium, Cefoselis Sulfate, Cefotaxime Sodium, Cefotetan Disodium, Cefotiam Hexetil, Cefotiam Hexetil Hydrochloride, Cefotiam Hydrochloride, Cefoxitin, Cefozopran, Cefozopran Hydrochloride, Cefpirome, Cefpodoxime Proxetil, Cefprozil, Cefprozil Monohydrate, Cefquinome, Ceftaroline, Ceftazidime, Cefteram Pivoxil, Ceftibuten, Ceftobiprole, Ceftobiprole Medocaril, Ceftrazonal Bopentil, Ceftrazonal Sodium, Ceftriaxone Sodium, Ceftrizoxime Alapivoxil, Cefuroxime, Cefuroxime Axetil, Cefuroxime Pivoxetil, Centanamycin, Cephalexin Monohydrate, Ceranapril, Ceruletide Diethylamine, Cetefloxacin, Chlorofusin, Chloroorienticin A, Chloroorienticin B, Chlorotetain, Cibrostatin 1, Cidofovir, Cilastatin Sodium, Cilengitide, Cimaterol, Cinitapride Hydrogen Tartrate, Cipamfylline, Circinamide, Cisapride Hydrate, Cispentacin, Citicoline, Citrullimycine A, Cladribine, Clitocine, Clofarabine, Clopidogrel Sulfate, Compound 301029, Coumamidine Gamma1, Coumamidine Gamma2, Cromoglycate Lisetil Hydrochloride, Cycallene, Cyclic-Cidofovir, Cycloserine, Cyclotheonamide A, Cyclothialidine, Cygalovir, Cypemycin, Cysmethynil, Cystamidin A, Cystamine, Cystazosin, Cystocin, Cytarabine, Cytarabine Ocfosfate, Cytaramycin, Cytochlor, Cytomodulin, Dabigatran, Dabigatran Etexilate, Dacopafant, Dactimicin, Dactinomycin, Dactylocycline A, Dactylocycline B, DADME-Immucillin-G, Dalargin, Danegaptide Hydrochloride, Dapropterin Dihydrochloride, Dapsone, Darbufelone Mesilate, Darifenacin Hydrobromide, Darinaparsin, Darunavir, Daunorubicin, Davasaicin, Davunetide, Debrisoquine Sulfate, Decahydromoenomycin A, Decaplanin, Deferoxamine, Degarelix Acetate, Delafloxacin, Delta-Aminolevulinic Acid Hydrochloride, Deltibant, Denagliptin Hydrochloride, Denibulin Hydrochloride, Denufosol Tetrasodium, Deoxymethylspergualin, Deoxynegamycin, Deoxyvariolin B, Desacetylvinblastinehydrazide/Fo late Conjugate, Des-F-Sitagliptin, Desglugastrin Tromethamine, Deslorelin, Desmopressin Acetate, Detiviciclovir Diacetate, Dexelvucitabine, Dexibuprofen Lysine, Dextroamphetamine Sulfate, Dezinamide, Dezocitidine, Diadenosine Tetraphosphate, Diaveridine, Dichlorobenzoprim, Dicloguamine Maleate, Didemnin X, Didemnin Y, Dideoxycytidine, Difurazone, Dilevalol, Dilevalol Hydrochloride, Disermolide, Disopyramide Phosphate, DI-VAL-L-DC, Docosyl Cidofovir, Dolastatin 14, Dolastatin C, Donitriptan Hydrochloride, Donitriptan Mesilate, Dovitinib Lactate, Doxazosin Mesylate, Doxorubicin Hydrochloride, Doxycycline Hyclate, D-Penicillamine, Draflazine, Droxidopa, DTPA-Adenosylcobalamin, Ebrotidine, Ecenofloxacin Hydrochloride, Efegatran Sulfate Hydrate, Eflornithine Hydrochloride, Eglumegad Hydrate, Eicosyl Cidofovir, Elacytarabine, Elastatinal B, Elastatinal C, Elpetrigine, Elvucitabine, Emtricitabine, Enalkiren, Enigmol, Eniporide Mesilate, Entecavir, Entinostat, Epinastine Hydrochloride, Epiroprim, Epirubicin Hydrochloride, Epithalon, Epofolate, Epostatin, Epsilon Aminocaproic Acid, Eremomycin, Eribulin Mesylate, Erucamide, Esafloxacine Hydrochloride, Eslicarbazepine Acetate, Etaquine, Ethanolamine, Ethylthio-DADME-Immucillin-A, Ethynylcytidine, Etravirine, Etriciguat, Exalamide, Examorelin, Exatecan Mesilate, Ezatiostat Hydrochloride, Famciclovir, Famotidine, Famotidine Bismuth Citrate, Favipiravir, Feglymycin, Felbamate, Fenleuton, Fidarestat, Fidexaban, Filaminast, Filarizone, Fingolimod Hydrochloride, Flucytosine, Fludarabine Phosphate, Fluorobenzyltriamterene, Fluorominoxidil, Fluoroneplanocin A, Flupiritine Maleate, Fluvirucin B2, Fluvoxamine Maleate, Folinic Acid, Fortimicin A, Fosamprenavir Calcium, Fosamprenavir Sodium, Fosfomycin Trometamol, Fradafiban, Freselestat, Frovatriptan, Fudosteine, Furamidine, G1 Peptide, Gabadur, Gabapentin, Gabexate Mesilate, Galarubicin Hydrochloride, Galmic, Galnon, Ganciclovir, Ganciclovir Elaidic Acid, Ganciclovir Monophosphate, Ganciclovir Sodium, Ganirelix, Ganirelix Acetate, Garomefrine Hydrochloride, Gemcitabine, Gemcitabine Elaidate, Gemifloxacin Mesilate, Gilatide, Girodazole, Glaspimod, Glucosamine Sulfate, Gludopa, Glutathione Monoethylester, Glutathione Monoisopropylester, Glycine-Proline- Melphalan, Glycopin, Glycothiohexide alpha, Golotimod, Goserelin, Growth Factor Antagonist-116, Growth Hormone Releasing Peptid 2, Guanabenz Acetate, Guanadrel Sulfate, Guanethidine Monosulfate, Guanfacine Hydrochloride, Gusperimus Hydrochloride, Halovir A, Halovir B, Halovir C, Halovir D, Halovir E, Hayumicin B, Hayumicin C1, Hayumicin C2, Hayumicin D, Helvecardin A, Helvecardin B, Hepavir B, Heptaminol AMP Amidate, Hexa-D-Arginine, Hexadecyl Cidofovir, Hexadecyloxypropyl-Cidofovir, Histamine Dihydro chloride, Histaprodifen, Histrelin, Histrelin Acetate, Human Angiotensin II, Hydrostatin A, Hydroxyakalone, Hydroxyurea, Hypeptin, Ibutamoren Mesilate, Icatibant Acetate, Iclaprim, Icofungipen, Idarubicin Hydrochloride, Ilatreotide, Ilonidap, Imetit, Imidafenacin, Imidazenil, Imiquimod, Immunosine, Impentamine, Incyclinide, Indanocine, Indantadol Hydrochloride, Indoxam, Inogatran, Intrifiban, Iobenguane[131I], Iodorubidazone (P), Iotriside, Isepamicin Sulfate, Isobatzelline A, Isobatzelline B, Isobatzelline C, Isobatzelline D, Isobutyramide, Isodoxorubicin, Isopropamide Iodide, Ispinesib Mesylate, Istaroxime, Janthinomycin A, Janthinomycin B, Janthinomycin C, Jaspine B, Kahalalide F, Kaitocephalin, Kanamycin, Karnamicin B1, Katanosin A, Katanosin B, Kistamicin A, L-4-Oxalysine, Labetalol Hydrochloride, Labradimil, Lagatide, Lamifiban, Lamivudine, Lamotrigine, Lanicemine 2(S)-Hydroxysuccinate, Lanicemine Hydrochloride, Lanomycin, Larazotide Acetate, Lazabemide Hydrochloride, L-Dopa Methyl Ester Hydrochloride, L-Dopamide, Lecirelin, Lenalidomide, Lenampicillin Hydrochloride, Leucettamine A, Leucovorin Calcium, Leuprolide Acetate, Leurubicin, Leustroducsin A, Leustroducsin B, Leustroducsin C, Leustroducsin H, Levetiracetam, Levodopa, Levodopa 3-O-Glucoside, Levodopa 4-O-Glucoside, Levo leucovorin Calcium, L-Histidinol, L-Homothiocitrulline, Liblomycin, Linagliptin, Linifanib, Lintopride, Lirexapride, Lirimilast, Lisinopril, L-Lysine-D-Amphetamine Dimesylate, Lobophorin A, Lobucavir, Lodenosine, Loloatin B, Lomeguatrib, Lometrexol, Lonafarnib, Loracarbef Hydrate, Loviride, Loxoribine, L-Simexonyl Homocysteine, L-Thiocitrulline, Lymphostin, Lysobactin, Mabuterol Hydrochloride, Makaluvamine A, Makaluvamine A, Makaluvamine B, Makaluvamine C, Managlinat Dialanetil, Matristatin A2, Melagatran, Melanotan II, Memantine Hydrochloride, Memno-Peptide A, Meprobamate, Meriolin-3, Mersacidin, Metaraminol, Metazosin, Metformin Hydrochloride, Methotrexate, Methyl Bestatin, Methyldopa, Methylthio-DADME-Immucillin-A, Metoclopramide Hydrochloride, Metyrosine, Mexiletine Hydrochloride, Micafungin Sodium, Midaxifylline, Mideplanin, Midoriamin, Milacainide Tartrate, Milacemide-[2H], Milnacipran Hydrochloride, Minamestane, Minocycline Hydrochloride, Minoxidil, Mirabegron, Mitomycin, Mivazerol, Mivobulin Isethionate, Mizoribine, Mocetinostat Dihydrobromide, Modafinil, Modafinil Sulfone, Moenomycin A Chloride Bismuth Salt, Mofegiline, Mofegiline Hydrochloride, Monamidocin, Monodansyl Cadaverine, Montirelin Tetrahydrate, Mosapride Citrate, Moxilubant, Moxilubant Maleate, Mozenavir Mesilate, M-Phenylene Ethynylene, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl Dipeptide C, Mureidomycin A, Mureidomycin B, Mureidomycin C, Mureidomycin D, Mycestericin E, Myriocin, Nafamostat Mesylate, Nafarelin Acetate, Naglivan, Namitecan, Napsagatran, Nebostinel, Nebracetam Fumarate, Neldazosin, Nelzarabine, Nemonoxacin, Neomycin B-Hexaarginine Conjugate, Neomycin-Acridine, Nepafenac, Nepicastat Hydrochloride, Neramexane Hydrochloride, Neridronic Acid, Netamiftide Trifluoroacetate, Netilmicin Sulfate, Nocathiacin I, Nocathiacin II, Nocathiacin III, Nocathiacin IV, NO-Gabapentin, Nolatrexed Hydrochloride, NO-Mesalamine, Noraristeromycin, Nuvanil, 06-Benzylguanine, Ocimumoside A, Octacosamicin A, Octacosamicin B, Octreother, Octreotide Acetate, Oglufanide Disodium, Olamufloxacin, Olamufloxacin Mesilate, Olcegepant, Olradipine Hydrochloride, Omaciclovir, Ombrabulin, Ombrabulin Hydrochloride, Onnamide A, Opiorphin, Orbofiban Acetate, Orienticin A, Orienticin B, Orienticin C, Orienticin D, Oritavancin, Oseltamivir Carboxylate, Oseltamivir Phosphate, Otamixaban, Otenabant Hydrochloride, Ovothiol A, Oxazofurin, Oxcarbazepine, Oxiglutatione Sodium, Oxiracetam, Oxolide, Oxynor, Oxyphenarsine, Ozarelix, Pachymedusa Dacnicolor Tryptophyllin-1, Paecilaminol, Pafuramidine Maleate, PalauAmine, Paldimycin B, Pamidronate Sodium, Pancopride, Papuamide A, Papuamide B, Papuamide C, Papuamide D, Parasin I, Paromomycin, Pasireotide, Paulomycin, Paulomycin A2, Paulomycin B, Paulomycin C, Paulomycin D, Paulomycin E, Paulomycin F, Pazufloxacin, Pazufloxacin Mesilate, PEG-Vancomycin, Pelagiomicin C, Peldesine, Pelitrexol, Pemetrexed Disodium, Penciclovir, Penicillin G Procaine, Pentamidine Gluconate, Pentamidine Isethionate, Pentamidine Lactate, Peplomycin, Peramivir, Perphanazine 4-Aminobutyrate, Phakellistatin 5, PHE-ARG-Beta-Naphthylamide, Phentermine, Phortress, Pholcoline, Pibutidine Hydrochloride, Pimeloylanilide O-Aminoanilide, Piracetam, Pirarubicin, Pivampicillin, Pixantrone Maleate, Pluraflavin A, Pluraflavin B, Plusbacin A1, Plusbacin A2, Plusbacin A3, Plusbacin A4, Plusbacin B1, Plusbacin B2, Plusbacin B3, Plusbacin B4, PMEO-5-ME-DAPY, Pneumocandin A0, Pneumocandin B0, Pneumocandin B0 2-Phosphate, Pneumocandin D0, Polaprezinc, Polydiscamide A, Polymer Bound Human Leukocyte Elastase Inhibitor, Poststatin, PPI17-24, Pradimicin E, Pradimicin FA-2, Pralatrexate, Pramipexole Hydrochloride, Pranedipine Tartrate, Prazosin Hydrochloride, Prefolic A, Pregabalin, Preladenant, Primaquine Phosphate, Probestin, Procainamide Hydrochloride, Procaine Hydrochloride, Pro-Diazepam, Prostatin, Prucalopride, Prucalopride Hydrochloride, Prucalopride Succinate, Pseudomycin A', Pseudomycin B', Pyloricidin B, Pyradizomycin, Pyrazinamide, Pyrazinoylguanidine, Pyriferone, Pyrimethamine, Quinelorane Hydrochloride, R-(+)-Aminoindane, Ralfinamide, Ramoplanin A'1, Ramoplanin A'2, Ramoplanin A'3, Ramorelix, Ravidomycin N-oxide, Razaxaban Hydrochloride, Reblastatin, Regadenoson, Relcovaptan, Remacemide Hydrochloride, Resiquimod, Restricticin, Retaspimycin Hydrochloride, Retigabine Hydrochloride, Rhodopeptin C1, Rhodopeptin C2, Rhodopeptin C3, Rhodopeptin C4, Rhodostreptomycin A, Rhodostreptomycin B, Ribavirin, Ribavirin Eicosenate cis, Ribavirin Eicosenate trans, Ribavirin Elaidate, Ribavirin Oleate, Rilmazafone Hydrochloride Dihydrate, Riluzole, Rimacalib Hydrochloride, Rimeporide Hydrochloride, Riociguat, Ritipenem Acoxil, Robalzotan Hydrochloride, Robalzotan Tartrate Hydrate, Rociclovir, Romurtide, Rotigaptide, Roxifiban Acetate, Ruboxyl, Rufinamide, Rumycin 1, Rumycin 2, Sabarubicin Hydrochloride, Sabiporide Mesilate, Safinamide Mesilate, Safingol, Sagamacin, Sampatrilat, Sampirtine, Saprisartan, Saquinavir, Saquinavir Mesilate, Sardomizide Hydrochloride, Sardomozide, Saussureamine C, Saxagliptin, Secobatzelline A, Secobatzelline B, Seglitide, Selank, Seletracetam, Semapimod Hydrochloride, Senicapoc, Sepimostat Mesilate, Seproxetine, Seraspenide, Sevelamer Carbonate, Sevelamer Hydrochloride, Shepherdin, Sibrafiban, Silo dosin, Silver Sulfadiazine, Sipatrigine, Sitafloxacin Hydrate, Sitagliptin Phosphate Monohydrate, S-Nitrosoglutathione, Sofigatran, Sonedenoson, Sotirimod, Sparfloxacin, Sperabillin A, Sperabillin B, Sperabillin C, Sperabillin D, Sphingofungin F, Spinorphin, Spisulosine, Squalamine Lactate, Streptomycin, Styloguanidine, Substance P(8-11), Sufinosine, Sulcephalosporin, Sulfostin, Sulphazocine, Sultamicilline Tosylate, Sunflower Trypsin Inhibitor-1, Surfen, Synadenol, Synguanol, Tabimorelin, Tacedinaline, Tacrine Hydrochloride, Tageflar, Talabostat, Talaglumetad Hydrochloride, Talampanel, Talipexole Dihydrochloride, Tallimustine Hydrochloride, Talopterin, Taltirelin, Tanespimycin, Tanogitran, Targinine, Technetium (99MTC) Depreotide, Teicoplanin-A2-1, Teicoplanin-A2-2, Teicoplanin-A2-3, Teicoplanin-A2-3, Teicoplanin-A2-5, Telavancin Hydrochloride, Telinavir, Temozolomide, Temurtide, Tenidap, Tenidap Sodium, Tenofovir, Tenofovir DF, Terazosin Hydrochloride, Tetracosyl Cidofovir, Tetracycline Hydrochloride, Tetrafibricin, Texenomycin A, Tezacitabine, TGP, Thioacet, Thiothio, Thrazarine, Thymoctonan, Thymopentin, Tiamdipine, Tigecycline, Tilarginine Hydrochloride, Timirdine Diethanesulfonate, Timodepressin, Tipifarnib, TNF-Alpha Protease Enzyme Inhibitor, Tobramycin, Tocainide Hydrochloride, Tokaramide A, Tomopenem, Topostatin, Torcitabine, Tosufloxacin, Tosufloxacin Tosilate, Tranexamic Acid, Trantinterol Hydrochloride, Tranylcypromine Sulfate, Trelanserin, Tresperimus Triflutate, Trichomycin A, Triciribine, Triciribine Phosphate, Trientine Hydrochloride, Trimazosin Hydrochloride, Trimetrexate Glucuronate, Trimexautide, Trimidox, Trovafloxacin, Trovafloxacin Hydrate, Trovafloxacin Hydrochloride Mesylate, Trovafloxacin Mesilate, Troxacitabine, Trybizine Hydrochloride, Tubastrine, Tuftsin, Tyroservatide, Tyrphostin 47, Ubenimex, Valacyclovir, Valganciclovir Hydrochloride, Valnemulin, Valomaciclovir Stearate, Valonomycin A, Valopicitabine, Valpromide, Valrocemide, Vamicamide, Vancomycin Hydrochloride, Vancoresmycin, Vapitadine Hydrochloride, Varespladib, Varespladib Methyl, Varespladib Mofetil, Velnacrine Maleate, Venorphin, Vigabatrin, Vilazodone Hydrochloride, Vindesine, Viramidine Hydrochloride, Viranamycin-B, Vitamin B3, W Peptide, Xemilofiban, Xylocydine, Zanamivir, Zileuton, Zoniporide Hydrochloride, Zorubicin Hydrochloride.

Suitable small molecule drugs comprising a secondary amine functional group are, for example, (−)-3-O-Acetylspectaline hydrochloride, (−)-3-O-tert-Boc-spectaline hydrochloride, (−)-Cicloprolol, (−)-Norchloro-[18F]fluorohomoepibatidine, (−)-Salbutamol hydrochloride, (−)-Salmeterol, (+)-(S)-Hydroxychloroquine, (+)-Isamoltan, (+)-R-Pramipexole, (R)-(+)-Amlodipine, (R)-Clevidipine, (R)-NSP-307, (R)-Teludipine, (R)-Thionisoxetine, (S)-Clevidipine, (S)—N-Desmethyltrimebutine, (S)-Noremopamil, [99Tc]Demobesin 4, [Glu10,Nle17,Nle30]-Pancreatic polypeptide(2-36), [Nle17,Nle30]-Pancreatic polypeptide(2-36), [psi[CH2NH]Tpg4]Vancomycin aglycon, 15bbeta-Methoxyardeemin, 3-Bromomethcathinone, 4,5-Dianilinophthalimide, 4-Hydroxyatomoxetine, 5-Methylurapidil, 7-Oxostaurosporine, 99mTc-c(RGDfK*)2HYNIC, A-42867 pseudoaglycone, Abacavir succinate, Abacavir sulfate, Abarelix, Acarbose, Acebutolol hydrochloride, Aceclofenac, Acyline, Adaphostin, Adaprolol maleate, Adaprolol oxalate, Adecypenol, Adrogolide hydrochloride, Aglaiastatin C, Alchemix, Alinidine, Alkasar-18, Alminoprofen, Alniditan, alpha-Methylepinephrine, Alprafenone hydrochloride, Alprenolol hydrochloride, Alprenoxime hydrochloride, Altromycin A, Altromycin C, Alvespimycin hydrochloride, Ambroxol nitrate, Amfebutamone hydrochloride, Amibegron hydrochloride, Amifostine hydrate, Amineptine, Aminocandin, Aminochinol, Amitivir, Amlodipine, Amlodipine besylate, Amocarzine, Amodiaquine, Amosulalol hydrochloride, Amoxapine, Amsacrine, Anabasine hydrochloride, Anisperimus, Antide-1, Aranidipine, Araprofen, Arbutamine hydrochloride, Ardeemin, Arformoterol tartrate, Argatroban monohydrate, Argiopine, Arotinolol hydrochloride, Asperlicin E, Atenolol, Atevirdine mesylate, Azathioprine, Azelnidipine, Azepino statin, Balamapimod, Balhimycin, Balofloxacin, Balofloxacin dihydrate, Bambuterol, Bamirastine hydrate, Banoxantrone, Baogongteng A, Barixibat, Barnidipine hydrochloride, Batoprazine, Batzelline A, Batzelline B, Batzelline C, Becampanel, Bederocin, Bedoradrine sulfate, Befunolol hydrochloride, Belactin B, Belotecan hydrochloride, Benazepril hydrochloride, Bendroflumethiazide, Benidipine hydrochloride, Berlafenone hydrochloride, Betaxolol hydrochloride, Bevantolol hydrochloride, Biemnidin, Bifemelane hydrochloride, Binospirone mesylate, Bioxalomycin alpha 1, Bis(7)-cognition, Bisantrene hydrochloride, Bisnafide mesilate, Bisoprolol fumarate, Bitolterol mesylate, Bleomycin A2 sulfate, Boholmycin, Bopindolol, Bosutinib, Brinazarone, Brinzolamide, Bulaquine, Bumetanide, Buteranol, Butofilolol, Cadrofloxacin hydrochloride, Caldaret hydrate, Calindol Dihydrochloride, Capridine beta, Carmoterol hydrochloride, Carteolol hydrochloride, Carvedilol, Caspofungin acetate, Ceftaroline fosamil acetate, Ceftizoxime sodium, Ceftobiprole, Celiprolol hydrochloride, Cerebrocrast, Ceruletide diethylamine, Cevipabulin, Chinoin-169, Chloptosin, Chlordiazepoxide hydrochloride, Chloroorienticin A, Chloroorienticin B, Cilazapril, Cilnidipine, Ciluprevir, Cimaterol, Cinacalcet hydrochloride, Cinnamycin, Ciprofloxacin hydrochloride, Ciprofloxacin silver salt, Clevidipine butyrate, Clitocine, Clopenphendioxan, Cloranolol hydrochloride, Clozapine, Conantokin-R, Conophylline, Crisnatol mesilate, Cronidipine, Dabelotine mesilate, Dabigatran, Dabigatran etexilate, Dalbavancin, Dapivirine, Dapropterin dihydrochloride, Dasantafil, Debromoshermilamine, Decaplanin, Degarelix acetate, Delapril hydrochloride, Delavirdine mesilate, Delfaprazine hydrochloride, Delucemine hydrochloride, Demethylallosamidin, Demexiptiline hydrochloride, Denopamine, Deoxymethylspergualin, Deoxyspergualin Hydrochloride, Desacetylvinblastine-hydrazide/folate conjugate, Desbutyl benflumetol, Desbutylhalofantrine hydrochloride, Desferri-salmycin A, Desferri-salmycin B, Desferri-salmycin C, Desferri-salmycin D, Desipramine hydrochloride, Desloratadine, Dexfenfluramine hydrochloride, Dexketoprofen meglumine, Dexmethylphenidate hydrochloride, Dexniguldipine hydrochloride, Dexsotalol, Diazepinomicin, Dichlorobenzoprim, Diclofenac potassium, Diclofenac sodium, Diclofenac zinc salt, Diethylnorspermine, Dihydrexidine, Dilevalol, Dilevalol hydrochloride, Dinapsoline, Dinoxyline, Dipivefrine hydrochloride, Discodermide, Discodermide acetate, Discorhabdin D, Discorhabdin P, Discorhabdin S, Discorhabdin T, Discorhabdin U, Dobutamine hydrochloride, Dobutamine phosphate, Dopexamine, Dopexamine hydrochloride, Doripenem, Dorzolamide hydrochloride, d-Pseudoephedrine hydrochloride, Droxinavir, Duloxetine hydrochloride, Duocarmycin A, Duocarmycin B1, Duocarmycin B2, Duocarmycin C1, Duocarmycin C2, Dynemicin A, Dynemicin C, Ebanicline, Ecteinascidin 1560, Ecteinascidin 722, Ecteinascidin 729, Ecteinascidin 736, Ecteinascidin 745, Ecteinascidin 770, Ecteinascidin 875, Efaroxan, Efegatran sulfate hydrate, Efepristin, Efonidipine hydrochloride ethanol, Elagolix sodium, Elansolid C1, Elaroflban, Elbanizine, Elgodipine hydrochloride, Elinafide mesilate, Elinogrel potassium, Elnadipine, Enalapril maleate, Enalapril nitrate, Enalaprilat, Enazadrem, Enkastin (D), Enkastin (D), Enkastin (D), Enkastin AD, Enkastin AE, Enkastin ID, Enkastin IE, Enkastin VD, Enkastin VE, Enoxacin, Epibatidine, Epostatin, Eremomycin, Ersentilide, Ersentilide hydrochloride, Ertapenem sodium, Esculeogenin A, Esculeoside A, Esmolol hydrochloride, Esperamicin A1, Etamsylate, Ethoxy-idazoxan, Eugenodilol, Ezlopitant, Falnidamol, Farglitazar, Fasobegron hydrochloride, Fasudil hydrochloride, Felodipine, Fenoldopam mesilate, Fenoterol hydrobromide, Fepradinol, Ferroquine, Ferulinolol, Finafloxacin hydrochloride, Flecainide acetate, Florbetaben, Florbetapir F 18, Flufenoxine, Flumezapine, Fluodipine, Fluoxetine hydrochloride, Fluparoxan, Flupirtine maleate, Foetidine 1, Foetidine 2, Folinic acid, Formoterol fumarate, Forodesine hydrochloride, Fosaprepitant dimeglumine, Fosopamine, Frovatriptan, Furnidipine, Furosemide, Gaboxadol, Gadobenic acid dimeglumine salt, Gadopentetate dimeglumine, Gadoterate meglumine, Galactomycin I, Galactomycin II, Garenoxacin mesilate, Gatifloxacin, Gefitinib, Glucolanomycin, Glutapyrone, Gosogliptin hydrochloride, Grepafloxacin hydrochloride, Gypsetin, Halofuginone hydrobromide, Helvecardin A, Helvecardin B, Herquline B, Hesperadin, Himastatin, Hispidospermidin, Homoepibatidine, Hydrochlorothiazide, Hydroflumethiazide, Hydroxychloroquine sulfate, Ibopamine, Idazoxan hydrochloride, Iganidipine hydrochloride, Imidapril, Imidapril hydrochloride, Imidazoacridinone, Imisopasem manganese, Immepip, Immepyr, Incadronate, Indacaterol, Indantadol hydrochloride, Indeloxazine hydrochloride, Indolmycin, Inogatran, Intoplicine, Iofetamine hydrochloride I-123, Iptakalim hydrochloride, Isavuconazonium chloride hydrochloride, Isepamicin sulfate, Isofagomine tartrate, Isoquine, Ispronicline, Isradipine, Iturelix, Kaitocephalin, Ketamine hydrochloride, Kopsinine, Korupensamine A, Korupensamine B, Korupensamine C, Kosinostatin, Labedipinedilol A, Labedipinedilol B, Labetalol hydrochloride, Labradimil, Lacidipine, Ladasten, Ladostigil tartrate, Lagatide, Landiolol, Lapatinib ditosylate, Lenapenem hydrochloride, Lenapenem hydrochloride hydrate, Lerisetron, Leucovorin calcium, Levobetaxolol hydrochloride, Levobunolol hydrochloride, Levo leucovorin calcium, Levonebivolol, Liblomycin, Linaprazan, Lisinopril, Litoxetine, Lobenzarit sodium, Lodamin, Lofexidine hydrochloride, Lomefloxacin hydrochloride, Lorcaserin, Lotrafiban, Loviride, Lubazodone hydrochloride, Lumiracoxib, Mabuterol hydrochloride, Makaluvamine D, Makaluvamine E, Makaluvamine F, Makaluvone, Manidipine hydrochloride, Manifaxine hydrochloride, Manzamine B, Manzamine D, Maprotiline hydrochloride, Maropitant, Masnidipine hydrochloride, Mecamylamine hydrochloride, Meclofenamate sodium, Mefenamic acid, Mefloquine hydrochloride, Melagatran, Melogliptin, Meluadrine, Meluadrine tartrate, Memoquin, Mepindolol sulfate, Mepindolol transdermal patch, Meropenem, Methamphetamine hydrochloride, Methoctramine, Methyclothiazide, Methylhistaprodifen, Methylphenidate hydrochloride, Metipranolol, Metolazone, Metoprolol fumarate, Metoprolol succinate, Metoprolol tartrate, Mezacopride, Michellamine B, Microcin J25, Micronomicin sulfate, Midafotel, Milacemide-[2H], Minaprine hydrochloride, Mirabegron, Mitomycin, Mitoxantrone hydrochloride, Mivobulin isethionate, Modipafant, Moexipril hydrochloride, Moexiprilat, Montirelin tetrahydrate, Moranolin, Motesanib diphosphate, Moxifloxacin hydrochloride, Moxonidine hydrochloride hydrate, Muraminomicin I, Mureidomycin E, Mureidomycin F, Mureidomycins, N1,N8-Bisnorcymserine, Nadolol, Naproxen piperazine, Napsamycin A, Napsamycin B, Napsamycin C, Napsamycin D, Nardeterol, N-demethylated sildenafil, Nebivolol, Nemonapride, Neomycin-acridine, Neratinib, Netilmicin sulfate, Nicardipine hydrochloride, Nifedipine, Nifekalant hydrochloride, Niguldipine hydrochloride, Nilvadipine, Nimodipine, Nipradilol, Nisoldipine, Nitracrine dihydrochloride hydrate, Nitrendipine, Nitrofenac, Nitroso-nifedipine, Noberastine, Noberastine citrate, NO-ciprofloxacin, N-Octyl-beta-valienamine, Nolomirole hydrochloride, Norfloxacin, Norsegoline, Nortopixantrone hydrochloride, Nortriptyline hydrochloride, N-tert butyl isoquine, Oberadilol, Oberadilol monoethyl maleate, Odanacatib, Olanzapine, Olanzapine pamoate, Olradipine hydrochloride, Ontazolast, OPC-17083, Orbifloxacin, Orciprenaline sulphate, Orienticin A, Orienticin B, Orienticin C, Oritavancin, Osemozotan hydrochloride, Osutidine, Otenabant hydrochloride, Ovothiol B, Oxprenolol hydrochloride, Ozenoxacin, Pafenolol, Palau'amine, Palindore fumarate, Panobinostat, Parodilol hemifumarate, Parogrelil hydrochloride, Paroxetine, Paroxetine ascorbate, Paroxetine camsilate, Paroxetine hydrochloride, Paroxetine mesilate, Pazelliptine trihydrochloride, Pazelliptine trihydrochloride monohydrate, Pelitinib, Pelitrexol, Penbutolol sulfate, Pentostatin, Peplomycin, Perindopril, Perzinfotel, Phendioxan, Pibutidine hydrochloride, Picumeterol fumarate, Pindolol, Pirbuterol hydrochloride, Pittsburgh Compound B, Pixantrone maleate, Plerixafor hydrochloride, Polyglutamate camptothecin, Pozanicline hydrochloride, Pradimicin A, Pradimicin B, Pradimicin D, Pradimicin FA-1, Pradimicin FL, Pradimicin FS, Pradimicin L, Pradimicin S, Pradofloxacin, Pramipexole hydrochloride, Pranedipine tartrate, Pranidipine, Prefolic A, Premafloxacin, Premafloxacin hydrochloride, Premafloxacin magnesium, Primaquine phosphate, Prisotinol, Procaterol Hydrochloride Hemihydrate, Propafenone hydrochloride, Propranolol hydrochloride, Protriptyline hydrochloride, Proxodolol, Pumaprazole, Pyrindamycin A, Pyrindamycin B, Quinapril hydrochloride, Quinpramine, rac-Debromoflustramine E, Radezolid, Rafabegron, Ralfinamide, Ramipril, Rasagiline mesilate, Razupenem, Reboxetine mesilate, Repinotan, Repinotan hydrochloride, Reproterol hydrochloride, Retaspimycin hydrochloride, Retigabine hydrochloride, Rhodostreptomycin A, Rhodostreptomycin B, Rifabutin, Rilmenidine dihydrogen phosphate, Rimoterol hydrobromide, Risotilide, Rivanicline, Robenacoxib, Rolapitant hydrochloride, Safinamide mesilate, Sagandipine, Salbostatin, Salbutamol nitrate, Salbutamol sulfate, Salmaterol, Salmeterol xinafoate, Sarizotan hydrochloride, Saussureamine C, Sazetidine-A, Selodenoson, Sertraline, Sertraline hydrochloride, Setazindol, Sezolamide hydrochloride, Shishijimicin A, Shishijimicin B, Shishijimicin C, Sibanomicin, Sibenadet hydrochloride, Silodosin, Sitamaquine hydrochloride, Sivelestat sodium hydrate, Sofinicline, Solabegron hydrochloride, Solpecainol hydrochloride, Soraprazan, Sotalol hydrochloride, Sparfloxacin, Spermine dialdehyde, Spirapril, Spiroquinazoline, Squalamine lactate, Streptomycin, Stressinl -A, Sumanirole maleate, Suprofenac 1, Suprofenac 2, Suprofenac 3, Suronacrine maleate, Tafamidis meglumine, Tafenoquine succinate, Talarozole, Talibegron, Talibegron hydrochloride, Talniflumate, Talotrexin, Taltobulin, Taludipine hydrochloride, Tamsulosin hydrochloride, Tanespimycin, Tanogitran, Tauropyrone, Tazopsine, Tecalcet hydrochloride, Tecastemizole, Technetium (99mTc) apcitide, Technetium (99mTc) bicisate, Telatinib, Telavancin hydrochloride, Temacrazine mesilate, Temafloxacin hydrochloride, Temocapril hydrochloride, Terbutaline sulfate, Terodiline hydrochloride, Tertatolol hydrochloride, Tetracaine hydrochloride, Tetrahydrodercitin 1, Tetrindole, Tezampanel, Thiamet-G, Thiofedrine, Tiamdipine, Tiamenidine, Tianeptine sodium, Tiapafant, Tienoxolol hydrochloride, Tigecycline, Tilisolol hydrochloride, Timolol hemihydrate, Timolol maleate, Tinazoline hydrohloride, Tirofiban hydrochloride, Tizanidine hydrochloride, Toborinone, Tolfenamic acid, Tomatine, Tomoxetine hydrochloride, Topixantrone hydrochloride, Torasemide, Trabectedin, Trandolapril, Trandolaprilat, Trantinterol hydrochloride, Treprostinil diethanolamine, Tresperimus triflutate, Triacetyl dynemicin C, Trientine hydrochloride, Trifluproxim, Trimetazidine, Trimetrexate glucuronate, Trombodipine, Troxipide, Tulathromycin A, Tulathromycin B, Tulobuterol hydrochloride, Ufenamate, Ulifloxacin, Ulimorelin, Uncialamycin, Urapidil, Utibapril, Utibaprilat, Vabicaserin hydrochloride, Vancomycin hydrochloride, Vandetanib, Vanidipinedilol, Vaninolol, Vapitadine hydrochloride, Varenicline tartrate, Varlitinib, Vatalanib succinate, Vatanidipine, Vatanidipine hydrochloride, Vestipitant mesylate, Vicenistatin, Vildagliptin, Viloxazine hydrochloride, Vofopitant hydrochloride, Voglibose, Voreloxin, Xamoterol fumarate, Ximelagatran, Yttrium-90 edotreotide, Zabicipril hydrochloride, Zabiciprilat hydrochloride ( ), Zabofloxacin hydrochloride, Zanapezil fumarate, Zelandopam hydrochloride, Zilpaterol, Zolmitriptan.

Suitable small molecule drugs comprising an aromatic hydroxyl group are, for example, (−)-cis-Resorcylide, (−)-Indocarbazostatin B, (−)-Salmeterol, (−)-Subersic acid, (+)-alpha-Viniferin, (+)-Etorphine, (+)-Indocarbazostatin, (+)-SCH-351448, (R)-Gossypol, (S)-(+)-Curcuphenol, (S)-Methylnaltrexone bromide, [8]-Gingerol, [Arg(Me)9] MS-10, [D-Tyr1,Arg(Me)9] MS-10, [D-Tyr1,AzaGly7,Arg(Me)9] MS-10, [D-Tyr1] MS-10, [psi[CH2NH]Tpg4]Vancomycin aglycon, [Trp19] MS-10, 13-Deoxyadriamycin hydrochloride, 14-Methoxymetopon, 14-Phenylpropoxymetopon, 18,19-Dehydrobuprenorphine hydrochloride, 2,12-Dimethyleurotinone, 2'-Hydroxymatteucinol, 2-Methoxyestradiol, 2-Methyleurotinone, 3,5-Dicaffeoylquinic acid, 3-Bromodiosmetine, 3-Bromodiosmine, 3-Chlorodiosmetine, 3-Chlorodiosmine, 4',7,8-Trihydroxyisoflavone, 4-Aminosalicylic acid, 4-Hydroxyatomoxetine, 4-Iodopropofol, 5-Iodofredericamycin A, 5Z-7-Oxozeaenol, 6-Carboxygenistein, 6-O-mPEG4-Nalbupine, 6-O-mPEG5-Nalbuphine, 7-Methylcapillarisin, 8(R)-Fluoroidarubicin hydrochloride, 8',9'-Dehydroascochlorin, 8-Carboxy-isoiantheran A, 8-Paradol, 8-Prenylapigenin, 8-Prenylnaringenin, 9-Hydroxycrisamicin A, A-42867 pseudoaglycone, Abarelix, Acacetin, Aclarubicin, Acolbifene hydrochloride, Acotiamide hydrochloride hydrate, Acrovestone, Actinoplanone A, Actinoplanone B, Aculeacin Agamma, Adaphostin, Adarotene, Adxanthromycin A, Aerothricin 1, Aerothricin 16, Aerothricin 41, Aerothricin 45, Aerothricin 50, Aerothricin 55, Ajulemic acid, Alchemix, Aldifen, alpha-Mangostin, alpha-Methylepinephrine, alpha-Methylnorepinephrine, Alpha-Peltatin, Altromycin A, Altromycin B, Altromycin C, Altromycin D, Altromycins, Alvimopan hydrate, Alvocidib hydrochloride, Amamistatin A, Amamistatin B, Amarogentin, Amelubant, Amidox, Aminocandin, Amodiaquine, Amoxicillin trihydrate, Amrubicin Hydrochloride, Amurensin H, Anguillosporal, Anidulafungin, Ankinomycin, Annamycin, Annulin C, Antimycin A11, Antimycin A12, Antimycin A13, Antimycin A14, Antimycin A15, Antimycin A16, Apicularen A, Apicularen B, Apigenin, Apomine, Apomorphine hydrochloride, Arbidol, Arbutamine hydrochloride, Arformoterol tartrate, Artepillin C, Arzoxifene hydrochloride, Aspoxicillin, Atalaphillidine, Atalaphillinine, Atraric acid, Avorelin, Axitirome, Azaresveratrol, Azatoxin, Azepinostatin, Baicalein, Baicalin, Balhimycin, Balsalazide disodium, Banoxantrone, Bazedoxifene acetate, Bazedoxifene hydrochloride, Bedoradrine sulfate, Benadrostin, Benanomicin A, Benanomicin B, Benastatin A, Benastatin B, Benastatin C, Benastatin D, Benzbromarone, Berefrine, Berupipam maleate, beta-Mangostin, Biemnidin, Biochanin A, Bioxalomycin alpha 1, Bioxalomycin alpha2, Bismuth subsalicylate, Bisphenol, Bix, Bizelesin, Bogorol A, Brandisianin A, Brandisianin B, Brandisianin C, Brasilicardin A, Brevifolin carboxylic acid, Breynin A, Breynin B, Bromotopsentin, Buflomedil pyridoxalphosphate, Buprenorphine hydrochloride, Buserelin acetate, Butein, Buteranol, Butorphan, Butorphanol tartrate, Calebin A, Calocoumarin A, Caloporoside D, Caloporoside E, Caloporoside F, Calphostin A, Calphostin B, Calphostin C, Calphostin D, Calphostin I, Capillarisin, Capsazepine, Carbazomadurin A, Carbazomadurin B, Carbetocin, Carbidopa, Carmoterol hydrochloride, Caspofungin acetate, Cassigalol A, Cefetecol, Cefoperazone sodium, Cefpiramide sodium, Cefprozil, Cefprozil monohydrate, Cetrorelix Acetate, Chaetoatrosin A, Chafuroside, Chloroorienticin A, Chloroorienticin B, Chondramide A, Chondramide B, Chondramide C, Cinnatriacetin A, Cinnatriacetin B, cis-6-Shogaol, Citpressine I, Citreamicin-Alpha, Citreamicin-eta, Citrusinine-I, Clausenamine A, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Coniferol Alcohol, Conophylline, Corynecandin, Cosalane, Crisamicin C, Crobenetine, Crobenetine hydrochloride, Curtisian A, Curtisian B, Curtisian D, Cyanidin Chloride Monohydrate, Cyclocommunol, Cyclopropaparadicicol, Cyclotheonamide A, Cyclothialidine, Cyrtominetin, Cytogenin, Cytosporone B, Cytotrienin I, Cytotrienin II, Dactylocycline A, Dactylocycline B, Dalargin, Dalbavancin, Damunacantal, Daphnodorin A, Daphnodorin B, Daphnodorin C ((−)-enantiomer), Darbufelone, Darbufelone mesilate, Daunorubicin, Daurichromenic acid, Davidigenin, Deacetyl moxisylyte hydrochloride, Decaplanin, Decyl gallate, Deferasirox, Dehydrozingerone, Delphinidin, Denopamine, Deoxymulundocandin, Dersalazine, Desacetylravidomycin N-oxide, Desglugastrin tromethamine, Deslorelin, Desmopressin acetate, Desvenlafaxine succinate, Dexanabinol, Dextrorphan, Dexylosylbenanomycin A, D-Fluviabactin, Diazaphilonic acid, Diazepinomicin, Dieckol, Diflunisal, Dihydrexidine, Dihydroavenanthramide D, Dihydrogranaticin B, Dihydrohonokiol B, Dihydroraloxifene, Dilevalol, Dilevalol hydrochloride, Dinapsoline, Dinoxyline, Dioncoquinone A, Dioncoquinone B, Dipotassium gossypolate, Dobutamine hydrochloride, Dobutamine Phosphate, Dopexamine, Dopexamine hydrochloride, Dosmalfate, Doxorubicin Hydrochloride, Doxorubicin, Morpholinyl, DoxoTam 12, Doxycycline hyclate, Dronabinol, Droxidopa, Duocarmycin B1, Duocarmycin B2, Duocarmycin C1, Duocarmycin C2, Dutomycin, Dynemicin A, Dynemicin C, Econazole Sulfosalicylate, Ecopipam, Ecteinascidin 1560, Ecteinascidin 722, Ecteinascidin 729, Ecteinascidin 736, Ecteinascidin 745, Ecteinascidin 757, Ecteinascidin 770, Ecteinascidin 875, Edotecarin, Edotreotide yttrium, Eflucimibe, Eflumast, Elansolid C1, Eldacimibe, Ellagic acid-4-gallate, Elliptinium acetate, Elsibucol, Eltrombopag olamine, Emodin, Enazadrem, Enofelast, Entacapone, ent-Estriol, Epidoxoform, Epigallocatechin-3-gallate, Epirubicin hydrochloride, Eplivanserin, Eplivanserin fumarate, Eplivanserin mesilate, Epocarbazolin A, Epocarbazolin B, Eprotirome, Eptazocine hydrobromide, Erabulenol A, Erabulenol B, Eremomycin, Estetrol, Estradiol, Estriol, Etalocib sodium, Etamsylate, Ethinylestradiol, Ethyl gallate, Etoposide, Eurotinone, Euxanthone, Evernimicin, Exifone, Ezetimibe, Fadolmidine hydrochloride, Feglymycin, Fenoldopam mesilate, Fenoterol hydrobromide, Fidaxomicin, Fidexaban, Fluostatin A, Fluostatin B, Foetidine 1, Foetidine 2, Folipastatin, Formobactin, Formoterol fumarate, Fosopamine, Frederine, Fulvestrant, Furaquinocin A, Furaquinocin B, Fusacandin A, Fusacandin B, Fusidienol, Galactomycin I, Galactomycin II, Galarubicin hydrochloride, Galocitabine, Gambogic acid, gamma-Mangostin, gamma-Tocotrienol, Ganirelix, Ganirelix acetate, Garvalone C, Garveatin E, Garveatin F, Genistein-7-phosphate, Gigantol, Gilvusmycin, Glucopiericidinol A1, Glucopiericidinol A2, Gludopa, Glycothiohexide alpha, Goserelin, Graniticin B, Griseusin C, Hatomarubigin A, Hatomarubigin B, Hatomarubigin C, Hatomarubigin D, Hayumicin A, Hayumicin B, Hayumicin C1, Hayumicin C2, Hayumicin D, Heliquinomycin, Helvecardin A, Helvecardin B, Hericenal A, Hericenal B, Hericenal C, Hidrosmin, Histrelin, Histrelin acetate, Hongoquercin A, Hongoquercin B, Honokiol diepoxide, Honokiol diepoxide, Human angiotensin II, Hydromorphone methiodide, Hymenistatin 1, Hypeptin, Hypericin, Hyperoside, Icariin, Idarubicin hydrochloride, Idronoxil, Ifenprodil, Imidazoacridinone, Incyclinide, Indacaterol, Indanocine, Integracin A, Integracin B, Integracin C, Integramycin, Integrastatin A, Integrastatin B, Intoplicine, Iodochlorhydroxyquin, Iododiflunisal, Iorubidazone (p), Iolopride (123I), Ioxipride, Iralukast, Iralukast sodium, Irciniastatin A, Irciniastatin B, Isalmadol, Isobavachalcone, Isodoxorubicin, Iso-iantheran A, Isoliquiritigenin, Isomolpan Hydrochloride, Isoquine, Isovanihuperzine A, Jadomycin B, Jasplakinolide, Kadsuphilin C, Kaitocephalin, Kampanol A, Kampanol B, Kanglemycin A, Kapurimycin A1, Kapurimycin A3, Kapurimycin A3, Kehokorin D, Kehokorin E, Kigamicin A, Kigamicin B, Kigamicin C, Kigamicin D, Kigamicin E, Kigamicinone, Kistamicin A, Klainetin A, Klainetin B, Kodaistatin A, Kodaistatin B, Kodaistatin C, Kodaistatin D, Korupensamine A, Korupensamine B, Korupensamine C, Korupensamine D, Kosinostatin, Labetalol hydrochloride, Laccaridione A, Lactonamycin, Lactosylphenyl trolox, Ladirubicin, Lamellarin alpha 20-sulfate sodium salt, Lamifiban, Lanreotide acetate, Lasofoxifene, Lasofoxifene tartrate, Latamoxef sodium, L-Chicoric acid, L-Dopamide, Lecirelin, Ledazerol, Leuprolide acetate, Leurubicin, Levalbuterol hydrochloride, Levodopa, Levodopa 3-O-glucoside, Levodopa 4-O-glucoside, Levorphanol tartrate, L-Fluviabactin, Lipiarmycin B3, Lipiarmycin B4, Liquiritin apioside, Lithospermic acid B magnesium salt, Lobatamide C, Lobatamide F, Loloatin B, Luminacin D, Luteolin, Macrocarpin A, Macrocarpin B, Makaluvamine D, Makaluvamine E, Malonoben, Maltolyl p-coumarate, Mannopeptimycin beta, Manzamine F, Marinopyrrole A, Marmelin, Masoprocol, Mastprom, Matteuorienate A, Matteuorienate B, Matteuorienate C, Medicarpin, Melevodopa hydrochloride, Mellein, Meluadrine, Meluadrine tartrate, Memno-peptide A, Meptazinol hydrochloride, Mesalazine, Metaraminol, Methanobactin, Methyl gallate, Methyldopa, Methylnaltrexone bromide, Metirosine, Micacocidin A, Micacocidin B, Micafungin sodium, Michellamine B, Mideplanin, Mimopezil, Minocycline hydrochloride, Miproxifene, Mitoxantrone hydrochloride, Mivazerol, Modecainide, Mollugin, Monohydroxyethylrutoside, Morphine Glucuronide, Morphine hydrochloride, Morphine sulfate, Moxifetin hydrogen maleate, Mumbaistatin, Mureidomycin A, Mureidomycin B, Mureidomycin C, Mureidomycin D, Mureidomycin E, Mureidomycin F, Mureidomycins, Mycophenolate Mofetil, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, Naamidine A, Nabilone, N-Acetylcolchinol, Nafarelin acetate, Nalbuphine hydrochloride, Nalfurafine hydrochloride, N-Allylsecoboldine, Nalmefene, Naloxone hydrochloride, Naltrexone hydrochloride, Naltrindole, Napsamycin A, Napsamycin B, Napsamycin C, Napsamycin D, Nardeterol, N-Cyclopentyl-tazopsine, Nebicapone, Nelfinavir mesilate, Nemorubicin, Neparensinol A, Neparensinol B, Neparensinol C, Nerfilin I, Nicanartine, Nitecapone, Nocardione A, Nocathiacin I, Nocathiacin III, Nocathiacin IV, NO-Mesalamine, Nordamunacantal, Nostocyclopeptide M1, Nothramicin, N-tert butyl isoquine, Obelmycin H, Ochromycinone, Octyl gallate, Odapipam acetate, O-Demethylchlorothricin, O-Demethylmurrayafoline A, Oenothein B, Okicenone, Olanzapine pamoate, Olcegepant, Olsalazine sodium, Onjixanthone I, Onjixanthone II, Oolonghomobisflavan A, Oolonghomobisflavan C, Orciprenaline sulphate, Orienticin A, Orienticin B, Orienticin C, Orienticin D, Oritavancin, Orniplabin, Orthosomycin A, Orthosomycin B, Orthosomycin C, Orthosomycin D, Orthosomycin E, Orthosomycin F, Orthosomycin G, Orthosomycin H, Osutidine, Oximidine III, Oxymetazoline hydrochloride, Oxymorphazole dihydrochloride, Oxymorphone hydrochloride, Oxyphenarsine, Ozarelix, Paeciloquinine A, Paeciloquinine D, Paeciloquinone B, Paeciloquinone D, Pancratistatin-3,4-cyclic phosphate sodium salt, Pannorin, Papuamide A, Papuamide B, Papuamide C, Papuamide D, Paracetamol, Parvisporin B, PEG-vancomycin, Penicillide, Pentazocine hydrochloride, Pepticinnamin E, Phaffiaol, Phakellistatin 7, Phakellistatin 8, Phakellistatin 9, Phenochalasin A, Phentolamine mesilate, Phlorofucofuroeckol, Phomopsichalasin, Phthalascidin, Physostigmine salicylate, Piceatannol, Pidobenzone, Pinocembrin, Pipendoxifene, Pirarubicin, Pittsburgh Compound B, Platencin, Platensimycin, Pluraflavin A, Pluraflavin B, Pluraflavin E, Pneumocandin A0, Pneumocandin B0, Pneumocandin B0 2-phosphate, Pneumocandin D0, Polyestradiol phosphate, Polyketomycin, Popolohuanone E, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Prinaberel, Probucol, Procaterol Hydrochloride Hemihydrate, Propofol, Propyl gallate, Protocatechuic acid, Protocatechuic aldehyde, Pseudohypericin, Purpuromycin, Pyrindamycin A, Pyrindamycin B, Quercetin-3-O-methyl ether, Quinagolide hydrochloride, Quinobene, rac-Apogossypolone, Rac-Tolterodine, Raloxifene hydrochloride, Ramoplanin A'1, Ramoplanin A'2, Ramoplanin A'3, Ramorelix, Ravidomycin N-oxide, Rawsonol, Reblastatin, Reproterol hydrochloride, Resobene, Resorthiomycin, Retaspimycin hydrochloride, Rhodiocyanoside B, Rhododaurichromanic acid A, Rifabutin, Rifalazil, Rifamexil, Rifampicin, Rifapentine, Rifaximin, Rimoterol hydrobromide, Riodoxol, Rohitukine, Rotigaptide, Rotigotine, Roxindole Mesilate, Ruboxyl, Rufigallol, Rumycin 1, Rumycin 2, Russuphelin A, Sabarubicin hydrochloride, Saintopin, Saintopin E, Sakyomicin A, Sakyomicin E, Salazopyridazin, Salbutamol nitrate, Salbutamol sulfate, Salcaprozic acid sodium salt, Salicylazobenzoic acid, Salicylihalamide A, Salicylihalamide B, Saliphenylhalamide, Salmaterol, Salmeterol xinafoate, Saloxin, Salvianolic acid L, Sampatrilat, Sanglifehrin A, Sanglifehrin B, Sanglifehrin C, Sanglifehrin D, Saptomycin D, Sapurimycin, Saricandin, Secoisolariciresinol diglucoside, Seglitide, Semorphone hydrochloride, Shishijimicin A, Shishijimicin B, Shishijimicin C, Sibenadet hydrochloride, Silychristin, Sinomenine, Sivifene, Siwenmycin, Sootepenseone, Spinorphin, Spinosulfate A, Spinosulfate B, Spiroximicin, Stachybocin A, Stachybocin B, Stachybocin C, Stachybotrin C, Stachybotrydial, Staplabin, Sterenin A, Sterenin C, Sterenin D, Streptopyrrole, Succinobucol, Sulfasalazine, Sulphazocine, Susalimod, Symbioimine, Syriacusin A, Syriacusin B, Syriacusin C, Tageflar, Taiwanhomoflavone A, TAP-doxorubicin, Tapentadol hydrochloride, Taramanon A, Tazofelone, Tazopsine, Tebufelone, Technetium Tc 99m depreotide, Teicoplanin-A2-1, Teicoplanin-A2-2, Teicoplanin-A2-3, Teicoplanin-A2-3, Teicoplanin-A2-5, Telavancin hydrochloride, Temoporfin, Teniposide, Tenuifoliside A, Tenuifoliside B, Tenuifoliside C, Terbutaline sulfate, Terprenin, Tetracycline hydrochloride, Tetragalloylquinic acid, Tetrahydrocurcumin, Tetrahydroechinocandin B, Tetrahydroswertianolin, Thenorphine, Theophylline rutoside, Thiazinotrienomycin B, Thiazinotrienomycin F, Thiazinotrienomycin G, Thielavin G, Thielocin B3, Thymopentin, Tigecycline, Tipelukast, Tocotrienol, Tokaramide A, Tolcapone, Tolterodine Tartrate, Topotecan Acetate, Topotecane Hydrochloride, Topsentine B1, Trabectedin, trans-Resveratrol, Traxoprodil, Traxoprodil mesylate, Trimidox, Triphendiol, Troglitazone, Tubastrine, Tubulysin A, Tubulysin B, Tubulysin C, Tucaresol, Tyropeptin A10, Tyropeptin A6, Tyropeptin A9, Tyroservatide, Tyrphostin 47, Uncarinic acid A, Uncarinic acid B, Uncialamycin, Valrubicin, Vancomycin hydrochloride, Veinamitol, Venorphin, Verticillatine, Vexibinol, Vialinin B, Vinaxanthone, W Peptide, Wiedendiol A, Wiedendiol B, Woodorien, Xamoterol Fumarate, Xanthoangelol E, Xanthofulvin, Xanthomegnin, Xipamide, Yatakemycin, Zelandopam hydrochloride, Zorubicin hydrochloride.

Suitable small molecule drugs comprising a hydroxyl functional group are, for example, (−)-(2R*,3R*,11bS*)-Dihydrotetrabenazine, (−)-(2R*,3S*,11bR*)-Dihydrotetrabenazine, (−)-2-(2-Bromohexadecanoyl)paclitaxel, (−)-4',5'-Didemethoxypicropodophyllin, (−)-4'-Demethoxypicropodophyllin, (−)-9-Dehydrogalanthaminium bromide, (−)-Calicheamicinone, (−)-Cicloprolol, (−)-cis-Resorcylide, (−)-Indocarbazostatin B, (−)-Kendomycin, (−)-Kolavenol, (−)-Salmeterol, (−)-Subersic acid, (+)-(2R*,3R*,11bS*)-Dihydrotetrabenazine, (+)-(2R*,3S*,11bR*)-Dihydrotetrabenazine, (+)-(S)-Hydroxychloroquine, (+)-23,24-Dihydrodiscodermolide, (+)-Almuheptolide A, (+)-alpha-Viniferin, (+)-Azacalanolide A, (+)-Dihydrocalanolide A, (+)-Etorphine, (+)-Indocarbazostatin, (+)-Isamoltan, (+)-SCH-351448, (+)-Sotalol, (E)-p-Coumaroylquinic acid, (R)-Almokalant, (R)-Dixyrazine dihydrochloride, (R)-Gossypol, (R)-Sulfinosine, (S)-(+)-Curcuphenol, (S)-Almokalant, (S)-Methylnaltrexone bromide, (S)-Oxiracetam, (S)-Sulfinosine, (Z)-Indenaprost, [8]-Gingerol, [Arg(Me)9] MS-10, [D-Tyr1,Arg(Me)9] MS-10, [D-Tyr1, AzaGly7,Arg(Me)9] MS-10, [D-Tyr1] MS-10, [N-MeIle4]-cyclosporin, [psi[CH2NH]Tpg4]Vancomycin aglycon, [Trp19] MS-10, 111In-Pentetreotide, 11-Hydroxyepothilone D, 11-Keto-Beta-Boswellic Acid, 13-Deoxyadriamycin hydrochloride, 14alpha-Lipoyl andrographolide, 14beta-Hydroxydocetaxel-1,14-acetonide, 14beta-Hydroxytaxotere, 14-Demethylmycoticin A, 14-Hydroxyclarithromycin, 14-Isobutanoylandrographolide, 14-Methoxymetopon, 14-Phenylpropoxymetopon, 14-Pivaloylandrographolide, 15-Methylepothilone B, 16-Methyloxazolomycin, 17-Aminogeldanamycin, 17beta-Hydroxywortmannin, 18,19-Dehydrobuprenorphine hydrochloride, 18-Hydroxycoronaridine, 19-O-Demethylscytophycin C, 19-O-Methylgeldanamycin, 1alpha,25-Dihydroxyvitamin D3-23,26-lactone, 1alpha-Hydroxyvitamin D4, 1-Oxorapamycin, 2,12-Dimethyleurotinone, 21-Aminoepothilone B, 22-Ene-25-oxavitamin D, 22-Oxacalcitriol, 24(S)-Ocotillol, 24-Deoxyascomycin, 25-Anhydrocimigenol-3-O-beta-D-xylopyranoside, 26-Fluoroepothilone, 2-Aminoaristeromycin, 2-Aminoneplanocin A, 2'-Hydroxymatteucinol, 2-Methoxyestradiol, 2-Methyleurotinone, 2'-Palmitoylpaclitaxel, 3,5-Dicaffeoylquinic acid, 3,7a-Diepialexine, 36-Dihydroisorolliniastatin 1,3-Allyl farnesol, 3-Bromodiosmetine, 3-Bromodiosmine, 3-Chlorodiosmetine, 3-Chlorodiosmine, 3-Deazaadenosine, 3-Epimaxacalcitol, 4,6-diene-Cer, 4',7,8-Trihydroxyisoflavone, 41-Demethylhomooligomycin B, 44-Homooligomycin B, 4-Aminosalicylic acid, 4-Chlorophenylthio-DADMe-immucillin-A, 4-Demethylepothilone B, 4-Demethylpenclomedine, 4'-Ethynylstavudine, 4-Hydroxyatomoxetine, 4"-Hydroxymevastatin lactone, 4-Iodopropofol, 5(R)-Hydroxytriptolide, 5,4'-Diepiarbekacin, 5,6-Dehydroascomycin, 5'-Epiequisetin, 5-Ethylthioribose, 5-Iodofredericamycin A, 5-N-Acetyl-15balpha-hydroxyardeemin, 5-Phenylthioacyclouridine, 5-Thiaepothilone, 5Z-7-Oxozeaenol, 6alpha-7-Epipaclitaxel, 6alpha-Fluorursodeoxycholic acid, 6-Carboxygenistein, 6'-Homoneplanocin A, 6-Hydroxyscytophycin B, 6-O-mPEG4-Nalbupine, 6-O-mPEG5-Nalbuphine, 7,7a-Diepialexine, 7-Chlorokynurenic acid, 7-Deoxytaxol, 7-Methylcapillarisin, 8(R)-Fluoroidarubicin hydrochloride, 8',9'-Dehydroascochlorin, 8-Carboxy-iso-iantheran A, 8-Paradol, 8-Prenylapigenin, 8-Prenylnaringenin, 9,11-Dehydrocortexolone 17alpha-butyrate, 9,9-Dihydrotaxol, 9-[18F]Fluoropropyl-(+)-dihydrotetrabenazine, 99mTc-c(RGDfK*)2HYNIC, 9-Aminocamptothecin, 9-Hydroxycrisamicin A, 9-Hydroxyrisperidone, A-42867 pseudoaglycone, Abacavir succinate, Abacavir sulfate, Abaperidone hydrochloride, Abarelix, Abietaquinone methide, Abiraterone, Acacetin, Acadesine, Acarbose, Acaterin, Acebutolol hydrochloride, Acemannan, Aceneuramic acid sodium salt, Aciclovir, Aclarubicin, Acolbifene hydrochloride, Acotiamide hydrochloride hydrate, Acrovestone, Actinoplanone A, Actinoplanone B, Aculeacin Agamma, Acyline, Adamantyl globotriaosylceramide, Adaphostin, Adaprolol maleate, Adaprolol Oxalate, Adarotene, Adecypenol, Adelmidrol, Ademetionine tosylate sulfate, Adenophostin A, Adenophostin B, Adenosine, Adlupulon, Adxanthromycin A, Aerothricin 1, Aerothricin 41, Aerothricin 45, Aerothricin 5, Aerothricin 50, Aerothricin 55, Afeletecan hydrochloride, Agelasphin 517, Agelasphin 564, Aglaiastatin A, Aglaiastatin B, Ajulemic acid, Albaconazole, Albifylline, Albitiazolium bromide, Albocycline K3, Alchemix, Alclometasone dipropionate, Alcuronium chloride, Aldecalmycin, Aldifen, Alemcinal, Alfacalcidol, Alisamycin, Aliskiren fumarate, Alkasar-18, Allixin, Almokalant, Alogliptin benzoate, alpha-C-Galactosylceramide, alpha-Galactosylceramide, alpha-Galactosylceramide-BODIPY, alpha-Lactosylceramide, alpha-Mangostin, alpha-Methylepinephrine, alpha-Methylnorepinephrine, Alpha-Peltatin, alpha-Pyrone I, Alprafenone hydrochloride, Alprenolol hydrochloride, Alprostadil, Altemicidin, Altorhyrtin C, Altromycin A, Altromycin B, Altromycin C, Altromycin D, Altromycins, Alvespimycin hydrochloride, Alvimopan hydrate, Alvocidib hydrochloride, Amamistatin A, Amamistatin B, Amarogentin, Ambroxol nitrate, Amdoxovir, Amelometasone, Amelubant, Amibegron hydrochloride, Amidox, Amikacin, Aminocandin, Amlexanox, Ammocidin A, Amodiaquine, Amosulalol Hydrochloride, Amoxicillin trihydrate, Amphidinolide E, Amphidinolide T1, Amphinidin A, Amphotericin B, Amprenavir, Amrubicin Hydrochloride, Amurensin H, Amycolamicin, Amycomycin, Anandamide, Andenallene, ANDREA-1, Androstanolone, Anguillosporal, Anguinomycin C, Anguinomycin D, Anidulafungin, Ankinomycin, Annamycin, Annocherimolin, Annulin C, Antheliatin, Antide, Antide-1, Antide-2, Antide-3, Antiflammin-1, Antiflammin-3, Antimycin A11, Antimycin A12, Antimycin A13, Antimycin A14, Antimycin A15, Antimycin A16, Apadenoson, Apalcillin sodium, Apaziquone, Aphidicolin, Aphidicolin Glycinate, Apicularen A, Apicularen B, Apigenin, Aplaviroc hydrochloride, Apomine, Apomorphine hydrochloride, Apricitabine, Aragusterol A, Aragusterol C, Aranorosin, Aranorosinol A, Aranorosinol B, Aranose, Arbekacin, Arbekacin sulfate, Arbidol, Arborcandin A, Arborcandin B, Arborcandin C, Arborcandin D, Arborcandin E, Arborcandin F, Arbutamine hydrochloride, Archazolid A, Archazolid B, Arformoterol tartrate, Argiotoxin-636, Arimoclomol maleate, Arisostatin A, Arisugacin A, Arotinolol hydrochloride, Artepillin C, Artilide fumarate, Arundifungin, Arzoxifene hydrochloride, Ascosteroside, Asiatic acid, Asiaticoside, Asimadoline, Asperlicin B, Asperlicin E, Aspoxicillin, Assamicin I, Assamicin II, Astromicin sulfate, Atalaphillidine, Atalaphillinine, Atazanavir sulfate, Atenolol, Atigliflozin, Atorvastatin, Atorvastatin calcium, Atorvastatin-Aliskiren, Atosiban, Atovaquone, Atraric acid, Atrinositol, Auristatin E, Aurothioglucose, Australifungin, Australine, Avicenol A, Avicequinone A, Avicin D, Avicin G, Avorelin, Axitirome, Azacitidine, Azaresveratrol, Azaromycin SC, Azatoxin, Azelastine embonate, Azepinostatin, Azithromycin, Azithromycin Copper Complex, Bactobolin, Bafilomycin A1, Bafilomycin C1, Baicalein, Baicalin, Balhimycin, Balofloxacin, Balofloxacin dihydrate, Balsalazide disodium, Bambuterol, Banoxantrone, Baogongteng A, Barixibat, Barusiban, Bazedoxifene acetate, Bazedoxifene hydrochloride, Becatecarin, Beciparcil, Beclometasone dipropionate, Becocalcidiol, Bedoradrine sulfate, Befloxatone, Befunolol hydrochloride, Begacestat, Belactin B, Belotecan hydrochloride, Benadrostin, Benanomicin A, Benanomicin B, Benastatin A, Benastatin B, Benastatin C, Benastatin D, Benexate cyclodextrin, Bengazole A, Bengazole B, Benzbromarone, Beraprost sodium, Berefrine, Berupipam maleate, Bervastatin, Besifloxacin hydrochloride, Beta-Boswellic Acid, beta-Mangostin, Betamethasone butyrate propionate, Betamethasone dipropionate, Beta-Sialosylcholesterol Sodium Salt, Betaxolol hydrochloride, Bevantolol hydrochloride, Biapenem, Biemnidin, Bimatoprost, Bimoclomol, Bimoclomol 1-oxide, Bimosiamose, Binfloxacin, Binodenoson, Biochanin A, Bioxalomycin alpha 1, Bioxalomycin alpha2, Bipranol hydrochloride, Bisabosqual B, Bisabosqual D, Bismuth subsalicylate, Bisoprolol fumarate, Bisphenol, Bitolterol mesylate, Bix, Bizelesin, Bleomycin A2 sulfate, Bogorol A, Bohemine, Boholmycin, Bolinaquinone, Borrelidin, Bosentan, Brandisianin A, Brandisianin B, Brandisianin C, Brasilicardin A, Brasilinolide A, Brasilinolide B, Brecanavir, Breflate, Brevifolin carboxylic acid, Breynin A, Breynin B, Brivanib, Brivudine, Bromotopsentin, Bryostatin 1, Bryostatin 10, Bryostatin 11, Bryostatin 12, Bryostatin 13, Bryostatin 9, Budesonide, Buflomedil pyridoxalphosphate, Bungeolic acid, Buprenorphine hydrochloride, Buserelin acetate, Butalactin, Butein, Buteranol, Butixocort, Butofilolol, Butorphan, Butorphanol tartrate, Byssochlamysol, Cabazitaxel, Cabin 1, Cadralazine, Cadrofloxacin hydrochloride, Caffeine citrate, Calanolide A, Calanolide B, Calbistrin A, Calbistrin B, Calbistrin C, Calbistrin D, Calcipotriol, Calcitriol, Calcium-like peptide 1, Calebin A, Calocoumarin A, Caloporoside B, Caloporoside C, Caloporoside D, Caloporoside E, Caloporoside F, Calphostin A, Calphostin B, Calphostin C, Calphostin D, Calphostin I, Calteridol calcium, Cambrescidin 800, Cambrescidin 816, Cambrescidin 830, Cambrescidin 844, Camiglibose, Campestanol ascorbyl phosphate, Canadensol, Canagliflozin, Candelalide B, Candelalide C, Cangrelor tetrasodium, Canventol, Capadenoson, Capecitabine, Capillarisin, Caprazamycin A, Caprazamycin B, Caprazamycin C, Caprazamycin E, Caprazamycin F, Capridine beta, Capsazepine, Carabersat, Carbazomadurin A, Carbazomadurin B, Carbetocin, Carbidopa, Carbovir, Caribaeoside, Carisbamate, Carmoterol hydrochloride, Carpesterol, Carquinostatin A, Carsatrin, Carteolol hydrochloride, Carteramine A, Carvastatin, Carvedilol, Caspofungin acetate, Cassigalol A, Castanospermine, Cefbuperazone sodium, Cefcanel, Cefetecol, Cefonicid sodium, Cefoperazone sodium, Cefoselis sulfate, Cefpiramide sodium, Cefprozil, Cefprozil monohydrate, Celgosivir, Celikalim, Celiprolol hydrochloride, Cephalostatin 1, Cephalostatin 2, Cephalostatin 3, Cephalostatin 4, Cephalostatin 7, Cephalostatin 8, Cephalostatin 9, Ceramidastin, Cerebroside A, Cerebroside B, Cerebroside C, Cerebroside D, Cerivastatin sodium, Ceruletide diethylamine, Cetefloxacin, Cethromycin, Cetrorelix Acetate, Chackol, Chaetoatrosin A, Chafuroside, Chenodeoxycholic acid, Chetocin, Chinoin-169, Chloptosin, Chlorazicomycin, Chlorofusin, Chlorogentisylquinone, Chloroorienticin A, Chloroorienticin B, Cholerae Autoinducer-1, Choline alfoscerate, Chondramide A, Chondramide B, Chondramide C, Ciclesonide, Cicletanine, Cidofovir, Cimaterol, Cimetropium bromide, Cinatrin A, Cinatrin B, Cinatrin C1, Cinatrin C2, Cinnabaramide A, Cinnatriacetin A, Cinnatriacetin B, Cinolazepam, Ciprofloxacin hydrochloride, Ciprokiren, cis-6-Shogaol, Citicoline, Citpressine I, Citreamicin-Alpha, Citreamicin-eta, Citropeptin, Citrullimycine A, Citrusinine-I, Cladribine, Clarithromycin, Clausenamine A, Clavaric acid, Clavarinone, Clavulanate potassium, Clazosentan, Clevudine, Clindamycin hydrochloride, Clitocine, Clobenoside, Clofarabine, Clopithepin, Cloranolol hydrochloride, Cocositol, Colabomycin A, Coleneuramide, Coleophomone B, Colestimide, Colforsin, Colforsin daproate hydrochloride, Colletoic acid, Colupulon, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Conagenin, Coniferol Alcohol, Coniosetin, Conocurvone, Conophylline, Contignasterol, Contulakin G, Cortexolone 17alpha-propionate, Corynecandin, Cosalane, Cositecan, Costatolide, Coumamidine Gamma1, Coumamidine Gamma2, Crassicauline A, Crellastatin A, Crisamicin C, Crisnatol mesilate, Crobenetine, Crobenetine hydrochloride, Cromakalim, Crossoptine A, Crossoptine B, Curtisian A, Curtisian B, Curtisian D, Curvularol, Cyanidin Chloride Monohydrate, Cyclamenol, Cyclandelate, Cyclipostin A, Cyclocommunol, Cyclohexanediol, Cyclomarin A, Cyclooctatin, Cycloplatam, Cycloproparadicicol, Cyclosporin A, Cyclosporin J, Cyclotheonamide A, Cyclothialidine, Cygalovir, Cypemycin, Cyrtominetin, Cystocin, Cystothiazole C, Cystothiazole D, Cystothiazole F, Cytallene, Cytarabine, Cytaramycin, Cytoblastin, Cytochalasin B, Cytochlor, Cytogenin, Cytosporic acid, Cytosporone B, Cytostatin, Cytotrienin I, Cytotrienin II, Cytotrienin III, Cytotrienin IV, Cytoxazone, DACH-Pt(II)-bis-ascorbate, Dacinostat, Dactimicin, Dactylfungin A, Dactylfungin B, Dactylocycline A, Dactylocycline B, Dactylorhin B, DADMe-Immucillin-G, DADMe-Immucillin-H, Dalargin, Dalbavancin, Dalfopristin mesilate, Dalvastatin, Damunacantal, Danofloxacin, Dapagliflozin, Daphnodorin A, Daphnodorin B, Daphnodorin C ((−)-enantiomer), Dapropterin dihydrochloride, Darbufelone, Darbufelone mesilate, Darunavir, Dasantafil, Dasatinib, Daunorubicin, Daurichromenic acid, Davidigenin, Davunetide, Deacetyl moxisylyte hydrochloride, Decahydromoenomycin A, Decaplanin, Decarestrictine C, Decarestrictine D, Decatromicin A, Decatromicin B, Decitabine, Decursinol, Decyl gallate, Deferasirox, Deferiprone, Deflazacort, Deforolimus, Degarelix acetate, Dehydelone, Dehydrodolastatin-13, Dehydrozingerone, Delafloxacin, Delaminomycin A, Delaminomycin B, Delaminomycin C, Delimotecan sodium, Delphinidin, delta-Tocopherol glucoside, Deltibant, Demethimmunomycin, Demethomycin, Demethylallosamidin, Demethylasterriquinone B-1, Denopamine, Denufosol tetrasodium, Deoxyenterocin, Deoxylaidlomycin, Deoxymulundocandin, Deoxynojirimycin, Deoxyspergualin Hydrochloride, Deprodone propionate, Dersalazine, Desacetyleleutherobin, Desacetylravidomycin N-oxide, Desacetylvinblastinehydrazide, Desacetylvinblastinehydrazide/folate conjugate, Desbutyl benflumetol, Desbutylhalofantrine hydrochloride, Desferri-danoxamine, Desferri-nordanoxamine, Desferri-salmycin A, Desferri-salmycin B, Desferri-salmycin C, Desferri-salmycin D, Desglugastrin tromethamine, Desisobutyrylciclesonide, Deslorelin, Desmethyleleutherobin, Desmin-370, Desmopressin acetate, Desoxyepothilone E, Desoxyepothilone F, Desoxylaulimalide, Desvenlafaxine succinate, Dexamethasone, Dexamethasone beloxil, Dexamethasone cipecilate, Dexamethasone Palmitate, Dexamethasone sodium phosphate, Dexanabinol, Dexelvucitabine, Dextrorphan, Dexylosylbenanomycin A, D-Fluviabactin, DHA-paclitaxel, Diadenosine tetraphosphate, Diazaphilonic acid, Diazepinomicin, Dicoumarol, Dictyostatin 1, Didemnin X, Didemnin Y, Dideoxyinosine, Dieckol, Diepoxin-sigma, Diflomotecan, Diflunisal, Digalactosyldiacylglycerol, Digoxin, Diheteropeptin, Dihydrexidine, Dihydroavenanthramide D, Dihydrocostatolide, Dihydroeponemycin, Dihydrogranaticin B, Dihydroheptaprenol, Dihydrohonokiol B, Dihydroisosteviol, Dihydroraloxifene, Dilevalol, Dilevalol hydrochloride, Dilmapimod, Dimelamol, Dimethandrolone, Dimethylcurcumin, di-mPEG5-Atazanavir, Dinaphine, Dinapsoline, Dinoxyline, Dioncoquinone A, Dioncoquinone B, Dioxolane thymine nucleoside, Dipivefrine hydrochloride, Dipotassium gossypolate, Dipyridamole, Dipyridamole beta-cyclodextrin complex, Diquafosol tetrasodium, Dirithromycin, Discodermide, Discodermide acetate, Disermolide, Disodium cromproxate, Disodium lettusate, Disorazol E1, Dobutamine hydrochloride, Dobutamine Phosphate, Docetaxel, Docosanol, Docosyl cidofovir, Dofequidar fumarate, Dolastatin 13, Dopexamine, Dopexamine hydrochloride, Doqualast, Doramectin, Doranidazole, Doretinel, Doripenem, Dorrigocin A, Dorrigocin B, Dosmalfate, Dovitinib Lactate, Doxefazepam, Doxercalciferol, Doxifluridine, Doxorubicin Hydrochloride, Doxorubicin, Morpholinyl, DoxoTam 12, Doxycycline hyclate, Dridocainide, Dronabinol, Droxidopa, Droxinavir, DTPA-adenosylcobalamin, Duocarmycin B1, Duocarmycin B2, Duocarmycin C1, Duocarmycin C2, Duramycin, Dutomycin, Dynemicin A, Dynemicin C, Ecdysterone, Ecenofloxacin hydrochloride, Ecomustine, Econazole Sulfosalicylate, Ecopipam, Ecraprost, Ecteinascidin 1560, Ecteinascidin 722, Ecteinascidin 729, Ecteinascidin 736, Ecteinascidin 745, Ecteinascidin 757, Ecteinascidin 770, Ecteinascidin 875, Edotecarin, Edotreotide yttrium, Efepristin, Eflucimibe, Eflumast, Eicosyl cidofovir, Elacytarabine, Elansolid C1, Eldacimibe, Eldecalcitol, Eleutherobin, Eleutheroside B, Eliprodil, Elisapterosin B, Ellagic acid-4-gallate, Elliptinium acetate, Elocalcitol, Elomotecan hydrochloride, Elsibucol, Eltanolone, Eltrombopag olamine, Elvitegravir, Elvucitabine, Emakalim, Embelin, Emestrin C, Emodin, Emtricitabine, Enalkiren, Enazadrem, Enfumafungin, Englerin A, Enigmol, Enkastin (D), Enkastin AD, Enkastin AE, Enkastin ID, Enkastin IE, Enkastin VD, Enkastin VE, Enocitabine, Enofelast, Enoloxone, Enoxacin, Enprostil, Enrasentan, Enrofloxacin, Entacapone, Entecavir, ent-Estriol, Eperezolid, Eperezolid N-oxide, Epervudine, Epicochlioquinone A, Epidoxoform, Epigallocatechin-3-gallate, Epirubicin hydrochloride, Epispongiadiol, Eplivanserin, Eplivanserin fumarate, Eplivanserin mesilate, Epocarbazolin A, Epocarbazolin B, Epofolate, Eponemycin, Epoprostenol sodium, Epothilone A, Epothilone A N-oxide, Epothilone B N-oxide, Epothilone E, Epoxomicin, Epoxyvibsanin B, Eprotirome, Eptaloprost, Eptastatin sodium, Eptastigmine Tartrate, Eptazocine hydrobromide, Erabulenol A, Erabulenol B, Erectumin A, Eremomycin, Eremophyllene A, Eribulin mesilate, Eriocalyxin B, Eritoran tetrasodium, Ersentilide, Ersentilide hydrochloride, Ertapenem sodium, Eryloside A, Eryloside F, Erythritol, Erythrodiol, Erythromycin, Erythromycin Acistrate, Erythromycin salnacedin, Erythromycin stinoprate, Esafloxacin Hydrochloride, Esculeogenin A, Esculeoside A, Esmolol hydrochloride, Espatropate hydrate, Esperatrucin, Estetrol, Estradiol, Estradiol acetate, Estren, Estriol, Etalocib sodium, Etamsylate, Ethanolamine, Ethinylestradiol, Ethyl gallate, Ethylthio-DADMe-immucillin-A, Ethynylcytidine, Etiprednol diclo acetate, Etoposide, Etoposide phosphate disodium salt, Eugenodilol, Eugenosedin A, Euphodendroidin D, Eurotinone, Euxanthone, Evernimicin, Everolimus, Exatecan mesilate, Exifone, Ezetimibe, Ezetimibe glucuronide, Fadolmidine hydrochloride, Faeriefungin A, Faeriefungin B, Fandofloxacin hydrochloride, Faropenem medoxomil, Faropenem sodium, Fasobegron hydrochloride, Fattiviracin A1, Favipiravir, Febradinol, Febuprol, Feglymycin, Fenoldopam mesilate, Fenoterol hydrobromide, Ferpifosate sodium, Ferulinolol, Fesoterodine fumarate, Fexofenadine hydrochloride, Fidaxomicin, Fidexaban, Filibuvir, Fimbrigal P, Finafloxacin hydrochloride, Fingolimod hydrochloride, Finrozole, Fleroxacin, Flomoxef Sodium, Flopristin, Floxuridine, Fludarabine phosphate, Fludelone, Fludeoxyglucose (18F), Flunisolide, Flunoprost, Fluocinonide, Fluoroindolocarbazole A, Fluoroindolocarbazole B, Fluoroindolocarbazole C, Fluoroneplanocin A, Fluostatin A, Fluostatin B, Flupentixol hydrochloride, Fluphenazine hydrochloride, Flurithromycin, Fluticasone furoate, Fluticasone propionate, Fluvastatin sodium, Fluvirucin B2, Foetidine 1, Foetidine 2, Folinic acid, Folipastatin, Fondaparinux sodium, Formamicin, Formestane, Formobactin, Formosyn A, Formoterol fumarate, Forodesine hydrochloride, Fosopamine, Fosteabine sodium hydrate, Frederine, Fucoxanthin, Fudosteine, Fuladectin component A3, Fuladectin component A4, Fulvestrant, Fumagalone, Furaquinocin A, Furaquinocin B, Fusacandin A, Fusacandin B, Fuscoside B, Fusidate silver, Fusidienol, Gaboxadol, Gabusectin, Gabusectin methyl ester, Gadobutrol, Gadocoletic acid trisodium salt, Gadomelitol, Gadoterate meglumine, Gadoteridol, Galactomycin I, Galactomycin II, Galactosyllactose, Galamustine hydrochloride, Galantamine hydrobromide, Galarubicin hydrochloride, Galocitabine, Gambogic acid, gamma-Mangostin, gamma-Tocotrienol, Ganciclovir, Ganciclovir elaidic acid, Ganciclovir monophosphate, Ganciclovir Sodium, Ganefromycin Alpha, Ganefromycin Beta, Ganglio side GM1, Ganirelix, Ganirelix acetate, Ganoderic acid X, Garenoxacin mesilate, Garomefrine hydrochloride, Garvalone C, Garveatin E, Garveatin F, Gatifloxacin, Gemcitabine, Gemcitabine elaidate, Gemeprost, Gemifloxacin mesilate, Genipin, Genistein-7-phosphate, Gigantol, Gilatide, Gilvusmycin, Gimestat, Girodazole, Glaucocalyxin A, Glemanserin, Glenvastatin, Glidobactin PF-1, Glucarolactam potassium, Glucolanomycin, Glucolipsin A, Glucolipsin B, Glucopiericidinol A1, Glucopiericidinol A2, Glucosamine sulfate, Gludopa, Glufosfamide, Glycopin, Glycothiohexide alpha, Glycyrrhizinic acid, Gomphostenin, Goodyeroside A, Goodyeroside B, Goralatide, Goserelin, Granaticin B, Grepafloxacin hydrochloride, Griseusin C, Halistatin 1, Halistatin 2, Halistatin 3, Halobetasol propionate, Halofantrine hydrochloride, Halofuginone hydrobromide, Halometasone, Halopredone Acetate, Halovir A, Halovir B, Halovir C, Halovir D, Halovir E, Halxazone, Haperforine B1, Hatomamicin, Hatomarubigin A, Hatomarubigin B, Hatomarubigin C, Hatomarubigin D, Hattalin, Hayumicin A, Hayumicin B, Hayumicin C1, Hayumicin C2, Hayumicin D, Hederacolchiside E, Heliquinomycin, Helvecardin A, Helvecardin B, Heptaminol AMP Amidate, Hericenal A, Hericenal B, Hericenal C, Hexadecyl cidofovir, Hexadecyloxypropyl-cidofovir, Hexafluorocalcitriol, Hidrosmin, Himastatin, Histrelin, Histrelin acetate, Hongoquercin A, Hongoquercin B, Honokiol diepoxide, Human angiotensin II, Hyaluronate sodium, Hydrocortisone Aceponate, Hydromorphone methiodide, Hydrostatin A, Hydroxyakalone, Hydroxychloroquine sulfate, Hydroxymycotrienin A, Hydroxymycotrienin B, Hydroxyphoslactomycin B, Hydroxyzine hydrochloride, Hymenistatin 1, Hypeptin, Hypericin, Hyperoside, Hypocholamide, Hypocholaride, Ibutilide fumarate, Icariin, Icatibant acetate, Idarubicin hydrochloride, Idebenone, Idremcinal, Idronoxil, Ifenprodil, Ilatreotide, Iliparcil, Ilonidap, Iloprost, Imidazoacridinone, Imipenem, Immunosine, Implitapide, Incyclinide, Indacaterol, Indanaprost (S), Indanocine, Indinavir sulfate, Indomethacin-Simvastatin, Indynaprost, Ingenol mebutate, Inophyllum B, Inophyllum P, Inosiplex, Integracide A, Integracide B, Integracin A, Integracin B, Integracin C, Integramycin, Integrastatin A, Integrastatin B, Intoplicine, Iobitridol, Iodixanol, Iodochlorhydroxyquin, Iododiflunisal, Iodorubidazone (p), Iofratol, Iohexol, Iolopride (123I), Iomeprol, Iopamidol, Iopentol, Iopromide, Iotriside, Iotrol, Ioversol, Ioxilan, Ioxipride, Ipratropium bromide, Iralukast, Iralukast sodium, Irciniastatin A, Irciniastatin B, Irinotecan hydrochloride, Irofulven, Isalmadol, Isepamicin sulfate, Isobavachalcone, Isodoxorubicin, Isoeleutherobin A, Isofagomine tartrate, Isofloxythepin, Isohomohalichondrin B, Iso-iantheran A, Isoliquiritigenin, Isomolpan Hydrochloride, Isoquine, Isosorbide 5-mononitrate, Isospongiadiol, Isovanihuperzine A, Isoxazoledehydelone, Isoxazolefludelone, Itavastatin calcium, Itrocinonide, Ixabepilone, Jadomycin B, Janthinomycin A, Janthinomycin B, Janthinomycin C, Jasplakinolide, Jorumycin, Kadsuphilin C, Kahalalide F, Kaitocephalin, Kampanol A, Kampanol B, Kanamycin, Kanglemycin A, Kansuinin B, kappa-Conotoxin P VIIA, Kapurimycin A1, Kapurimycin A3, Karalicin, Karnamicin B1, Katanosin A, Katanosin B, Kehokorin D, Kehokorin E, Khafrefungin, Kifunensine, Kigamicin A, Kigamicin B, Kigamicin C, Kigamicin D, Kigamicin E, Kigamicinone, Kijimicin, Kinsenoside, Kistamicin A, Klainetin A, Klainetin B, Kobifuranone B, Kobiin, Kodaistatin A, Kodaistatin B, Kodaistatin C, Kodaistatin D, Korupensamine A, Korupensamine B, Korupensamine C, Korupensamine D, Kosinostatin, Kuehneromycin A, Kurasoin B, Kynostatin-227, Kynostatin-272, Labedipinedilol A, Labedipinedilol B, Labetalol hydrochloride, Labradimil, Laccaridione A, Lactonamycin, Lactosylphenyl trolox, Ladirubicin, Lagatide, Laherradurin, Lamellarin alpha 20-sulfate sodium salt, Lamifiban, Lamivudine, Landiolol, Lanreotide acetate, Lanthiopeptin, Larotaxel dihydrate, Lasinavir, Lasofoxifene, Lasofoxifene tartrate, Lasonolide A, Latamoxef sodium, Latanoprost, Latrunculin S, Lavanduquinocin, L-Chicoric acid, L-Dopamide, Lecirelin, Ledazerol, Leinamycin, Lemuteporphin, Lenapenem hydrochloride, Lenapenem hydrochloride hydrate, Leptofuranin A, Leptofuranin B, Lersivirine, Lestaurtinib, Leuprolide acetate, Leurubicin, Leustroducsin A, Leustroducsin B, Leustroducsin C, Leustroducsin H, Levalbuterol hydrochloride, Levobetaxolol hydrochloride, Levobunolol hydrochloride, Levodopa, Levodopa 3-O-glucoside, Levodopa 4-O-glucoside, Levodropropizine, Levofloxacin, Levonadifloxacin arginine salt, Levonebivolol, Levorphanol tartrate, Lexacalcitol, L-Fluviabactin, L-Histidinol, Liblomycin, Licoricesaponin C2, Lificiguat, Limaprost alfadex, Linaprazan, Linopristin, Lipiarmycin B3, Lipiarmycin B4, Liquiritin apioside, Lisofylline, Lithospermic acid B magnesium salt, Lobatamide C, Lobatamide F, Lobophorin A, Lobophorin B, Lobucavir, Lodenafil, Lodenosine, Loloatin B, Lomefloxacin hydrochloride, Lometrexol, Longestin, Lopinavir, Lorazepam, Lormetazepam, Lornoxicam, Losartan, Losartan potassium, Losigamone, Loteprednol etabonate, Lovastatin, Loxoribine, L-threitol ceramide, L-threo-C6-pyridinium-ceramide-bromide, Lubeluzole, Lumefantrine, Luminacin D, Lupulone, Lurtotecan, Luteolin, Lu-Tex bis(gluconate), Lysobactin, Mabuterol hydrochloride, Macquarimycin B, Macrocarpin A, Macrocarpin B, Macrolactine M, Madecassic acid, Madecassoside, Makaluvamine D, Makaluvamine E, Malonoben, Maltolyl p-coumarate, Manitimus, Mannopeptimycin alpha, Mannopeptimycin beta, Mannopeptimycin delta, Mannopeptimycin epsilon, Mannopeptimycin gamma, Manoalide, Manumycin A, Manumycin B, Manumycin C, Manumycin E, Manumycin F, Manumycin G, Manzamine F, Marbofloxacin, Maribavir, Marimastat, Marinopyrrole A, Marmelin, Maslinic acid, Masoprocol, Mastprom, Matteuorienate A, Matteuorienate B, Matteuorienate C, Mazokalim, Medicarpin, Mefloquine hydrochloride, Megovalicin A, Megovalicin B, Megovalicin C, Megovalicin D, Megovalicin G, Megovalicin H, Melevodopa hydrochloride, Mellein, Meloxicam, Meluadrine, Meluadrine tartrate, Memno-peptide A, Mepindolol sulfate, Mepindolol transdermal patch, Meptazinol hydrochloride, Meropenem, Mesalazine, Metaraminol, Metesind glucuronate, Methanobactin, Methoxatone, Methscopolamine bromide, Methyl bestatin, Methyl gallate, Methyldopa, Methylnaltrexone bromide, Methylprednisolone, Methylprednisolone aceponate, Methylpredniso lone suleptanate, Methylthio-DADMe-immucillin-A, Methysergide maleate, Metildigoxin, Metipranolol, Metirosine, Metoprolol Fumarate, Metoprolol succinate, Metoprolol tartrate, Metrifonate, Metronidazole, Micacocidin A, Micacocidin B, Micafungin sodium, Michellamine B, Michigazone, Microbisporicin A2, Microcolin A, Micronomicin sulfate, Midecamycin acetate, Mideplanin, Miglitol, Miglustat, Milataxel, Milbemycin alpha-9, Milrinone Lactate, Mimopezil, Minerval, Minocycline hydrochloride, Miporamicin, Mipragoside, Miproxifene, Mirabegron, Mirodenafil hydrochloride, Misakinolide, Misoprostol, Mitemcinal fumarate, Mitoxantrone hydrochloride, Mivazerol, Mizoribine, Modecainide, Modithromycin, Moenomycin A chloride bismuth salt, Mollugin, Mometasone furoate, Momordin Ic, Monamidocin, Monlicin A, Monogalactosyldiacylglycerol, Monohydroxyethylrutoside, Monophosphoryl lipid A, Montelukast sodium, Morphine Glucuronide, Morphine hydrochloride, Morphine sulfate, Motexafin gadolinium, Motexafin lutetium, Moxidectin, Moxifetin hydrogen maleate, Moxifloxacin hydrochloride, Mozenavir mesilate, Multiforisin A, Mumbaistatin, Mupirocin, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl dipeptide C, Mureidomycin A, Mureidomycin B, Mureidomycin C, Mureidomycin D, Mureidomycin E, Mureidomycin F, Mureidomycins, Mycalamide A, Mycestericin E, Mycolactone A, Mycolactone B, Mycophenolate Mofetil, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, N4-Hexadecyl-dC-AZT, N-9-Oxadecyl-6-methyl-DGJ, Naamidine A, Nabilone, N-Acetylcolchinol, N-Acetylsperamycin A1, N-Acetylsperamycin A1B, N-Acetylsperamycin A2, Nadifloxacin, Nadolol, Nafarelin acetate, Naftopidil, Nafuredin, Nafuredin-gamma, Nagstatin, Nalbuphine hydrochloride, Nalfurafine hydrochloride, N-Allylsecoboldine, Nalmefene, Naloxone hydrochloride, Naltrexone hydrochloride, Naltrindole, Namitecan, Napsamycin A, Napsamycin B, Napsamycin C, Napsamycin D, Nardeterol, Naroparcil, Navuridine, N-Cyclopentyl-tazopsine, Nebicapone, Nebivolol, Nectrisine, Neldazosin, Nelfinavir mesilate, Nelivaptan, Nelzarabine, Nemifitide ditriflutate, Nemonoxacin, Nemorubicin, Neocimicigenoside A, Neocimicigenoside B, Neolaulimalide, Neomycin B-arginine conjugate, Neomycin-acridine, Nepadutant, Neparensinol A, Neparensinol B, Neparensinol C, Nerfilin I, Neristatin 1, Nesbuvir, Netilmicin sulfate, Netivudine, Neu5Ac2en, Ngercheumicin A, Ngercheumicin B, N-hexacosanol, Nicanartine, Nifekalant hydrochloride, Nileprost beta-cyclodextrin clathrate, Nipradolol, Nitecapone, Nitropravastatin, N-Nonyl-deoxygalactojirimycin, Nocardione A, Nocathiacin I, Nocathiacin II, Nocathiacin III, Nocathiacin IV, N-Octyl-beta-valienamine, NO-hydrocortisone, Noladin ether, NO-Mesalamine, Nooglutil, Noraristeromycin, Nordamunacantal, Norfloxacin, Norfloxacin succinil, Nortopixantrone hydrochloride, Nostocyclopeptide M1, Nothramicin, NO-Ursodeoxycholic acid, N-Retinoyl-D-glucosamine, N-tert butyl isoquine, Nubiotic 2, Nutlin-2, Obelmycin H, Oberadilol, Oberadilol Monoethyl Maleate, Obeticholic acid, Ochromycinone, Ocimumoside A, Ocimumoside B, Octacosamicin A, Octacosamicin B, Octreotide Acetate, Octyl gallate, Odapipam acetate, O-Demethylchlorothricin, O-Demethylmurrayafoline A, Odiparcil, Oenothein B, Ofloxacin, Okicenone, Olamufloxacin, Olamufloxacin mesilate, Olanzapine pamoate, Olcegepant, Oleanolic acid, Oleoyl-L-Valinol amide, Olsalazine sodium, Omaciclovir, Ombrabulin, Ombrabulin hydrochloride, Onjixanthone I, Onjixanthone II, Onnamide A, Oolonghomobisflavan A, Oolonghomobisflavan C, OPC-17083, Opiorphin, Opipramol hydrochloride, Orbifloxacin, Orciprenaline sulphate, Orienticin A, Orienticin B, Orienticin C, Orienticin D, Oritavancin, Orniplabin, Ornoprostil, Ortataxel, Orthosomycin A, Orthosomycin B, Orthosomycin C, Orthosomycin D, Orthosomycin E, Orthosomycin F, Orthosomycin G, Orthosomycin H, Ospemifene, Osutidine, Oxaspirol A, Oxaspirol B, Oxazepam, Oxazofurin, Oxeclosporin, Oximidine III, Oxiracetam, Oxitropium bromide, Oxolide, Oxprenolol hydrochloride, Oxymetazoline hydrochloride, Oxymethacyl, Oxymorphazole dihydrochloride, Oxymorphone hydrochloride, Oxynor, Oxyphenarsine, Ozarelix, Ozenoxacin, Pachastrissamine, Pachymedusa dacnicolor Tryptophyllin-1, Paciforgine, Paclitaxel, Paclitaxel ceribate, Paeciaminol, Paeciloquinine A, Paeciloquinine D, Paeciloquinone B, Paeciloquinone D, Pafenolol, Palau'amine, Paldimycin B, Palinavir, Palmidrol, Pamapimod, Pamaqueside, Pancratistatin disodium phosphate, Pancratistatin-3,4-cyclic phosphate sodium salt, Panipenem, Pannorin, Pantethine, Papuamide A, Papuamide B, Papuamide C, Papuamide D, Paquinimod, Paracetamol, Parasin I, Paricalcitol, Parodilol Hemifumarate, Paromomycin, Parvisporin B, Patellazole A, Patellazole B, Patellazole C, Patupilone, Paulomycin, Paulomycin A2, Paulomycin B, Paulomycin C, Paulomycin D, Paulomycin E, Paulomycin F, Pazufloxacin, Pazufloxacin mesilate, Pefloxacin, PEG40000-Paclitaxel, PEG5000-Paclitaxel, PEG-conjugated camptothecin, PEG-vancomycin, Pelitrexol, Peloruside A, Penasterol, Penbutolol sulfate, Penciclovir, Penicillide, Pentazocine hydrochloride, Pentostatin, Peplomycin, Pepticinnamin E, Peramivir, Percyquinnin, Periciazine, Perillyl alcohol, Perphenazine, Persin, Petrosaspongiolide M, PG-camptothecin, Phaffiaol, Phakellistatin 7, Phakellistatin 8, Phakellistatin 9, Phaseolinone, Phenochalasin A, Phenprocoumon, Phentolamine mesilate, Philinopside A, Phlorofucofuroeckol, Phomactin A, Phomactin B, Phomoidride A, Phomopsichalasin, Phorboxazole A, Phorboxazole B, Phospholine, Phthalascidin, Physostigmine salicylate, Piceatannol, Picumeterol fumarate, Pidobenzone, Pimecrolimus, Pimilprost, Pindolol, Pinitol, Pinocembrin, Pipendoxifene, Pipotiazine, Pirarubicin, Pirbuterol hydrochloride, Pirfenoxone, Pirodomast, Pironetin, Piroxicam, Pittsburgh Compound B, Pladienolide A, Pladienolide B, Pladienolide C, Pladienolide D, Pladienolide E, Plantagoside, Platencin, Platensimycin, Plaunotol, Plevitrexed, Plitidepsin, Pluraflavin A, Pluraflavin B, Pluraflavin E, Plusbacin A1, Plusbacin A2, Plusbacin A3, Plusbacin A4, Plusbacin B1, Plusbacin B2, Plusbacin B3, Plusbacin B4, Pneumocandin A0, Pneumocandin B0, Pneumocandin B0 2-phosphate, Pneumocandin D0, Podophyllotoxin, Polyestradiol phosphate, Polyketomycin, Polymer bound human leukocyte elastase inhibitor, Ponalrestat, Popolohuanone E, Posaconazole, Posizolid, Potassium embelate, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pradofloxacin, Prasterone, Prednicarbate, Prednisolone, Prednisolone acetate, Prednisolone farnesylate, Prednisone, Prefolic A, Premafloxacin, Premafloxacin hydrochloride, Preussin, Prinaberel, Prisotinol, Pristinamycin IA, Pristinamycin HA, Proamipide, Probestin, Probucol, Procaterol Hydrochloride Hemihydrate, Prolylmeridamycin, Propafenone hydrochloride, Propeptin T, Propofol, Propranolol hydrochloride, Propyl gallate, Prostanit, Prostatin, Prostratin, Protocatechuic acid, Protocatechuic aldehyde, Proxodolol, Prulifloxacin, Prulifloxacin Hydrochloride, Prulifloxacin Mesylate, Pseudoephedrine hydrochloride, Pseudohypericin, Pseudomycin A', Pseudomycin B', Purpuromycin, Purvalanol A, Pycnanthuquinone A, Pycnanthuquinone B, Pyloricidin B, Pyridavone, Pyrindamycin A, Pyrindamycin B, Pyripyropene A, Pyripyropene B, Pyripyropene C, Pyripyropene D, Pyrrolosporin A, Quartromicin A1, Quartromicin A2, Quartromicin A3, Quartromicin D1, Quartromicin D2, Quartromicin D3, Quercetin-3-O-methyl ether, Quetiapine fumarate, Quinagolide hydrochloride, Quinidine, Quinobene, Quinoxapeptin C, Quinupristin Mesilate, rac-Apogossypolone, Rac-Tolterodine, Rafabegron, Raloxifene hydrochloride, Raltitrexed, Raluridine, Rameswaralide, Ramoplanin A'1, Ramoplanin A'2, Ramoplanin A'3, Ramorelix, Ranimustine, Ranolazine, Rapamycin, Ravidomycin N-oxide, Rawsonol, Razupenem, Rebamipide bismuth citrate tetramethyledamine, Reblastatin, Regadenoson, Remikiren mesilate, Remiprostol, Remogliflozin etabonate, Repandiol, Reproterol hydrochloride, Resobene, Resorthiomycin, Retapamulin, Retaspimycin hydrochloride, Revatropate, Reveromycin A, Rhodiocyanoside A, Rhodiocyanoside B, Rhododaurichromanic acid A, Rhodostreptomycin A, Rhodostreptomycin B, Ribavirin, Ribavirin eicosenate cis, Ribavirin eicosenate trans, Ribavirin elaidate, Ribavirin oleate, Rifabutin, Rifalazil, Rifamexil, Rifampicin, Rifapentine, Rifaximin, Rilmakalim hemihydrate, Rimexo lone, Rimoterol hydrobromide, Riodoxol, Ritipenem acoxil, Ritonavir, Rivastigmine tartrate, Rivenprost, Rocagloic acid, Rocuronium bromide, Rofleponide, Rofleponide palmitate, Rohitukine, Rokitamycin, Rolliniastatin 1, Romurtide, Roquinimex, Rosaprostol sodium, Roscovitine, Roselipin 1A, Roselipin 1B, Roselipin 2A, Roselipin 2B, Rostafuroxine, Rosuvastatin calcium, Rosuvastatin sodium, Rotigaptide, Rotigotine, Roxatidine bismuth citrate, Roxindole Mesilate, Roxithromycin, Rubiginone A1, Rubiginone A2, Rubiginone B1, Rubiginone C1, Rubitecan, Ruboxyl, Rufigallol, Rufloxacin Gluconate, Rufloxacin hydrochloride, Rumycin 1, Rumycin 2, Russuphelin A, Sabarubicin hydrochloride, Safingol, Saintopin, Saintopin E, Saishin N, Sakyomicin A, Sakyomicin E, Salazopyridazin, Salbostatin, Salbutamol nitrate, Salbutamol sulfate, Salcaprozic acid sodium salt, Salicylazobenzoic acid, Salicylihalamide A, Salicylihalamide B, Salinamide A, Salinosporamide A, Saliphenylhalamide, Salmaterol, Salmeterol xinafoate, Saloxin, Salvianolic acid L, Samaderine X, Sampatrilat, Sanfetrinem, Sanfetrinem cilexetil, Sanfetrinem sodium, Sanglifehrin A, Sanglifehrin B, Sanglifehrin C, Sanglifehrin D, Sapacitabine, Saptomycin D, Sapurimycin, Saquinavir, Saquinavir mesilate, Sarcophytol A, Sarcophytol B, Saricandin, Saussureamine D, Saussureamine E, Sazetidine-A, Scopinast fumarate, Scopolamine, Scyphostatin, Secalciferol, Secobatzelline A, Secobatzelline B, Secoisolariciresinol diglucoside, Securioside A, Securioside B, Seglitide, Selamectin, Selank, Selodenoson, Semagacestat, Semduramicin, Semorphone hydrochloride, Seocalcitol, Seprilose, Sergliflozin etabonate, Serofendic acid, Sessiloside, Setamycin, Setazindol, Shepherdin, Shishijimicin A, Shishijimicin B, Shishijimicin C, Sialosylcholesterol-Alpha Sodium Salt, Sibanomicin, Sibenadet hydrochloride, Sibiskoside, Sildenafil citrate, Silodosin, Siltenzepine, Silychristin, Simotaxel, Simvastatin, Sinomenine, Sitafloxacin hydrate, Sitostanol ascorbyl phosphate, Sivifene, Siwenmycin, Sizofiran, Smilagenin, Socorromycin, Sodium cromoglycate, Sodium oxybate, Solabegron hydrochloride, Solpecainol hydrochloride, Sonedenoson, Sootepenseone, Soraprazan, Sorbicillactone A, Sorivudine, so-Simvastatin-6-one, Sotalol hydrochloride, Sparfloxacin, Sparoxomycin A1, Sparoxomycin A2, Sperabillin A, Sperabillin B, Sperabillin C, Sperabillin D, Sphingofungin F, Spinorphin, Spinosulfate A, Spinosulfate B, Spirocardin A, Spirocardin B, Spiroximicin, Spiruchostatin A, Spiruchostatin B, Spisulosine, Spongiadiol, Spongistatin 1, Spongistatin 3, Spongistatin 4, Spongistatin 5, Spongistatin 6, Spongistatin 7, Spongistatin 8, Spongistatin 9, Sporeamicin A, Sporeamicin B, Squalamine lactate, Squalestatin I, Stachybocin A, Stachybocin B, Stachybocin C, Stachybotrin C, Stachybotrydial, Staplabin, Starrhizin, Stavudine, Stelleramacrin A, Stelleramacrin B, Sterenin A, Sterenin C, Sterenin D, Streptomycin, Streptopyrrole, Styloguanidine, Suberosenol A, Succinobucol, Sugammadex sodium, Sulfasalazine, Sulfinosine, Sulfircin C, Sulopenem, Sulopenem etzadroxil, Sulphazocine, Sulphoquinovosyldiacylglycerol, Sulprostone, Sulukast, Sunflower trypsin inhibitor-1, Suplatast tosilate, Suronacrine maleate, Susalimod, Swiftiapregnene, Symbioimine, Synadenol, Synguanol, Syriacusin A, Syriacusin B, Syriacusin C, Syzygiol, Tacalcitol, Tacapenem pivoxil, Taccalonolide E, Tacrolimus, Tafluprost, Tageflar, Taiwanhomoflavone A, Takanawaene A, Takanawaene B, Takanawaene C, Talibegron, Talibegron hydrochloride, Talnetant, Tamandarin A, Tamandarin B, Tamolarizine Hydrochloride, Tanespimycin, TAP-doxorubicin, Tapentadol hydrochloride, Taramanon A, Tasquinimod, Taurohyodeoxycholic acid, Tautomycin, Taxuyunnanine, Tazofelone, Tazopsine, Tebipenem, Tebipenem cilexetyl, Tebipenem pivoxil, Tebufelone, Tecadenoson, Technetium Tc 99m depreotide, Teicoplanin-A2-1, Teicoplanin-A2-2, Teicoplanin-A2-3, Teicoplanin-A2-5, Telavancin hydrochloride, Telbivudine, Telinavir, Telithromycin, Temafloxacin hydrochloride, Temazepam, Temoporfin, Tempol, Temsirolimus, Temurtide, Tenidap, Teniposide, Tenoxicam, Tenuifoliside A, Tenuifoliside B, Tenuifoliside C, Tenuifoliside D, Terbutaline sulfate, Terestigmine tartrate, Terfenadine, Teriflunomide, Terlakiren, Ternatin, Terprenin, Terreulactone A, Terreulactone B, Terreulactone C, Terreulactone D, Tertatolol hydrochloride, Tesetaxel, Testosterone glucoside, Tetracosyl cidofovir, Tetracycline hydrochloride, Tetrafibricin, Tetragalloylquinic acid, Tetrahydrocortisol, Tetrahydrocurcumin, Tetrahydroechinocandin B, Tetrahydroswertianolin, Tetrahydroxyquinone, Tetromycin A, Tetromycin B, Tetronothiodin, Texenomycin A, Tezacitabine, Tezosentan, Tezosentan disodium, Thenorphine, Theopederin D, Theoperidin E, Theophylline rutoside, Thermozymocidin, Thiamet-G, Thiamphenicol, Thiarubrine E, Thiarubrine F, Thiarubrine G, Thiarubrine H, Thiazinotrienomycin B, Thiazinotrienomycin F, Thiazinotrienomycin G, Thiazohalostatin, Thielavin G, Thielocin B3, Thiofedrine, Thiomarinol, Thiomarinol B, Thiomarinol C, Thiomarinol D, Thiomarinol E, Thiomarinol F, Thioviridamide, Thioxamycin, Thrazarine, Thymallene, Thymectacin, Thymopentin, Tidembersat, Tienoxolol hydrochloride, Tigecycline, Tilisolol hydrochloride, Timolol hemihydrate, Timolol maleate, Tipelukast, Tipranavir, Tiqueside, Tisocalcitate, Tixocortol buryrate propionate, Toborinone, Tobramycin, Tocotrienol, Tokaramide A, Tolcapone, Toloxatone, Tolterodine Tartrate, Tolvaptan, Tolytoxin, Tomatine, Tomeglovir, Tonabersat, Topixantrone hydrochloride, Topotecan Acetate, Topotecane Hydrochloride, Topovale, Topsentine B1, Torcitabine, Torezolid, Tosedostat, Tosufloxacin, Tosufloxacin Tosilate, Trabectedin, Tradecamide, trans-Resveratrol, Trantinterol hydrochloride, Travoprost, Traxoprodil, Traxoprodil mesylate, Trecadrine, Trecetilide fumarate, Treprostinil diethanolamine, Treprostinil sodium, Triamcinolone acetonide, Triamcinolone hexacetonide, Trichodimerol, Trichomycin A, Trichostatin D, Triciferol, Triciribine, Triciribine phosphate, Trifluridine, Trilostane, Trimegestone, Trimidox, Trimoprostil, Triphendiol, Tripterin, Triptolide, Troglitazone, Trovafloxacin, Trovafloxacin hydrate, Trovafloxacin hydrochloride mesylate, Trovafloxacin mesilate, Troxacitabine, Tsukubamycin A, Tubastrine, Tubelactomicin A, Tuberactomycin B, Tuberactomycin D, Tuberactomycin E, Tubingensin B, Tubulysin A, Tubulysin B, Tubulysin C, Tucaresol, Tuftsin, Tulathromycin A, Tulathromycin B, Tulobuterol hydrochloride, Turbostatin 1, Turbostatin 2, Turbostatin 3, Turbostatin 4, Tyropeptin A10, Tyropeptin A6, Tyropeptin A9, Tyroservatide, Tyrphostin 47, Ubenimex, Ukrain, Ulifloxacin, Uncarinic acid A, Uncarinic acid B, Uncialamycin, Unoprostone, Unoprostone isopropyl ester, Ursodeoxycholic acid, Ustilipid A, Ustilipid B, Ustilipid C, Uvalol, Vadimezan, Valganciclovir hydrochloride, Valnemulin, Valonomycin A, Valopicitabine, Valrubicin, Vancomycin hydrochloride, Vancoresmycin, Vanidipinedilol, Vaninolol, Variapeptin, Vebufloxacin, Veinamitol, Velnacrine Maleate, Velusetrag, Venorphin, Vermisporin, Vernakalant hydrochloride, Verticillatine, Vexibinol, Vialinin B, Vicenistatin, Vinaxanthone, Vindesine, Vinfosiltine sulfate, Vinleucinol, Vinylamycin, Viquidacin, Viramidine Hydrochloride, Viranamycin-A, Viranamycin-B, Viscosin, Vitilevuamide, Voclosporin, Voglibose, Volinanserin, Volpristin, Voreloxin, W Peptide, Wiedendiol A, Wiedendiol B, Woodorien, Xamoterol Fumarate, Xanthoangelol E, Xanthofulvin, Xanthomegnin, Xenovulene A, Xipamide, Xylocydine, Yatakemycin, Yohimbine, Zabofloxacin hydrochloride, Zahavin B, Zalcitabine, Zampanolide, Zanamivir, Zankiren, Zaragozic acid D3, Zelandopam hydrochloride, Z-Eleutherobin, Zenarestat, Zidovudine, Zilascorb (2H), Zilpaterol, Zonampanel, Zorubicin hydrochloride, Zosuquidar trihydrochloride, Zotarolimus, Zoticasone propionate, Zuclopenthixol hydrochloride.

Suitable small molecule drugs comprising a carboxyl functional group are, for example, (−)-Subersic acid, (+)-Deoxoartelinic acid, (+)-Hemipalmitoylcarnitinium, (+)-Indobufen, (+)-SCH-351448, (E)-p-Coumaroylquinic acid, (Z)-Indenaprost, [111In-DTPA-Pro1,Tyr4]bombesin, [90Y]-DOTAGA-substance P, [psi[CH2NH]Tpg4]Vancomycin aglycon, 111In-Pentetreotide, 11-Keto-Beta-Boswellic Acid, 15-Methoxypinusolidic acid, 1-Methyl-D-tryptophan, 3,5-Dicaffeoylquinic acid, 3-MATIDA, 3-O-Acetyloleanolic acid, 4-Aminosalicylic acid, 6alpha-Fluoroursodeoxycholic acid, 6-Carboxygenistein, 7-Chlorokynurenic acid, 8-Carboxy-iso-iantheran A, 99mTc-c(RGDfK*)2HYNIC, A-42867 pseudoaglycone, Aceclofenac, Acemetacin, Aceneuramic acid sodium salt, Acetyl-11-Keto-Beta-Boswellic Acid, Acetyl-Beta-Boswellic Acid, Acetylcysteine, Achimillic Acids, Acipimox, Acitazanolast, Acrivastine, Actarit, Adapalene, Adarotene, Ademetionine tosylate sulfate, Adxanthromycin A, Ajulemic acid, Alacepril, Aladapcin, Aleglitazar, Alitretinoin, Alminoprofen, Alogliptin benzoate, alpha-Linolenic acid, alpha-Lipoic acid, alpha-Methyltryptophan, Alprostadil, Altemicidin, Alutacenoic acid B, Alvimopan hydrate, Amiglumide, Amineptine, Aminocaproic acid, Aminolevulinic acid hydrochloride, Amlexanox, Amoxicillin trihydrate, Amphotericin B, Amsilarotene, Anakinra, Antiflammin-1, Antiflammin-2, Antiflammin-3, Apalcillin sodium, Aplaviroc hydrochloride, Argatroban monohydrate, Argimesna, Artelinate, Artepillin C, Artesunate, Arundifungin, Ascosteroside, Asiatic acid, Aspirin, Aspoxicillin, Assamicin I, Assamicin II, Ataluren, Atorvastatin, Atorvastatin calcium, Atrasentan, Azaromycin SC, Azelaic Acid, Azepinostatin, Azilsartan, Azoxybacilin, Aztreonam, Aztreonam L-lysine, Azumamide E, Baclofen, Bafilomycin C1, Baicalin, Balhimycin, Balofloxacin, Balofloxacin dihydrate, Balsalazide disodium, Bamirastine hydrate, Belactosin A, Belactosin C, Benanomicin A, Benanomicin B, Benastatin A, Benastatin B, Benazepril hydrochloride, Benthocyanin A, Bepotastine besilate, Beraprost sodium, Besifloxacin hydrochloride, Beta-Boswellic Acid, beta-Hydroxy beta-methylbutyrate, Betamipron, Beta-Sialosylcholesterol Sodium Salt, Bevirimat, Bexarotene, Bezafibrate, Biapenem, Bilastine, Bimosiamose, Bindarit, Binfloxacin, Biphenyl-indanone A, Boc-Belactosin A, Borrelidin, Brasilicardin A, Brasilinolide A, Bremelanotide, Brevifolin carboxylic acid, Bucillamine, Bumetanide, Bungeolic acid, Buprenorphine hemiadipate, Buprenorphine-Val-carbamate, Butibufen, Butoctamide hemisuccinate, Butyzamide, Cabin 1, Cadrofloxacin hydrochloride, Calbistrin A, Calbistrin B, Calbistrin C, Calbistrin D, Calcium-like peptide 1, Calcium-like peptide 2, Caloporoside B, Caloporoside C, Caloporoside D, Caloporoside E, Caloporoside F, Calpinactam, Calteridol calcium, Camprofen, Candesartan, Candoxatril, Candoxatrilat, Canfosfamide hydrochloride, Canrenoate potassium, Caprazamycin A, Caprazamycin B, Caprazamycin C, Caprazamycin E, Caprazamycin F, Captopril, Carbidopa, Carmoxirole hydrochloride, Carprofen, Cefaclor, Cefalexin monohydrate, Cefbuperazone sodium, Cefcanel, Cefdaloxime, Cefdinir, Cefetecol, Cefixime, Cefmatilen hydrochloride hydrate, Cefmenoxime hydrochloride, Cefminox sodium, Cefodizime, Cefonicid sodium, Cefoperazone sodium, Cefoselis sulfate, Cefotiam hydrochloride, Cefoxitin, Cefpimizole sodium, Cefpiramide sodium, Cefprozil, Cefprozil monohydrate, Ceftaroline fosamil acetate, Ceftazidime, Ceftibuten, Ceftobiprole, Cefuroxime, Ceranapril, Cerivastatin sodium, Ceruletide diethylamine, Cetefloxacin, Cetirizine hydrochloride, Chenodeoxycholic acid, Chinoin-169, Chlorambucil, Chloroorienticin A, Chloroorienticin B, Choline fenofibrate, Choline thioctate, Chrolactomycin, Cilastatin sodium, Cilazapril, Cilengitide, Cilomilast, Ciluprevir, Cinaciguat, Cinalukast, Cinatrin A, Cinatrin B, Cinatrin C1, Cinatrin C2, Cinatrin C3, Cinnatriacetin A, Cinnatriacetin B, Ciprofibrate, Ciprofloxacin hydrochloride, Circinamide, Cispentacin, Citrullimycine A, Clavaric acid, Clavulanate potassium, Clinofibrate, Clopidogrel Sulfate, Colletoic acid, Complestatin, Conagenin, Cosalane, Creatine phosphate, Cyclocreatine, Cycloplatam, Cyclothialidine, Cytomodulin, Cytosporic acid, Dabigatran, Daglutril, Dalargin, Dalbavancin, Danegaptide hydrochloride, Danofloxacin, Darinaparsin, Daunorubicin Sulfate, Daurisentan, Daurichromenic acid, Davunetide, Decahydromoenomycin A, Decaplanin, Decatromicin A, Decatromicin B, Deferasirox, Delafloxacin, Delapril Hydrochloride, Deltibant, Deoxylaidlomycin, Deoxynegamycin, Dersalazine, Desacetylvinblastinehydrazide/folate conjugate, Desferri-danoxamine, Desferri-nordanoxamine, Desglugastrin tromethamine, Desmin-370, Dexibuprofen, Dexibuprofen lysine, Dexketoprofen, Dexketoprofen choline, Dexketoprofen D,L-lysine, Dexketoprofen lysine, Dexketoprofen meglumine, Dexketoprofen trometamol, Dexloxiglumide, Dexpemedolac, dextro-Ciprofibrate, Dexylosylbenanomycin A, Diacerein, Diazaphilonic acid, Di-Calciphor, Difenoxin, Diflunisal, Dihydroavenanthramide D, Dihydrogranaticin B, Dihydroisosteviol, Dihydrolipoic acid, Disalazine, Disila-bexarotene, Disodium cromproxate, Disodium lettusate, Doqualast, Doripenem, Dormitroban, Dorrigocin A, Dorrigocin B, Droxidopa, DTPA-adenosylcobalamin, Duramycin, Dynemicin A, Ecabet Sodium, Ecenofloxacin hydrochloride, Econazole Sulfosalicylate, Edetic acid, Edotreotide yttrium, Efletirizine, Eflornithine hydrochloride, Eglumetad hydrate, Elansolid C1, Elarofiban, Elastatinal B, Elastatinal C, Elsibucol, Eltrombopag olamine, Elvitegravir, Emricasan, Enalapril maleate, Enalapril nitrate, Enalaprilat, Enfumafungin, Enkastin (D), Enkastin AD, Enkastin AE, Enkastin ID, Enkastin IE, Enkastin VD, Enkastin VE, Enoloxone, Enoxacin, Enrasentan, Enrofloxacin, Epalrestat, Epidioxymanadic acid A, Epidioxymanadic acid B, Epithalon, Epofolate, Epoprostenol sodium, Epostatin, Episteride, Eprosartan mesilate, Eprotirome, Eptaloprost, Eptastatin sodium, Eptastigmine Tartrate, Eptifibatide, Erdosteine, Eremomycin, Ertapenem sodium, Ertiprotafib, Eryloside F, Esafloxacin Hydrochloride, Esonarimod, Etacrynic acid, Etalocib sodium, Etodolac, Etretin, Evatanepag, Evernimicin, Exisulind, Ezetimibe glucuronide, Fandofloxacin hydrochloride, Faranoxi, Farglitazar, Faropenem sodium, Fasobegron hydrochloride, Febuxostat, Feglymycin, Felbinac, Felbinac Lysine Salt, Fenbufen, Fexofenadine hydrochloride, Fidexaban, Finafloxacin hydrochloride, Fleroxacin, Flobufen, Flomoxef Sodium, Flunoprost, Flunoxaprofen, Flurbiprofen, Fluvastatin sodium, Folinic acid, Fondaparinux sodium, Fosfosal, Fradafiban, Frusemide, Fudosteine, Furprofen, G1 peptide, Gabadur, Gabapentin, Gabapentin enacarbil, Gabusectin, Gadobenic acid dimeglumine salt, Gadobutrol, Gadocoletic acid trisodium salt, Gadodenterate, Gadomelitol, Gadopentetate dimeglumine, Gadoterate meglumine, Gadoteridol, Gambogic acid, Gamendazole, Gamma-Linolenic Acid, Ganefromycin Alpha, Ganefromycin Beta, Ganglioside GM1, Ganoderic acid X, Garenoxacin mesilate, Gastrazole, Gatifloxacin, Gemfibrozil, Gemifloxacin mesilate, Gemopatrilat, Gilatide, Gimatecan, Giripladib, Glaspimod, Glucarolactam potassium, Gludopa, Glutathione Monoethyl Ester, Glutathione Monoisopropyl Ester, Glycine-proline-Melphalan, Glycopin, Glycyrrhizinic acid, Golotimod, Goodyeroside B, Goralatide, Grepafloxacin hydrochloride, GS-143, Haterumadioxin A, Haterumadioxin B, Helvecardin A, Helvecardin B, Heptelidic acid chlorohydrin, Hericenal A, Hericenal B, Hericenal C, Homoindanomycin, Hongoquercin A, Hongoquercin B, Human angiotensin II, Hyaluronate sodium, Hydrostatin A, Ibuprofen, Icatibant acetate, Icofungipen, Idrapril, Ifetroban, Ilepatril, Iloprost, Imidapril, Imidapril hydrochloride, Imiglitazar, Imipenem, Indanaprost (S), Indanomycin, Indeglitazar, Indobufen, Indole-3-propionic acid, Indometacin, Indomethacin trometamol, Indoxam, Indynaprost, Inogatran, Inosiplex, Iododiflunisal, Iodofiltic acid-[123I], Iodostearic Acid, Iralukast, Iralukast sodium, Isalsteine, Isobongkrekic acid, Isotretinoin, Itavastatin calcium, Itriglumide, Kaitocephalin, Kanglemycin A, Kapurimycin A1, Kapurimycin A3, Ketoprofen, Ketoprofen lysine, Ketorolac, Ketorolac tromethamine, Khafrefungin, Kijimicin, Kistamicin A, L-4-Oxalysine, Labradimil, Lamectacin, Lamifiban, Lanthiopeptin, Lapaquistat acetate, Larazotide acetate, Laropiprant, Latamoxef sodium, L-Chicoric acid, Lenapenem hydrochloride, Lenapenem hydrochloride hydrate, Levocabastine hydrochloride, Levocetirizine dihydrochloride, levo-Ciprofibrate, Levodopa, Levodopa 3-O-glucoside, Levodopa 4-O-glucoside, Levofloxacin, Levonadifloxacin arginine salt, L-Homothiocitrulline, Licofelone, Licorice-saponin C2, Lidorestat, Limaprost alfadex, Limazocic, Linoleic acid 18:2w6-cis,9-cis, Linotroban, Lintitript, Lipohexin, Lisinopril, Lithium succinate, Lithospermic acid B magnesium salt, Loloatin B, Lomefloxacin hydrochloride, Lometrexol, Longestin, Lonidamine, Loracarbef hydrate, Lorglumide, Lotrafiban, Loxiglumide, L-Simexonyl homocysteine, L-Thiocitrulline, Lubiprostone, Lumiracoxib, Lu-Tex bis (gluconate), Lysinated-betulonic acid, Lysine acetylsalicylate, Macrocarpin B, Madecassic acid, Maracenin A1, Maracenin A2, Maracenin B1, Maracenin B2, Maracenin C1, Maracenin C2, Maracenin D1, Maracenin D2, Marbofloxacin, Maslinic acid, Matristatin A1, Matristatin A2, Matteuorienate A, Matteuorienate B, Matteuorienate C, Mebrofenin, Meclinertant, Mefenamic acid, Melagatran, Memnopeptide A, Meptazinol-Val-carbamate, Meropenem, Mersacidin, Mesalazine, Metesind glucuronate, Methanobactin, Methotrexate, Methoxatin, Methyldopa, Methylenolactocin, Methylhomoindanomycin, Metiapril, Metirosine, Micacocidin A, Micacocidin B, Midafotel, Midoriamin, Milrinone Lactate, Minerval, Mipitroban, Mispyric acid, Mixanpril, Moenomycin A chloride bismuth salt, Moexipril hydrochloride, Moexiprilat, Mofezolac, Momordin Ic, Monamidocin, Monoethanolamine oleate, Montelukast sodium, Morphine Glucuronide, Moxifloxacin hydrochloride, Mumbaistatin, Mupirocin, Muraglitazar, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Mureidomycin A, Mureidomycin B, Mureidomycin C, Mureidomycin D, Mureidomycin E, Mureidomycin F, Mureidomycins, Mycaperoxide A, Mycaperoxide B, Mycestericin E, Mycophenolic acid sodium salt, Myriceric acid A, Mytolbilin acid, Nadifloxacin, Nafagrel hydrochloride, Nafagrel hydrochloride hemihydrate, Nagstatin, Napirimus, Napsagatran, Napsamycin A, Napsamycin B, Napsamycin C, Napsamycin D, Nateglinide, Naveglitazar, Nebostinel, Nemonoxacin, Neu5Ac2en, Niacin, Niglizin, Nileprost beta-cyclodextrin clathrate, Nooglutil, Norfloxacin, Norfloxacin succinil, Obeticholic acid, Octacosamicin A, Octacosamicin B, O-Demethylchlorothricin, Ofloxacin, Olamufloxacin, Olamufloxacin mesilate, Olanzapine pamoate, Oleanolic acid, Olmesartan, Olopatadine Hydrochloride, Olsalazine sodium, Omapatrilat, Onnamide A, OPC-17083, Opiorphin, Orbifloxacin, Oreganic acid, Orienticin A, Orienticin B, Orienticin C, Orienticin D, Oritavancin, Orniplabin, Oseltamivir carboxylate, Ovothiol A, Ovothiol B, Ovothiol C, Oxaprozin, Oxeglitazar, Oxiglutatione sodium, Oxymorphone-Val-carbamate, Oxynor, Ozagrel hydrochloride, Ozenoxacin, Pactimibe, Padoporfin, Paeciloquinone B, Paeciloquinone D, Paldimycin B, Palovarotene, Panipenem, Parasin I, Parinaric acid, Paulomycin, Paulomycin A2, Paulomycin B, Paulomycin C, Paulomycin D, Paulomycin E, Paulomycin F, Pazufloxacin, Pazufloxacin mesilate, Pefloxacin, PEG-vancomycin, Pelagiomicin C, Peliglitazar, Pelitrexol, Pelretin, Penasterol, Penicillamine, Peramivir, Perindopril, PG-camptothecin, Phomallenic acid C, Phomoidride A, Phomoidride B, Phosphinic cyclocreatine, Phosphosalsalate, Physostigmine salicylate, Pibaxizine, Pidotimod, Piraxostat, Piretanide, Pirfenoxone, Pirprofen, Pivagabine, Pixantrone maleate, Plakotenin, Platencin, Platensimycin, Plevitrexed, Pluraflavin E, Plusbacin A1, Plusbacin A2, Plusbacin A3, Plusbacin A4, Plusbacin B1, Plusbacin B2, Plusbacin B3, Plusbacin B4, Polyalthidin, Pomisartan, Ponalrestat, Poststatin, PPI17-24, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pradofloxacin, Pralatrexate, Pranoprofen, Prefolic A, Pregabalin, Premafloxacin, Premafloxacin hydrochloride, Prezatide copper acetate, Proamipide, Probenecid, Probestin, Procysteine, Proglumide, Propagermanium, Propofol hemisuccinate, Prostatin, Prostratin succinate, Protocatechuic acid, Protoporphyrin IX gallium(III) complex, Prulifloxacin, Prulifloxacin Hydrochloride, Prulifloxacin Mesylate, Pseudomycin A', Pseudomycin B', Pycnanthuquinone A, Pycnanthuquinone B, Pyloricidin B, Pyridazomycin, Pyrrolosporin A, Quiflapon Sodium, Quinapril hydrochloride, Quinlukast, Rafabegron, Ragaglitazar, Raltitrexed, Ramatroban, Ramipril, Raxofelast, Razupenem, Rebamipide bismuth citrate tetramethyledamine, Rebamipide bismuth L-tartrate tetramethyledamine, Repaglinide, Resobene, Reveromycin A, Rhododaurichromanic acid A, Ridogrel, Robenacoxib, Rocagloic acid, Rolafagrel, Romazarit, Romurtide, Rosaprostol sodium, Rosuvastatin calcium, Rosuvastatin sodium, Rufloxacin Gluconate, Rufloxacin hydrochloride, Rumycin 1, Rumycin 2, Salazopyridazin, Salcaprozic acid sodium salt, Salicylazobenzoic acid, S-Allylmercaptocaptopril, Salmisteine, Salvianolic acid L, Samixogrel, Sampatrilat, Sanfetrinem, Sanfetrinem sodium, Sapurimycin, Sarpogrelate hydrochloride, Saussureamine A, Saussureamine B, Saussureamine C, Saussureamine D, Saussureamine E, Scabronine G, Scopadulcic acid B, Securioside A, Securioside B, Selank, Semduramicin, Seocalcitol, Seratrodast, Serofendic acid, Sessiloside, Shepherdin, Sialosylcholesterol-Alpha Sodium Salt, Sitafloxacin hydrate, S-Nitrosocaptopril, S-Nitrosoglutathione, Sodelglitazar, Sodium cromoglycate, Sodium oxybate, Sofalcone, Solabegron hydrochloride, Sorbicillactone A, Sparfloxacin, Sphingofungin F, Spinorphin, Spirapril, Spiriprostil, Spiroglumide, Spiroximicin, Squalestatin I, Stachybocin A, Stachybocin B, Stachybocin C, Staplabin, Starrhizin, Sterenin D, Subtilopentadecanoic acid, Succinobucol, Sufotidine bismuth citrate, Sugammadex sodium, Sulfasalazine, Sulindac, Sulopenem, Sulukast, Sunflower trypsin inhibitor-1, Susalimod, Tafamidis meglumine, Tageflar, Talaglumetad hydrochloride, Talibegron, Talibegron hydrochloride, Talopterin, Taltobulin, Tamibarotene, Tanogitran, Tanomastat, TAP-doxorubicin, Tarenflurbil, Targinine, Tazarotenic Acid, Tebipenem, Teicoplanin-A2-1, Teicoplanin-A2-2, Teicoplanin-A2-3, Teicoplanin-A2-5, Telavancin hydrochloride, Telmesteine, Telmisartan, Temafloxacin hydrochloride, Temocapril hydrochloride, Temurtide, Tenosal, Terbogrel, Terestigmine tartrate, Terikalant fumarate, Tesaglitazar, Tetomilast, Tetradecylselenoacetic acid, Tetrafibricin, Tetragalloylquinic acid, Tetrahydroechinocandin B, Tetronothiodin, Tezampanel, Thermozymocidin, Thiazohalostatin, Thielavin G, Thielocin, Thielocin B3, Thio foscarnet, Thioxamycin, Thrazarine, Thymic humoral factor gamma-2, Thymopentin, Tiagabine hydrochloride, Tibenelast, Ticolubant, Tilarginine hydrochloride, Tiliquinatine, Timodepressin, Tipelukast, Tiplasinin, Tirofiban hydrochloride, Tisartan, Tolfenamic acid, Tolmetin, Tolrestatin, Tomopenem, Tosufloxacin, Tosufloxacin Tosilate, Trandolapril, Trandolaprilat, Tranexamic acid, Tranilast, Treprostinil diethanolamine, Treprostinil sodium, Tretinoin, Triacetylshikimic acid, Trichomycin A, Triflusal, Trimexautide, Trimoprostil, Tripterin, Tropesin, Trovafloxacin, Trovafloxacin hydrate, Trovafloxacin hydrochloride mesylate, Trovafloxacin mesilate, Tubelactomicin A, Tuberactomycin D, Tuberactomycin E, Tubulysin A, Tubulysin B, Tubulysin C, Tucaresol, Tuftsin, Turbinaric acid, Tyroservatide, Ubenimex, Ulifloxacin, Uncarinic acid A, Uncarinic acid B, Unoprostone, Ursodeoxycholic acid, Ursolic acid phosphate, Utibapril, Utibaprilat, Vadimezan, Valonomycin A, Valproate Semisodium, Valproic acid, Valsartan, Vancomycin hydrochloride, Varespladib, Vebufloxacin, Vedaprofen, Veliflapon, Verlukast, Vinaxanthone, Viquidacin, Viranamycin-A, Viscosin, Vitilevuamide, Voreloxin, W Peptide, Xanthofulvin, Zabicipril Hydrochloride, Zabiciprilat Hydrochloride, Zabofloxacin hydrochloride, Zaltoprofen, Zanamivir, Zaragozic acid D3, Zenarestat, Zofenoprilat, Zofenoprilat arginine, Zolasartan, Zonampanel.

Suitable small molecule drugs comprising a phosphate functional group are, for example, Adenophostin A, Adenophostin B, Atrinositol, Buflomedil pyridoxalphosphate, Cytostatin, Fludarabine phosphate, Fosfluconazole, Fosfonochlorin, Fosfosal, Fosopamine, Fosquidone, Fostamatinib, Ganciclovir monophosphate, Genistein-7-phosphate, Hydroxyphoslactomycin B, Leustroducsin A, Leustroducsin B, Leustroducsin C, Leustroducsin H, Mangafodipir trisodium, Menadiol sodium diphosphate, Miproxifene phosphate, Monophosphoryl lipid A, Phospholine, Phosphosalsalate, Pneumocandin B0 2-phosphate, Tafluposide, Triciribine phosphate, Ursolic acid phosphate.

Suitable small molecule drugs comprising a thiol functional group are, for example, Acetylcysteine, Antileukinate, Argimesna, Bucillamine, Butixocort, Captopril, Dihydrolipoic acid, Gemopatrilat, Glutathione monoethyl ester, Glutathione monoisopropyl ester, Midoriamin, Omapatrilat, Ovothiol A, Ovothiol B, Ovothiol C, Penicillamine, Rebimastat, Shepherdin, Zofenoprilat, Zofenoprilat arginine.

In one embodiment the drug is a protein or peptide drug. Preferably, such protein or peptide drug is selected from the group consisting of ACTH, adenosine deaminase, agalsidase, albumin, alfa-1 antitrypsin (AAT), alfa-1 proteinase inhibitor (API), alglucosidase, alteplase, anistreplase, ancrod serine protease, antibodies (monoclonal or polyclonal and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), chorionic gonadotropin (hCG), hemoglobins, hepatitis B vaccines, hirudin, hyaluronidases, idurnonidase, immune globulins, influenza vaccines, interleukines (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), lactase, leuprolide, levothyroxine, luteinizing hormone, lyme vaccine, natriuretic peptide, pancrelipase, papain, parathyroid hormone, PDGF, pepsin, phospholipase-activating protein (PLAP), platelet activating factor alcetyl-hydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrothropin, transforming growth factors, tumor necrosis factor (TNF), TNF receptor-IgG Fc, tissue plasminogen activator (tPA), transferrin, TSH, urate oxidase, and urokinase.

In a preferred embodiment the drug is an antibody, such as a monoclonal or polyclonal antibody or a fragment or fusion thereof. Preferred antibody fragments are selected from the group consisting of Fab (fragment, antigen-binding), F(ab)$_2$ fragments, Fc (fragment, crystallizable), pFc' fragment, Fv (fragment, variable), scFv (single-chain variable fragment), di-scFv/diabodies, bi-specific T-cell engager, CDRs (complementarity determining regions), single-domain antibodies (sdABs/Nanobodies), heavy chains ($\alpha$, $\delta$, $\delta$, $\gamma$, $\mu$) or heavy chain fragments, light chains ($\lambda$, $\theta$) or light chain fragments, VH fragments (variable region of the heavy chain), VL fragments (variable region of the light chain), VHH fragments and VNAR fragments.

In another preferred embodiment the protein drug is preferably a protein drug that modulates the activity of one or more of the biological target(s) selected from the group consisting of basic fibroblast growth factors (bFGF), acidic fibroblast growth factors (aFGF), transforming growth factors alpha (TGFa), transforming growth factors beta (TGFβ), platelet-derived growth factor (PDGF), angiogenin, platelet-derived endothelial cell growth factor (PD-ECGF), interleukin-1 (IL-1) interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin (plasminogen fragment), antiangiogenic anti-thrombin III, cartilage-derived inhibitor (CDI), CDS9 complement fragment, endostatin (collagen XVIII fragment), fibronectin fragment, gro-beta, heparinases, heparin hexasaccharide fragment, human chorionic gonadotropin (hCG), interferon alpha/beta/gamma, interferon inducible protein (IP-IO), kringle S (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, and vasostatin (calreticulin fragment), prostaglandin, growth hormone, insulin-like growth factor-I (IGF-I), sphingosine-1-phosphate, factor D, RTP801, inhibitors of complement, including C1, C3 and C5, $\alpha_2$ adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), and pigment epithelium-derived factor (PEDF).

If the drug is an affinity scaffold protein it is preferably selected from the group consisting of shark-derived affinity scaffold proteins, Kunitz domain-derived affinity scaffold proteins, centyrin-derived affinity scaffold proteins, ubiquitin-derived affinity scaffold proteins, lipocalin-derived affinity scaffold proteins, ankyrin-derived affinity scaffold proteins, versabodies (disulfide-rich affinity scaffold proteins), fibronectin-derived affinity scaffold proteins, cameloid-derived antibody fragments and affinity scaffold proteins, llama-derived antibody fragments and affinity scaffold proteins, transferrin-derived affinity scaffold proteins, and squash-type protease inhibitors with cysteine-knot scaffold-derived affinity scaffold proteins.

Tag Moiety

In one embodiment, the tag moiety T is a small molecule.

Preferably, T is W; $C_{1-50}$ alkyl; $C_{2-50}$ alkenyl; or $C_{2-50}$ alkynyl, which W; $C_{1-50}$ alkyl; $C_{2-50}$ alkenyl; and $C_{2-50}$ alkynyl are optionally substituted with one or more $R^{10}$, which are the same or different and which $C_{1-50}$ alkyl; $C_{2-50}$ alkenyl; and $C_{2-50}$ alkynyl are optionally interrupted by one or more group(s) selected from the group consisting of W, —C(O)O—; —O—; —C(O)—; —C(O)N($R^9$)—; —S(O)$_2$N($R^9$)—; —S(O)N($R^9$)—; —S(O)$_2$—; —S(O)—; —N($R^9$) S(O)$_2$N($R^{9a}$)—; —S—; —N($R^9$)—; —OC(O)$R^9$; —N($R^9$) C(O)—; —N($R^9$)S(O)$_2$—; —N($R^9$)S(O)—; —N($R^9$)C(O) O—; —N($R^9$)C(O)N($R^{9a}$)—; and —OC(O)N($R^9R^{9a}$);
wherein $R^9$, $R^{9a}$, $R^{9b}$ are independently of each other H; W; $C_{1-50}$ alkyl; $C_{2-50}$ alkenyl; or $C_{2-50}$ alkynyl, wherein W; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more group(s) selected from the group consisting of W, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O) O—; —N($R^{11}$)C(O)N($R^{11a}$)—; and —OC(O)N ($R^{11}R^{11a}$);

W is phenyl; naphthyl; indenyl; indanyl; tetralinyl; $C_{3-10}$ cycloalkyl; 4 to 7 membered heterocyclyl; or 8- to 11-membered heterobicyclyl, wherein W is optionally substituted with one or more $R^{10}$, which are the same or different;

$R^{10}$ is halogen; CN; oxo (=O); COO$R^{12}$; O$R^{12}$; C(O)$R^{12}$; C(O)N($R^{12}R^{12a}$); S(O)$_2$N($R^{12}R^{12a}$); S(O)N($R^{12}R^{12a}$); S(O)$_2R^{12}$; S(O)$R^{12}$; N($R^{12}$)S(O)$_2$N($R^{12a}R^{12b}$); S$R^{12}$; N($R^{12}R^{12a}$); NO$_2$; OC(O)$R^{12}$; N($R^{12}$)C(O)$R^{12a}$; N($R^{12}$)S(O)$_2R^{12a}$; N($R^{12}$)S(O)$R^{12a}$; N($R^{12}$)C(O) O$R^{12a}$; N($R^{12}$)C(O)N($R^{12a}R^{12b}$); OC(O)N($R^{12}R^{12a}$);

or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently of each other H; or $C_{1-6}$alkyl, wherein $C_{1-6}$ alkyl is optionally substituted with one or more halogen, which are the same or different.

In one embodiment $R^9$, $R^{9a}$, $R^{9b}$ may be independently of each other H.

In one embodiment $R^{10}$ is $C_{1-6}$ alkyl.

In one embodiment W is phenyl.

Preferably, T is a linear, branched, or dendritic polymer.

In another embodiment the tag moiety T is a polymer which comprises one or more polymer(s) selected from the group consisting of polypeptides, 2-methacryloyl-oxyethyl phosphoyl cholins, poly(acrylic acids), poly(acrylates), poly (acrylamides), poly(alkyloxy) polymers, poly(amides), poly (amidoamines), poly(amino acids), poly(anhydrides), poly (aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(imino carbonates), poly(lactic acids), poly (lactic-co-glycolic acids), poly(methacrylamides), poly (methacrylates), poly(methyloxazolines), poly (organophosphazenes), poly(ortho esters), poly(oxazolines), polypropylene glycols, poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylan, and copolymers thereof.

Preferably, T is a polymer with a molecular weight ranging from 0.5 to 50 kDa, more preferably from 0.5 to 40 kDa, even more preferably from 1 to 30, even more preferably from 1 to 20 kDa and most preferably from 2 to 15 kDa.

In a preferred embodiment T is a PEG-based polymer comprising at least 70% PEG or a hyaluronic acid-based polymer comprising at least 70% hyaluronic acid. More preferably, T is a PEG-based polymer comprising at least 70% PEG, even more preferably comprising at least 80% PEG and most preferably comprising at least 90% PEG.

Preferred moieties T are a linear or branched PEG-based polymer with a molecular weight ranging from 0.5 to 50 kDa and $C_{1-20}$ alkyl wherein said $C_{1-20}$ alkyl is optionally interrupted with by one or more group(s) selected from the group consisting of W, —C(O)O—; —O—; —C(O)—; —C(O)N ($R^9$)—; —S(O)$_2$N($R^9$)—; —S(O)N($R^9$)—; —S(O)$_2$—; —S(O)—; —N($R^9$)S(O)$_2$N($R^{9a}$)—; —S—; —N($R^9$)—; —OC(O)$R^9$; —N($R^9$)C(O)—; —N($R^9$)S(O)$_2$—; —N($R^9$)S (O)—; —N($R^9$)C(O)O—; —N($R^9$)C(O)N($R^{9a}$)—; and —OC(O)N($R^9R^{9a}$);
wherein $R^9$, $R^{9a}$, $R^{9b}$ are independently of each other H; W; $C_{1-50}$ alkyl; $C_{2-50}$ alkenyl; or $C_{2-50}$ alkynyl.

It is especially advantageous if T is a polymer, in particular a PEG-based polymer, in case the drug is not water-soluble or has only limited water-solubility. The polymeric moiety increases the solubility of the biologically active moiety which may result in higher conjugation yields in process step (d).

Other Aspects

The present invention further relates to a hydrogel-linked prodrug releasing a tag moiety-biologically active moiety conjugate obtainable by a process of the present invention.

Preferably, the hydrogel is obtainable by a process wherein process step (d) is selected from (d-i), (d-ii), (d-iii) or (d-iv).

In another preferred embodiment the hydrogel is obtainable by a process wherein step (d) is selected from (d-v), (d-vi), (d-vii) or (d-viii).

Another aspect of the present invention is a pharmaceutical composition comprising the prodrug of the present invention or a pharmaceutical salt thereof together with a pharmaceutically acceptable excipient.

In one embodiment the release of the tag moiety-biologically active moiety conjugate from the hydrogel-linked prodrugs of the present invention occurs with a half-life ranging from 1 hour to twelve months, e.g. from 6 hours to twelve months, from twelve hours to eleven months, from one day to ten months, from three days to nine months, from six days to nine months, from one week to nine months, from two weeks to seven months, from three weeks to eight months, from four weeks to eight months, from six weeks to seven months, from eight weeks to seven months, from ten weeks to six months, from twelve weeks to six months or from sixteen weeks to five months.

Yet another aspect of the present invention is a hydrogel-linked prodrug releasing a tag moiety-biologically active moiety conjugate of the present invention or a pharmaceutical composition comprising the hydrogel-linked prodrugs releasing a tag moiety-biologically active moiety conjugate of the present invention for use as a medicament.

Yet another aspect of the present invention is a method of treating, controlling, delaying or preventing in a mammalian patient, preferably in a human, in need of the treatment of one or more conditions comprising administering to said patient a therapeutically effective amount of the hydrogel-linked prodrugs releasing a tag moiety-biologically active moiety conjugate of the present invention or the pharmaceutical composition comprising the hydrogel-linked prodrugs releasing a tag moiety-biologically active moiety conjugate of the present invention or a pharmaceutically acceptable salt thereof.

EXAMPLES

Materials and Methods

Amino 4-arm PEG 5 kDa was obtained from JenKem Technology, Beijing, P. R. China. Cithrol™ DPHS was obtained from Croda International Pic, Cowick Hall, United Kingdom. cis-1,4-cyclohexanedicaboxylic acid was obtained from TCI EUROPE N.V., Boerenveldseweg 6-Haven 1063, 2070 Zwijndrecht, Belgium.

Isopropylmalonic acid was obtained from ABCR GmbH & Co. KG, 76187 Karlsruhe, Germany.

N-(3-maleimidopropionyl)-39-amino-4,7,10,13,16,19,22, 25,28,31,34,37-dodecaoxa-nonatriacontanoic acid pentafluorophenyl ester (Mal-NH-PEG12-PFE) was obtained from Biomatrik Inc., Jiaxing, P. R. China.

N-(3-maleimidopropionyl)-21-amino-4,7,10,13,16,19-hexaoxa-heneicosanoic acid NHS ester (Mal-PEG6-NHS) and t-boc-Amido-dPEG 12-alcohol was obtained from Celares GmbH, Berlin, Germany.

6-(S-Tritylmercapto)hexanoic acid was purchased from Polypeptide, Strasbourg, France.

15-Tritylthio-4,7,10,13-tetraoxa-pentadecanoic acid (Trt-S-PEG4-COOH) is obtained from Iris Biotech GmbH, Marktredwitz, Germany.

Oxyma pure, Fmoc-L-Asp(OtBu)-OH and Fmoc-L-Asp(OBn)-OH were purchased from Merck Biosciences GmbH, Schwalbach/Ts, Germany.

(5-methyl-2-oxo-1,3-dioxol-4-yl)-methyl 4-nitrophenyl carbonate was purchased from Chemzon Scientific Inc., Lachine, QC, Canada.

ω-Maleimido-α-methoxy-PEG 750 Da was obtained from Rapp Polymere, Tubingen, Germany Human growth hormone releasing factor fragment 1-29 with a C-terminally added cysteine amide (GRF(1-29)-Cys; sequence: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Cys-$NH_2$) e.g. synthesized by Fmoc-strategy can be obtained from any custom peptide synthesis supplier, such as, for example, Peptide Specialty Laboratories GmbH, Heidelberg, Germany.

All other chemicals were from Sigma-ALDRICH Chemie GmbH, Taufkirchen, Germany.

Methods:

Fmoc Deprotection:

For Fmoc protecting-group removal, the resin was agitated with 2/2/96 (v/v/v) piperidine/DBU/DMF (two times, 10 min each) and washed with DMF (ten times).

RP-HPLC Purification:

RP-HPLC was done on a 100×20 mm or 100×40 mm C18 ReproSil-Pur 300 ODS-3 5 μm column (Dr. Maisch, Ammerbuch, Germany) connected to a Waters 600 HPLC System and Waters 2487 Absorbance detector unless otherwise stated. Linear gradients of solution A (0.1% TFA in $H_2O$) and solution B (0.1% TFA in acetonitrile) were used. HPLC fractions containing product were pooled and lyophilized.

Flash Chromatography:

Flash chromatography purifications were performed on an Isolera One system from Biotage AB, Sweden, using Biotage KP-Sil silica cartridges and n-heptane, ethyl acetate, and methanol as eluents. Products were detected at 254 nm. For products showing no absorbance above 240 nm fractions were screened by LC/MS.

For hydrogel beads, syringes equipped with polyethylene frits were used as reaction vessels or for washing steps.

Analytical ultra-performance LC (UPLC) was performed on a Waters Acquity system equipped with a Waters BEH300 C18 column (2.1×50 mm, 1.7 μm particle size) coupled to a LTQ Orbitrap Discovery mass spectrometer from Thermo Scientific.

HPLC-Electrospray ionization mass spectrometry (HPLC-ESI-MS) was performed on a Waters Acquity UPLC with an Acquity PDA detector equipped with a Waters ACQUITY UPLC BEH300 C18 RP column (2.1×50 mm, 300 Å, 1.7 μm, flow: 0.25 mL/min; solvent A: UP-$H_2O$+ 0.04% TFA, solvent B: UP-Acetonitrile+0.05% TFA) and coupled to a Thermo LTQ Orbitrap Discovery high resolution/high accuracy mass spectrometer or a Waters ZQ 4000 ESI mass spectrometer.

MS of PEG products showed a series of $(CH_2CH_2O)_n$ moieties due to polydispersity of PEG starting materials. For easier interpretation only one single representative m/z signal is given in the examples.

Example 1

Synthesis of Backbone Reagent 1g

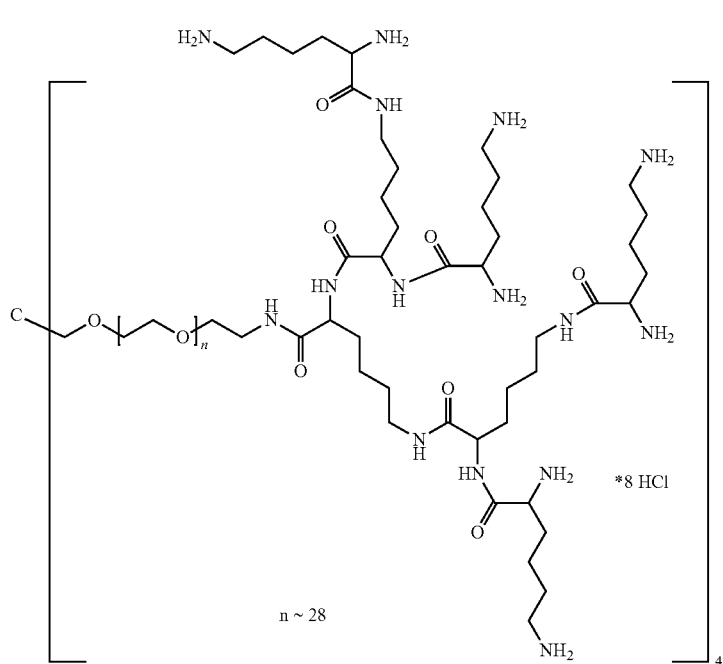

Backbone reagent 1g was synthesized from amino 4-arm PEG5000 1a according to following scheme:

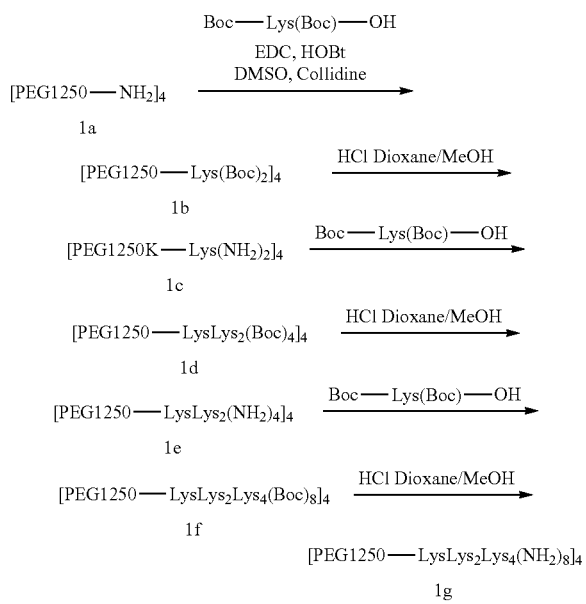

For synthesis of compound 1b, amino 4-arm PEG5000 1a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC.HCl (1.15 g, 6.00 mmol), HOBt.H$_2$O (0.96 g, 6.25 mmol), and collidine (5.20 mL, 40 mmol) were added. The reaction mixture was stirred for 30 min at RT.

The reaction mixture was diluted with 1200 mL of DCM and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1b was purified by RP-HPLC.

Yield: 3.85 g (59%) colorless glassy product 1b.

MS: m/z 1294.4=[M+5H]$^{5+}$ (calculated=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the next step without further purification.

MS: m/z 1151.9=[M+5M]$^{5+}$ (calculated=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC.HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 1d, which was used in the next step without further purification.

MS: m/z 1405.4=[M+6H]$^{7+}$ (calculated=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the next step without further purification. MS: m/z 969.6=[M+7H]$^{7+}$ (calculated=969.7).

For the synthesis of compound 1f, compound 1e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product if as colorless oil.

Product was dissolved in DCM and precipitated with cooled (−18° C.) diethylther. This step was repeated twice and the precipitate was dried in vacuo.

Yield: 4.72 g (82%) colourless glassy product if which was used in the next step without further purification.

MS: m/z 1505.3=[M+8H]$^{8+}$ (calculated=1505.4).

Backbone reagent 1g was obtained by stirring a solution of compound if (MW ca. 12035 g/mol, 4.72 g, 0.39 mmol) in 20 mL of methanol and 40 mL of 4 N HCl in dioxane at RT for 30 min. Volatiles were removed in vacuo.

Yield: 3.91 g (100%), glassy product backbone reagent 1g.

MS: m/z 977.2=[M+9H]$^{9+}$ (calculated=977.4).

Alternative Synthetic Route for 1g

For synthesis of compound 1b, to a suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIPEA (20.9 mL, 120 mmol) were added at 45° C. and the mixture was stirred for 30 min.

Subsequently, n-propylamine (2.48 mL, 30.0 mmol) was added. After 5 min the solution was diluted with 1000 mL of MTBE and stored overnight at −20° C. without stirring. Approximately 500 mL of the supernatant were decanted and discarded. 300 mL of cold MTBE (nominal −20° C.) were added and after 1 min shaking the product was collected by filtration through a (Por. 3) filter and washed with 500 mL of cold MTBE. The product was dried in vacuo for 16 h.

Yield: 65.6 g (74%) 1b as a white lumpy solid

MS: m/z 937.4=[M+7H]$^{7+}$ (calculated=937.6).

Compound 1c was obtained by stirring of compound 1b from the previous step (48.8 g, 7.44 mmol) in 156 mL of 2-propanol at 40° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.

Yield: 38.9 g (86%) 1c as a white powder

MS: m/z 960.1=[M+6H]$^{6+}$ (calculated=960.2).

For synthesis of compound 1d, boc-Lys(boc)-OSu (16.7 g, 37.7 mmol) and DIPEA (13.1 mL, 75.4 mmol) were added to a suspension of 1c from the previous step (19.0 g, 3.14 mmol) in 80 ml 2-propanol at 45° C. and the mixture was stirred for 30 min at 45° C. Subsequently, n-propylamine (1.56 mL, 18.9 mmol) was added. After 5 min the solution was precipitated with 600 mL of cold MTBE and centrifuged (3000 min$^{-1}$, 1 min) The precipitate was dried in vacuo for 1 h and dissolved in 400 mL THF. 200 mL of diethyl ether were added and the product was cooled to −30° C. for 16 h without stirring. The suspension was filtered through a glass filter and washed with 300 mL cold MTBE. The product was dried in vacuo for 16 h.

Yield: 21.0 g (80%) 1d as a white solid

MS: m/z 1405.4=[M+6H]$^{6+}$ (calculated=1405.4).

Compound 1e was obtained by dissolving compound 1d from the previous step (15.6 g, 1.86 mmol) in 3 N HCl in methanol (81 mL, 243 mmol) and stirring for 90 min at 40° C. 200 ml of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE. The product was dried in vacuo.

Yield: 13.2 g (96%) 1e as a white powder

MS: m/z 679.1=[M+10H]$^{10+}$ (calculated=679.1).

For the synthesis of compound 1f, boc-Lys(boc)-OSu (11.9 g, 26.8 mmol) and DIPEA (9.34 mL, 53.6 mmol) were added to a suspension of 1e from the previous step, (8.22 g, 1.12 mmol) in 165 ml 2-propanol at 45° C. and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4×200 mL of cold MTBE/iPrOH 4:1 and 1×200 mL of cold MTBE. The product was dried in vacuo for 16 h.

Yield: 12.8 g, MW (90%) if as a pale yellow lumpy solid

MS: m/z 1505.3=[M+8H]$^{8+}$ (calculated=1505.4).

Backbone reagent 1g was obtained by dissolving 4ArmPEG5kDa(-LysLys$_2$Lys$_4$(boc)$_8$)$_4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifuged at 3000 rpm for 1 min. The precipitate was dried in vacuo for 1 h and redissolved in 90 mL of MeOH, precipitated with 240 ml of cold MTBE and the suspension was centrifuged at 3000 rpm for 1 min. The product 1g was dried in vacuo.

Yield: 11.5 g (89%) as pale yellow flakes.

MS: m/z 1104.9=[M+8H]$^{8+}$ (calculated=1104.9).

Example 2

Synthesis of Crosslinker Reagent 2d

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

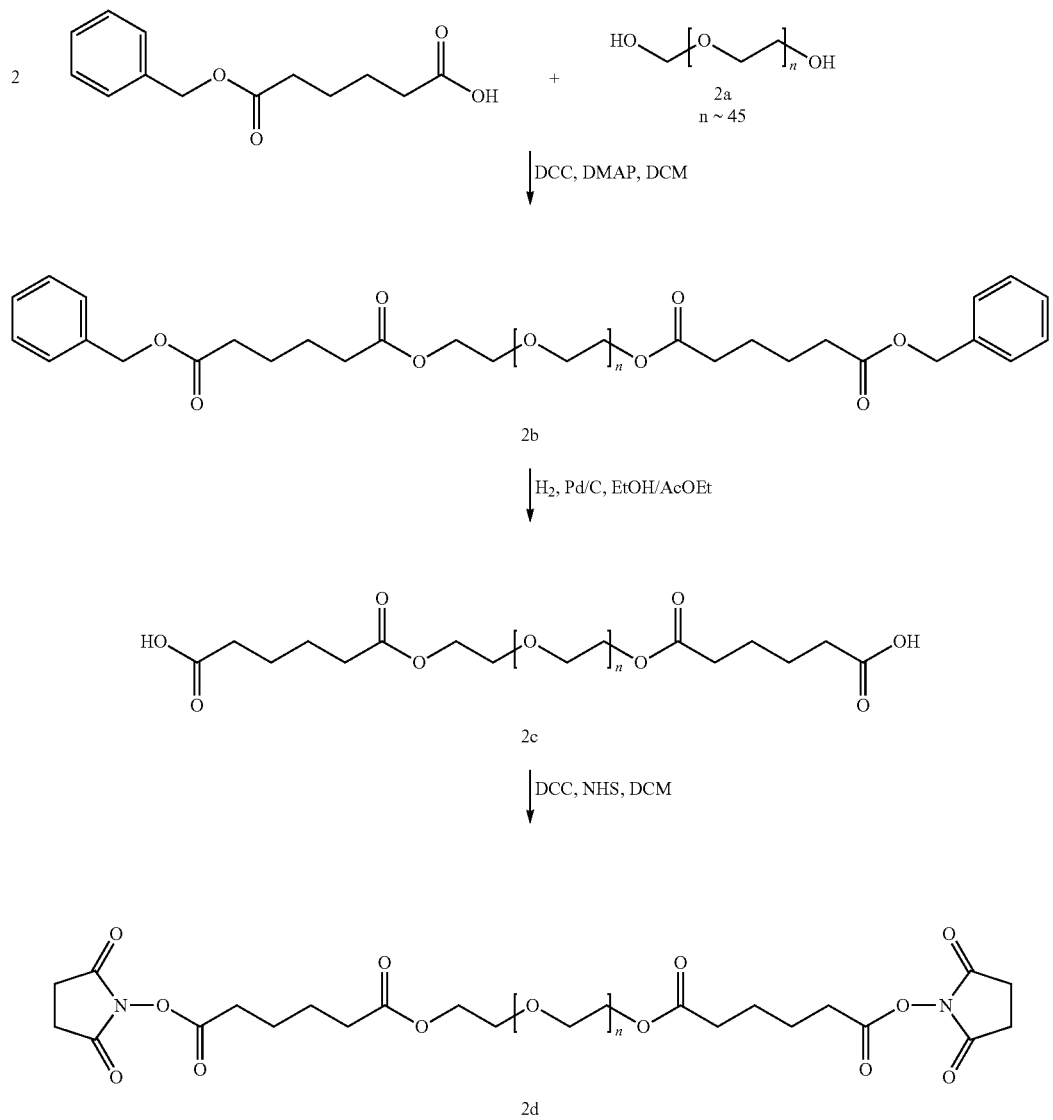

A solution of PEG 2000 (2a) (11.0 g, 5.5 mmol) and benzyl adipate half-ester (4.8 g, 20.6 mmol) in DCM (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by distillation in vacuo. The residue was dissolved in 1000 mL 1/1 (v/v) diethyl ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled diethyl ether (−30° C.). The filter cake was dried in vacuo.

Yield: 11.6 g (86%) 2b as a colorless solid. The product was used without further purification in the next step.

MS: m/z 813.1=$[M+3M]^{3+}$ (calculated=813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo.

Yield: 12.3 g (quantitative) 2c as yellowish oil. The product was used without further purification in the next step.

MS: m/z 753.1=$[M+3H]^{3+}$ (calculated=753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 ml of DCM (anhydrous) was stirred over night at room temperature. The reaction mixture was cooled to 0° C. and precipitate was filtered off. DCM was evaporated and the residue was recrystallized from THF.

Yield: 8.73 g (85%) crosslinker reagent 2d as colorless solid.

MS: m/z 817.8=$[M+3H]^{3+}$ (calculated=817.9 g/mol).

Synthesis of 2e

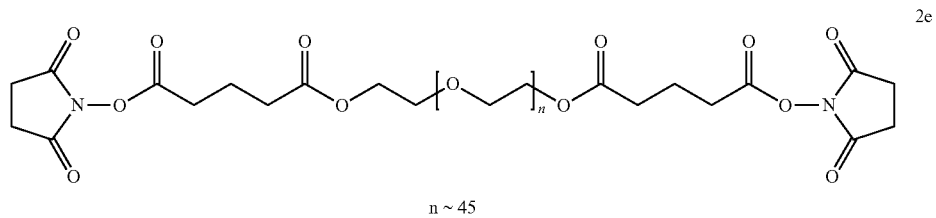

n ~ 45

2e was synthesized as described for 2d except for the use of glutaric acid instead of adipic acid MS: m/z 764.4=[M+3H]$^{3+}$ (calculated=764.5).

Example 3

Preparation of hydrogel beads 3 containing free amino groups

A solution of 1200 mg 1g and 3840 mg 2e in 28.6 mL DMSO was added to a solution of 425 mg Arlacel P135 (Croda International Plc) in 100 mL heptane. The mixture was stirred at 650 rpm with a propeller stirrer for 10 min at 25° C. to form a suspension in a 250 ml reactor equipped with baffles. 4.3 mL TMEDA was added to effect polymerization. After 2 h, the stirrer speed was reduced to 400 rpm and the mixture was stirred for additional 16 h. 6.6 mL of acetic acid were added and then after 10 min 50 mL of water and 50 mL of saturated aqueous sodium chloride solution were added. After 5 min, the stirrer was stopped and the aqueous phase was drained.

For bead size fractionation, the water-hydrogel suspension was wet-sieved on 75, 50, 40, 32 and 20 μm mesh steel sieves. Bead fractions that were retained on the 32, 40, and 50 μm sieves were pooled and washed 3 times with water, 10 times with ethanol and dried for 16 h at 0.1 mbar to give 3 as a white powder.

Amino group content of hydrogel was determined by coupling of a fmoc-amino acid to the free amino groups of the hydrogel and subsequent fmoc-determination as described by Gude, M., J. Ryf, et al. (2002) *Letters in Peptide Science* 9(4): 203-206.

The amino group content of 3 was determined to be between 0.11 and 0.16 mmol/g.

Example 4

Preparation of Maleimide Functionalized Hydrogel Suspension 4 and Determination of Maleimide Substitution Hydrogel 3 was pre-washed with 99/1 (v/v) DMSO/DIPEA, washed with DMSO and incubated for 45 min with a solution of Mal-PEG6-NHS (2.0 eq relative to theoretical amount of amino groups on hydrogel) in DMSO. Hydrogel were washed five times with DMSO and five times with pH 3.0 succinate (20 mM, 1 mM EDTA, 0.01% Tween-20). The sample was washed three times with pH 6.0 sodium phosphate (50 mM, 50 mM ethanolamine, 0.01% Tween-20) and incubated in the same buffer for 1 h at RT. Then hydrogel was washed five times with pH 3.0 sodium succinate (20 mM, 1 mM EDTA, 0.01% Tween-20) and kept in that buffer to yield maleimide functionalized hydrogel 4 in suspension.

For determination of maleimide content, an aliquot of hydrogel 4 was washed three times with water and ethanol each. The aliquot was dried under reduced pressure and the weight of hydrogel in the aliquot was determined. Another aliquot of hydrogel 4 was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). A maleimide content of 0.10-0.15 mmol/g dried hydrogel was calculated.

Example 5

Synthesis of Linker Reagent 5c

Linker reagent 5c was synthesized according to the following scheme:

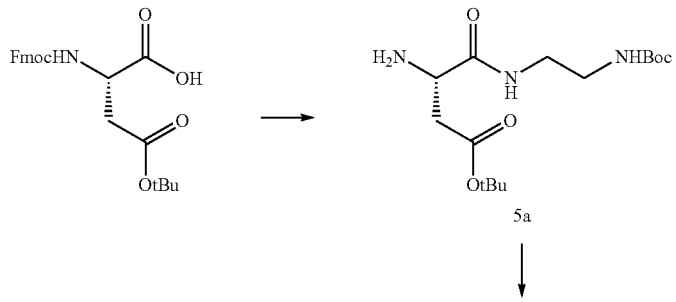

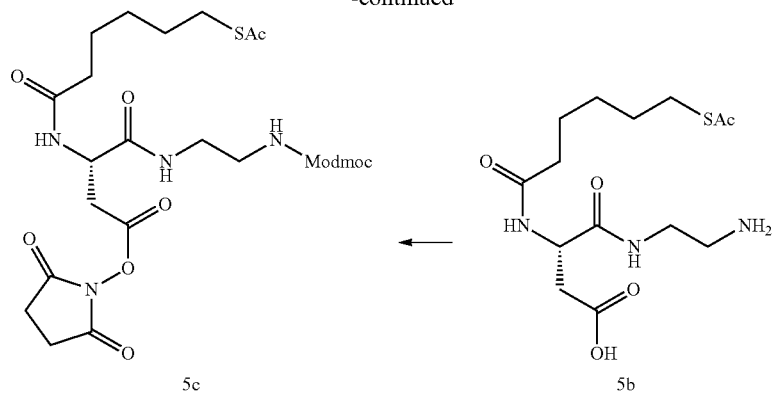

5c       5b

Synthesis of 5a

Fmoc-L-Asp(OtBu)-OH (1.00 g, 2.43 mmol) was dissolved with DCC (0.70 g, 3.33 mmol) in DCM (25 mL, anhydrous, mol. sieve). Oxyma pure (0.51 g, 3.58 mmol) and collidine (0.50 mL, 3.58 mmol) were added in one portion and a solution of N-Boc-ethylenediamine (0.41 g, 2.56 mmol) in DCM (15 mL, anhydrous, mol. sieve) was added slowly. After stirring the mixture for 90 min at RT the formed precipitate was filtered off and the filtrate washed with 0.1 M HCl. The aqueous layer was extracted with DCM (2×) and the combined organic fractions were washed with sat. aqueous $NaHCO_3$ (3×) and brine (1×), dried over $Na_2SO_4$, filtered and concentrated in vacuo. The crude solid was purified by flash chromatography. The intermediate N-boc-N'—(N-fmoc-4-tert.-butyl-L-aspartoyl)-ethylenediamine was obtained as a white solid (0.98 g, 1.77 mmol, 73%).

MS: m/z 554.29=$[M+H]^+$, (calculated=554.29).

N-boc-N'—(N-fmoc-4-tert.-butyl-L-aspartoyl)-ethylenediamine (0.98 g, 1.77 mmol) was dissolved in THF (15 mL), DBU (0.31 mL) was added and the solution was stirred for 12 min at RT. The reaction was quenched with AcOH (0.5 ml), concentrated in vacuo and the residue purified by flash chromatography to give 5a (0.61 g, 1.77 mmol, 73% over 2 steps) as a white solid.

MS: m/z 332.38=$[M+H]^+$, (calculated=332.22).

Synthesis of 5b

6-Acetylthiohexanoic acid (0.37 g, 1.95 mmol) was dissolved in DCM (19.5 mL, anhydrous, mol. sieve) and Oxyma pure (0.35 g, 2.48 mmol) and DCC (0.40 g, 1.95 mmol) added in one portion. The solution was stirred for 30 min at RT, filtered, and the filtrate added to a solution of 5a (0.61 g, 1.77 mmol) in DCM (10.5, mL anhydrous, mol. sieve). DIPEA (0.46 mL, 2.66 mmol) was added to the solution and the reaction stirred for 2 h at RT. The solution was washed with 0.1 M $H_2SO_4$ (2×), sat. aqueous $NaHCO_3$ (2×) and brine. The organic layer was dried over $Na_2SO_4$, filtered and concentrated in vacuo. The crude material was purified by flash chromatography to give N-boc-N'—(N-6-acetylthiohexyl-4-tert.-butyl-L-aspartoyl)-ethylenediamine (0.65 g, 1.30 mmol, 73% over 2 steps) as white solid.

MS: m/z 504.27=$[M+H]^+$, (calculated=504.28).

N-boc-N'—(N-6-Acetylthiohexyl-4-tert.-butyl-L-aspartoyl)-ethylenediamine (0.60 g, 1.18 mmol) was dissolved in TFA (5 mL) and TES (0.13 mL) and water (0.13 mL) were added. The mixture was stirred for 30 min at RT. TFA was removed in a stream of $N_2$, and crude 5b dissolved in $H_2O$/ACN 1:1 and purified by RP-HPLC.

Yield: 0.39 g, 0.85 mmol (TFA salt), 72%.

MS: m/z 348.25=$[M+H]^+$, (calculated=348.16).

Synthesis of 5c 5b (TFA salt, 0.38 g, 0.80 mmol) was dissolved in DMF (5 mL, anhydrous, mol. sieve) and Modmoc-ONp ((5-methyl-2-oxo-1,3-dioxol-4-yl)-methyl 4-nitrophenyl carbonate, 0.26 g, 0.88 mmol) and DIPEA (0.28 mL, 1.6 mmol) were added. The resulting suspension was diluted with DCM (5 mL, anhydrous, mol. sieve) and stirred for 3 h at RT. More DIPEA (0.28 mL 1.6 mmol) was added and stirring continued for 2 h. DCM was concentrated in vacuo. The residue was purified by RP-HPLC to give Modmoc-N'—(N-6-acetylthiohexyl-L-aspartyl)-ethylenediamine (0.31 g, 0.62 mmol, 77%) as a colorless oil.

MS: m/z 504.16=$[M+H]^+$, (calculated=504.17).

Modmoc-N'—(N-6-acetylthiohexyl-L-aspartyl)-ethylene-diamine (150 mg, 0.30 mmol) was dissolved in DCM (17.5 mL, anhydrous, mol. sieve) and NHS (41 mg, 0.36 mmol), DCC (74 mg, 0.36 mmol) and DMAP (4 mg, 0.03 mmol) were added in one portion. The reaction was stirred for 1 h at RT and the resulting suspension filtered. The precipitate was washed with a small amount of DCM and the combined filtrates were concentrated in vacuo. 5c was purified by RP-HPLC to give after lyophilization a colorless oil (144 mg, 0.24 mmol, 80%). MS: m/z 601.18=$[M+H]^+$, (calculated=601.18).

Example 6

Synthesis of Linker Reagent 6e

Linker reagent 6e was synthesized according to the following scheme:

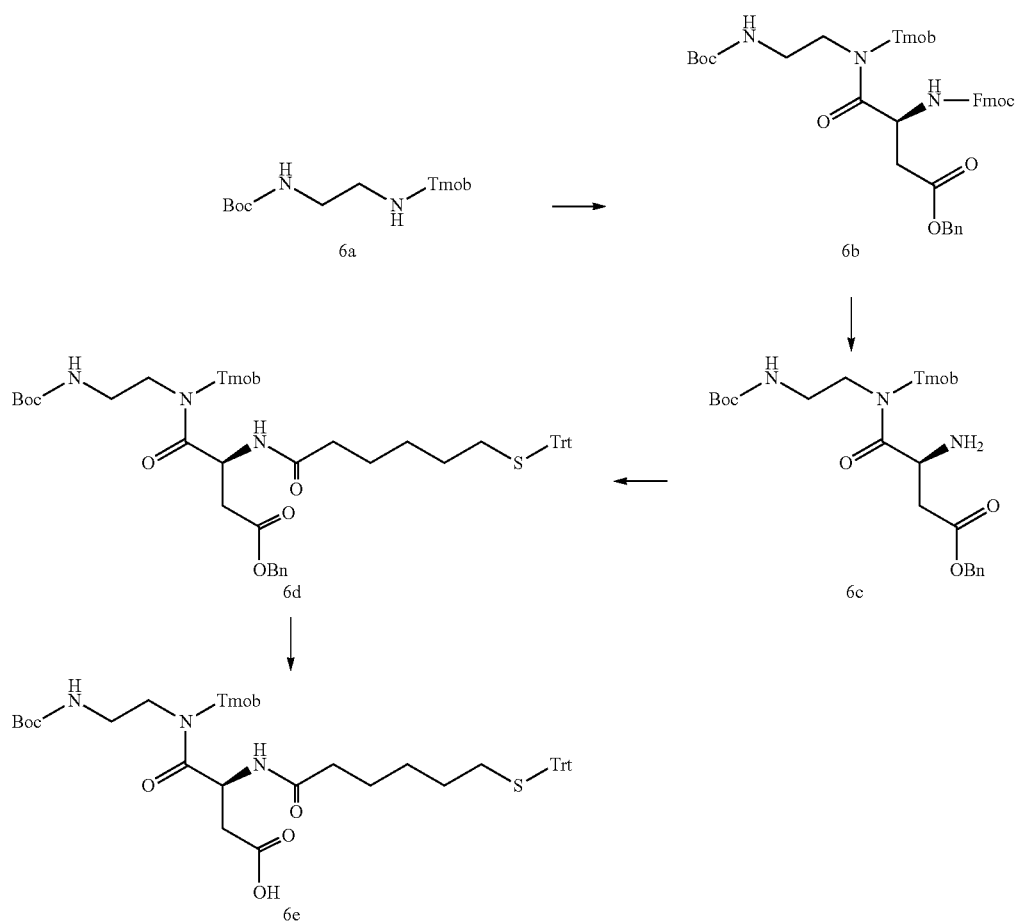

To a solution of N-Boc-ethylenediamine (2.08 g, 12.98 mmol) and NaCNBH$_3$ (775 mg, 12.33 mmol) in MeOH (20 mL, anhydrous) a solution of 2,4,6-trimethoxybenzaldehyde (2.29 g, 11.68 mmol) in 40 mL anhydrous MeOH/DCM 1/1 (v/v) was added over 2 h via syringe pump. The mixture was stirred at RT for 90 min, acidified with 0.4 M HCl (60 mL) and stirred further 15 min. The reaction mixture was extracted with ethyl acetate (5×). The combined organic phases were washed with saturated NaHCO$_3$ and brine and dried over Na$_2$SO$_4$. Solvents were removed in vacuo and the residue was dried in high vacuum (<0.1 mbar). Crude N-Boc-N'-Tmob-ethylenediamine 6a was used in the next reaction step without further purification. Yield: 3.70 g (10.87 mmol, 84%) of a colorless solid. MS: m/z 341.21=[M+H]+, (calculated=341.21).

A solution of 6a (1.7 g, 4.99 mmol) in DCM (40 ml, anhydrous, mol. sieve) was added to a solution of DCC (1.34 g, 6.50 mmol), Oxyma pure (995 mg, 7.00 mmol), Fmoc-L-Asp(OBn)-OH (2.22 g, 4.98 mmol) and collidine (1.24 mL, 9.53 mmol) in DCM (40 ml, anhydrous, mol. sieve). The reaction mixture was stirred for 3 h at RT. The precipitate was filtered off and the filtrate was washed with 0.1 M HCl, sat. NaHCO$_3$ and brine. Organic phase was dried over Na$_2$SO$_4$ and solvents were removed in vacuo. The crude material was purified by flash chromatography to give 6b (3.19 g, 4.15 mmol, 83%) as off white solid. MS:m/z 768.35=[M+H]+, (calculated=768.35).

To a solution of 6b (8.59 g, 11.19 mmol) in THF (98 mL) DBU (2 mL) was added. The solution was stirred for 12 min at RT, and the solvent was concentrated in vacuo. Flash chromatography afforded 4.89 g 6c (8.96 mmol, 80%). MS: m/z 546.28=[M+1-1]+, (calculated=546.28).

6-Tritylmercaptohexanoic acid (2.04 g, 5.22 mmol) was dissolved in DCM (20 mL, anhydrous, mol. sieve) and DCC (1.08 g, 5.22 mmol) and Oxyma pure (945 mg, 6.65 mmol) were added. After 30 min, 6c (2.59 g, 4.75 mmol) and DIPEA (1.24 mL, 7.12 mmol) were added. The reaction mixture was stirred for 22 h at RT. The mixture was extracted with 1 N H$_2$SO$_4$ (2×), sat. NaHCO$_3$ (2×) and brine. The organic phase was dried over Na$_2$SO$_4$, concentrated in vacuo and 6d was purified by flash chromatography. Yield: 4.10 g (4.47 mmol, 94%). MS: m/z 940.12=[M+Na]+, (calculated=940.43).

To a solution of 6d (4.10 g, 4.47 mmol) in i-PrOH (60 mL), water (20 mL) and LiOH (322 mg, 13.41 mmol) was added and the reaction mixture was stirred for 1 h at RT. Toluene (300 mL) was added and the organic phase was with 0.1 N HCl and with brine. The organic phase was dried over Na$_2$SO$_4$, filtrated and concentrated in vacuo. 6e was purified by flash chromatography. Yield: 3.53 g (4.26 mmol, 95%). MS: m/z 827.93=[M+H]+, (calculated=828.39).

Example 7

Synthesis of Linker Reagent 7c

Linker reagent 7c was synthesized according to the following scheme:

133

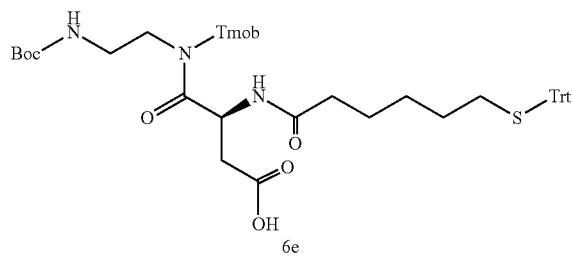

6e

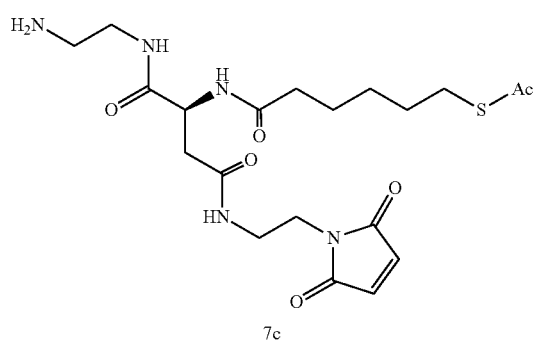

7c

134

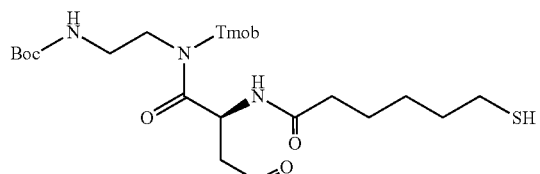

7a

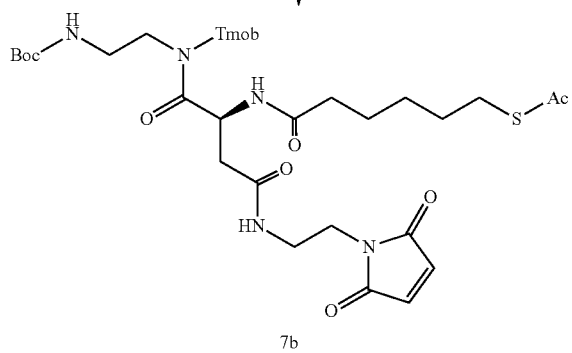

7b

Linker reagent 6e (420 mg, 0.508 mmol) was dissolved in HFIP (9 mL), and acetic acid (0.5 mL) and TES (0.5 mL) were added. The reaction was stirred for 15 min at RT an volatiles were removed in vacuo. 7a was isolated by RP-HPLC to give a white substance after lyophilization (216 mg, 0.369 mmol, 73%). MS: m/z 608.26=[M+Na]$^+$, (calculated=608.26).

To a solution of 7a (216 mg, 0.369 mmol) in DCM (15 ml, anhydous, mol. sieve) was added triethylamine (257 µl, 1.845 mmol), DMAP (45 mg, 0.037 mmol) and acetic anhydride (140 µl, 1.476 mmol). Reaction mixture was stirred for 40 min. Reaction was quenched with sat. NaHCO$_3$ (30 mL) and extracted with DCM (2×). Combined organics were dried over MgSO$_4$ and concentrated in vacuo. Residue was dissolved in DCM (15 mL, anhydrous, mol. sieve). PyBOP (384 mg, 0.738 mmol), DIPEA (257 µl, 1.476 mmol) and a solution of aminoethylmaleimide (TFA salt, 188 mg, 0.738 mmol) in DMF (2 mL) were added. Mixture was stirred for 40 min. Reaction was quenched with acetic acid. Volatiles were removed in vacuo. 7b was purified by RP-HPLC to give a white substance after lyophilization (154 mg, 0.205 mmol, 56%). MS: m/z 772.32=[M+Na]$^+$, (calculated=772.32).

7b (154 mg, 0.205 mmol) was dissolved in 16.2 mL of a mixture of HFIP/water/TES/TFA 39/1/1/3.3 (v/v/v/v) and stirred for 90 min at RT. Volatiles were removed in vacuo and 7c was purified by RP-HPLC to give a white substance after lyophilization (48 mg, 50%). MS: m/z 470.21=[M+H]$^+$, (calculated=470.21).

Example 8

Synthesis of Linker Maleimide Reagent 8d

Linker maleimide reagent 8d was synthesized according to the following scheme:

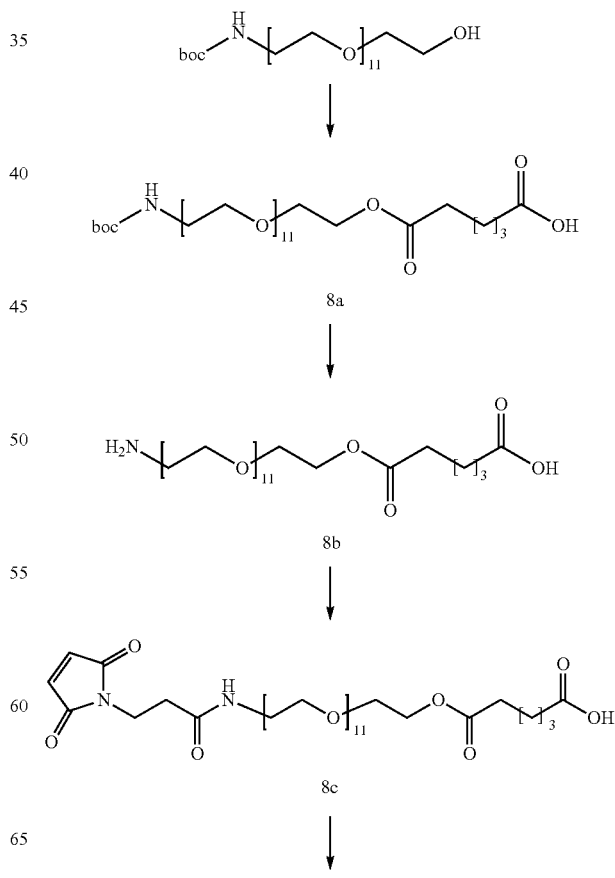

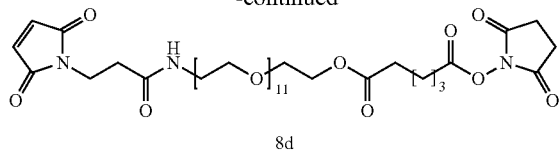

8d

To a solution of t-boc-Amido-dPEG 12-alcohol (1 mmol) in DCM (10 mL, anhydrous, mol. sieve) is added adipic anhydride (2 mmol), DIPEA (4 mmol) and DMAP (0.05 mmol). Volatiles are removed in vacuo, the residue is dissolved in ACN/water, acidified with acetic acid and 8a is purified by RP HPLC. Product containing fractions are pooled and lyophilized.

8a (1 mmol) is dissolved in 10 mL HFIP/TFA 9/1 (v/v) and stirred at RT until complete removal of the boc protecting group. Volatiles are removed in a stream of nitrogen and residue is dissolved in ACN/water and 8b is purified by RP HPLC. Product containing fractions are pooled and lyophilized.

8b (1 mmol) is dissolved in 10 mL ACN/water 9/1 (v/v). A solution of 3-(Maleimido)propionic acid N-hydroxysuccinimide ester (1 mmol) in ACN (5 mL) is added and the pH is adjusted to pH 6-7.5 by adding 0.1 M phosphate buffer pH 7.4. After conversion, 8c is purified by RP HPLC. Product containing fractions are pooled and lyophilized.

8c (1 mmol) is dissolved in 10 mL DCM (anhydrous, mol. sieve). DCC (2 mmol) and HOSu (2 mmol) is added. After conversion, volatiles are removed in vacuo and 8d is purified by RP HPLC. Product containing fractions are pooled and lyophilized.

Example 9

Preparation of GRF(1-29)-Cys-PEG 9

GRF(1-29)-Cys-PEG 9 is prepared by PEGylation of GRF(1-29)-Cys via its reactive thiol group according to the following scheme:

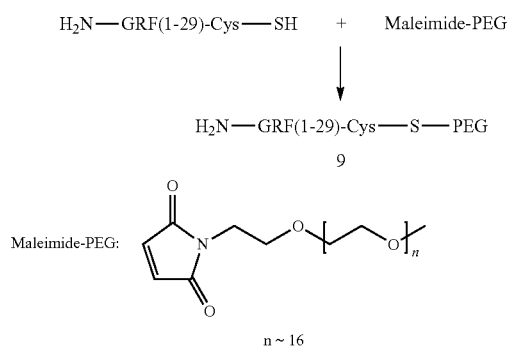

A solution of ω-maleimido-α-methoxy-PEG 750 Da (2.25 mg, 3 μmol) in 0.5 mL PBS buffer containing 0.01% Tween20 is added to a solution of 7 mg GRF(1-29)-Cys in 0.5 mL PBS buffer. The mixture is incubated for 30 min at RT. 9 is purified by SEC (Äkta Purifier System equipped with a SD75 GL10/300 column, GE Healthcare, running buffer: pH 7.4 PBS containing 0.01% Tween20, flow rate 0.75 ml/min).

Example 10

Preparation of linker-GRF(1-29)-Cys-PEG 10b

Linker-GRF(1-29)-Cys-PEG 10b is prepared from GRF(1-29)-Cys-PEG 9 by amidation reaction with linker reagent 5c according to the following scheme:

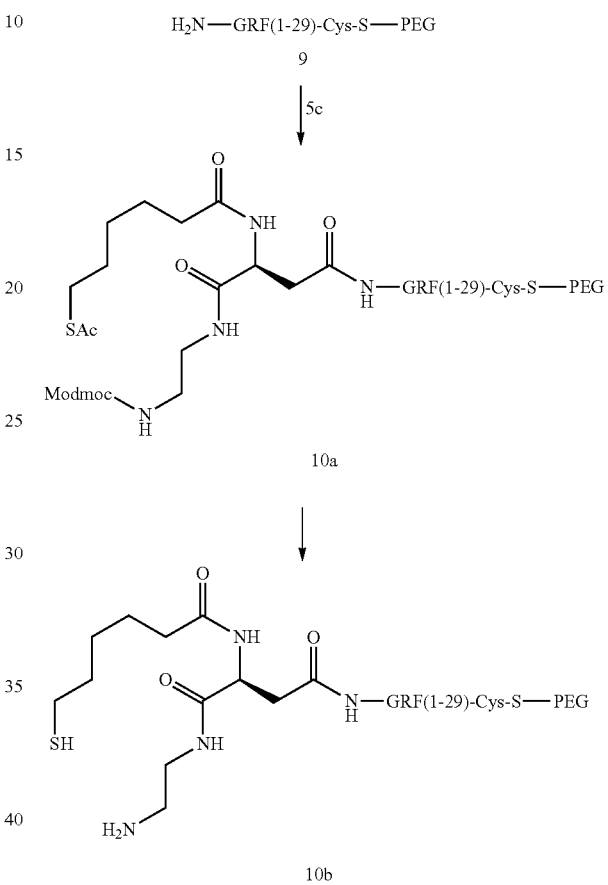

The reaction scheme depicts an amidation reaction on the N-terminus of the GRF-peptide. It is understood that the amidation reaction can take place at any of the free amino groups of GRF(1-29)-Cys-PEG (i.e. amino terminus or Lys side chains).

6 mg of Linker reagent 5c is dissolved in 100 μL DMSO to yield a concentration of 100 mM. 1 molar equivalent of linker reagent 5c relative to the amount of GRF(1-29)-Cys-PEG is added to a solution of 9 mg GRF(1-29)-Cys-PEG 9 in 2 mL pH 7.4 PBS containing 0.01% Tween20. The reaction is mixed carefully and incubated for 5 min at room temperature. Subsequently, further molar equivalents of linker reagent 5c are added to the solution in 1 molar equivalent steps and after addition of each equivalent the reaction mixture is incubated for 5 min at room temperature, until an approx. 2/1 mixture (as determined by MS) of unmodified 9 and the protected linker monoconjugate 10a is obtained.

The pH of the reaction mixture is adjusted to pH 6.5 by addition of 1 M sodium citrate, pH 5.0. 0.5 M $NH_2OH$ ($NH_2OH$ hydrochloride dissolved in 10 mM sodium citrate, 140 mM sodium chloride, 5 mM $Na_2EDTA$, adjusted to pH 6.5 with NaOH) is added to a final concentration of 45 mM and the deprotection reaction is incubated at room temperature for 4 h yielding the linker-GRF(1-29)-Cys-PEG conjugate 10b. The mixture of GRF(1-29)-Cys-PEG 9 and linker-GRF(1-29)-Cys-PEG conjugate 10b is buffer exchanged to pH 7.4 PBS containing 0.01% Tween and the overall concentration of the two species is adjusted to 1 mg/mL. The content of 10b in the mixture is determined by ESI-MS.

Example 11

Preparation of GRF(1-29)-Cys-linker 11b

GRF(1-29)-Cys-linker with aminoethyl tag 11b is prepared by reaction with linker reagent 7c according to the following scheme:

A solution of 0.8 mg GRF(1-29)-Cys in 0.2 mL 10 mM Citrat pH 6.5, 140 mM NaCl, 0.5 mM EDTA, 0.1% Tween 80 is mixed with linker reagent 7c (4.7 µl of a 100 mM solution in DMSO). After 10 min incubation, 10 µl 2-mercaptoethanol solution (4.7 µl 2-mercaptoethanol in 1 mL water) is added and incubated for further 15 min.

For removal of acetyl protecting group, 22 µl of 0.5 M $NH_2OH$ ($NH_2OH$ hydrochloride dissolved in 10 mM sodium citrate, 140 mM sodium chloride, 5 mM $Na_2EDTA$, adjusted to pH 6.5 with NaOH) is added. Mixture is incubated for 3 h at RT. 11b is purified/buffer exchanged by SEC (Äkta Purifier System equipped with a SD75 GL10/300 column, GE Healthcare, running buffer: pH 7.4 PBS containing 0.01% Tween20, flow rate 0.75 ml/min). Solution is concentrated to 300 µl by ultrafiltration.

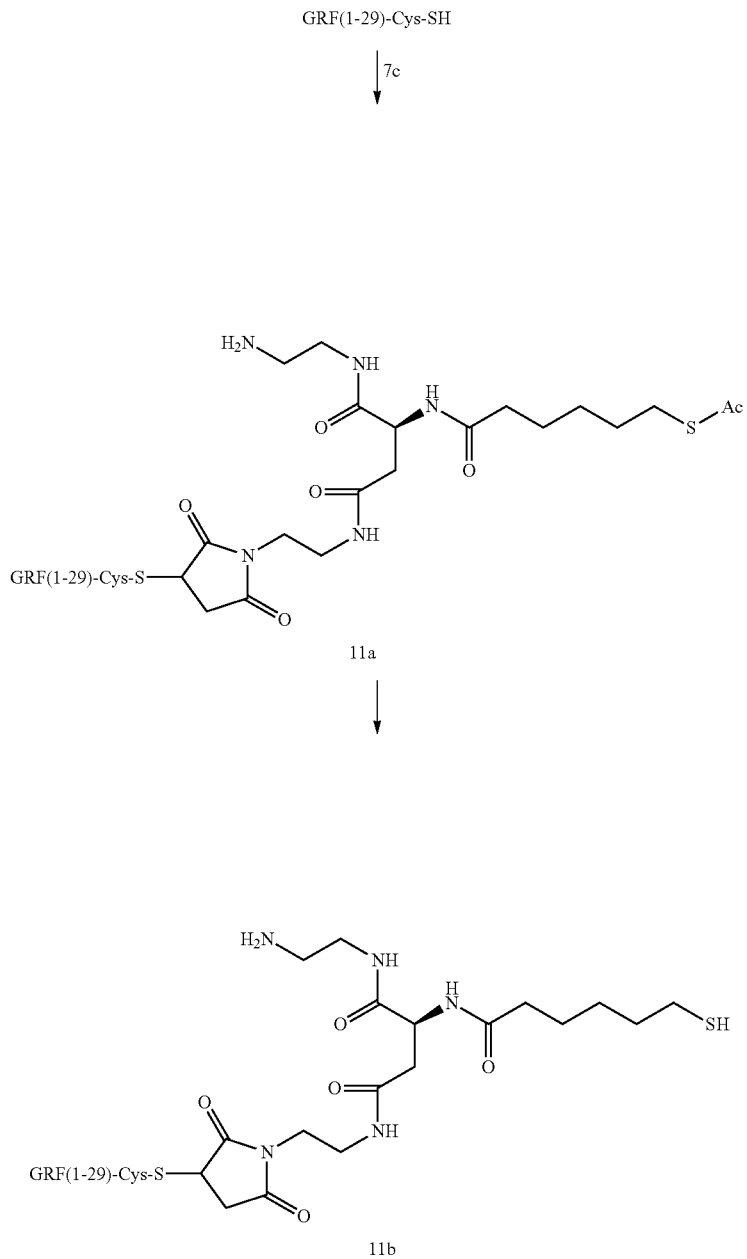

Example 12
Synthesis of Backbone Reagent 12a and 12g
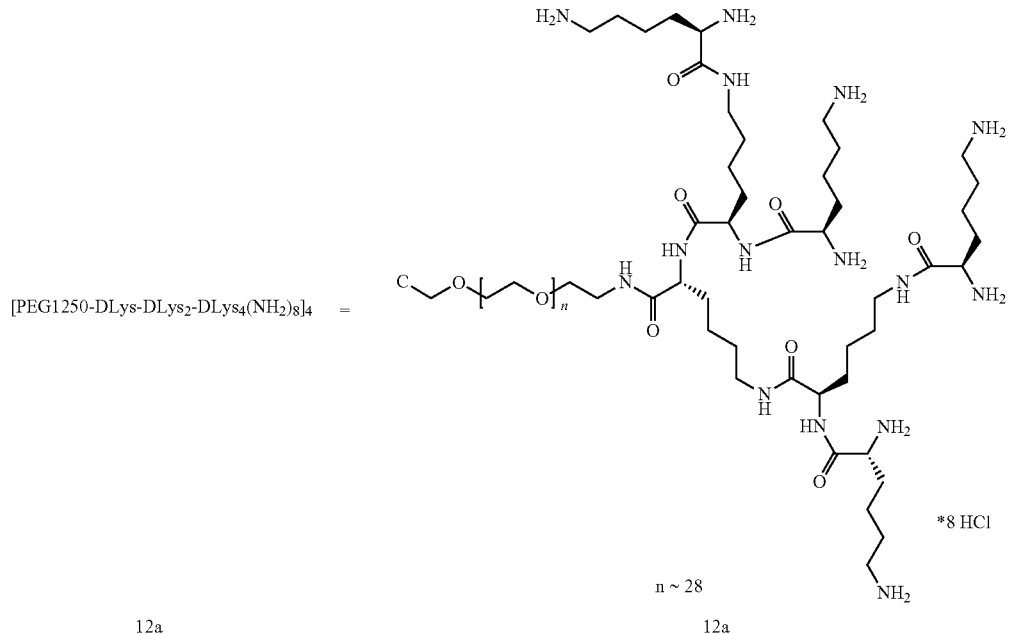
12a
Backbone reagent 12a was synthesized as described in example 1 of WO 2011/012715 A1 except for the use of Boc-DLys(Boc)-OH instead of Boc-LLys(Boc)-OH.
MS: m/z 888.50=$[M+10H^+]^{10+}$ (calculated=888.54)
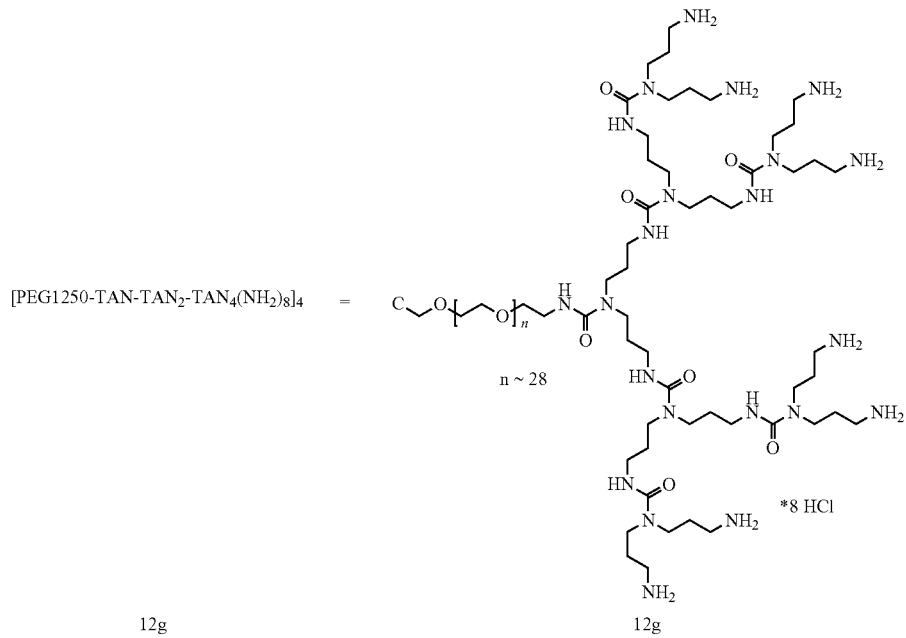
12g Backbone reagent 12g was synthesized from amino 4-arm PEG5000 12b according to the following scheme:

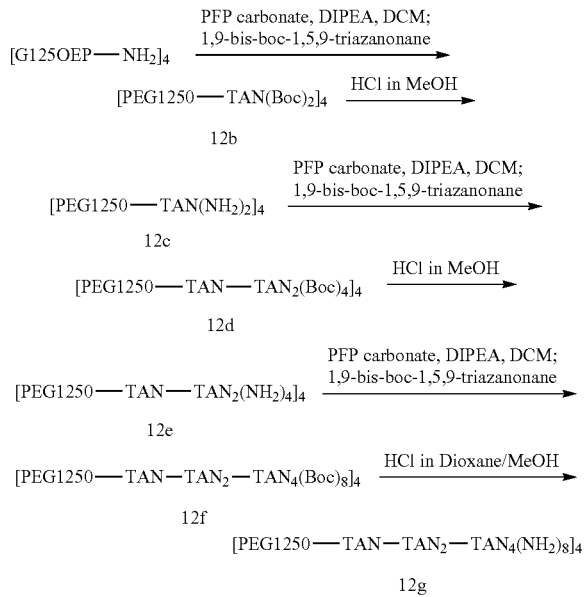

For synthesis of compound 12b, amino 4-arm PEG5000 (MW ca. 5350 g/mol, 10.7 g, 2.00 mmol, HCl salt) and bis(pentafluorophenyl)carbonate (4.73 g, 12.0 mmol) were dissolved in 43 mL of DCM (anhydrous) and DIPEA (3.10 g, 24.0 mmol, 4.18 mL) was added at room temperature. After 10 min, 1,9-bis-boc-1,5,9-triazanonane (5.30 g, 16.0 mmol) was added and the mixture was stirred for 15 min. Then additional 1,9-bis-boc-1,5,9-triazanonane (0.33 g, 1.0 mmol) was added. After complete dissolution, the reaction mixture was filtered and the solvent was evaporated at room temperature.

The residue was dissolved in 40 mL iPrOH and diluted with 320 mL MTBE. The product was precipitated over night at −20° C. The precipitate was collected by filtration through a glass filter Por. 3, and washed with 200 mL of cooled MTBE (0° C.). The product was dried in vacuo over night.

Yield 11.1 g (83%) white solid 12b.

MS: m/z 1112.86=$[M+6H]^{6+}$ (calculated=1113.04).

For synthesis of compound 12c, the boc-protected compound 12b (11.1 g, 1.66 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night.

Yield 9.14 g (89%) white powder 12c (HCl salt).

MS: m/z 979.45=$[M+6H]^{6+}$ (calculated=979.55).

For synthesis of compound 12d, compound 12c (9.06 g, 1.47 mmol, HCl salt) and bis(pentafluorophenyl)carbonate (6.95 g, 17.6 mmol) were dissolved in 50 mL of DCM (anhydrous) and DIPEA (4.56 g, 35.3 mmol, 6.15 mL) was added at room temperature. After 10 min, 1,9-bis-boc-1,5,9-triazanonane (7.80 g, 23.5 mmol) was added and the mixture was stirred for 15 min. Then, additional 1,9-bis-boc-1,5,9-triazanonane (0.49 g, 1.5 mmol) was added. After complete dissolution, the solvent was evaporated at room temperature.

The residue was dissolved in 35 mL iPrOH at 40° C. and diluted with 200 mL MTBE. The product was precipitated over night at −20° C. The precipitate was collected by filtration through a glass filter Por. 3, and washed with 200 mL of cooled MTBE (0° C.). The product was dried in vacuo over night to give 12d as a white solid.

Yield 11.6 g (90%) white solid 12d.

MS: m/z 1248.08=$[M+7H]^{7+}$ (calculated=1248.27).

For synthesis of compound 12e, the boc-protected compound 12d (11.4 g, 1.31 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night to give white powder 12e.

Yield 7.60 g (75%) white powder 12e (HCl salt).

MS: m/z 891.96=$[M+8H]^{8+}$ (calculated=892.13).

For synthesis of compound 12f, compound 12e (7.56 g, 0.980 mmol, HCl salt) and bis(pentafluorophenyl)carbonate (9.27 g, 23.0 mmol) were dissolved in 250 mL of DCM (anhydrous) and DIPEA (6.08 g, 47.0 mmol, 8.19 mL) was added at 35° C. After 10 min, 1,9-bis-boc-1,5,9-triazanonane (5.30 g, 16.0 mmol) was added and the mixture was stirred for 15 min. Then additional 1,9-bis-boc-1,5,9-triazanonane (0.33 g, 1.0 mmol) was added. After complete dissolution, the solvent was evaporated at room temperature.

The residue was dissolved in 250 mL iPrOH at 60° C. and diluted with 1350 mL MTBE. The product was precipitated over night at −20° C. The precipitate was collected by filtration through a glass filter Por. 3, and washed with 400 mL of cooled MTBE (0° C.). The product was dried in vacuo over night to give 12f as a glassy solid.

Yield 11.1 g (83%) glassy solid 12f.

MS: m/z 1312.01=$[M+10H]^{10+}$ (calculated=1312.21).

For synthesis of backbone reagent 12g, the boc-protected compound 12f (7.84 g, 0.610 mmol) was dissolved in 16 mL of MeOH at 37° C. and 55 mL of a precooled solution of 4 M HCl (4° C.) in dioxane was added at room temperature. The mixture was stirred without cooling for 20 min. After 20 min, 110 mL of 3M HCl in MeOH was added. The solution was partitioned in 24 Falcon tubes (50 mL) and precipitated with by adding 40 mL cold MTBE (−20° C.) to each Falcon tube. After centrifugation at 3214 rcf for 1 min, the supernatant was decanted and the glassy solid was dissolved in 5 mL MeOH per Falcon tube and precipitated by adding 40 mL cold MTBE (−20° C.) to each Falcon tube again. The supernatant was discarded and the remaining solid was dried in vacuo over night.

Yield 5.74 g (87%) white glassy solid 12g (HCl salt).

MS: m/z 965.46=$[M+10H]^{10+}$ (calculated=965.45).

Example 13

Synthesis of Crosslinker Reagents 13d, 13g, 13k, and 13o

Crosslinker reagent 13e was prepared from azelaic acid monobenzyl ester and PEG10000 according to the following scheme:

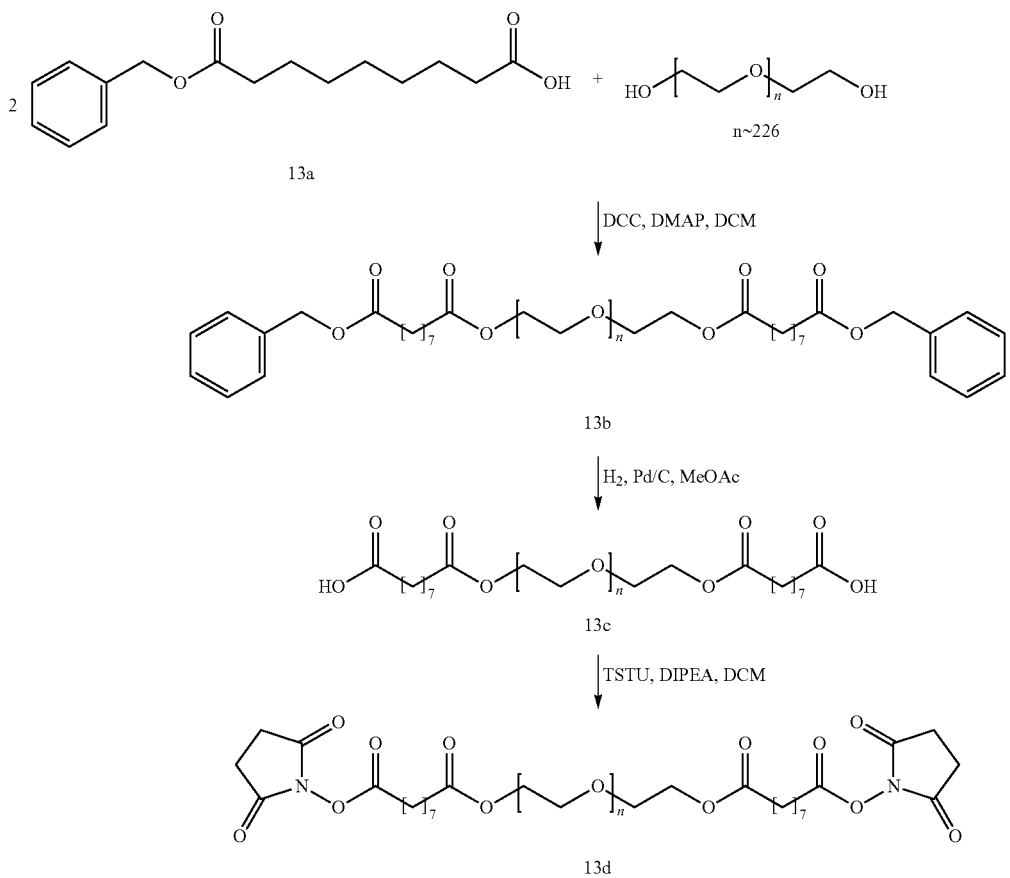

13d

For the synthesis of azelaic acid monobenzyl ester 13a, a mixture of azelaic acid (37.6 g, 200 mmol), benzyl alcohol (21.6 g, 200 mmol), p-toluenesulfonic acid (0.80 g, 4.2 mmol), and 240 mL toluene was refluxed for 7 h in a Dean-Stark apparatus. After cooling down, the solvent was evaporated and 300 mL sat. aqueous NaHCO$_3$ solution were added. This mixture was extracted with 3×200 mL MTBE. The combined organic phases were dried over Na$_2$SO$_4$ and the solvent was evaporated. The product was purified on 2×340 g silica using ethyl acetate/heptane (10:90→25:75) as eluent. The eluent was evaporated and the residue was dried in vacuo over night.

Yield 25.8 g (46%) colorless oil 13a.

MS: m/z 279.16=[M+H]$^+$ (calculated=279.16).

For synthesis of compound 13b, azelaic acid monobenzyl ester 13a (3.90 g, 14.0 mmol) and PEG 10000 (40.0 g, 4.00 mmol) were dissolved in 64 mL dichloromethane and cooled with an ice bath. A solution of DCC (2.89 g, 14.0 mmol) and DMAP (0.024 g, 0.020 mmol) in 32 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 65 mL dichloromethane and diluted with 308 mL MTBE at room temperature. The mixture was stored over night at −20° C. The precipitate was collected by filtration through a glass filter Por. 3, and washed with 250 mL of cooled MTBE (−20° C.). The product was dried in vacuo over night.

Yield 40.8 g (97%) white powder 13b.

MS: m/z 835.50=[M+14H]$^{14+}$ (calculated=835.56).

For synthesis of compound 13c, compound 13b (40.6 g, 3.86 mmol) was dissolved in methyl acetate (250 mL) and 203 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 37.2 g (93%) glassy solid 13c.

MS: m/z 882.53=[M+13H]$^{13+}$ (calculated=882.51).

For synthesis of compound 13d, compound 13c (32.0 g, 3.10 mmol) and TSTU (3.73 g, 12.4 mmol) were dissolved in 150 mL dichloromethane at room temperature. Then DIPEA (1.60 g, 12.4 mmol) was added and the mixture was stirred for 1 h. The resulting suspension was filtered and the filtrate was diluted with 170 mL dichloromethane, washed with 140 mL of a solution of 750 g water/197 g NaCl/3 g NaOH. The organic phase was dried over MgSO$_4$ and the solvent was evaporated in vacuo.

The residue was dissolved in 200 mL toluene, diluted with 180 mL MTBE at room temperature and stored over night at −20° C. The precipitate was collected by filtration through a glass filter Por. 3, and washed with 100 mL of cooled MTBE (−20° C.). The product was dried in vacuo over night.

Yield 28.8 g (88%) white powder 13d.

MS: m/z 795.47=[M+15H]$^{15+}$ (calculated=795.54).

Crosslinker reagent 13g was prepared from azelaic acid monobenzyl ester and PEG6000 according to the following scheme:

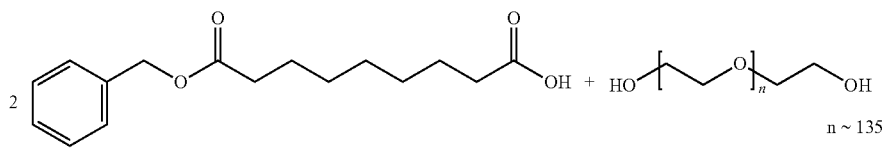

13a

↓ DCC, DMAP, DCM

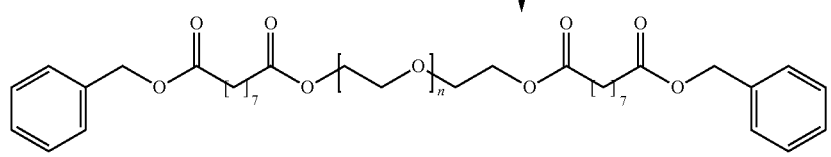

13e

↓ H2, Pd/C, MeOAc

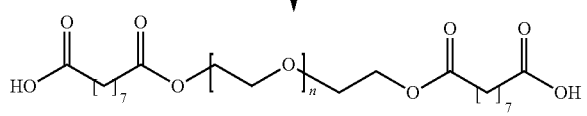

13f

↓ TSTU, DIPEA, DCM

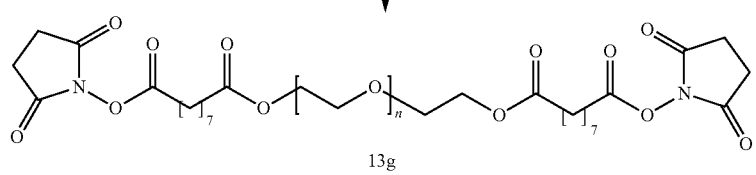

13g

For synthesis of compound 13e, azelaic acid monobenzyl ester 13a (6.50 g, 23.3 mmol) and PEG 6000 (40.0 g, 6.67 mmol) were dissolved in 140 mL dichloromethane and cooled with an ice bath. A solution of DCC (4.81 g, 23.3 mmol) and DMAP (0.040 g, 0.33 mmol) in 40 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 300 mL MTBE at room temperature. The mixture was stored over night at −20° C. The precipitate was collected by filtration through a glass filter Por. 3, and washed with 500 mL of cooled MTBE (−20° C.). The product was dried in vacuo over night.

Yield: 41.2 g (95%) white powder 13e.

MS: m/z 833.75=$[M+8H]^{8+}$ (calculated=833.74).

For synthesis of compound 13f, compound 13e (41.2 g, 6.32 mmol) was dissolved in methyl acetate (238 mL) and ethanol (40 mL), then 400 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 38.4 g (96%) glassy solid 13f.

MS: m/z 750.46=$[M+9H]^{9+}$ (calculated=750.56).

For synthesis of compound 13g, compound 13f (38.2 g, 6.02 mmol) and TSTU (7.25 g, mmol) were dissolved in 130 mL dichloromethane at room temperature. Then DIPEA (3.11 g, 24.1 mmol) was added and the mixture was stirred for 1 h. The resulting suspension was filtered, the filtrate was diluted with 100 mL dichloromethane and washed with 200 mL of a solution of 750 g water/197 g NaCl/3 g NaOH. The organic phase was dried over MgSO$_4$ and the solvent was evaporated in vacuo.

The residue was dissolved in 210 mL toluene, diluted with 430 mL MTBE at room temperature and stored over night at −20° C. The precipitate was collected by filtration through a glass filter Por. 3, and washed with 450 mL of cooled MTBE (−20° C.). The product was dried in vacuo over night.

Yield 35.8 g (91%) white powder 13g.

MS: m/z 857.51=$[M+8H]^{8+}$ (calculated=857.51).

Crosslinker reagent 13k was prepared from isopropylmalonic acid monobenzyl ester and PEG10000 according to the following scheme:

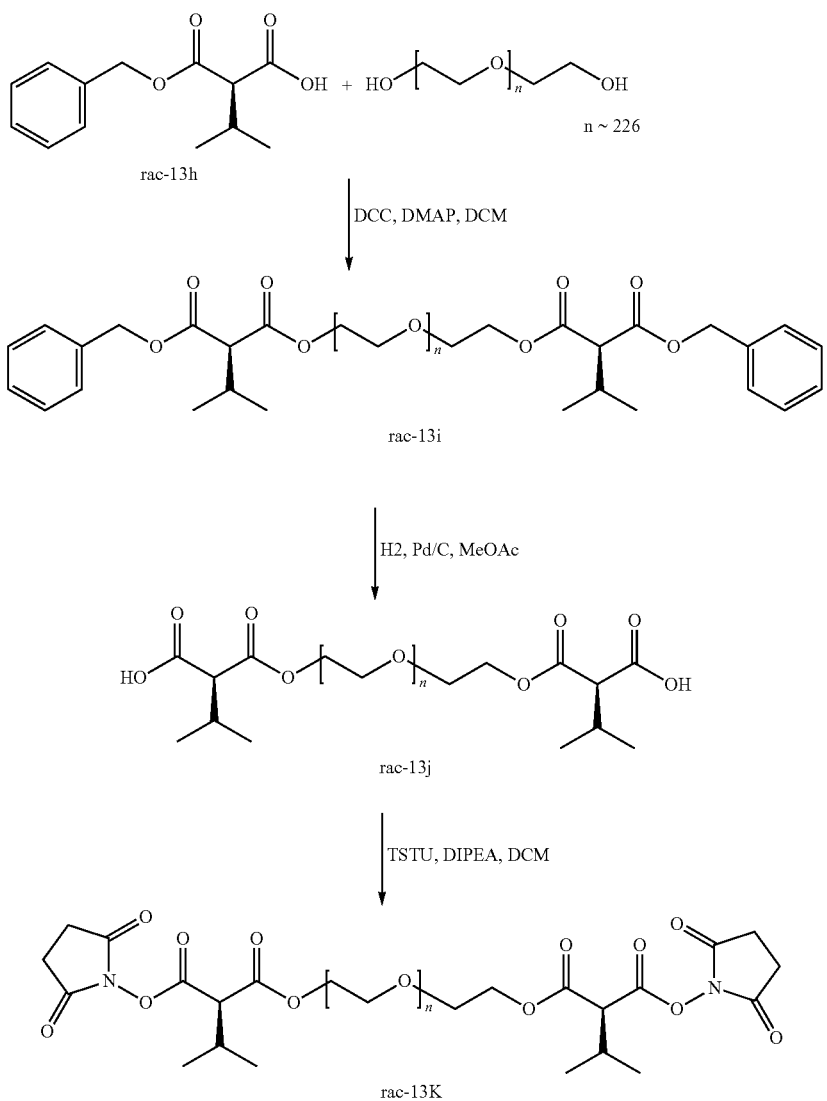

rac-13K

For the synthesis of isopropylmalonic acid monobenzyl ester rac-13h, isopropylmalonic acid (35.0 g, 239 mmol), benzyl alcohol (23.3 g, 216 mmol) and DMAP (1.46 g, 12.0 mmol) were dissolved in 100 mL acetonitrile. Mixture was cooled to 0° C. with an ice bath. A solution of DCC (49.4 g, 239 mmol) in 150 mL acetonitrile was added within 15 min at 0° C. The ice bath was removed and the reaction mixture was stirred over night at room temperature, then the solid was filtered off. The filtrate was evaporated at 40° C. in vacuo and the residue was dissolved in 300 mL MTBE. This solution was extracted with 2×300 mL sat. aqueous NaHCO$_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over MgSO$_4$. The product was purified on 340 g silica using ethyl acetate/heptane (10:90→20:80) as eluent. The eluent was evaporated and the residue was dried in vacuo over night.

Yield: 9.62 g (17%) colorless oil rac-13h.

MS: m/z 237.11=[M+H]$^+$ (calculated=237.11).

For synthesis of compound 13i, isopropylmalonic acid monobenzyl ester rac-13h (945 mg, 4.00 mmol) and PEG 10000 (10.0 g, 4.00 mmol) were dissolved in 20 mL dichloromethane and cooled with an ice bath. A solution of DCC (825 mg, 4.00 mmol) and DMAP (6 mg, 0.05 mmol) in 10 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 20 mL dichloromethane and diluted with 150 mL MTBE at room temperature. The mixture was stored over night at −20° C. The precipitate was collected by filtration through a glass filter Por. 3, and washed with 500 mL of cooled MTBE (−20° C.).

The product was dried in vacuo over night.

Yield: 9.63 g (92%) white powder 13i.

MS: m/z 742.50=[M+16H]$^{16+}$ (calculated=742.51).

For synthesis of compound 13j, compound 13i (3.38 g, 0.323 mmol) was dissolved in methyl acetate (100 mL) and 105 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield: 3.25 g (98%) glassy solid 13j.

MS: m/z 731.25=[M+16H]$^{16+}$ (calculated=731.25).

For synthesis of compound 13k, compound 13j (3.10 g, 0.302 mmol) and TSTU (0.364 g, 1.21 mmol) were dissolved in 15 mL dichloromethane at room temperature. Then DIPEA (0.156 g, 1.21 mmol) was added and the mixture was stirred for 45 min. The resulting suspension was filtered and the filtrate was washed with 2×10 mL of a 0.5 M phosphate buffer pH=6.5. The organic phase was dried over MgSO$_4$ and the solvent was evaporated in vacuo. The residue was dissolved in 20 mL toluene, diluted with 10 mL MTBE at room temperature and stored over night at −20° C. The precipitate was collected by filtration through a glass filter Por. 3, and washed with 250 mL of cooled MTBE (−20° C.). The product was dried in vacuo over night.

Yield: 2.66 g (84%) white powder 13k.

MS: m/z 743.37=[M+16H]$^{16+}$ (calculated=743.38).

Crosslinker reagent rac-13o was prepared from cis-1,4-cyclohexanedicarboxylic acid and PEG10000 according to the following scheme:

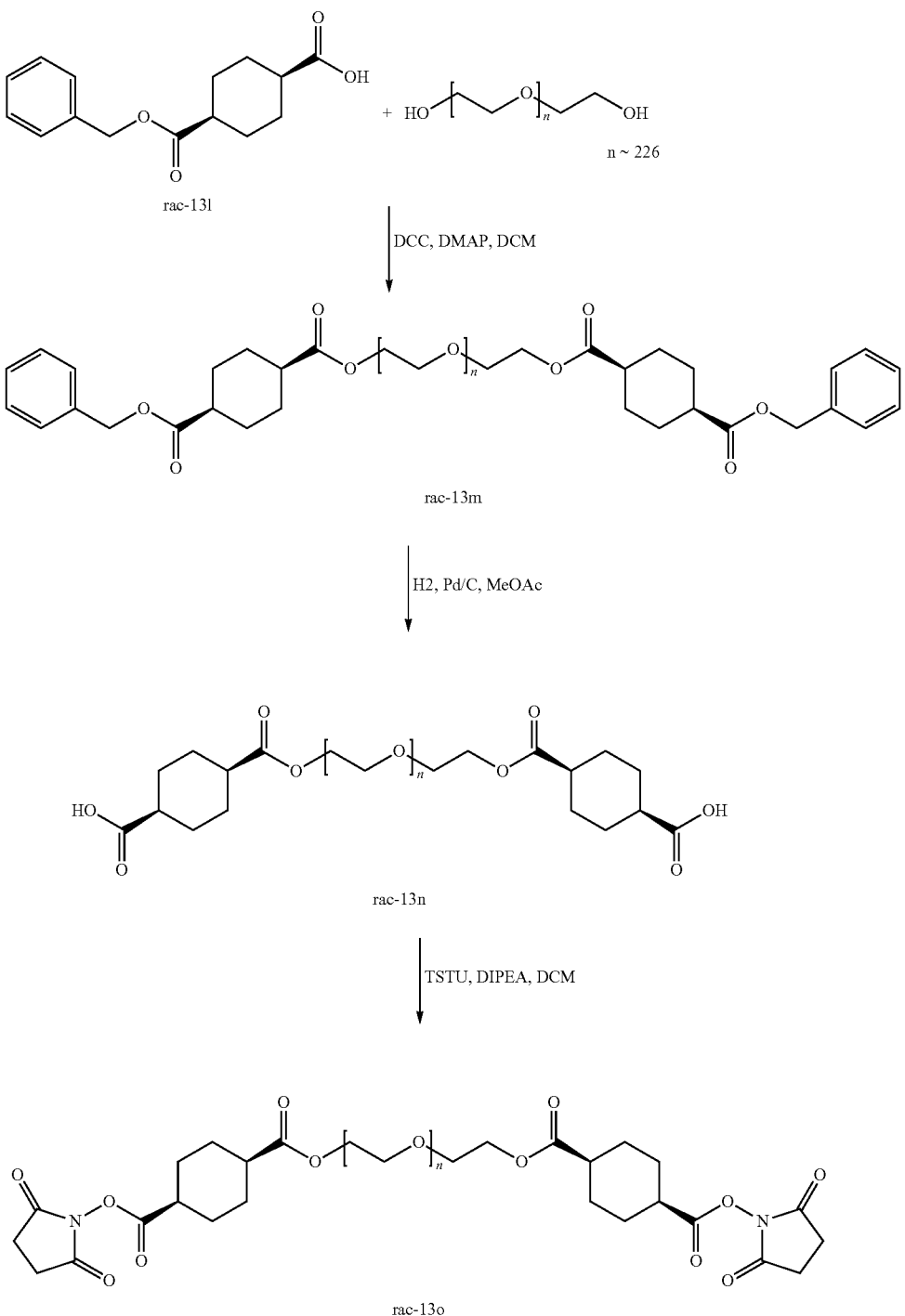

For the synthesis of cis-1,4-cyclohexanedicarboxylic acid monobenzyl ester rac-13l, cis-1,4-cyclohexanedicarboxylic acid (20.0 g, 116 mmol), benzyl alcohol (11.3 g, 105 mmol) and DMAP (710 mg, 5.81 mmol) were dissolved in 200 mL THF. Mixture was cooled to 0° C. with an ice bath. A solution of DCC (49.4 g, 239 mmol) in 100 mL THF was added within 15 min at 0° C. The ice bath was removed and the reaction mixture was stirred over night at room temperature, then the solid was filtered off. The filtrate was evaporated at 40° C. and the residue was dissolved in 300 mL MTBE. This solution was extracted with 2×300 mL sat. aqueous $NaHCO_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over $MgSO_4$. The product was purified on 340 g silica using ethyl acetate/heptane (10:90→20:80) as eluent. The eluent was evaporated and the colorless oily residue crystallized during drying in vacuo over night.

Yield: 4.82 g (16%) colorless crystals rac-13l.

MS: m/z 263.13=$[M+H]^+$ (calculated=263.13).

For synthesis of compound 13m, cis-1,4-cyclohexanedicarboxylic acid monobenzyl ester rac-21 (2.10 g, 8.00 mmol) and PEG 10000 (20.0 g, 10.0 mmol) were dissolved in 50 mL dichloromethane and cooled with an ice bath. A solution of DCC (1.65 g, 8.00 mmol) and DMAP (0.012 g, 0.10 mmol) in 25 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 55 mL dichloromethane and diluted with 300 mL MTBE at room temperature. The mixture was stored over night at −20° C. The precipitate was collected by filtration through a glass filter Por. 3, and washed with 250 mL of cooled MTBE (−20° C.). The product was dried in vacuo over night.

Yield: 18.2 g (87%) white powder 13m.

MS: m/z 745.76=$[M+16H]^{16+}$ (calculated=745.77).

For synthesis of compound 13n, compound 13m (9.00 g, 0.857 mmol) was dissolved in methyl acetate (100 mL) and 157 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield: 8.83g (100%) glassy solid 13n.

MS: m/z 734.50=$[M+16H]^{16+}$ (calculated=734.50).

For synthesis of compound 13o, compound 13n (8.92 g, 0.864 mmol) and TSTU (1.04 g, 3.64 mmol) were dissolved in 35 mL dichloromethane at room temperature. Then DIPEA (0.447 g, 3.46 mmol) was added and the mixture was stirred for 45 min. The resulting suspension was filtered and the filtrate was washed with 2×10 mL of a 0.5 M phosphate buffer pH=6.5. The organic phase was dried over $MgSO_4$ and the solvent was evaporated in vacuo.

The residue was dissolved in 50 mL toluene, diluted with 25 mL MTBE at room temperature and stored over night at −20° C. The precipitate was collected by filtration through a glass filter Por. 3, and washed with 400 mL of cooled MTBE (−20° C.). The product was dried in vacuo over night.

Yield: 7.62 g (84%) white powder 13o.

MS: m/z 702.60=$[M+16H]^{16+}$ (calculated=702.59).

Example 14

Preparation of Hydrogel Beads 14a, 14b, 14c, and 14d Containing Free Amino Groups In a cylindrical 250 mL reactor with bottom outlet, diameter 60 mm, equipped with baffles, an emulsion of 218 mg Cithrol™ DPHS in 100 mL undecane was stirred with an isojet stirrer, diameter 50 mm at 580 rpm, at ambient temperature. A solution of 250 mg 12a and 2205 mg 13d in 22.1 g DMSO was added and stirred for 10 min at RT to form a suspension. 1.1 mL TMEDA were added to effect polymerization. The mixture was stirred for 16 h. 1.7 mL of acetic acid were added and then after 10 min 100 mL of a 15 wt % solution of sodium chloride in water was added. After 10 min, the stirrer was stopped and phases were allowed to separate. After 2 h the aqueous phase containing the hydrogel was drained.

For bead size fractionation, the water-hydrogel suspension was diluted with 40 mL ethanol and wet-sieved on 125, 100, 75, 63, 50, 40, and 32 µm steel sieves using a Retsch AS200 control sieving machine for 15 min. Sieving amplitude was 1.5 mm, water flow 300 mL/min. Bead fractions that were retained on the 63 and 75 µm sieves were pooled and washed 3 times with 0.1% AcOH, 10 times with ethanol and dried for 16 h at 0.1 mbar to give 670 mg of 14a as a white powder.

Amino group content of the hydrogel was determined to be 0.145 mmol/g by conjugation of a fmoc-amino acid to the free amino groups on the hydrogel and subsequent fmoc-determination.

14b was prepared as described for 14a except for the use of 350 mg 12a, 2548 mg 13g, 26.1 g DMSO, 257 mg Cithrol™ DPHS, 1.5 mL TMEDA, and 2.4 mL acetic acid, yielding 550 mg 14b as a white powder, free amino groups 0.120 mmol/g.

14c was prepared as described for 14a except for the use of 250 mg 12a, 3019 mg rac-13k, 32.7 g DMSO, 290 mg Cithrol™ DPHS, 1.1 mL ml TMEDA, and 1.7 mL acetic acid, yielding 770 mg 13c as a white powder, free amino groups 0.126 mmol/g.

14d was prepared as described for 14a except for the use of 250 mg 12a, 2258 mg rac-13o, 22.6 g DMSO, 222 mg Cithrol™ DPHS, 1.1 mL ml TMEDA, and 1.7 mL acetic acid, yielding 186 mg 14d as a white powder, free amino groups 0.153 mmol/g.

Example 15

Preparation of Maleimide Functionalized Hydrogel Beads 15

259.3 mg of dry hydrogel beads 14a was incubated for 15 min in 10 mL 1% n-propylamine in NMP and subsequently washed five times with NMP and two times with 2% DIPEA in NMP. 171 mg of Mal-NH-PEG12-PFE was dissolved in 1 mL NMP and added to the washed hydrogel beads 14a. The hydrogel suspension was incubated for 2 h at room temperature. Resulting maleimide functionalized hydrogel beads 15 were washed five times each with NMP, 20 mM succinate, 1 mM $Na_2EDTA$, 0.01% Tween20, pH 3.0, water, and with 0.1% acetic acid, 0.01% Tween20.

Example 16

Preparation of Linker Maleimide Functionalized Hydrogel Beads 16

259.3 mg of dry hydrogel beads 14a are incubated for 15 min in 10 mL 1% n-propylamine in NMP and subsequently washed five times with NMP and two times with 2% DIPEA in NMP. 169 mg of linker maleimide reagent 8d is dissolved in 1 mL NMP and added to the washed hydrogel beads 14a. The hydrogel suspension is incubated for 2 h at room temperature. Resulting maleimide functionalized hydrogel beads 16 are washed five times each with NMP, 20 mM succinate, 1 mM $Na_2EDTA$, 0.01% Tween20, pH 3.0, water, and with 0.1% acetic acid, 0.01% Tween20.

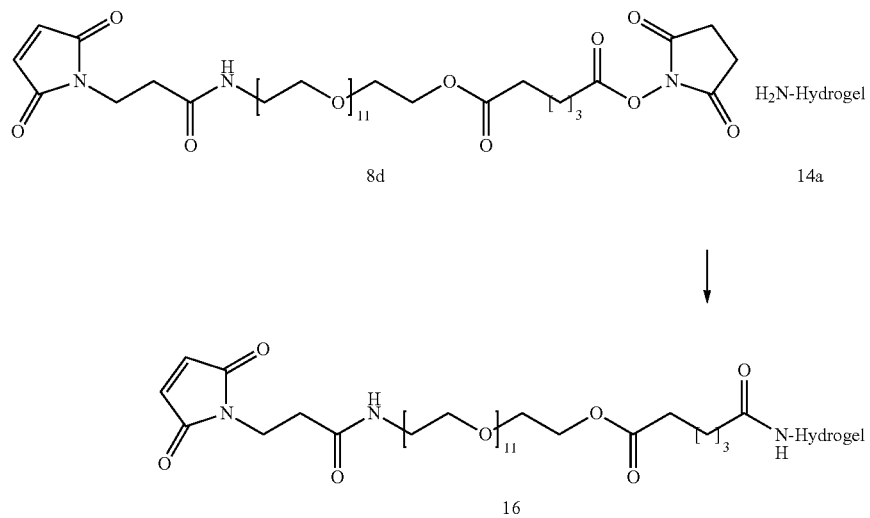

Example 17

Synthesis of Transient hydrogel-linker-GRF(1-29)-Cys-PEG Prodrug 17

1.5 mg of linker-GRF(1-29)-Cys-PEG 10b in pH 7.4 PBS containing 0.01% Tween20 are added to 5 mg of maleimide functionalized hydrogel beads 15 and incubated overnight at room temperature yielding transient hydrogel-linker-GRF-(1-29)-Cys-PEG prodrug 17. Hydrogel beads are washed several times with pH 7.4 PBS containing 0.01% Tween20.

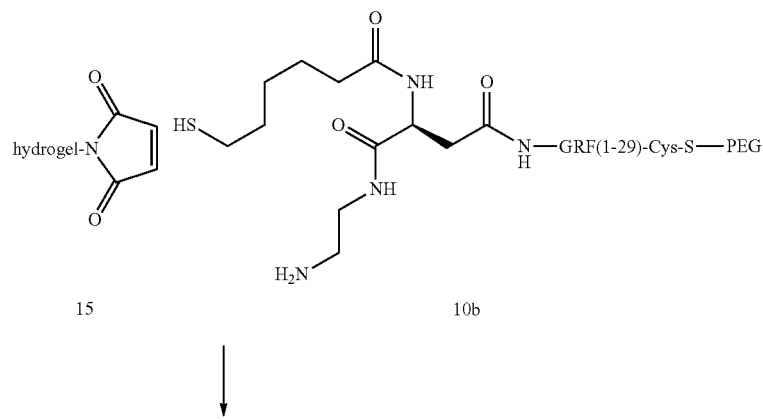

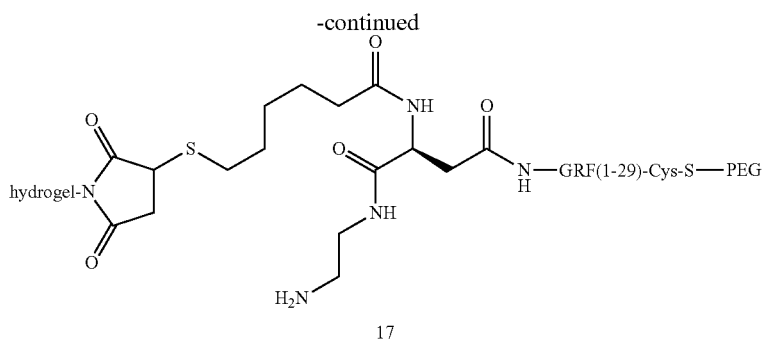

17

Example 18

Synthesis of Transient GRF(1-29)-Cys-Linker-Hydrogel Prodrug 18

1.5 mg of GRF(1-29)-Cys-linker with aminoethyl tag 11b in pH 7.4 PBS containing 0.01% Tween 20 are added to 5 mg of maleimide functionalized hydrogel beads 15 and incubated overnight at room temperature yielding transient GRF(1-29)-Cys-linker-hydrogel prodrug 18. Hydrogel beads are washed several times with pH 7.4 PBS containing 0.01% Tween20.

Example 19

Synthesis of Transient GRF(1-29)-Cys-PEG-linker-hydrogel Prodrug 19

1.5 mg of GRF(1-29)-Cys in pH 7.4 PBS containing 0.01% Tween20 are added to 5 mg of maleimide functionalized hydrogel beads 16 and incubated overnight at room temperature yielding transient GRF(1-29)-Cys-PEG-linker-hydrogel prodrug 19. Hydrogel beads are washed several times with pH 7.4 PBS containing 0.01% Tween20.

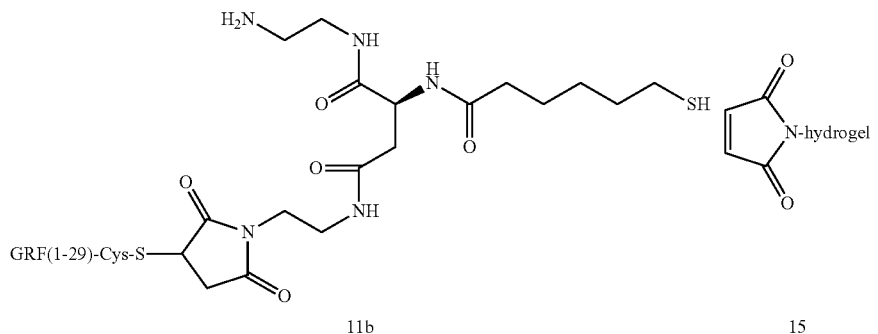

11b                                                                      15

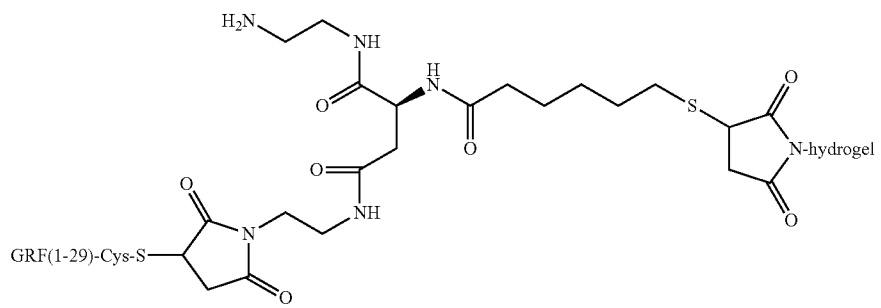

18

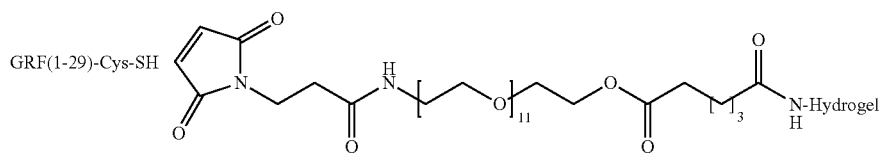

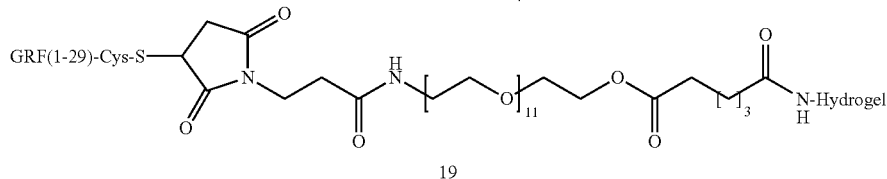

Example 20

In Vitro Release Kinetics—Determination of In Vitro Half-Life

GRF(1-29)-Cys -hydrogel prodrugs 17, 18 and 19 respectively are washed five times with pH 7.4 PBS buffer containing 0.01% Tween20, and suspended in 1 mL of the aforementioned buffer. The suspension is incubated at 37° C. The buffer of the suspension is exchanged after different time intervals and analyzed by HPLC-SEC at 220 nm. Peaks corresponding to the respective liberated tagged GRF(1-29)-Cys (see scheme below) are integrated and the total of liberated tagged GRF(1-29)-Cys is plotted against total incubation time. Curve fitting software is applied to determine first-order cleavage rates.

17
|pH 7.4 incubation

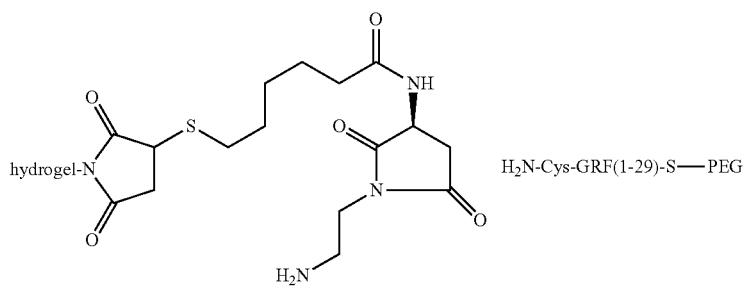

18
|pH 7.4 incubation

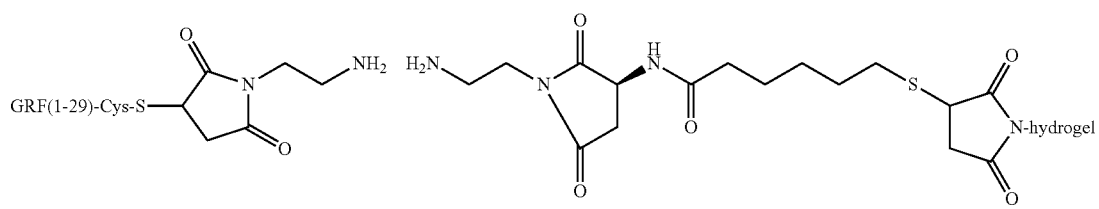

-continued

19

↓ pH 7.4 incubation

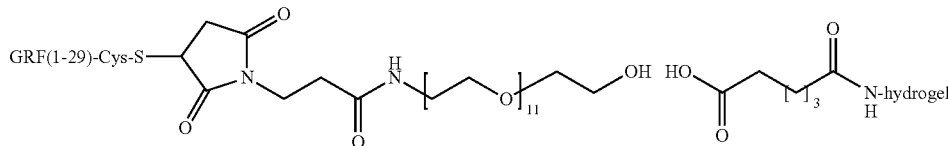

ABBREVIATIONS

Ac acetyl
ACN acetonitrile
AcOH acetic acid
AcOEt ethyl acetate
Asp aspartate
Bn benzyl
Boc t-butyloxycarbonyl
DBU 1,3-diazabicyclo[5.4.0]undecene
DCC N,N-dicyclohexylcarbodiimid
DCM dichloromethane
DIPEA diisopropylethylamine
DMAP dimethylamino-pyridine
DMF N,N-dimethylformamide
DMSO dimethylsulfoxide
DTT DL dithiotreitol
EDC 1-Ethyl-3-(3-dimethylaminopropyl)carbodiimid
EDTA ethylenediaminetetraacetic acid
eq stoichiometric equivalent
EtOH ethanol
Fmoc 9-fluorenylmethoxycarbonyl
HFIP 1,1,1,3,3,3-hexafluoroisopropanol
HPLC high performance liquid chromatography
HOBt N-hydroxybenzotriazole
iPrOH 2-propanol
LCMS mass spectrometry-coupled liquid chromatography
Mal 3-maleimido propyl
Mal-NH-PEG12-PFE N-(3-maleimidopropionyl)-39-amino-4,7,10,13,16,19,22,25,28,31,34,37-dodecaoxa-nonatriacontanoic acid pentafluorophenyl ester
Mal-PEG6-NHS N-(3-maleimidopropionyl)-21-amino-4,7,10,13,16,19-hexaoxa-heneicosanoic acid NHS ester
Me methyl
MeOAc methyl acetate
MeOH methanol
Mmt 4-methoxytrityl
Modmoc (5-methyl-2-oxo-1,3-dioxol-4-yl)-methyloxycarbonyl
MS mass spectrum/mass spectrometry
MTBE methyl tert.-butyl ether
MW molecular mass
NHS N-hydroxy succinimide
Oxyma Pure ethyl 2-cyano-2-(hydroxyimino)acetate
PEG poly(ethylene glycol)
PyBOP benzotriazole-1-yl-oxy-tris-pyrrolidino-phosphonium hexafluorophosphate
RP-HPLC reversed-phase high performance liquid chromatography
rpm rounds per minute
RT room temperature
SEC size exclusion chromatography
tBu tert.-butyl
TAN 1,5,9-triazanonane
TCEP tris(2-carboxyethyl)phosphine hydrochloride
TES triethylsilane
TFA trifluoroacetic acid
THF tetrahydrofurane
TMEDA N,N,N'N'-tetramethylethylene diamine
Tmob 2,4,6-trimethoxybenzyl
Trt triphenylmethyl, trityl
TSTU O—(N-succinimidyl)-N,N,N',N'-tetramethyluronium tetrafluoroborate
UPLC ultra performance liquid chromatography
V volume

The invention claimed is:

1. A process for the preparation of a hydrogel-linked prodrug releasing a tag moiety-biologically active moiety conjugate, comprising the steps of:
    (a) providing a mixture comprising:
        (a-i) at least one backbone reagent, wherein the at least one backbone reagent has a molecular weight ranging from 1 to 100 kDa, and comprises at least three functional groups $A^{x0}$, wherein each $A^{x0}$ is an amine (—$NH_2$ or —NH—), a hydroxyl (—OH), a carboxyl (—COOH), or an activated carboxyl of the formula —$COY^1$, wherein $Y^1$ is selected from formulas (f-i) to (f-vi):

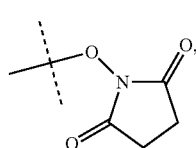

(f-i)

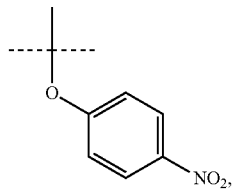

(f-ii)

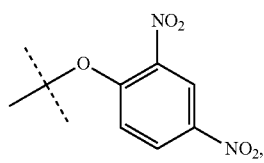

(f-iii)

-continued

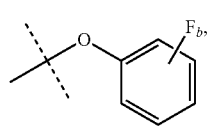

(f-iv)

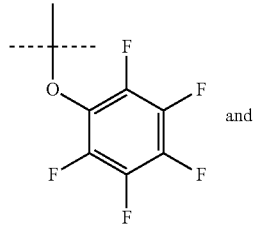

(f-v)

and

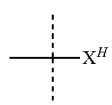

(f-vi)

wherein;
the dashed lines indicate attachment to the rest of the molecule;
b is 1, 2, 3, or 4; and
$X^H$ is Cl, Br, I, or F; and (a-ii) at least one crosslinker reagent, wherein the at least one crosslinker reagent has a molecular weight ranging from 0.2 to 40 kDa and comprises at least two functional end groups selected from the group consisting of activated ester groups, activated carbamate groups, activated carbonate groups, activated thiocarbonate groups, and amine groups;
wherein a weight ratio of the at least one backbone reagent to the at least one crosslinker reagent is from 1:99 to 99:1; and
wherein the molar ratio of $A^{x0}$ to functional end groups is >1;

(b) polymerizing the mixture of step (a) to a hydrogel;
(c) optionally covalently conjugating a spacer reagent of formula (VI) to $A^{x0}$ of the hydrogel from step (b), where the formula (VI) is:

$A^{x1}$-$SP^2$-$A^{x2}$  (VI);

wherein
$SP^2$ is $C_{1-50}$ alkyl, $C_{2-50}$ alkenyl, or $C_{2-50}$ alkynyl, which $C_{1-50}$ alkyl, $C_{2-50}$ alkenyl, and $C_{2-50}$ alkynyl is optionally interrupted by one or more group(s) selected from the group consisting of —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl, and naphthyl;
$A^{x1}$ is a functional group for reaction with $A^{x0}$ of the hydrogel; and
$A^{x2}$ is a functional group; and (d) covalently conjugating;
(d-i) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalently conjugating a drug to said reversible prodrug linker moiety resulting in a reversible prodrug linker moiety-biologically active moiety conjugate conjugated to the hydrogel of step (b) or (c), followed by covalently conjugating a tag reagent to the biologically active moiety resulting in a reversible prodrug linker moiety-biologically active moiety-tag moiety conjugate conjugated to the hydrogel of step (b) or (c); or (d-ii) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalently conjugating a biologically active moiety-tag moiety conjugate reagent to said reversible prodrug linker moiety through a functional group of the biologically active moiety resulting in a reversible prodrug linker moiety-biologically active moiety-tag moiety conjugate conjugated to the hydrogel of step (b) or (c); or (d-iii) a reversible prodrug linker moiety-biologically active moiety conjugate reagent to $A^{x0}$ or $A^{x2}$ of the hydrogel of step (b) or (c), respectively, through a functional group of the reversible prodrug linker moiety, followed by covalently conjugating a tag reagent to said biologically active moiety; or (d-iv) a reversible prodrug linker moiety-biologically active moiety-tag moiety conjugate reagent to $A^{x0}$ or $A^{x2}$ of the hydrogel of step (b) or (c), respectively, through a functional group of the reversible prodrug linker moiety; or (d-v) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalently conjugating a tag reagent to said reversible prodrug linker moiety resulting in a reversible prodrug linker moiety-tag moiety conjugate conjugated to the hydrogel of step (b) or (c), followed by covalently conjugating a drug to said tag moiety resulting in a reversible prodrug linker moiety-tag moiety-biologically active moiety conjugate conjugated to the hydrogel of step (b) or (c); or (d-vi) a reversible prodrug linker reagent to $A^{x0}$ or $A^{x2}$ of the hydrogel of step (b) or (c), respectively, resulting in a reversible prodrug linker moiety conjugated to the hydrogel of step (b) or (c), followed by covalently conjugating a tag moiety-biologically active moiety conjugate reagent to said reversible prodrug linker moiety through a functional group of the tag moiety;

(d-vii) a reversible prodrug linker moiety-tag moiety conjugate reagent to $A^{x0}$ or $A^{x2}$ of the hydrogel of step (b) or (c), respectively, through a functional group of the reversible prodrug linker moiety, followed by covalently conjugating a drug to said tag moiety; or (d-viii) a reversible prodrug linker moiety-tag moiety-biologically active moiety conjugate reagent to $A^{x0}$ or $A^{x2}$ of the hydrogel of step (b) or (c), respectively, through a functional group of the reversible prodrug linker moiety;

wherein the linkage between the reversible prodrug linker moiety and the biologically active moiety in the prodrug according to (d-i), (d-ii), (d-iii), and (d-iv) and the linkage between the reversible prodrug linker moiety and the tag moiety in the prodrug according to (d-v), (d-vi), (d-vii), and (d-viii) is reversible;

wherein the biologically active moiety is a small molecule drug in bound form having a molecular weight of between 50 Da and 1 kDa, a peptide drug in bound form, a protein drug in bound form, or an oligonucleotide drug in bound form; and wherein the tag moiety is a polymer with a molecular weight ranging from 0.5 to 50 kDa.

2. The process of claim 1;

wherein the at least one backbone reagent is selected from the group consisting of:

(i) a compound of formula (I):

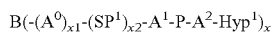 (I);

wherein:

B is a branching core selected from the group consisting of (a-i)
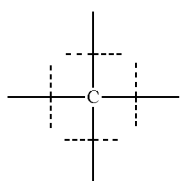

(a-ii)
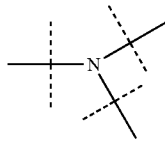

(a-iii)
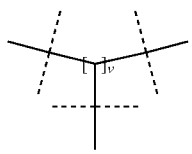

(a-iv)
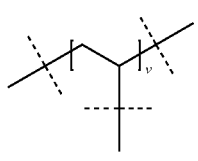

(a-v)
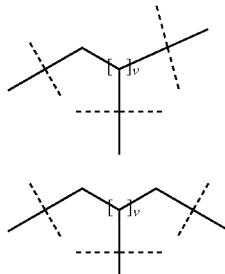

(a-vi)
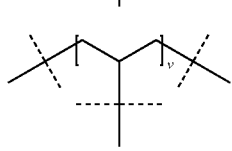

(a-vii)
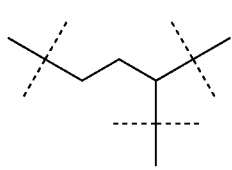

(a-viii)

-continued (a-ix)
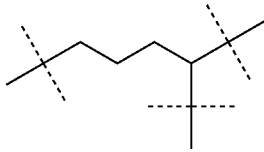

(a-x)
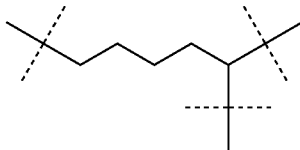

(a-xi)
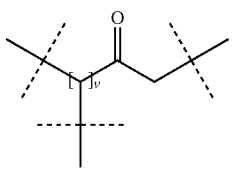

(a-xii)
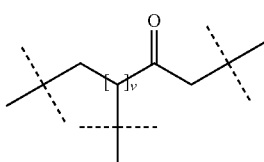

(a-xiii)
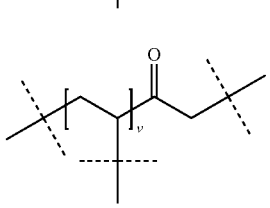

(a-xiv)

(a-xv)
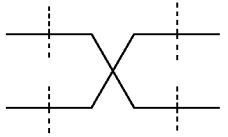

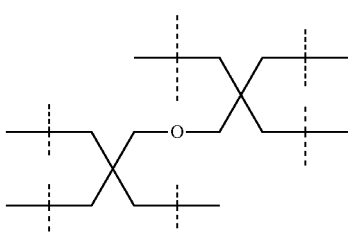

(a-xvi)
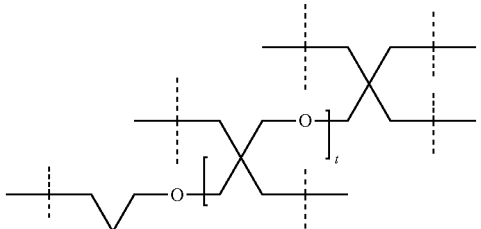

(a-xvii)
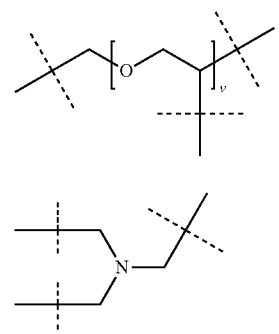

(a-xviii)
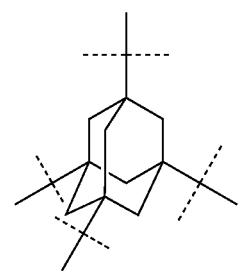

(a-xix)

(a-xx)
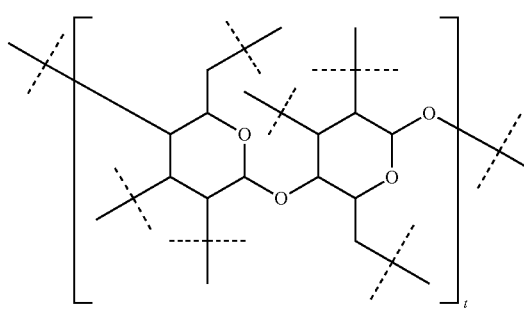

(a-xxi)
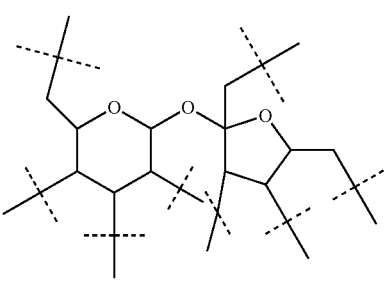

(a-xxii)
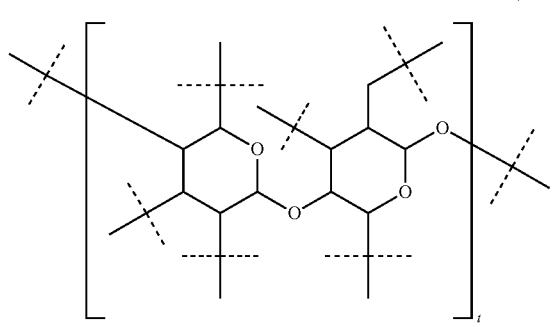

(a-xxiii)
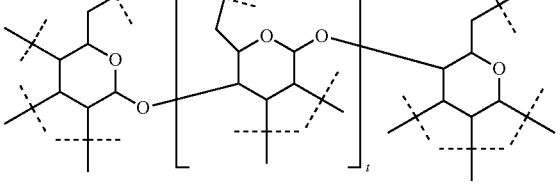

wherein
  dashed lines indicate attachment to $A^0$ or, if x1 and x2 are both 0, to $A^1$,
  t is 1 or 2;
  v is 1, 2, 3, 4, 5, 6, 7, 8, 9, 10, 11, 12, 13, or 14;
  $SP^1$ is a spacer moiety selected from the group consisting of $C_{1-6}$ alkyl, $C_{2-6}$ alkenyl, and $C_{2-6}$ alkynyl;
  P is a PEG-based polymeric chain comprising at least 80% PEG;
  $Hyp^1$ is a moiety comprising an amine (—$NH_2$ and/or —NH—) or a polyamine comprising at least two amines (—$NH_2$ and/or —NH—);
  x is an integer from 3 to 16;
  x1 and x2 are independently of each other 0 or 1, provided that x1 is 0, if x2 is 0;
  $A^0$, $A^1$, and $A^2$ are independently of each other selected from the group consisting of

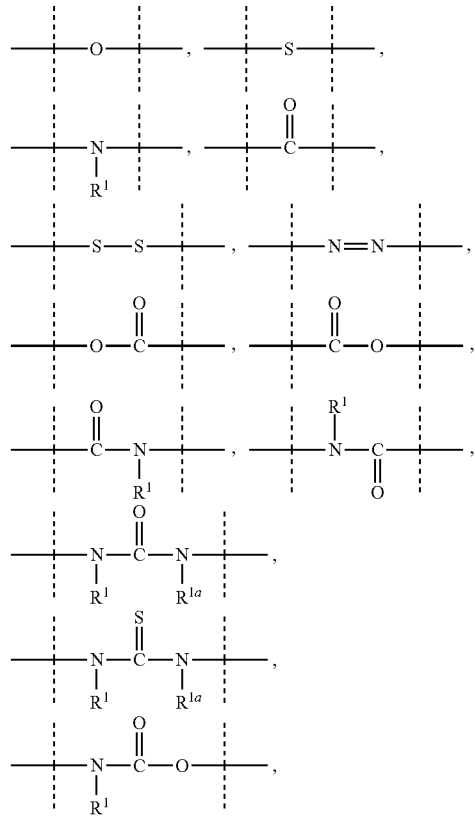

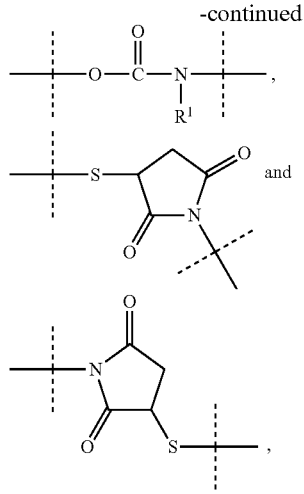

wherein $R^1$ and $R^{1a}$ are independently of each other H or $C_{1-6}$ alkyl;

(ii) a compound of formula (II):

$$\text{Hyp}^2\text{-}A^3\text{-}P\text{-}A^4\text{-}\text{Hyp}^3 \quad (II);$$

wherein:
P is defined as above in the compound of formula (I);
$\text{Hyp}^2$ and $\text{Hyp}^3$ are independently of each other a polyamine comprising at least two amines (—$NH_2$ and/or —NH—); and
$A^3$ and $A^4$ are independently selected from the group consisting of:

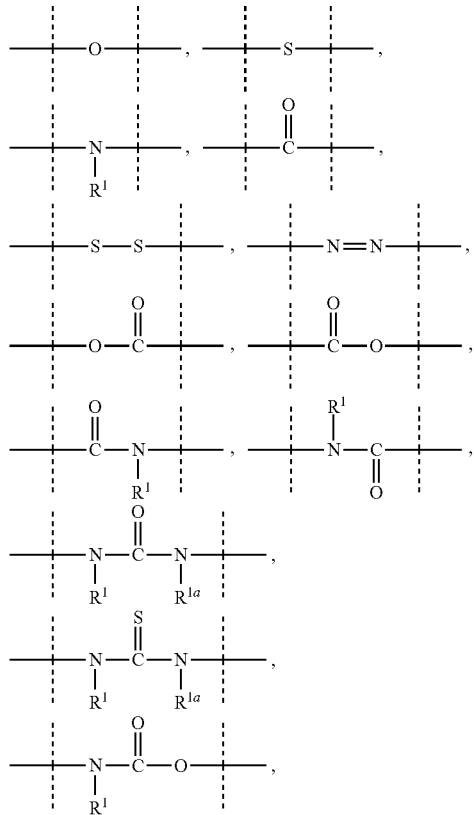

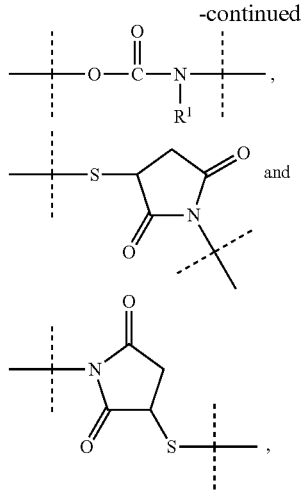

wherein $R^1$ and $R^{1a}$ are independently of each other H or $C_{1-6}$ alkyl;

(iii) a compound of formula (III):

$$P^1\text{-}A^5\text{-}\text{Hyp}^4 \quad (III);$$

wherein:
$P^1$ is a PEG-based polymeric chain comprising at least 80% PEG;
$\text{Hyp}^4$ is a polyamine comprising at least three amines (—$NH_2$ and/or —NH); and
$A^5$ is selected from the group consisting of:

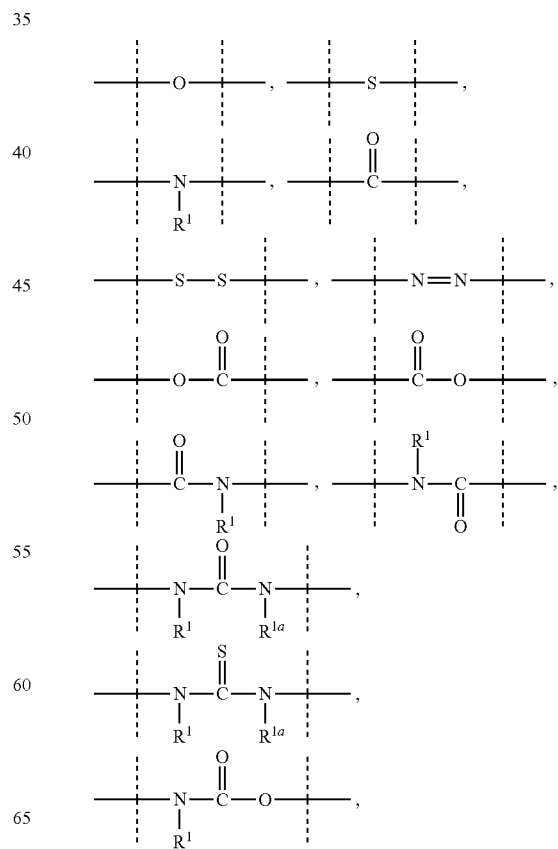

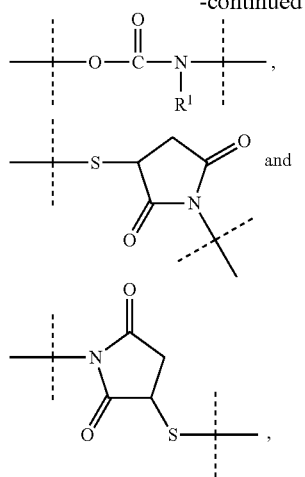

wherein $R^1$ and $R^{1a}$ are independently of each H or $C_{1-6}$ alkyl; and (iv) a compound of formula (IV):

$$T^1\text{-}A^6\text{-}Hyp^5 \qquad (IV);$$

wherein:
Hyp$^5$ is a polyamine comprising at least three amines (—NH$_2$ and/or —NH); and
$A^6$ is selected from the group consisting of:

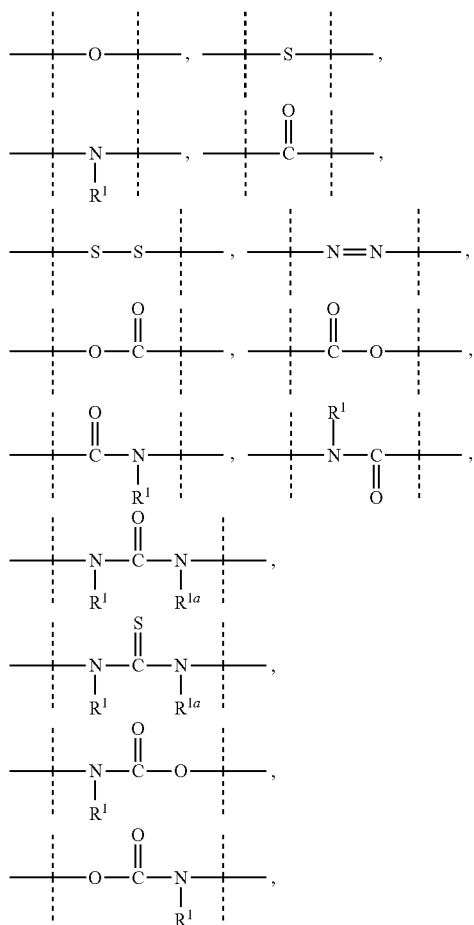

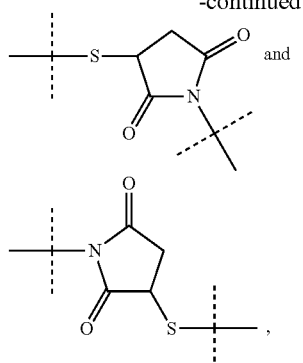

wherein $R^1$ and $R^{1a}$ are independently of each other H or $C_{1-6}$ alkyl; and $T^1$ is selected from the group consisting of $C_{1-50}$ alkyl, $C_{2-50}$ alkenyl and $C_{2-50}$ alkynyl, which $C_{1-50}$ alkyl, $C_{2-50}$ alkenyl and $C_{2-50}$ alkynyl are optionally interrupted by one or more group(s) selected from the group consisting of —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl, and naphthyl.

3. The process of claim 2;
wherein Hyp$^1$, Hyp$^2$, Hyp$^3$, Hyp$^4$, and Hyp$^5$ are selected from the group consisting of:
a moiety of formula (e-i):

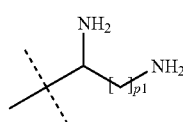

(e-i)

wherein:
p1 is an integer from 1 to 5; and
the dashed line indicates attachment to $A^2$ if the backbone reagent is of formula (I) and to $A^3$ or $A^4$ if the backbone reagent is of formula (II);
a moiety of formula (e-ii):

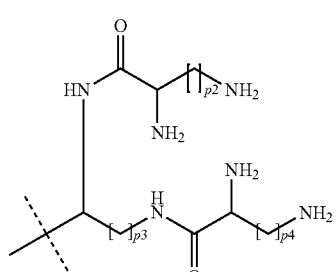

(e-ii)

wherein:
p2, p3, and p4 are identical or different and each is independently of the others an integer from 1 to 5; and
the dashed line indicates attachment to $A^2$ if the backbone reagent is of formula (I), to $A^3$ or $A^4$ if the backbone reagent is of formula (I), to $A^5$ if the backbone is of formula (III) and to $A^6$ if the backbone reagent is of formula (IV);

a moiety of formula (e-iii):

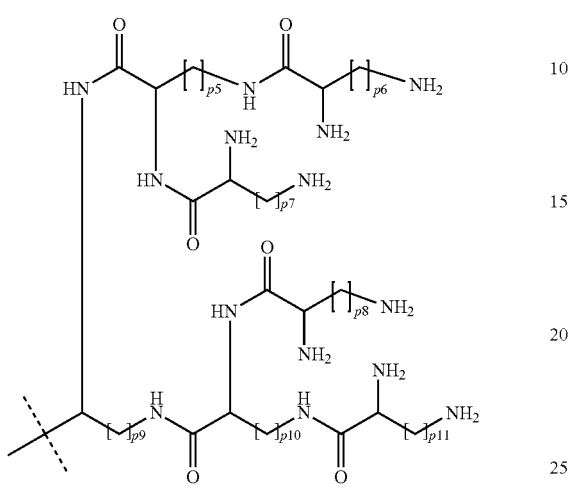

(e-iii)

wherein:
p5 to p11 are identical or different and each is independently of the others an integer from 1 to 5; and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-iv):

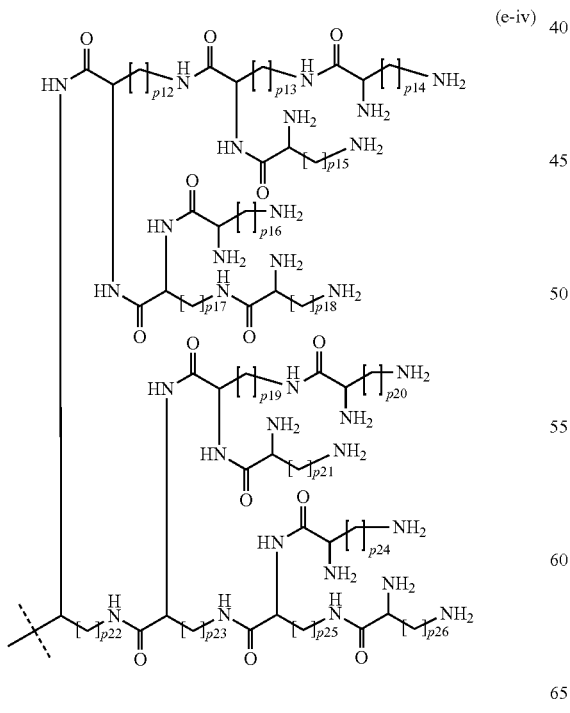

(e-iv)

wherein:
p12 to p26 are identical or different and each is independently of the others an integer from 1 to 5; and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-v):

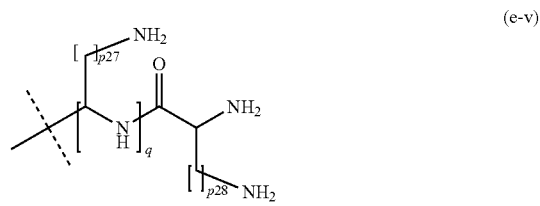

(e-v)

wherein:
p27 and p28 are identical or different and each is independently of the other an integer from 1 to 5;

q is an integer from 1 to 8; and the dashed line indicates attachment to $A^2$ if the backbone reagent is of formula (I), to $A^3$ or $A^4$ if the backbone reagent is of formula (II), to $A^5$ if the is of formula (III) and to $A^6$ if the backbone reagent is of formula (IV);

a moiety of formula (e-vi):

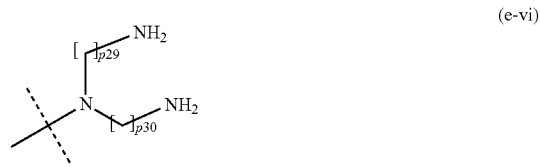

(e-vi)

wherein:
p29 and p30 are identical or different and each is independently of the other an integer from 2 to 5; and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-vii):

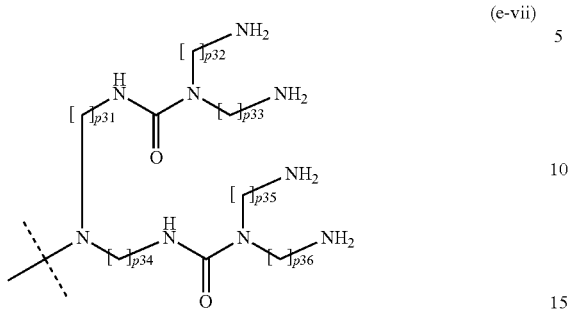

(e-vii)

wherein:

p31 to p36 are identical or different and each is independently of the others an integer from 2 to 5; and the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-viii):

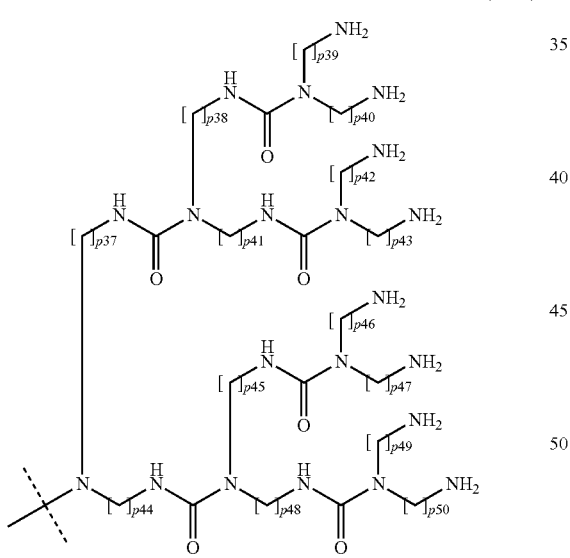

(e-viii)

wherein:

p37 to p50 are identical or different and each is independently of the others an integer from 2 to 5; and the dashed line indicates attachment to $A^2$ if the backbone reagent is of formula (I), to $A^3$ or $A^4$ if the backbone reagent is of formula (II), to $A^5$ if the is of formula (III) and to $A^6$ if the backbone reagent is of formula (IV); and a moiety of formula (e-ix):

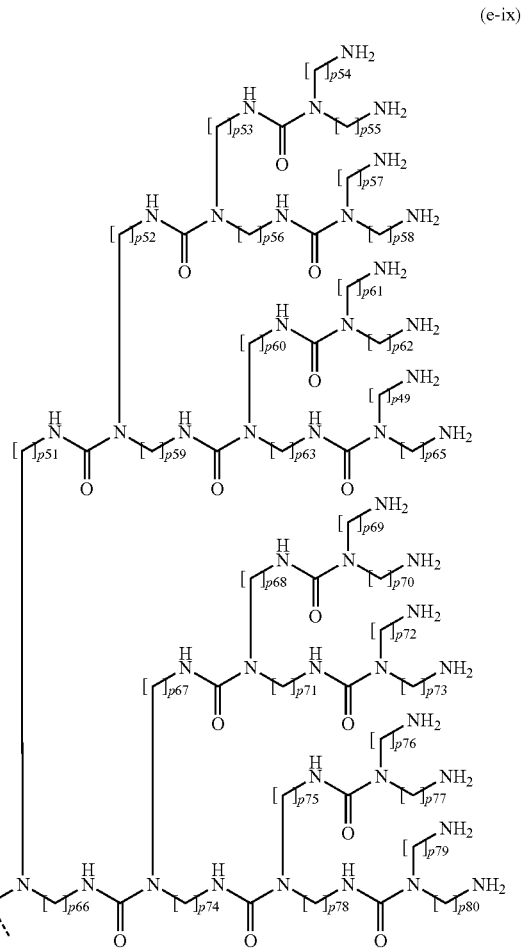

(e-ix)

wherein:

p51 to p80 are identical or different and each is independently of the others an integer from 2 to 5; and the dashed line indicates attachment to $A^2$ if the backbone reagent is of formula (I), to $A^3$ or $A^4$ if the backbone reagent is of formula (II), to $A^5$ if the backbone is of formula (III) and to $A^6$ if the backbone reagent is of formula (IV);

wherein the moieties (e-i) to (e-v) may at each chiral center be in either R- or S-configuration.

4. The process of claim 3;

wherein the moiety $-A^2-Hyp^1$ is:

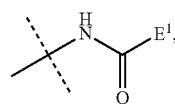

wherein:

the dashed line indicates attachment to P; and $E^1$ is selected from formulas (e-i) to (e-ix).

5. The process of claim 2;
wherein $A^0$ is:

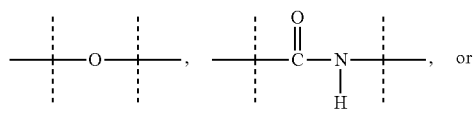

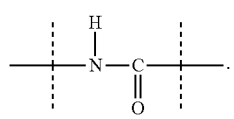

6. The process of claim 2;
wherein P is of formula (c-i):

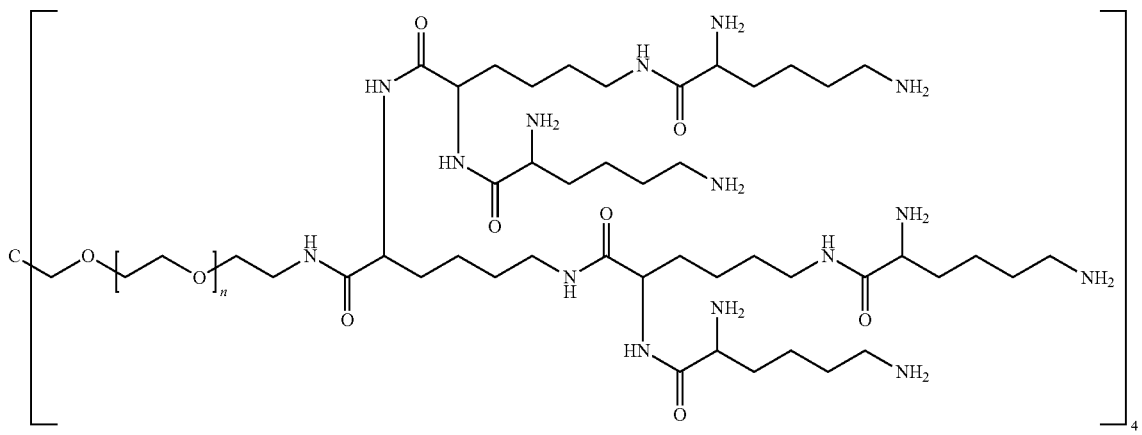

wherein n ranges from 6 to 900.

7. A method of claim 6; wherein n ranges from 20 to 700.

8. A method of claim 6; wherein n ranges from 20 to 250.

9. A method of claim 2; wherein P is a PEG-based polymeric chain comprising at least 85% PEG.

10. A method of claim 2; wherein P is a PEG-based polymeric chain comprising at least 90% PEG.

11. A method of claim 2; wherein P is a PEG-based polymeric chain comprising at least 95% PEG.

12. The process of claim 1;
wherein the backbone reagent has the following formula:

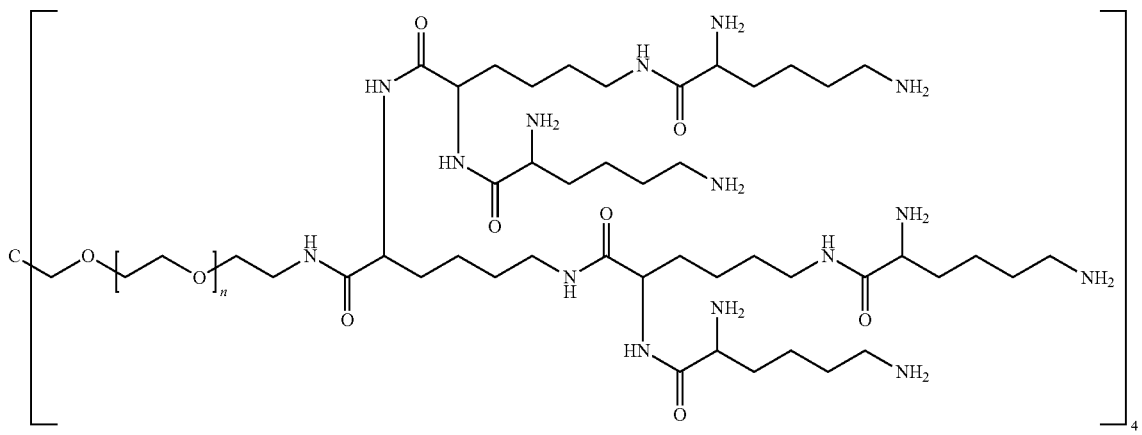

wherein:
n ranges from 10 to 40.

13. The process of claim 1;
wherein the crosslinker reagent is a compound of formula (V-II):

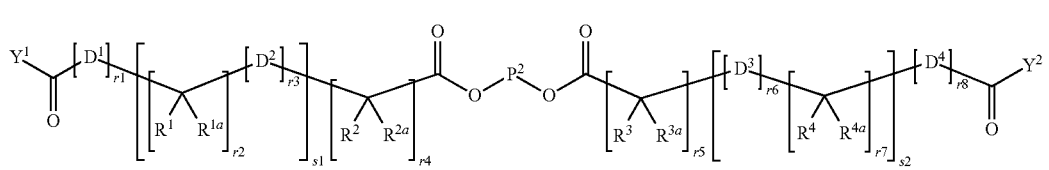

wherein:

D¹, D², D³, and D⁴ are identical or different and each is independently of the others O, NR⁵, S, or CR⁵R⁵ᵃ;

R¹, R¹ᵃ, R², R²ᵃ, R³, R³ᵃ, R⁴, R⁴ᵃ, R⁵, and R⁵ᵃ are identical or different and each is independently of the others H or C₁₋₆ alkyl; optionally, one or more of the pair(s) R¹/R¹ᵃ, R²/R²ᵃ, R³/R³ᵃ, R⁴/R⁴ᵃ, R¹/R², R³/R⁴, R¹ᵃ/R²ᵃ, and R³ᵃ/R⁴ᵃ form a chemical bond or are joined together with the atom to which they are attached to form a C₃₋₈ cycloalkyl or to form a ring A or are joined together with the atom to which they are attached to form a 4- to 7-membered heterocyclyl or 8- to 11-membered heterobicyclyl or adamantyl;

A is phenyl, naphthyl, indenyl, indanyl, or tetralinyl;

P² is:

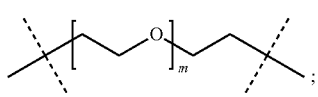

m ranges from 5 to 920;

r1, r2, r7, r8 are independently 0 or 1;

r3 and r6 are independently 0, 1, 2, 3, or 4;

r4 and r5 are independently 1, 2, 3, 4, 5, 6, 7, 8, 9, or 10;

s1 and s2 are independently 1, 2, 3, 4, 5, or 6;

Y¹ and Y² are identical or different and each is independently of the other selected from formulas (f-i) to (f-vi):

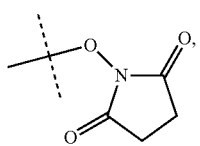
(f-i)

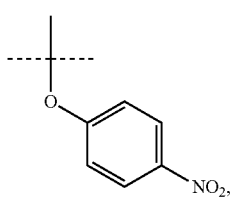
(f-ii)

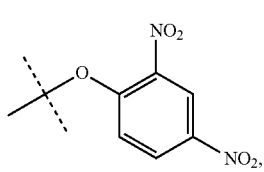
(f-iii)

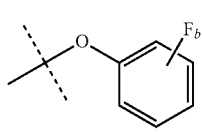
(f-iv)

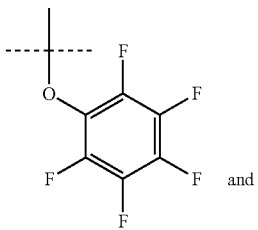
(f-v)

and

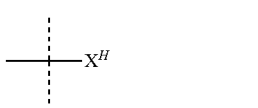
(f-vi)

wherein:
the dashed lines indicate attachment to the rest of the molecule;
b is 1, 2, 3, or 4; and
X^H is Cl, Br, I, or F.

14. A method of claim 13; wherein m ranges from 5 to 460.

15. A method of claim 13; wherein m ranges from 40 to 230.

16. The process of claim 1;
wherein
A^{x0} is an amine;
A^{x1} is ClSO₂—, R¹(C=O)—, I—, Br—, Cl—, SCN—, CN—, O=C=N—, Y¹—(C=O)—, Y¹—(C=O)—NH—, or Y¹—(C=O)—O—;
R¹ is H, C₁₋₆ alkyl, C₂₋₆ alkenyl, C₂₋₆ alkynyl, C₃₋₈ cycloalkyl, 4- to 7-membered heterocyclyl, 8- to 11-membered heterobicyclyl, phenyl, naphthyl, indenyl, indanyl, or tetralinyl; and
Y¹ is selected from formulas (f-i) to (f-vi):

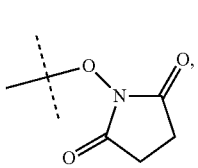
(f-i)

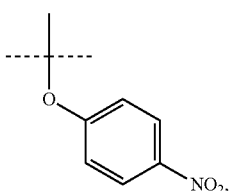
(f-ii)

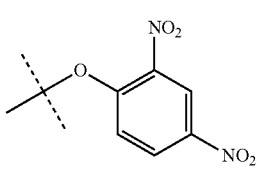
(f-iii)

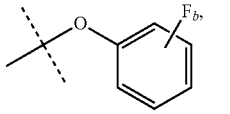
(f-iv)

-continued (f-v)

[structure: pentafluorophenyl ether]

and (f-vi)

―――X$^H$ wherein:
the dashed lines indicate attachment to the rest of the molecule;
b is 1, 2, 3, or 4; and
X$^H$ is Cl, Br, I, or F.

17. The process of claim 1;
wherein A$^{x2}$ is selected from the group consisting of -maleimide, —SH, —NH$_2$, —SeH, —N$_3$, —C≡CH, —CR$^1$=CR$^{1a}$R$^{1b}$, —OH, —(CH=X)—R$^1$, —(C=O)—S—R$^1$, —(C=O)—H, —NH—NH$_2$, —O—NH$_2$, —Ar—X$^0$, —Ar—Sn(R$^1$)(R$^{1a}$)(R$^{1b}$), —Ar—B(OH)(OH), Br, I,

[structures shown]

with optional protecting groups;
wherein:
dashed lines indicate attachment to SP$^2$;
X is O, S, or NH;
X$^0$ is —OH, —NR$^1$R$^{1a}$, —SH, or —SeH;

X$^H$ is Cl, Br, I, or F;
Ar is phenyl, naphthyl, indenyl, indanyl, or tetralinyl; and
R$^1$, R$^{1a}$, and R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocycyl, 8- to 11-membered heterobicyclyl, phenyl, naphthyl, indenyl, indanyl, or tetralinyl.

18. The process of claim 1;
wherein step (d) is (d-iv) and optionally comprises the step of covalently conjugating a reversible prodrug linker moiety-biologically active moiety-tag moiety conjugate reagent of formula (XIII) to A$^{x0}$ of step (b) or to A$^{x2}$ of step (c), wherein formula (XIII) is:

$$A^{x3}\text{-}L\text{-}A^{y3}\text{-}D\text{-}A^{y4}\text{-}T \qquad (XIII);$$

wherein
L is the reversible prodrug linker moiety,
D is the biologically active moiety;
T is the tag moiety;
A$^{x3}$ is a functional group selected from the group consisting of —SH, —NH$_2$, —SeH, -maleimide, —C≡CH, —N$_3$, —CR$^1$=CR$^{1a}$R$^{1b}$, —(C=X)—R$^1$, —OH, —(C=O)—S—R$^1$, —NH—NH$_2$, —O—NH$_2$, —Ar—Sn(R$^1$)(R$^{1a}$)(R$^{1b}$), —Ar—B(OH)(OH), —Ar—X$^0$,

[structures shown]

wherein:
dashed lines indicate attachment to L
X is O, S, or NH;
X$^0$ is —OH, —NR$^1$R$^{1a}$, —SH, or —SeH;
R$^1$, R$^{1a}$, R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl;

Ar is phenyl, naphthyl, indenyl, indanyl, or tetralinyl; and $Y^1$ is selected from formulas (f-i) to (f-vi):

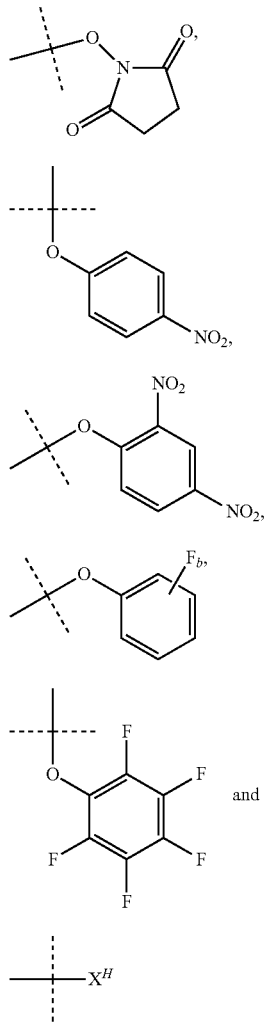

(f-i)

(f-ii)

(f-iii)

(f-iv)

(f-v)

(f-vi)

wherein:
  the dashed lines indicate attachment to the rest of the molecule
  b is 1, 2, 3, or 4; and
  $X^H$ is Cl, Br, I, or F;

$A^{y3}$ is a linkage selected from the group consisting of:

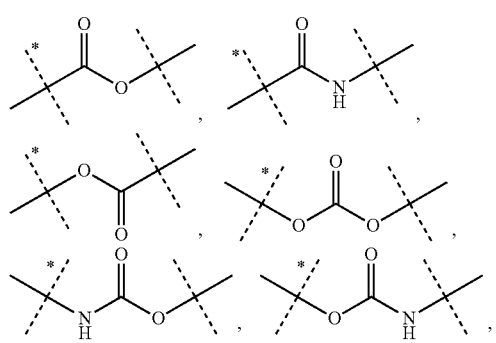

-continued

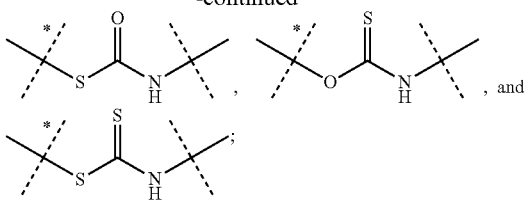

wherein:
  the dashed lines marked with an asterisk indicate attachment to L; and
  the unmarked dashed lines indicate attachment to D; and $A^{y4}$ is a linkage selected from the group consisting of:

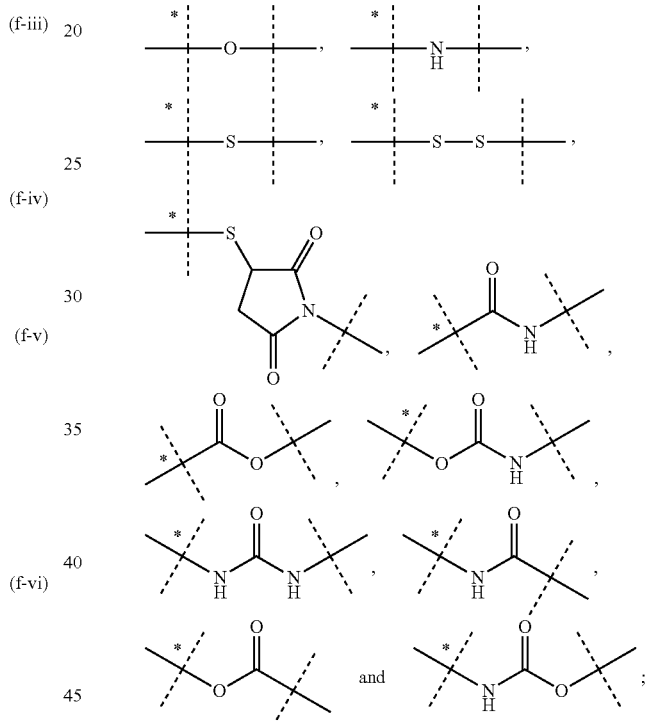

wherein:
  the dashed lines marked with an asterisk indicate attachment to D; and
  the unmarked dashed lines indicate attachment to T;
wherein $A^{x3}$ reacts with $A^{x0}$ or $A^{x2}$, respectively.

19. The process of claim 18;
wherein $A^{y3}$ is selected from the group consisting of:

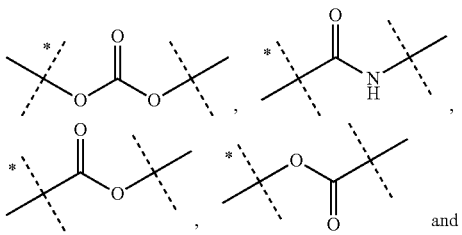

and

-continued

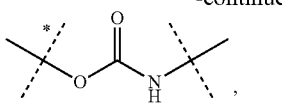

wherein:
the dashed lines marked with an asterisk indicate attachment to L; and
the unmarked dashed lines indicate attachment to D.

20. The process of claim 1;
wherein step (d) is (d-vii) and optionally comprises the steps of:
(i) covalently conjugating a reversible prodrug linker moiety-tag moiety conjugate reagent of formula (XVII) to $A^{x0}$ of step (b) or to $A^{x2}$ of step (c), where formula (XVII) is:

$$A^{x3}\text{-}L\text{-}A^{y5}\text{-}T\text{-}A^{x9} \qquad (XVII);$$

wherein:
L is the reversible prodrug linker moiety;
T is the tag moiety;
$A^{x3}$ is a functional group selected from the group consisting of —SH, —NH$_2$, —SeH, -maleimide, —C≡CH, —N$_3$, —CR$^1$=CR$^{1a}$R$^{1b}$, —(C=X)—R$^1$, —OH, —(C=O)—S—R$^1$, —NH—NH$_2$, —O—NH$_2$, —Ar—Sn(R$^1$)(R$^{1a}$)(R$^{1b}$), —Ar—B(OH)(OH), —Ar—X$^0$,

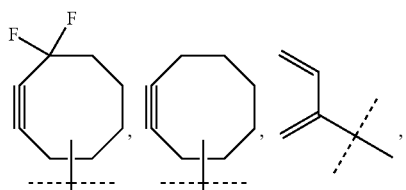

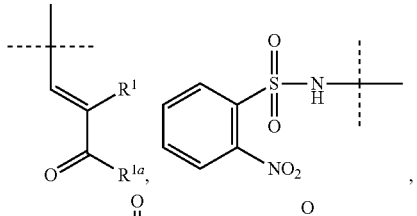

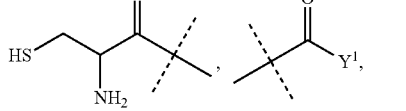

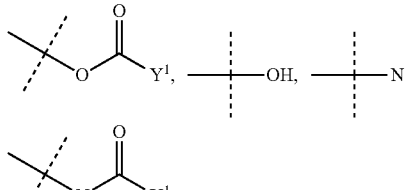

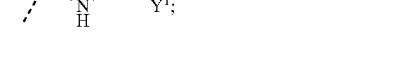

wherein
dashed lines indicate attachment to L;
X is O, S, or NH;
X$^0$ is —OH, —NR$^1$R$^{1a}$, —SH, or —SeH;
R$^1$, R$^{1a}$, R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl;
Ar is phenyl, naphthyl, indenyl, indanyl, or tetralinyl; and
Y$^1$ is selected from formulas (f-i) to (f-vi):

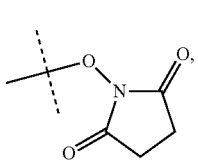 (f-i)

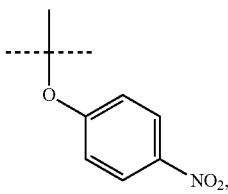 (f-ii)

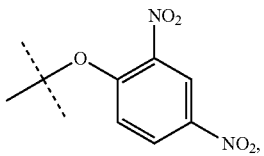 (f-iii)

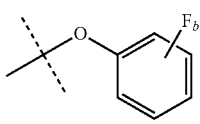 (f-iv)

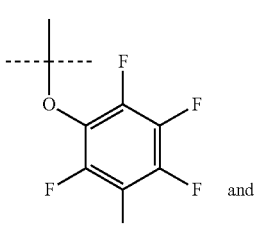 (f-v)

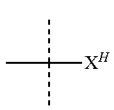 (f-vi)

wherein:
the dashed lines indicate attachment to the rest of the molecule;
b is 1, 2, 3, or 4; and
X$^H$ is Cl, Br, I, or F;
$A^{x9}$ is selected from the group consisting of -maleimide,

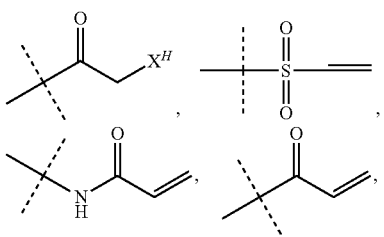

-continued

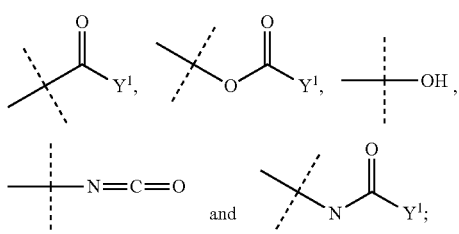

wherein;
dashed lines indicate attachment to T; and
Y$^1$ is selected from formulas (f-i) to (f-vi):

(f-i)

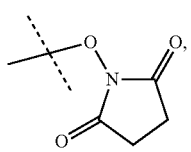

(f-ii)

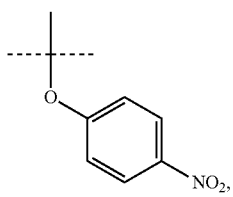

(f-iii)

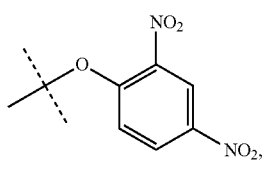

(f-iv)

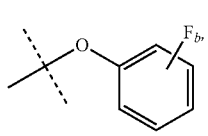

(f-v)

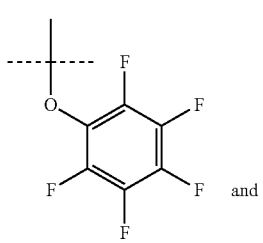 and (f-vi)

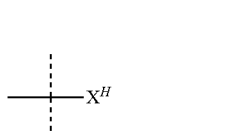

wherein:
the dashed lines indicate attachment to the rest of the molecule;
b is 1, 2, 3, or 4; and
X$^H$ is Cl, Br, I, or F; and A$^{y5}$ is selected from the group consisting of:

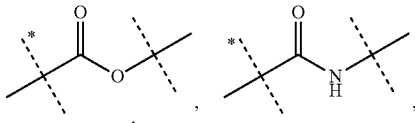

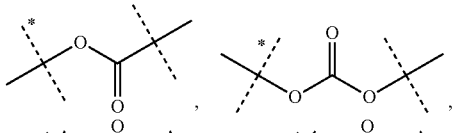

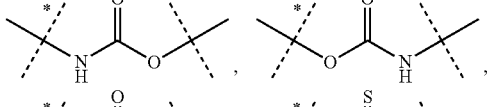

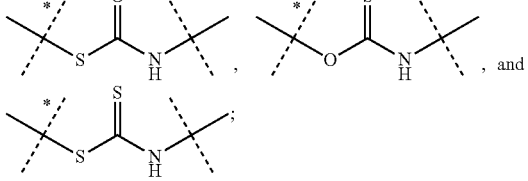

wherein
the dashed lines marked with an asterisk indicate attachment to L; and
the unmarked dashed lines indicate attachment to T; and
wherein A$^{x3}$ reacts with A$^{x0}$ or A$^{x2}$, respectively; and
(ii) covalently conjugating a drug of formula (VIIIa) to the conjugate of step (i), where formula (VIIIa) is:

$$A^{x5}\text{-}D \qquad \text{(VIIIa)};$$

wherein:
D is the biologically active moiety; and
A$^{x5}$ is a functional group of the drug and is selected from the group consisting of carboxylic acid, amine, thiol, sulfonic acid, carbonate, carbamate, hydroxyl, aldehyde, ketone, hydrazine, isocyanate, isothiocyanate, phosphoric acid, phosphonic acid, haloacetyl, alkyl halides, acryloyl, aryl fluorides, hydroxylamine, disulfides, vinyl sulfone, vinyl ketone, diazoalkanes, diazoacetyls, oxirane, and aziridine; and
wherein A$^{x5}$ reacts with A$^{x9}$.

21. The process of claim 1;
wherein step (d) is (d-viii) and optionally comprises the step of covalently conjugating a reversible prodrug linker moiety-tag moiety-biologically active moiety conjugate reagent of formula (XVIII) to A$^{x0}$ of step (b) or to A$^{x2}$ of step (c), where formula (XVIII) is:

$$A^{x3}\text{-}L\text{-}A^{y5}\text{-}T\text{-}A^{y6}\text{-}D \qquad \text{(XVIII)};$$

wherein:
L is the reversible prodrug linker moiety;
D is the biologically active moiety;
T is the tag moiety;
A$^{x3}$ is a functional group selected from the group consisting of —SH, —NH$_2$, —SeH, -maleimide, —C≡CH, —N$_3$, —CR$^1$=CR$^{1a}$R$^{1b}$, —(C=X)—R$^1$, —OH, —(C=O)—S—R$^1$, —NH—NH$_2$, —O—NH$_2$, —Ar—Sn(R$^1$)(R$^{1a}$)(R$^{1b}$), —Ar—B(OH)(OH), —Ar—X$^O$,

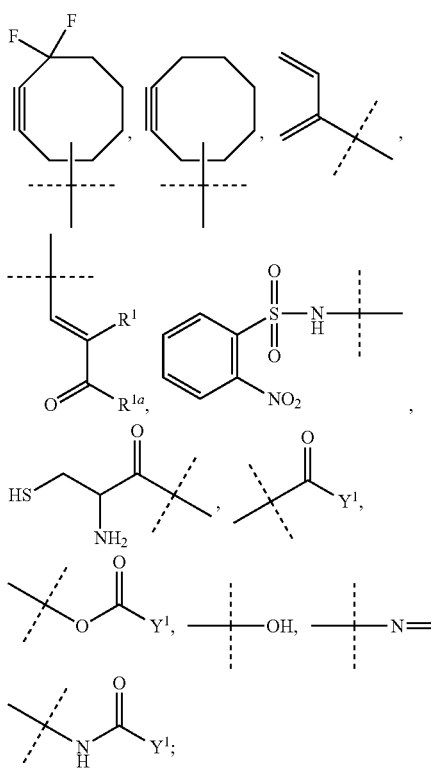

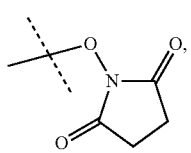

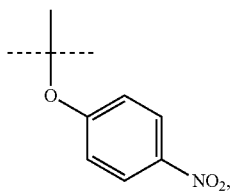

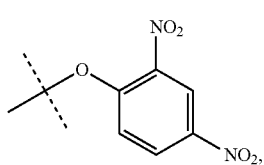

wherein:
 dashed lines indicate attachment to L;
 X is O, S, or NH;
 $X^0$ is —OH, —$NR^1R^{1a}$, —SH, or —SeH;
 $R^1$, $R^{1a}$, $R^{1b}$ are independently of each other H, C, alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl;
 Ar is phenyl, naphthyl, indenyl, indanyl, or tetralinyl; and
 $Y^1$ is selected from formulas (f-i) to (f-vi):

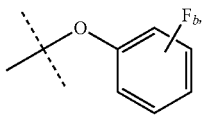
(f-iv)

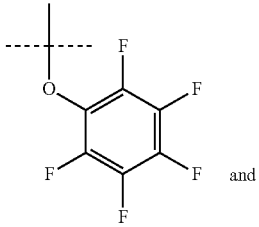 and
(f-v)

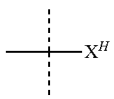
(f-vi)

wherein:
 the dashed lines indicate attachment to the rest of the molecule;
 b is 1, 2, 3, or 4; and
 $X^H$ is Cl, Br, I, or F;
$A^{y5}$ is selected from the group consisting of:

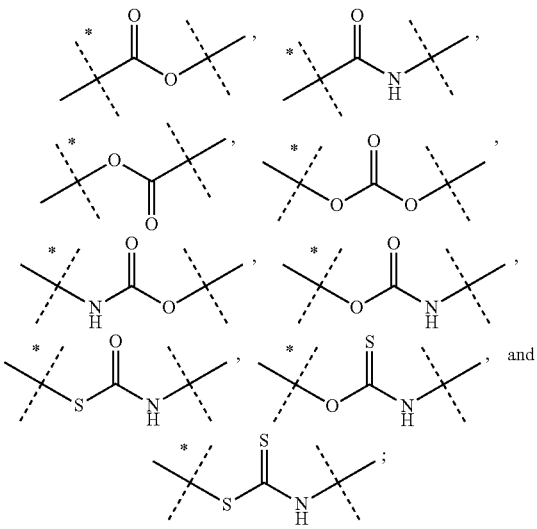

wherein:
 the dashed lines marked with an asterisk indicate attachment to L; and
 the unmarked dashed lines indicate attachment to T; and
$A^{y6}$ is a linkage selected from the group consisting of:

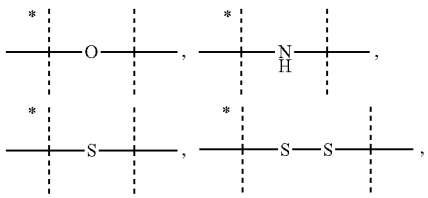

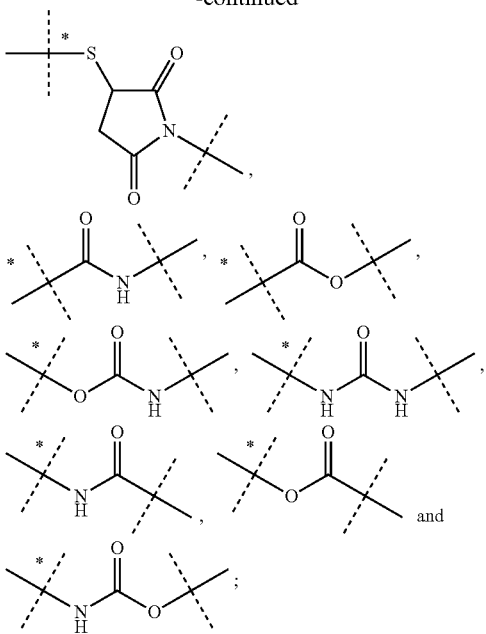

wherein
the dashed lines marked with an asterisk indicate attachment to D; and
the unmarked dashed lines indicate attachment to T;
wherein $A^{x3}$ reacts with $A^{x0}$ or $A^{x2}$, respectively.

22. A hydrogel-linked prodrug releasing a tag moiety-biologically active moiety conjugate obtained by the process of claim 1.

23. The prodrug of claim 22;
wherein process step (d) is selected from the group consisting of (d-i), (d-ii), (d-iii), and (d-iv).

24. The prodrug of claim 22;
wherein process step (d) is selected from the group consisting of (d-v), (d-vi), (d-vii), and (d-viii).

25. A pharmaceutical composition comprising:
the prodrug of claim 22 or a pharmaceutical salt thereof; and
a pharmaceutically acceptable excipient.

26. A method comprising:
utilizing the prodrug of claim 22 as a medicament.

27. A method comprising:
utilizing the pharmaceutical composition of claim 25 as a medicament.

* * * * *